United States Patent
Anand et al.

(10) Patent No.: US 10,407,416 B2
(45) Date of Patent: Sep. 10, 2019

(54) KAPPA OPIOID AGONISTS AND USES THEREOF

(71) Applicant: Nektar Therapeutics, San Francisco, CA (US)

(72) Inventors: Neel K. Anand, San Mateo, CA (US); Franco J. Duarte, Walnut Creek, CA (US); Wen Zhang, San Ramon, CA (US); Zhongxu Ren, Foster City, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 15/719,376

(22) Filed: Sep. 28, 2017

(65) Prior Publication Data

US 2018/0016266 A1    Jan. 18, 2018

Related U.S. Application Data

(63) Continuation of application No. 14/900,039, filed as application No. PCT/US2014/044535 on Jun. 27, 2014, now Pat. No. 9,815,824.

(60) Provisional application No. 61/929,685, filed on Jan. 21, 2014, provisional application No. 61/841,042, filed on Jun. 28, 2013.

(51) Int. Cl.
| | |
|---|---|
| *C07D 409/12* | (2006.01) |
| *C07D 333/48* | (2006.01) |
| *C07D 241/04* | (2006.01) |
| *C07D 207/12* | (2006.01) |
| *C07D 207/14* | (2006.01) |
| *C07D 213/56* | (2006.01) |
| *C07D 213/61* | (2006.01) |
| *C07C 233/40* | (2006.01) |
| *C07D 205/04* | (2006.01) |
| *C07D 295/125* | (2006.01) |
| *C07C 233/05* | (2006.01) |
| *C07D 207/09* | (2006.01) |
| *C07D 401/12* | (2006.01) |

(52) U.S. Cl.
CPC .......... *C07D 409/12* (2013.01); *C07C 233/05* (2013.01); *C07C 233/40* (2013.01); *C07D 205/04* (2013.01); *C07D 207/09* (2013.01); *C07D 207/12* (2013.01); *C07D 207/14* (2013.01); *C07D 213/56* (2013.01); *C07D 213/61* (2013.01); *C07D 241/04* (2013.01); *C07D 295/125* (2013.01); *C07D 333/48* (2013.01); *C07D 401/12* (2013.01)

(58) Field of Classification Search
CPC .. C07D 205/04; C07D 207/09; C07D 207/12; C07D 207/14; C07D 295/125
See application file for complete search history.

(56) References Cited

U.S. PATENT DOCUMENTS

| | | | |
|---|---|---|---|
| 5,232,978 | A | 8/1993 | Gottschlich et al. |
| 6,057,357 | A | 5/2000 | Horwell et al. |
| 7,915,228 | B2 | 3/2011 | Wiesner et al. |
| 2005/0136031 | A1 | 6/2005 | Bentley et al. |
| 2006/0178426 | A1 | 8/2006 | Stahle et al. |
| 2010/0048602 | A1 | 2/2010 | Riggs-Sauthier et al. |
| 2016/0145245 | A1 | 5/2016 | Anand et al. |

FOREIGN PATENT DOCUMENTS

| | | | |
|---|---|---|---|
| EP | 0 254 545 A2 | | 1/1988 |
| GB | 0254545 | * | 1/1988 |
| JP | 11-12250 | | 1/1999 |
| JP | 11012250 | | 1/1999 |
| WO | WO 94/06784 A1 | | 3/1994 |
| WO | WO 96/06078 A1 | | 2/1996 |
| WO | WO 00/14065 A1 | | 3/2000 |
| WO | WO 02/098949 A1 | | 12/2002 |
| WO | WO 2004/054970 A1 | | 7/2004 |
| WO | WO 2008/011551 A1 | | 1/2008 |
| WO | WO 2008/112288 A2 | | 9/2008 |

OTHER PUBLICATIONS

Barlow et al., "Structure/Activity Studies Related to 2-(3,4-Dichlorophenyl)-N-methyl-N-[2-(1-pyrrolidinyl)-1-substituted-ethyl]acetamides: A Novel Series of Potent and Selective $_\kappa$-Opioid Agonists", J. Med. Chem., vol. 34, No. 11, pp. 3149-3158, (Nov. 1991).
Bhuniya et a., "Design, Synthesis, and Application of Chiral Nonracemic Lithium Amide Bases in Enantioselective Deprotonation of Epoxides", J. Org. Chem., vol. 61, pp. 6108-6113, (1996).
Chang et al., "κ Opioid Receptor Selective Affinity Labels: Electrophilic Benzeneacetamides as κ-Selective Opioid Antagonists", J. Med. Chem., vol. 37, pp. 4490-4498, (1994).
Chen et al., "Synthesis and Properties of ABA Amphiphiles", J. Org. Chem., vol. 64, pp. 6870-6873, (1999).
Dehaven-Hudkins et al., "Peripherally Restricted Opioid Agonists as Novel Analgesic Agents", Current Pharmaceutical Design, vol. 10, pp. 743-757, (2004).

(Continued)

*Primary Examiner* — Valerie Rodriguez-Garcia
(74) *Attorney, Agent, or Firm* — Jacqueline F. Mahoney

(57) ABSTRACT

Provided are compounds of Formula I:

(Formula I)

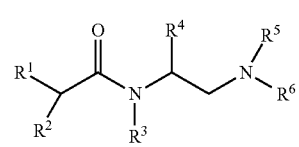

and pharmaceutically acceptable salts and solvates thereof, wherein $R^1$, $R^2$, $R^3$, $R^4$, $R^5$, and $R^6$ are as described herein. The compounds of Formula I are agonists of the kappa opioid receptor and relate to and/or have application(s) in (among others) the fields of drug discovery, pharmacotherapy, physiology, organic chemistry and polymer chemistry.

13 Claims, No Drawings

(56) References Cited

OTHER PUBLICATIONS

Ertl et al., "Fast Calculation of Molecular Polar Surface Area as a Sum of Fragment-Based Contributions and Its Application to the Prediction of Drug Transport Properties", J. Med. Chem., vol. 43, pp. 3714-3717, (2000).
Finley et al., "Opioid and nociception receptors regulate cytokine and cytokine receptor expression", Cellular Immunology, vol. 252, pp. 146-154, (2008).
Ghosh et al., "Synthesis of the kappa-agonist CJ-15,161 via a palladium-catalyzed cross-coupling reaction", Chem. Commun., pp. 1644-1645, (2002).
Kelder et al., "Polar Molecular Surface as a Dominating Determinant for Oral Absorption and Brain Penetration of Drugs", Pharmaceutical Research, vol. 16, No. 10, pp. 1514-1519, (1999).
Kumar et al., "Amino acid conjugates as κ opioid receptor agonists", Bioorganic & Medicinal Chemistry Letters, vol. 15, pp. 1279-1282, (2005).
Kumar et al., "Synthesis and evaluation of novel peripherally restricted κ-opioid receptor agonists", Bioorganic & Medicinal Chemistry Letters, vol. 15, pp. 1091-1095, (2005).
McAtee et al., "Potent and selective small-molecule human urotensin-II antagonists with improved pharmacokinetic profiles", Bioorganic & Medicinal Chemistry Letters, vol. 18, pp. 3716-3719, (2008).
Parkhill et al., "Reduction of lipopolysaccharide-induced interleukin-6 production by the kappa opioid U50,488 in a mouse monocyte-like cell line", International Immunopharmacology, vol. 6, pp. 1013-1019, (2006).
Riviere, "Peripheral kappa-opioid agonist for visceral pain", British Journal of Pharmacology, vol. 141, pp. 1331-1334, (2004).
Rogers et al., "Opioid G protein-coupled receptors: signals at the crossroads of inflammation", Trends in Immunology, vol. 24, No. 3, pp. 116-121, (Mar. 2003).
Rubin et al., "The Cell Biology of the Blood-Brain Barrier", Annu. Rev. Neurosci., vol. 22, pp. 11-28, (1999).
Summerfield et al., "Central Nervous System Drug Disposition: The Relationship between in Situ Brain Permeability and Brain Free Fraction", The Journal of Pharmacology and Experimental Therapeutics, vol. 322, No. 1, pp. 205-213, (2007).
Tang et al., "A κ Opioid Pharmacophore Becomes a Spinally Selective κ-δAgonist When Modified with a Basic Extender Arm", ACS Med. Chem. Lett., vol. 2, pp. 7-10, (2011).
Tsuji, "Small Molecular Drug Transfer across the Blood-Brain Barrier via Carrier-Mediated Transport Systems", NeuroRx: The Journal of the American Society for Experimental NeuroTherapeutics, vol. 2, pp. 54-62, (Jan. 2005).
Wang, "Chemistry with Chiral Lithium Amides: Enantiotopic Group- and Face Selective Reactions", MSc Thesis, 2007).
PCT International Search Report and Written Opinion in PCT/US2014/044535 dated Jan. 29, 2015.
PCT International Preliminary Report on Patentability in PCT/US2014/044535 dated Jan. 7, 2016.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
Nof Corporation, PEG Derivatives, Phospholipid and Drug Delivery Materials for Pharmaceuticals, 46 pages, Catalogue 2003-$1^{st}$, (Jan. 2003).
Nof Corporation, PEG Derivatives, Phospholipid and Drug Delivery Materials for Pharmaceuticals, 27 pages, Catalogue 2003-$2^{nd}$, (Mar. 2004).
Nof Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™Technology, 31 pages, (Nov. 5, 2004).
Quanta Biodesign, Ltd., Leading innovator, producer and provider of monodisperse discrete PEG™(dPEG™) derivatives, (Product Catalog), 26 pages, (Updated: Jul. 18, 2005).
Quanta Biodesign, Ltd., Leading innovator, producer and provider of monodisperse discrete PEG™(dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Examination Report in European Patent Application No. 14 740 120.2 dated Apr. 6, 2017.
European Examination Report corresponding to European Patent Application No. 14 740 120.2 dated Dec. 13, 2017.
European Examination Report corresponding to European Patent Application No. 14 740 120.2 dated Jul. 13, 2018.
English Translation of Notice of Reasons for Rejection corresponding to Japanese Patent Application No. 2016-524234 dated Jun. 6, 2018.

* cited by examiner

KAPPA OPIOID AGONISTS AND USES THEREOF

This application a Continuation of U.S. application Ser. No. 14/900,039, filed 18 Dec. 2015, now U.S. Pat. No. 9,815,824, which is a 35 U.S.C. § 371 application of International Application No. PCT/US2014/044535, filed 27 June 2014, designating the United States, which claims the benefit of priority under 35 U.S.C. § 119(e) to both U.S. Provisional Patent Application Serial No. 61/929,685, filed 21 Jan. 2014, and U.S. Provisional Patent Application Serial No. 61/841,042, filed 28 Jun. 2013, the disclosures of which are incorporated herein by reference in their entireties.

The present disclosure relates to novel compounds and to their use as agonists of the kappa opioid receptor. The disclosure also relates to methods for preparation of the compounds and to pharmaceutical compositions containing such compounds. The compounds described herein relate to and/or have application(s) in (among others) the fields of drug discovery, pharmacotherapy, physiology, organic chemistry and polymer chemistry.

Kappa opioid agonists that exhibit full agonist properties at the kappa opioid receptor have been widely shown to be efficacious in preclinical models of pain, particularly visceral pain. Kappa opioid agonists are understood to lack several of the side effects of mu opioid agonists, including abuse liability, gastrointestinal transit inhibition and respiratory depression. Kappa opioid agonists, however, are understood to produce complicating side effects, such as dysphoria and sedation at analgesic doses. As a result, the presence of these side effects has hindered the development of kappa opioid agonists as clinically useful analgesics.

Beyond analgesia, kappa agonists have shown anti-inflammatory effects both in vitro and in vivo. Additionally, asimadoline, a kappa opioid agonist that is moderately restricted to the periphery, is currently undergoing studies for the treatment of irritable bowel syndrome. Due to its limited CNS entry, asimadoline may reduce the extent of side effects associated with less restricted kappa agonists, though studies are still ongoing. Additional known kappa opioid agonists, such as enadoline and spiradoline, enter the CNS (Central Nervous System) causing dysphoria, and thus have not been developed clinically. Further, while mixed agonists (acting on kappa and mu receptors) have been marketed, to date, no full kappa agonist has been approved for use in humans.

The incorporation of a poly(ethylene glycol) moiety into a small molecule scaffold has been utilized to modify the rate of CNS entry of several classes of molecules. U.S. Patent Application Publication No. 2005/0136031 and U.S. Patent Application Publication No. 2010/0048602. The sites of incorporation and further modifications to the molecules, however, have differing effects on the overall activity and pharmacological properties of the resulting molecule.

In view of the above, there remains a need for peripherally acting kappa opioid agonists that retain sufficient efficacy to treat visceral pain and other symptoms or disease states associated with the kappa opioid receptor, while reducing the CNS side effects. The present invention seeks to address these and other needs.

In one or more embodiments of the invention a compound selected from Formula

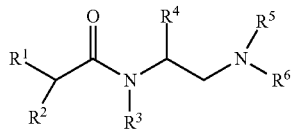

Formula I wherein $R^1$ is selected from optionally substituted aryl, optionally substituted amino, and optionally substituted aryloxy; $R^2$ is selected from hydrogen, optionally substituted aryl, and X-POLY; $R^3$ is selected from hydrogen and an optionally substituted alkyl; $R^4$ is selected from an optionally substituted aryl; $R^5$ is selected from hydrogen, optionally substituted alkyl, and X-POLY; $R^6$ is selected from hydrogen and an optionally substituted alkyl; or $R^5$ and $R^6$ may be taken together to form an optionally substituted heterocyclyl; provided at least one of $R^1$, $R^2$, $R^4$, $R^5$, and $R^6$ are substituted with an X-POLY group, wherein X is an optional linker and POLY is a water soluble, non-peptidic oligomer; and pharmaceutically acceptable salts and solvates thereof, is provided.

In one or more embodiments of the invention, a composition is provided, the composition comprising (i) a compound as described herein, and, optionally, (ii) a pharmaceutically acceptable excipient.

In one or more embodiments of the invention, composition of matter is provided, the composition of matter comprising a compound as described herein, wherein the compound is present in a dosage form.

In one or more embodiments of the invention, a method is provided, the method comprising administering a compound as described herein to a patient in need thereof.

Additional embodiments of the present compounds, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

As used in this specification, the singular forms "a," "an," and "the" include plural referents unless the context clearly dictates otherwise.

In describing and claiming the present invention, the following terminology will be used in accordance with the definitions described below.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like. As used herein, "lower alkyl" refers to an alkyl group having from 1 to 6 carbon atoms. Specific examples of lower alkyl include, but are not limited to, methyl, ethyl, n-propyl, iso-propyl, n-butyl, iso-butyl, t-butyl, n-hexyl, and the like.

The term "substituted alkyl" refers to an alkyl group having 1 to 5 substituents (in certain embodiments 1, 2, or 3) selected from of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxyl, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R is alkyl, aryl or heteroaryl and n is 0, 1, or 2. "Substituted lower alkyl" refers to a lower alkyl group defined above, substituted as defined for alkyl.

The term "alkylene" refers to a diradical of a branched or unbranched saturated hydrocarbon chain, in certain embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like. The term "lower alkylene" refers to a diradical of a branched or unbranched saturated hydrocarbon chain, in certain embodiments, having 1, 2, 3, 4, 5 or 6 carbon atoms.

The terms "substituted alkylene" and "substituted lower alkylene" refer to an alkylene group or lower alkylene group as defined above having 1 to 5 substituents (in certain embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in certain embodiments, from 2 to 10 carbon atoms, e.g. 2 to 6 carbon atoms) and having from 1 to 6 carbon-carbon double bonds, e.g. 1, 2 or 3 carbon-carbon double bonds. In certain embodiments, alkenyl groups include ethenyl (or vinyl, i.e. —CH═CH$_2$), 1-propylene (or allyl, i.e. —CH$_2$CH═CH$_2$), isopropylene (—C(CH$_3$)═CH$_2$), and the like. The term "lower alkenyl" refers to alkenyl as defined above having from 2 to 6 carbon atoms.

The term "substituted alkenyl" refers to an alkenyl group as defined above having 1 to 5 substituents (in certain embodiments, 1, 2, or 3 substituents) as defined for substituted alkyl.

The term "substituted lower alkenyl" refers to a lower alkenyl group as defined above having 1 to 5 substituents (in certain embodiments, 1, 2, or 3 substituents) as defined for substituted alkyl.

The term "alkenylene" refers to a diradical of a branched or unbranched unsaturated hydrocarbon group having from 2 to 20 carbon atoms (in certain embodiments, from 2 to 10 carbon atoms, e.g. 2 to 6 carbon atoms) and having from 1 to 6 carbon-carbon double bonds, e.g. 1, 2, or 3 carbon-carbon double bonds.

The term "alkynyl" refers to a monoradical of an unsaturated hydrocarbon, in certain embodiments, having from 2 to 20 carbon atoms (in certain embodiments, from 2 to 10 carbon atoms, e.g. 2 to 6 carbon atoms) and having from 1 to 6 carbon-carbon triple bonds e.g. 1, 2, or 3 carbon-carbon triple bonds. In certain embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in certain embodiments, 1, 2, or 3 substituents) as defined for substituted alkyl.

The term "alkynylene" refers to a diradical of an unsaturated hydrocarbon, in certain embodiments, having from 2 to 20 carbon atoms (in certain embodiments, from 2 to 10 carbon atoms, e.g. 2 to 6 carbon atoms) and having from 1 to 6 carbon-carbon triple bonds e.g. 1, 2, or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In certain embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like. The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is optionally substituted alkylene and Z is substituted alkenyl or substituted alkynyl, where substituted alkyl, substituted alkenyl and substituted alkynyl are as defined herein.

The term "C$_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In certain embodiments, C$_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, and 3-fluoropropyl.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in certain embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in certain embodiments, 1, 2 or 3 substituents), selected from alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)— heteroaryl, —S(O)$_2$-alkyl, —S(O)$_2$-cycloalkyl, —S(O)$_2$-heterocyclyl, —S(O)$_2$-aryl and —S(O)$_2$— heteroaryl.

The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

As used herein, "—X-POLY" refers to a water-soluble, nonpeptidic oligomer POLY attached through a linker "X".

"Water soluble oligomer" indicates a non-peptidic oligomer that is at least 35% (by weight) soluble, preferably greater than 70% (by weight), and more preferably greater than 95% (by weight) soluble, in water at room temperature. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. In certain embodiments, the oligomers used in connection with present the invention are homo-oligomers. The water-soluble oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 50 monomers, preferably from about 1 to about 30 monomers. In certain embodiments, an "oligomer" is a molecule possessing from about 2 to about 50 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or any polyethylene glycol is one in which substantially all (preferably all) monomeric subunits are ethylene oxide subunits, though, the oligomer may contain distinct end capping moieties or functional groups, e.g., for providing a site of covalent modification or reaction with another compound. PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. For the PEG oligomers, the variable (n) ranges from about 1 to 50, and the terminal groups and architecture of the overall PEG can vary. When PEG further comprises a functional group, A, for linking to, e.g., a small molecule, the functional group when covalently attached to a PEG oligomer does not result in formation of an oxygen-oxygen bond (—O—O—, a peroxide linkage).

The terms "end-capped" or "terminally capped" are interchangeably used herein to refer to a terminal or endpoint of an oligomer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, alkyl, heteroaryl, cyclo, heterocyclo, and the like. In addition, saturated, unsaturated, substituted and unsubstituted forms of each of the foregoing are envisioned. Moreover, the end-capping group can also be a silane. In addition, the end-capping group and be trifluoromethoxy. The end-capping group can also comprise a detectable label. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

In the context of describing the consistency of oligomers in a given composition, "substantially" or "essentially" means nearly totally or completely, for instance, 95% or greater, in certain embodiments 97% or greater, in certain embodiments 98% or greater, in certain embodiments 99% or greater, and in certain embodiments 99.9% or greater.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). In certain embodiments, a monodisperse oligomer composition possesses a MW/Mn value of 1.0005 or less, and in certain embodiments, a MW/Mn value of 1.0000. By extension, a composition comprised of monodisperse compounds means that substantially all oligomers of all compounds in the composition have a single and definable number (as a whole number) of monomers rather than a distribution and would possess a MW/Mn value of 1.0005, and in certain embodiments, a MW/Mn value of 1.0000 if the oligomer were not attached to a compound of the present invention. A composition comprised of monodisperse compounds can include, however, one or more substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. In certain embodiments, for a bimodal oligomer composition as described herein, each peak is generally symmetric about its mean, although the size of the two peaks may differ. Ideally, the polydispersity index of each peak in the bimodal distribution, Mw/Mn, is 1.01 or less, in certain embodiments 1.001 or less, in certain embodiments 1.0005 or less, and in certain embodiments a MW/Mn value of 1.0000. By extension, a composition comprised of bimodal compounds means that substantially all oligomers of all compounds in the composition have one of two definable and different numbers (as whole numbers) of monomers rather than a large distribution and would possess a MW/Mn value of 1.01 or less, in certain embodiments 1.001 or less, in certain embodiments 1.0005 or less, and in certain embodiments a MW/Mn value of 1.0000 if the oligomer were not attached to a compound of the present invention. A composition comprised of bimodal compounds can include, however, one or more substances such as solvents, reagents, excipients, and so forth.

"Branched", in reference to the geometry or overall structure of an oligomer, refers to an oligomer having two or more oligomers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

As used herein "X" is a spacer moiety including a covalent bond or a group of 1-20 atoms. X may include, but is not limited to optionally substituted alkylene, optionally substituted alkenylene, optionally substituted alkynylene, optionally substituted alkoxy, hydroxyl, optionally substituted amino, optionally substituted aryl, optionally substituted heterocyclyl, optionally substituted heteroaryl, optionally substituted ester, alkyl amine, dialkyl amine, keto, optionally substituted acyl, aminocarbonyl, carboxyalkyl, acyloxy, acylamino, alkoxycarbonylamino, aminocarbonylamino, and the like. It is understood that the spacer X will comprise diradicals of the respective groups. Exemplary spacer moieties include a covalent bond, —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—CH$_2$—CH$_2$—C(O)—NH—, —NH—C(O)—CH$_2$—, —NH—C(O)—CH$_2$—O—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, a bivalent cycloalkyl group, amino, substituted amino. Additional spacers include, acylamino, acyl, aryloxy, alkylene, amino, substituted amino, piperidino, and pyrrolidino. For purposes of the present invention, however, a group of atoms is not considered a spacer when it is immediately adjacent to an oligomeric segment, and the group of atoms is the same as a monomer of the oligomer such that the group would represent a mere extension of the oligomer chain.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In certain embodiments, aryls include phenyl, fluorenyl, naphthyl, anthryl, and the like.

Unless otherwise constrained by the definition for the aryl substituent, such aryl groups can optionally be substituted with 1, 2, 3, 4, or 5 substituents (In certain embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)— heteroaryl, —S(O)$_2$-alkyl, —S(O)$_2$-cycloalkyl, —S(O)$_2$-heterocyclyl, —S(O)$_2$-aryl and —S(O)$_2$— heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In certain embodiments, the "heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in certain embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)— heteroaryl, —S(O)$_2$-alkyl, —S(O)$_2$-cycloalkyl, —S(O)$_2$-heterocyclyl, —S(O)$_2$-aryl and —S(O)$_2$— heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in certain embodiments, 1, 2, or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)— heteroaryl, —S(O)$_2$-alkyl, —S(O)$_2$-cycloalkyl, —S(O)$_2$-heterocyclyl, —S(O)$_2$-aryl and —S(O)$_2$— heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$. The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl or alkynyl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "alkyl amine" refers to —NHR in which R is optionally substituted alkyl.

The term "dialkyl amine" refers to —NRR in which each R is independently an optionally substituted alkyl.

The term "cyano" refers to the group —CN.

The term "azido" refers to a group N=N=N.

The term "keto" or "oxo" refers to a group =O.

The term "carboxy" or "carboxyl" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, —X-POLY, cyano or —S(O)$_n$R$^a$, in which R$^a$ is alkyl, aryl or heteroaryl and n is 0, 1, or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, $CF_3$, amino, substituted amino, —X-POLY, cyano, cycloalkyl, heterocyclyl, aryl, heteroaryl, and —$S(O)_nR^a$, in which $R^a$ is alkyl, aryl or heteroaryl and n is 0, 1, or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, $CF_3$, amino, substituted amino, —X-POLY, cyano, cycloalkyl, heterocyclyl, aryl, heteroaryl, and —$S(O)_nR^a$, in which $R^a$ is alkyl, aryl or heteroaryl and n is 0, 1, or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, $CF_3$, amino, substituted amino, —X-POLY, cyano, cycloalkyl, heterocyclyl, aryl, heteroaryl, and —$S(O)_nR^a$, in which $R^a$ is alkyl, aryl or heteroaryl and n is 0, 1, or 2.

The term "alkoxycarbonylamino" refers to the group —$N(R^d)C(O)OR$ in which R is alkyl and $R^d$ is hydrogen or alkyl. Unless otherwise constrained by the definition, each alkyl may optionally be further substituted by 1, 2, or 3 substituents selected from alkyl, alkenyl, alkynyl, carboxy, carboxyalkyl, aminocarbonyl, hydroxy, alkoxy, halogen, $CF_3$, amino, substituted amino, —X-POLY, cyano, cycloalkyl, heterocyclyl, aryl, heteroaryl, and —$S(O)_nR^a$, in which $R^a$ is alkyl, aryl or heteroaryl and n is 0, 1, or 2.

The term "aminocarbonylamino" refers to the group —$NR^eC(O)NRR$, wherein $R^e$ is hydrogen or alkyl and each R is hydrogen, alkyl, cycloalkyl, aryl, heteroaryl or heterocyclyl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, $CF_3$, amino, substituted amino, —X-POLY, cyano, cycloalkyl, heterocyclyl, aryl, heteroaryl, and —$S(O)_nR^a$, in which $R^a$ is alkyl, aryl or heteroaryl and n is 0, 1, or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —$S(O)_2R$, in which R is alkyl, cycloalkyl, heterocyclyl, aryl or heteroaryl. "Substituted sulfone" refers to a group —$S(O)_2R$, in which R is substituted alkyl, substituted cycloalkyl, substituted heterocyclyl, substituted aryl or substituted heteroaryl, as defined herein.

The term "aminosulfonyl" refers to the group —$S(O)_2NRR$, wherein each R is independently hydrogen, alkyl, cycloalkyl, aryl, heteroaryl or heterocyclyl. Unless otherwise constrained by the definition, all substituents may optionally be further substituted by 1, 2, or 3 substituents selected from alkyl, alkenyl, alkynyl, carboxy, carboxyalkyl, aminocarbonyl, hydroxy, alkoxy, halogen, $CF_3$, amino, substituted amino, —X-POLY, cyano, cycloalkyl, heterocyclyl, aryl, heteroaryl, and —$S(O)_nR^a$, in which $R^a$ is alkyl, aryl or heteroaryl and n is 0, 1, or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. In certain contexts the term "biological membrane" does not include those membranes associated with the middle gastro-intestinal tract (e.g., stomach and small intestines) For example, in some instances it may be desirable for a compound of the invention to have a limited ability to cross the blood-brain barrier, yet be desirable that the same compound cross the middle gastro-intestinal tract.

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

"Pharmacologically effective amount," "physiologically effective amount," and "therapeutically effective amount"

are used interchangeably herein to mean the amount of a compound of the present invention alone or present in a composition that is needed to provide a threshold level of the compound in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

The term "patient," refers to a living organism suffering from or prone to a condition that can be prevented or treated by administration of a compound as described herein, and includes both humans and animals.

The compounds of the invention, if chiral, may be in a racemic mixture, or an optically active form, for example, a single optically active enantiomer, or any combination or ratio of enantiomers (i.e., scalemic mixture). In addition, the compound may possess one or more geometric isomers. With respect to geometric isomers, a composition can comprise a single geometric isomer or a mixture of two or more geometric isomers. A compound for use in the present invention can be in its customary active form, or may possess some degree of modification.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

The term "pharmaceutically acceptable salt" refers to non-toxic salts of the compounds of this invention. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Also included are salts with acidic amino acid such as aspartate and glutamate. Base addition salts include alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or solvates.

The term "solvate" refers to a complex formed by the combining of a compound of the present invention and a solvent.

The term "hydrate" refers to the complex formed by the combining of a compound of the present invention and water.

Selected substituents comprising the compounds of Formula I may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

Names of compounds of the present disclosure are provided using ACD/Name software for naming chemical compounds (Advanced Chemistry Development, Inc., Toronto, Canada). Other compounds or radicals may be named with common names or systematic or non-systematic names. In some instances a substituent for a given variable (e.g., $R^3$) within of a generic formula is shown with a dash ("-") as in "—$CH_3$," or with a squiggly line (e.g., "~") as in "~X-POLY;" each are used interchangeably herein. The naming and numbering of the compounds of the disclosure is illustrated with a representative compound of the formula

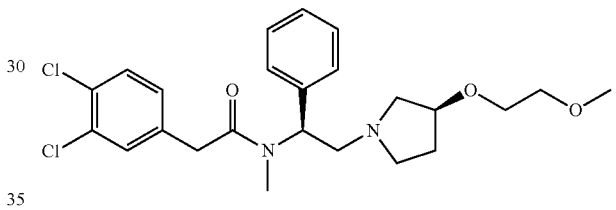

which is named 2-(3, 4-dichlorophenyl)-N-{(1S)-2-[(3S)-3-(2-methoxyethoxy)pyrrolidin-1-yl]-1-phenylethyl}-N-methylacetamide.

In certain embodiments, a compound selected from Formula I is provided

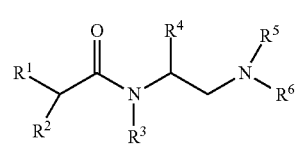

Formula I wherein $R^1$ is selected from optionally substituted aryl, optionally substituted amino, and optionally substituted aryloxy; $R^2$ is selected from hydrogen, optionally substituted aryl, and X-POLY; $R^3$ is selected from hydrogen and an optionally substituted alkyl; $R^4$ is selected from an optionally substituted aryl; $R^5$ is selected from hydrogen, optionally substituted alkyl, and X-POLY; $R^6$ is selected from hydrogen and an optionally substituted alkyl; or $R^5$ and $R^6$ may be taken together to form an optionally substituted heterocyclyl; provided at least one of $R^1$, $R^2$, $R^4$, $R^5$, and $R^6$ are an X-POLY group or are substituted with an X-POLY group, wherein X is an optional linker and POLY is a water soluble, non-peptidic oligomer; and provided that when $R^1$ is phenyl, $R^2$ is phenyl, $R^3$ is methyl, $R^4$ is phenyl, and $R^5$ and $R^6$ are taken together to form a pyrrolidinyl group, the pyrrolidinyl group is not substituted with X-POLY; and pharmaceutically acceptable salts and solvates thereof.

In certain embodiments of a compound of Formula I, $R^1$ is selected from an optionally substituted aryl. In certain embodiments, $R^1$ is an optionally substituted phenyl. In certain embodiments, $R^1$ is selected from phenyl, phenyl substituted with 1 to 3 halogens, and phenyl substituted with X-POLY. In certain embodiments, $R^1$ is optionally substituted amino. In certain embodiments, $R^1$ is amino substituted with an optionally substituted aryl. In certain embodiments, $R^1$ is amino substituted with an optionally substituted phenyl. In certain embodiments, $R^1$ is amino substituted with a phenyl group.

In certain embodiments of a compound of Formula I, $R^2$ is selected from hydrogen, optionally substituted aryl, and X-POLY. In certain embodiments, $R^2$ is hydrogen. In certain embodiments, $R^2$ is an optionally substituted aryl. In certain embodiments, $R^2$ is an optionally substituted phenyl. In certain embodiments, $R^2$ is phenyl. In certain embodiments, $R^2$ is $R^2$ is X-POLY.

In certain embodiments of a compound of Formula I, $R^3$ is selected from hydrogen and an optionally substituted alkyl. In certain embodiments, $R^3$ is an optionally substituted alkyl. In certain embodiments, $R^3$ is hydrogen. In certain embodiments, $R^3$ is an optionally substituted lower alkyl. In certain embodiments, $R^3$ is methyl.

In certain embodiments of a compound of Formula I, $R^4$ is selected from an optionally substituted phenyl. In certain embodiments, $R^4$ is selected from phenyl and phenyl substituted with —X-POLY.

In certain embodiments of a compound of Formula I, $R^5$ is hydrogen. In certain embodiments, $R^5$ is an optionally substituted alkyl. In certain embodiments, $R^5$ is an optionally substituted lower alkyl. In certain embodiments, $R^5$ is a lower alkyl or a lower alkyl substituted with a lower alkoxy group. In certain embodiments, $R^5$ is —X-POLY.

In certain embodiments of a compound of Formula I, $R^6$ is hydrogen. In certain embodiments, $R^6$ is an optionally substituted alkyl. In certain embodiments, $R^6$ is an optionally substituted lower alkyl. In certain embodiments, $R^6$ is a lower alkyl or a lower alkyl substituted with a lower alkoxy group.

In certain embodiments of a compound of Formula I, $R^5$ and $R^6$ are taken together to form an optionally substituted heterocyclyl. In certain embodiments, $R^5$ and $R^6$ are taken together to form an optionally substituted piperidinyl or an optionally substituted pyrrolidinyl. In certain embodiments, $R^5$ and $R^6$ are taken together to form an optionally substituted pyrrolidinyl. In certain embodiments, $R^5$ and $R^6$ are taken together to form a pyrrolidinyl substituted with a group selected from hydroxyl and X-POLY.

In certain embodiments of a compound of Formula I, X is an optional linker. In certain embodiments, X is selected from a covalent bond, —C(O)—NH—; —C(O)—NH—CH$_2$—; —C(O)—NH—CH$_2$CH$_2$—; —O—C(O)NH—, —C(O)—NH—; —O—; —NH—C(O)—; —NH—C(O)—CH$_2$—; —NHC(O)CH$_2$O—, —NH—C(O)—CH$_2$CH$_2$—; —NH—; and —NHS(O)$_2$—.

In certain embodiments of a compound of Formula I, POLY is a poly(alkylene oxide) oligomer. In certain embodiments, POLY is a poly(ethylene oxide) oligomer. In certain embodiments, POLY is end-capped with a hydroxyl group or a lower alkoxy group. In certain embodiments, POLY is made of 1 to 30 monomers. In certain embodiments, POLY is made of 1 to 15 monomers. In certain embodiments, POLY is made of 1 to 10 monomers.

In certain embodiments of a compound of Formula I, the compound has the structure:

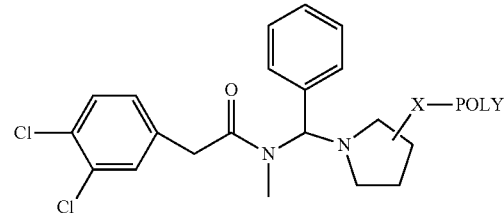

wherein X is an optional linker and POLY is —(CH$_2$CH$_2$O)$_n$—Y, wherein n is 1 to 30, and Y is selected from hydrogen and lower alkyl. In certain embodiments, X is selected from O, —O—C(O)N—, and a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

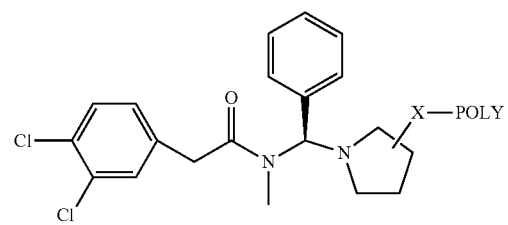

wherein X is an optional linker and POLY is —(CH$_2$CH$_2$O)$_n$—Y, wherein n is 1 to 30, and Y is selected from hydrogen and lower alkyl. In certain embodiments, X is selected from O, —O—C(O)N—, and a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

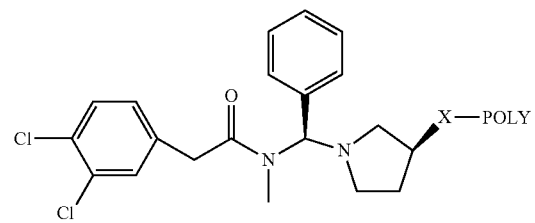

wherein X is an optional linker and POLY is —(CH$_2$CH$_2$O)$_n$—Y, wherein n is 1 to 30, and Y is selected from hydrogen and lower alkyl. In certain embodiments, X is selected from O, —O—C(O)N—, and a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

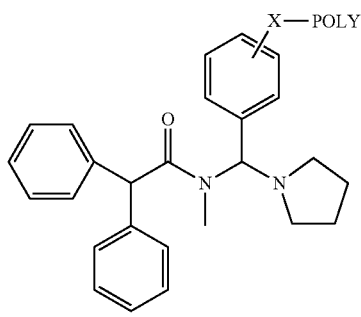

wherein X is an optional linker and POLY is —(CH$_2$CH$_2$O)$_n$—Y, wherein n is 1 to 30, and Y is selected from hydrogen and lower alkyl. In certain embodiments, X is selected from —NHC(O)CH$_2$O—NH—; O—; and NHS(O)$_2$—. In certain embodiments, X is —NHC(O)CH$_2$O—. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

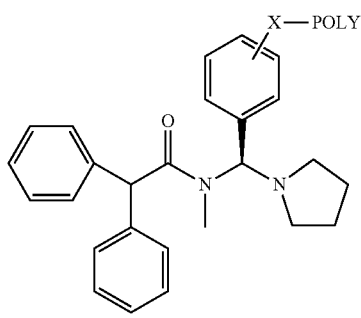

wherein X is an optional linker and POLY is —(CH$_2$CH$_2$O)$_n$—Y, wherein n is 1 to 30, and Y is selected from hydrogen and lower alkyl. In certain embodiments, X is selected from —NHC(O)CH$_2$O—NH—; O—; and NHS(O)$_2$—. In certain embodiments, X is —NHC(O)CH$_2$O—. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

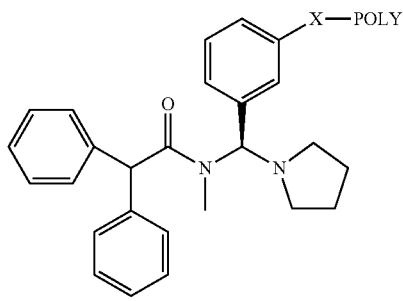

wherein X is an optional linker and POLY is —(CH$_2$CH$_2$O)$_n$—Y, wherein n is 1 to 30, and Y is selected from hydrogen and lower alkyl. In certain embodiments, X is selected from —NHC(O)CH$_2$O—NH—; O—; and NHS(O)$_2$—. In certain embodiments, X is —NHC(O)CH$_2$O—. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

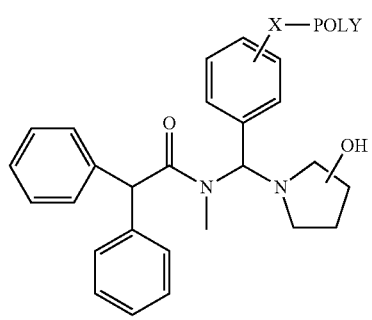

wherein X is an optional linker and POLY is —(CH$_2$CH$_2$O)$_n$—Y, wherein n is 1 to 30, and Y is selected from hydrogen and lower alkyl. In certain embodiments, X is selected from —NHC(O)CH$_2$O—NH—; O—; and NHS(O)$_2$—. In certain embodiments, X is —NHC(O)CH$_2$O—. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

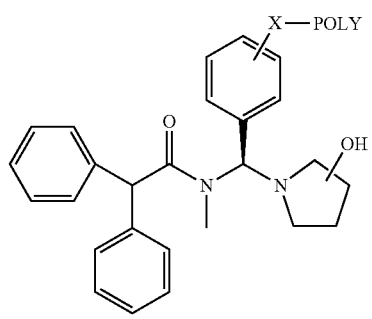

wherein X is an optional linker and POLY is —(CH$_2$CH$_2$O)$_n$—Y, wherein n is 1 to 30, and Y is selected from hydrogen and lower alkyl. In certain embodiments, X is selected from —NHC(O)CH$_2$O—NH—; O—; and NHS(O)$_2$—. In certain embodiments, X is —NHC(O)CH$_2$O—. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

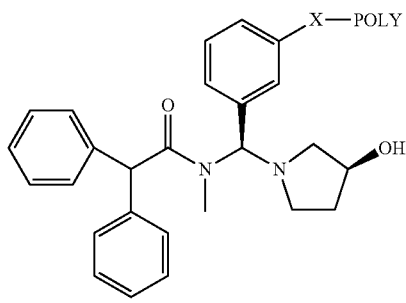

wherein X is an optional linker and POLY is —(CH₂CH₂O)ₙ—Y, wherein n is 1 to 30, and Y is selected from hydrogen and lower alkyl. In certain embodiments, X is selected from —NHC(O)CH₂O—NH—; O—; and NHS(O)₂—. In certain embodiments, X is —NHC(O)CH₂O—. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

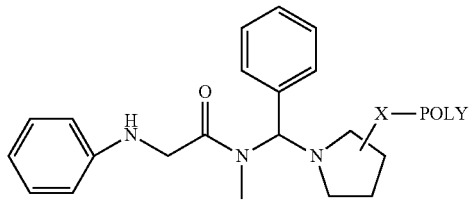

wherein X is an optional linker and POLY is —(CH₂CH₂O)ₙ—Y, wherein n is 1 to 30, and Y is selected from hydrogen and lower alkyl. In certain embodiments, X is O or a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

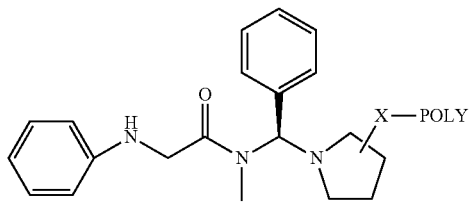

wherein X is an optional linker and POLY is —(CH₂CH₂O)ₙ—Y, wherein n is 1 to 30, and Y is selected from hydrogen and lower alkyl. In certain embodiments, X is O or a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

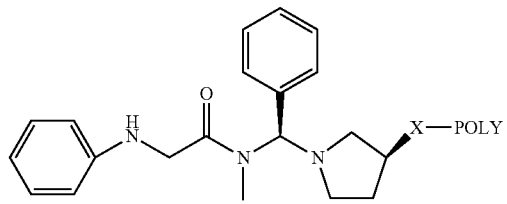

wherein X is an optional linker and POLY is —(CH₂CH₂O)ₙ—Y, wherein n is 1 to 30, and Y is selected from hydrogen and lower alkyl. In certain embodiments, X is O or a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

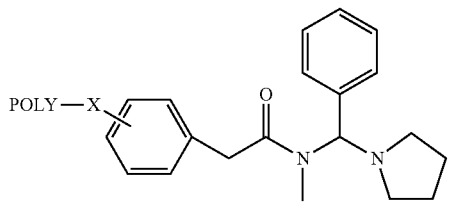

wherein X is an optional linker and POLY is —(CH₂CH₂O)ₙ—Y, wherein n is 1 to 30, and Y is selected from hydrogen and lower alkyl. In certain embodiments, X is O or a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

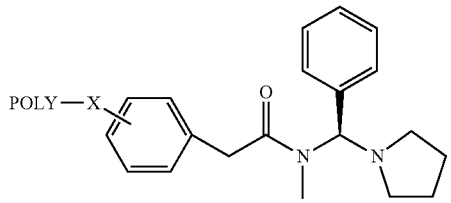

wherein X is an optional linker and POLY is —(CH₂CH₂O)ₙ—Y, wherein n is 1 to 30, and Y is selected from hydrogen and lower alkyl. In certain embodiments, X is O or a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

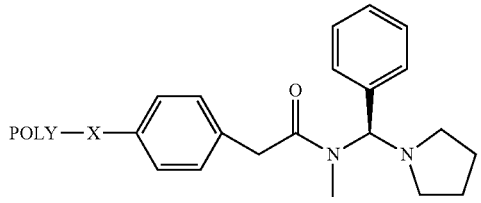

wherein X is an optional linker and POLY is —(CH$_2$CH$_2$O)$_n$—Y, wherein n is 1 to 30, and Y is selected from hydrogen and lower alkyl. In certain embodiments, X is O or a covalent bond. In certain embodiments, Y is hydrogen. In certain embodiments, Y is methyl. In certain embodiments, n is 1 to 20. In certain embodiments, n is 1 to 10.

In certain embodiments of a compound of Formula I, the compound has the structure:

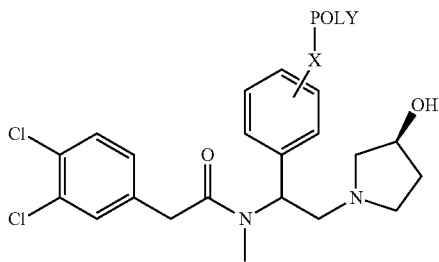

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

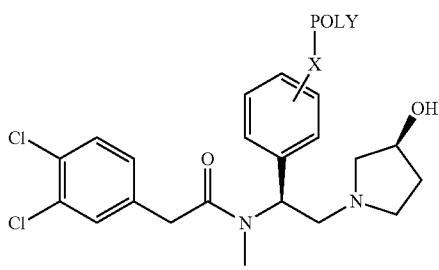

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

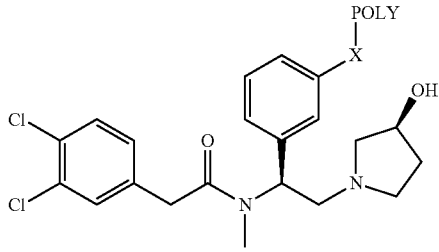

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

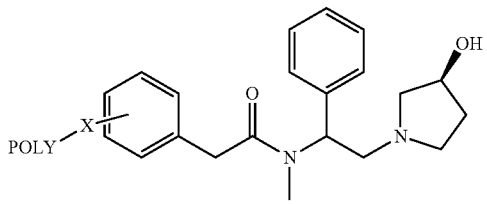

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

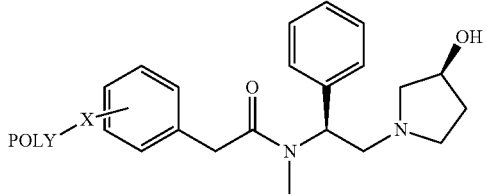

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

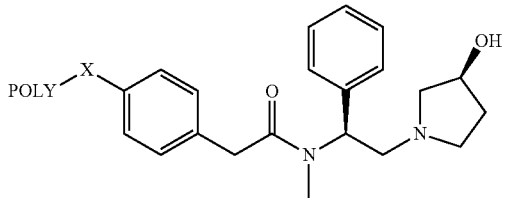

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure

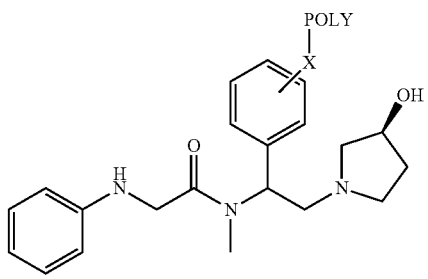

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure

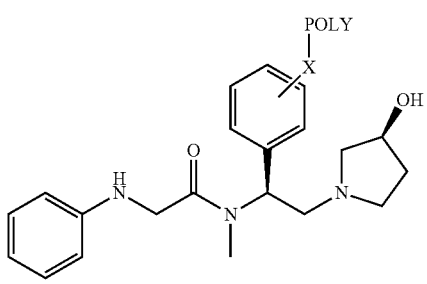

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

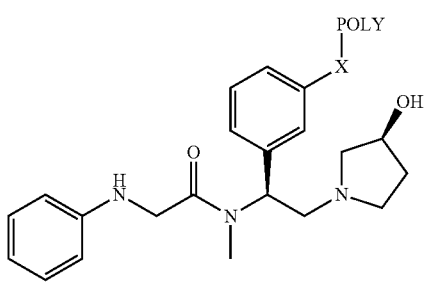

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

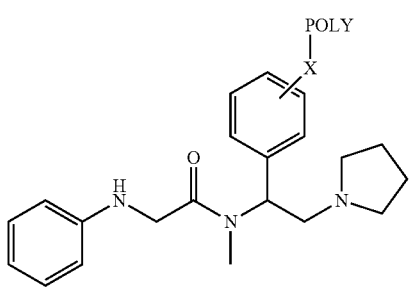

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

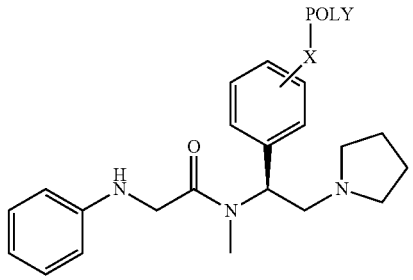

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

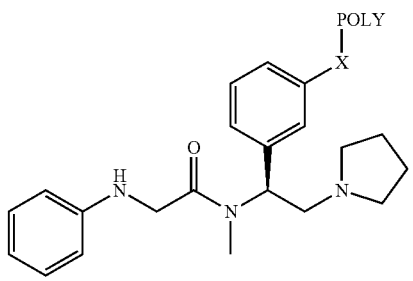

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

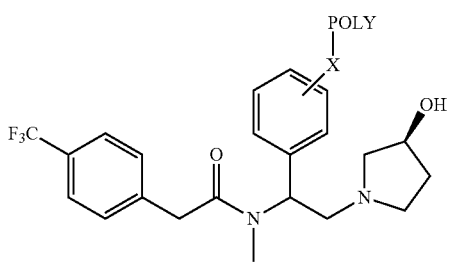

wherein X is an optional linker and POLY is —(CH$_2$CH$_2$O)$_n$—Y, wherein n is 1 to 30, and Y is selected from hydrogen and lower alkyl.

In certain embodiments of a compound of Formula I, the compound has the structure:

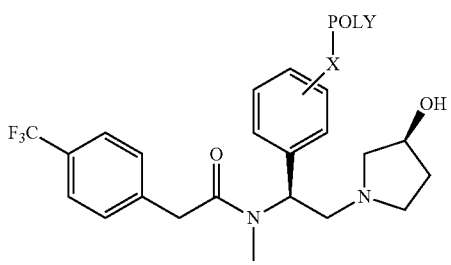

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

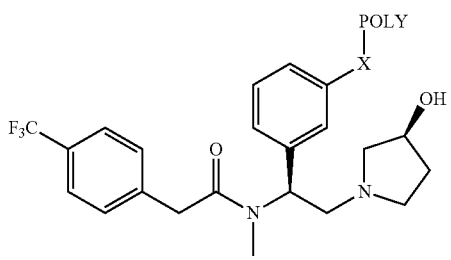

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

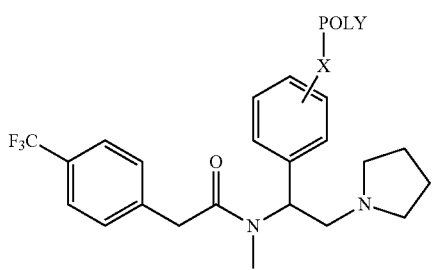

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

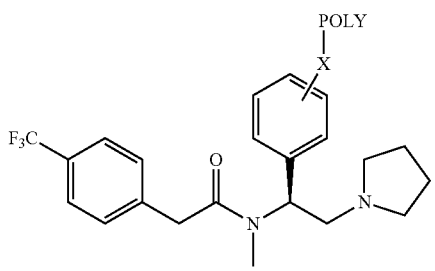

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

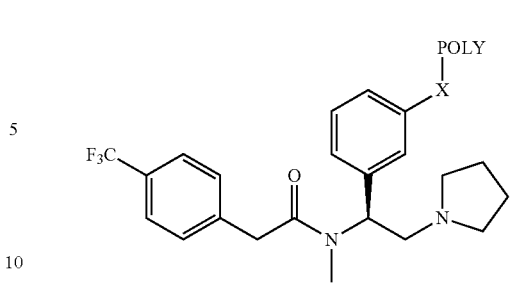

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

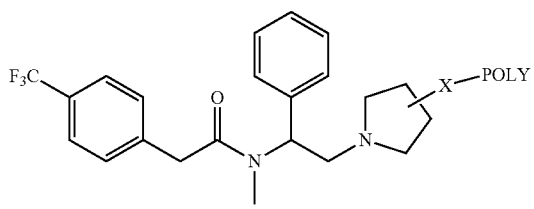

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

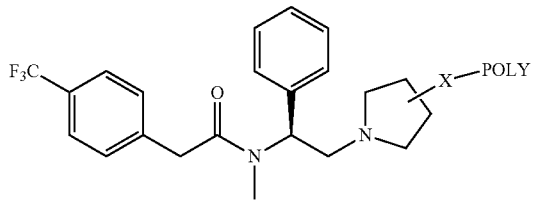

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

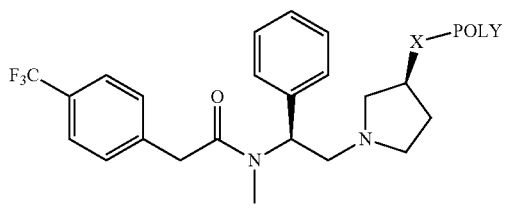

wherein X is an optional linker and POLY is —(CH₂CH₂O)ₙ—Y, wherein n is 1 to 30, and Y is selected from hydrogen and lower alkyl.

In certain embodiments of a compound of Formula I, the compound has the structure:

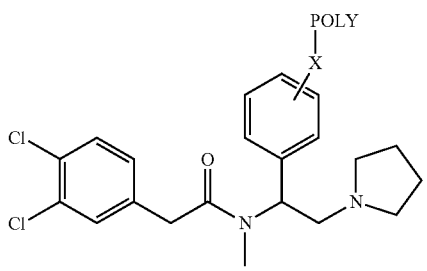

wherein X is an optional linker and POLY is
—(CH$_2$CH$_2$O)$_n$—Y, wherein n is 1 to 30, and Y is selected from hydrogen and lower alkyl.

In certain embodiments of a compound of Formula I, the compound has the structure:

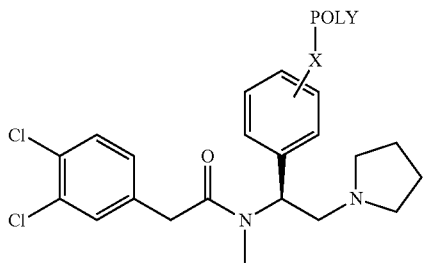

wherein X is an optional linker and POLY is
—(CH$_2$CH$_2$O)$_n$—Y, wherein n is 1 to 30, and Y is selected from hydrogen and lower alkyl.

In certain embodiments of a compound of Formula I, the compound has the structure:

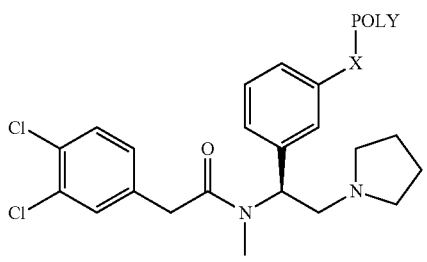

wherein X is an optional linker and POLY is
—(CH$_2$CH$_2$O)$_n$—Y, wherein n is 1 to 30, and Y is selected from hydrogen and lower alkyl.

In certain embodiments of a compound of Formula I, the compound has the structure:

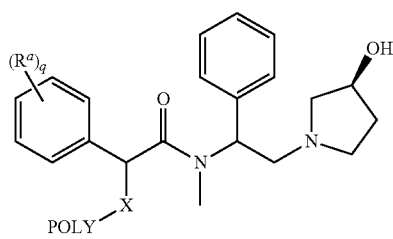

wherein each R$^a$ is independently selected from hydrogen, halo, lower alkyl, trifluoromethyl, cyano, lower alkoxy, and amino, q is 1 to 3, X is an optional linker and POLY is
—(CH$_2$CH$_2$O)$_n$—Y, wherein n is 1 to 30, and Y is selected from hydrogen and lower alkyl.

In certain embodiments of a compound of Formula I, the compound has the structure:

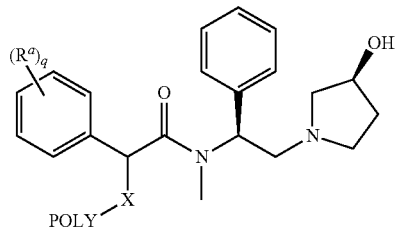

wherein each R$^a$ is independently selected from hydrogen, halo, lower alkyl, trifluoromethyl, cyano, lower alkoxy, and amino, q is 1 to 3, X is an optional linker and POLY is
—(CH$_2$CH$_2$O)$_n$—Y, wherein n is 1 to 30, and Y is selected from hydrogen and lower alkyl.

In certain embodiments of a compound of Formula I, the compound has the structure:

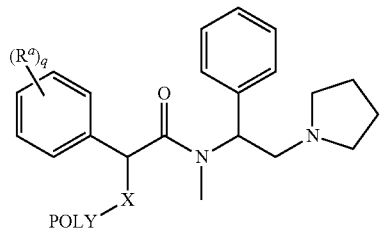

wherein each R$^a$ is independently selected from hydrogen, halo, lower alkyl, trifluoromethyl, cyano, lower alkoxy, and amino, q is 1 to 3, X is an optional linker and POLY is
—(CH$_2$CH$_2$O)$_n$—Y, wherein n is 1 to 30, and Y is selected from hydrogen and lower alkyl.

In certain embodiments of a compound of Formula I, the compound has the structure:

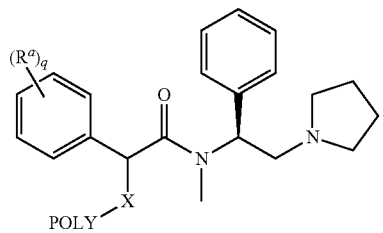

wherein each R$^a$ is independently selected from hydrogen, halo, lower alkyl, trifluoromethyl, cyano, lower alkoxy, and amino, q is 1 to 3, X is an optional linker and POLY is
—(CH$_2$CH$_2$O)$_n$—Y, wherein n is 1 to 30, and Y is selected from hydrogen and lower alkyl.

In certain embodiments of a compound of Formula I, the compound has the structure:

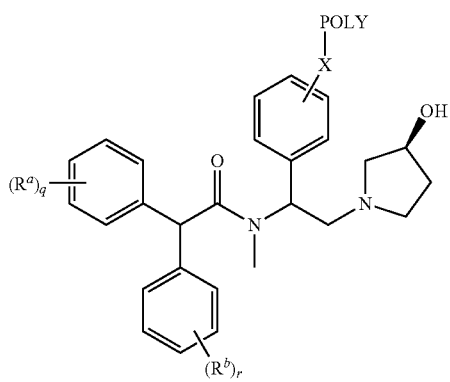

wherein each $R^a$ is independently selected from hydrogen, halo, lower alkyl, trifluoromethyl, cyano, lower alkoxy, and amino, q is 1 to 3, each $R^b$ is independently selected from hydrogen, halo, lower alkyl, trifluoromethyl, cyano, lower alkoxy, and amino, r is 1 to 3, X is an optional linker and POLY is —$(CH_2CH_2O)_n$—Y, wherein n is 1 to 30, and Y is selected from hydrogen and lower alkyl.

In certain embodiments of a compound of Formula I, the compound has the structure:

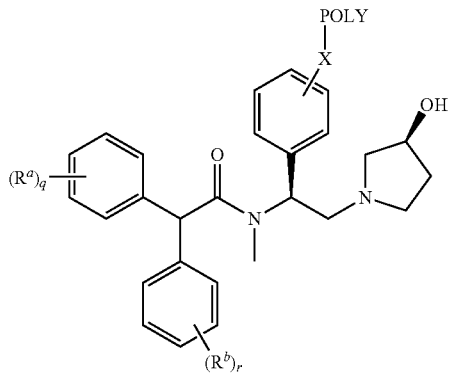

wherein each $R^a$ is independently selected from hydrogen, halo, lower alkyl, trifluoromethyl, cyano, lower alkoxy, and amino, q is 1 to 3, each $R^b$ is independently selected from hydrogen, halo, lower alkyl, trifluoromethyl, cyano, lower alkoxy, and amino, r is 1 to 3, X is an optional linker and POLY is —$(CH_2CH_2O)_n$—Y, wherein n is 1 to 30, and Y is selected from hydrogen and lower alkyl.

In certain embodiments of a compound of Formula I, the compound has the structure:

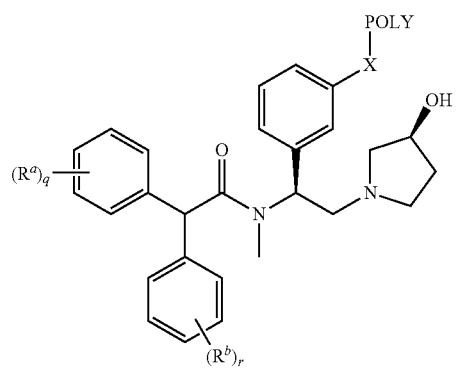

wherein each $R^a$ is independently selected from hydrogen, halo, lower alkyl, trifluoromethyl, cyano, lower alkoxy, and amino, q is 1 to 3, each $R^b$ is independently selected from hydrogen, halo, lower alkyl, trifluoromethyl, cyano, lower alkoxy, and amino, r is 1 to 3, X is an optional linker and POLY is —$(CH_2CH_2O)_n$—Y, wherein n is 1 to 30, and Y is selected from hydrogen and lower alkyl.

In certain embodiments of a compound of Formula I, the compound has the structure:

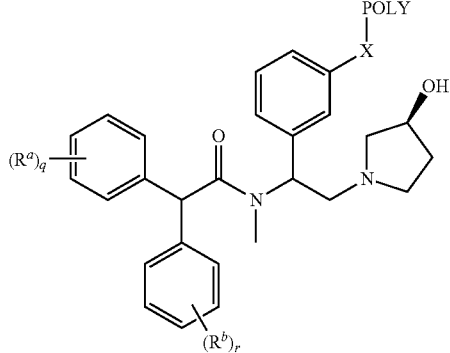

wherein each $R^a$ is independently selected from hydrogen, halo, lower alkyl, trifluoromethyl, cyano, lower alkoxy, and amino, q is 1 to 3, each $R^b$ is independently selected from hydrogen, halo, lower alkyl, trifluoromethyl, cyano, lower alkoxy, and amino, r is 1 to 3, X is an optional linker and POLY is —$(CH_2CH_2O)_n$—Y, wherein n is 1 to 30, and Y is selected from hydrogen and lower alkyl.

In certain embodiments of a compound of Formula I, the compound has the structure:

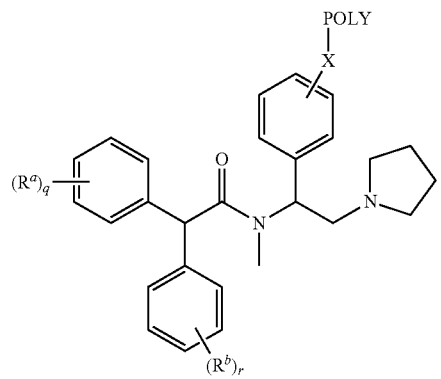

wherein each $R^a$ is independently selected from hydrogen, halo, lower alkyl, trifluoromethyl, cyano, lower alkoxy, and amino, q is 1 to 3, each $R^b$ is independently selected from hydrogen, halo, lower alkyl, trifluoromethyl, cyano, lower alkoxy, and amino, r is 1 to 3, X is an optional linker and POLY is —$(CH_2CH_2O)_n$—Y, wherein n is 1 to 30, and Y is selected from hydrogen and lower alkyl.

In certain embodiments of a compound of Formula I, the compound has the structure:

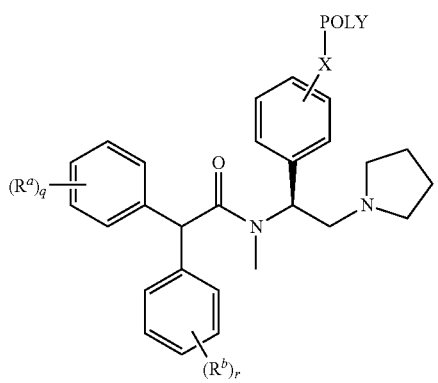

wherein each $R^a$ is independently selected from hydrogen, halo, lower alkyl, trifluoromethyl, cyano, lower alkoxy, and amino, q is 1 to 3, each $R^b$ is independently selected from hydrogen, halo, lower alkyl, trifluoromethyl, cyano, lower alkoxy, and amino, r is 1 to 3, X is an optional linker and POLY is —$(CH_2CH_2O)_n$—Y, wherein n is 1 to 30, and Y is selected from hydrogen and lower alkyl.

In certain embodiments of a compound of Formula I, the compound has the structure:

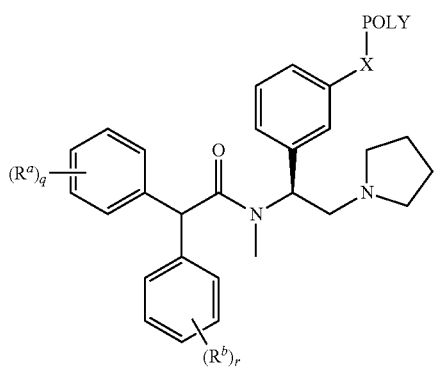

wherein each $R^a$ is independently selected from hydrogen, halo, lower alkyl, trifluoromethyl, cyano, lower alkoxy, and amino, q is 1 to 3, each $R^b$ is independently selected from hydrogen, halo, lower alkyl, trifluoromethyl, cyano, lower alkoxy, and amino, r is 1 to 3, X is an optional linker and POLY is —$(CH_2CH_2O)_n$—Y, wherein n is 1 to 30, and Y is selected from hydrogen and lower alkyl.

In certain embodiments of a compound of Formula I, Y is optionally substituted alkyl or hydrogen. In certain embodiments, Y is optionally substituted alkyl or hydrogen Y is hydrogen. In certain embodiments, Y is methyl. In certain embodiments, n is 1 to 20. In certain embodiments, n is 1 to 10.

In certain embodiments of compounds of the invention, a compound is provided, the compound having the following structure:

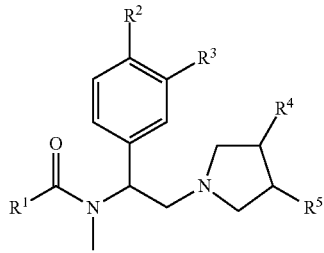

wherein:
$R^1$ is selected from the group consisting of

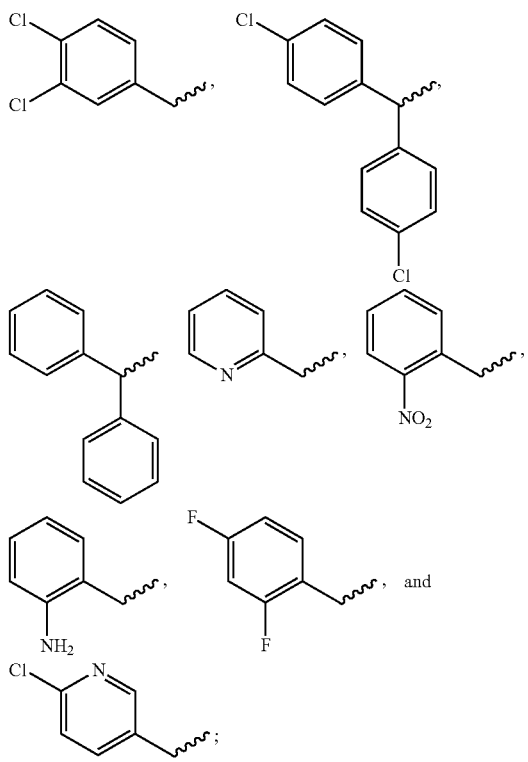

$R^2$ is selected from the group consisting of hydrogen, ~$CF_3$, and ~X-POLY;
$R^3$ is selected from the group consisting of ~X-POLY, ~$NHSO_2CH_3$,

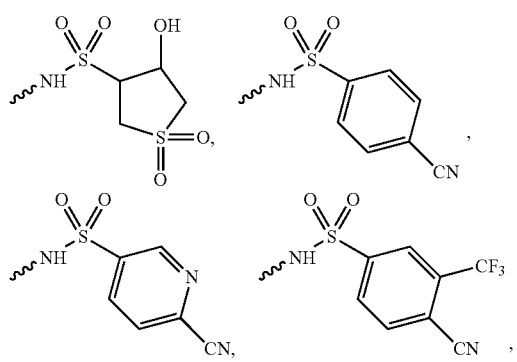

~NHSO$_2$CH$_2$CH$_2$OCH$_3$, ~NHSO$_2$CH$_2$CH$_2$OCH$_2$CF$_3$, ~NHSO$_2$CH$_2$CH(CH$_3$)OH, ~NH$_2$, and ~NHSO$_2$—(CH$_2$CH$_2$O)$_n$—Y, wherein n is 1 to 30, and Y is selected from hydrogen and lower alkyl;

R$^4$ is selected from the group consisting of hydrogen, hydroxyl, ~OCH$_2$COOH, ~OCH$_2$CH$_2$OH, ~OCH$_2$CH$_2$OCH$_2$COOH, ~OCH$_2$CH$_2$OCH$_2$CH$_2$OCH$_2$COOH, and ~X-POLY; and R$^5$ is selected from the group of hydrogen and hydroxyl, and pharmaceutically acceptable salts and solvates thereof.

In certain embodiments of compounds of the inventions, a compound is provided the compound having the following structure:

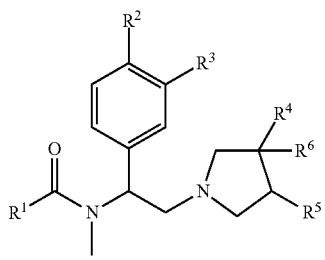

wherein:
R$^1$ is selected from the group consisting of

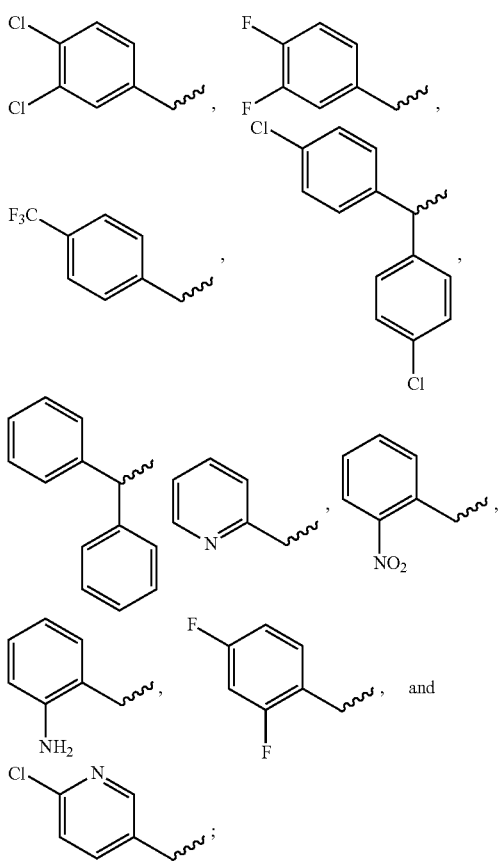

R$^2$ is selected from the group consisting of hydrogen, ~CF$_3$, ~X-POLY and ~OCH$_2$CH$_2$OH, ~OCH$_2$CH$_2$O;

R$^3$ is selected from the group consisting of hydrogen, ~X-POLY, ~NHSO$_2$CH$_3$,

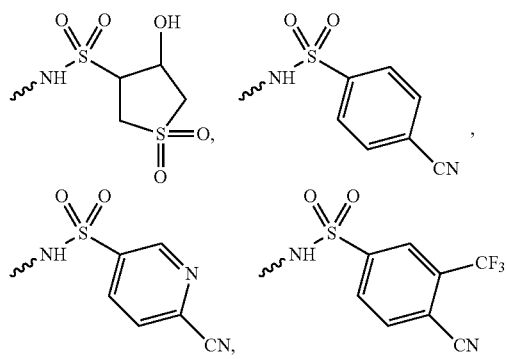

~NHSO$_2$CH$_2$CH$_2$OCH$_3$, ~NHSO$_2$CH$_2$CH$_2$OCH$_2$CF$_3$, ~NHSO$_2$CH$_2$CH(CH$_3$)OH, ~NH$_2$, and ~NHSO$_2$—(CH$_2$CH$_2$O)$_n$—Y, wherein n is 1 to 30, and Y is selected from hydrogen, lower alkyl and trifluoromethoxy, and ~NHC(O)NH—(CH$_2$CH$_2$O)$_n$—Y, wherein n is 1 to 30, and Y is selected from hydrogen, lower alkyl and trifluoromethoxy;

R$^4$ is selected from the group consisting of hydrogen, hydroxyl, ~OCH$_2$COOH, ~OCH$_2$CH$_2$OH, ~OCH$_2$CH$_2$OCH$_2$COOH, ~OCH$_2$CH$_2$OCH$_2$CH$_2$OCH$_2$COOH, and ~X-POLY;

X is an optional linker;

POLY is a water soluble, non-peptidic oligomer; and

R$^5$ is selected from the group of hydrogen, hydroxyl and fluoro; and

R$^6$ is fluoro only when R$^5$ is also fluoro, otherwise R$^5$ is hydrogen;

with the proviso the compound contains not more than one of the group ~X-POLY and ~(CH$_2$CH$_2$O)$_n$—Y, and pharmaceutically acceptable salts and solvates thereof.

In certain embodiments of compounds of the invention, a compound is provided, the compound having the following structure:

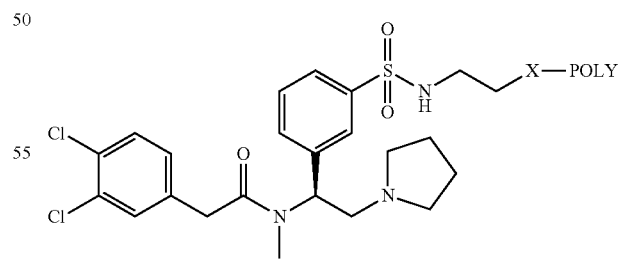

X is an optional linker; POLY is a water soluble, non-peptidic oligomer, and pharmaceutically acceptable salts and solvates thereof.

In certain embodiments of compounds of the invention, a compound is provided, the compound having the following structure:

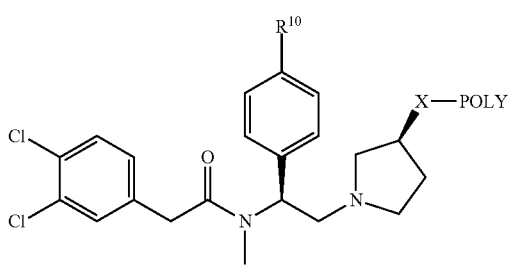

wherein R[10] is selected from the group consisting of ~H, ~OCH₂CH₂OH, ~OCH₂CH₂OCH₃, ~NHCH₂CH₂OH, and ~NHCH₂CH₂OCH₃, X is an optional linker, POLY is a water soluble, non-peptidic oligomer, and pharmaceutically acceptable salts and solvates thereof.

In certain embodiments of compounds of the invention, a compound is provided, the compound having the following structure:

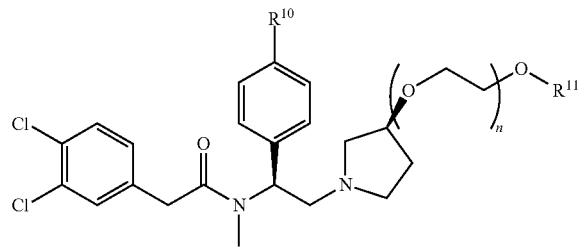

wherein:
(n) is an integer of from 1 to 30;
R[10] is selected from the group consisting of ~H, ~OCH₂CH₂OH, ~OCH₂CH₂OCH₃, ~NHCH₂CH₂OH, and ~NHCH₂CH₂OCH₃;
R[11] is selected from the group consisting of ~H, ~CH₃, and ~CF₃, and pharmaceutically acceptable salts and solvates thereof.

In certain embodiments of compounds of the invention, a compound is provided, the compound having the following structure:

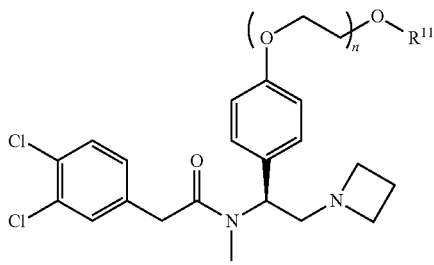

wherein (n) is an integer of from 1 to 30, and R[11] is seleted from the group consisting of ~H, ~CH₃, and ~CF₃, and pharmaceutically acceptable salts and solvates thereof.

In certain embodiments of the invention, the compound is selected from
2-(3, 4-dichlorophenyl)-N-{(1S)-2-[(3S)-3-(2-methoxyethoxy)pyrrolidin-1-yl]-1-phenylethyl}-N-methylacetamide;
2-(3, 4-Dichlorophenyl)-N-{(1S)-2-[(3S)-3-(2-(2-(2-methoxyethoxy) ethoxy] ethoxy) pyrrolidin-1-yl)-1-phenylethyl}-N-methylacetamide;
(3S)-1-[(2S)-2-{[(3,4-Dichlorophenyl)acetyl](methyl)amino}-2-phenylethyl]pyrrolidin-3-yl {2-[2-(2-methoxyethoxy)ethoxy]ethyl}carbamate;
(3S)-1-[(2S)-2-{[(3,4-Dichlorophenyl)acetyl](methyl)amino}-2-phenylethyl]pyrrolidin-3-yl 2,5,8,11,14-pentaoxahexadecan-16-ylcarbamate;
2-(3,4-Dichlorophenyl)-N-methyl-N-{(1S)-2-[(3S)-3-(2,5,8,11,14-pentaoxahexadecan-16-yloxy)pyrrolidin-1-yl]-1-phenylethyl}acetamide;
N-Methyl-N-{(1S)-2-[(3S)-3-(2,5,8,11,14-pentaoxahexadecan-16-yloxy)pyrrolidin-1-yl]-1-phenylethyl}-N²-phenylglycinamide;
2-(3,4-Dichlorophenyl)-N-{(1S)-2-[ethyl(2-methoxyethyl)amino]-1-phenylethyl}-N-methylacetamide;
N-[(1S)-2-[(3S)-3-Hydroxypyrrolidin-1-yl]-1-(3-{[(2-methoxyethoxy)acetyl]amino}phenyl)ethyl]-N-methyl-2,2-diphenylacetamide;
N-{3-[(1S)-1-[(Diphenylacetyl)(methyl)amino]-2-(pyrrolidin-1-yl)ethyl]phenyl}-2,5,8,11,14,17-hexaoxanonadecan-19-amide; and
N-Methyl-2-[4-(2, 5, 8, 11, 14-pentaoxahexadecan-16-yloxy)phenyl]-N-[(1S)-1-phenyl-2-(pyrrolidin-1-yl)ethyl]acetamide; and pharmaceutically acceptable salts thereof.

The compounds of the present invention may be prepared using techniques known to one of skill in the art. As disclosed herein, each compound of Formula I comprises at least one —X-POLY group. The incorporation of the X-POLY group into a compound of Formula I can be achieved by reacting a synthetic precursor/synthetic intermediate of a compound of Formula I with a POLY group having a functional group that is capable of reacting with a functional group on the synthetic intermediate to compound of Formula I. The synthetic intermediate of a compound of Formula I may in certain embodiments possess a group suitable for covalent attachment of the oligomer. Such groups include, but are not limited to, a free hydroxyl, carboxyl, carbonyl, thio, amino group, or the like. Such groups can be incorporated into the synthetic intermediate to provide a point of attachment for the oligomer. As such, the oligomer can be incorporated at a various stages of the synthesis, depending on the synthetic scheme. The introduction and conversion of functional groups in a synthetic intermediate are transformations that are generally known to those of skill in the art and can be found in the relevant texts. See e.g. M. Smith, *March's Advanced Organic Chemistry: Reactions, Mechanisms and Structure*, (7th ed. 2013); Carey and Sundberg, *Advanced Organic Chemistry*, (5th ed. 2007).

The group "X" adjacent to POLY in the compound of Formula I is typically formed by reaction of a functional group on a terminus of the oligomer (or one or more monomers when it is desired to "grow" the oligomer onto the compound of the present invention) with a corresponding functional group within synthetic precursor/intermediate to a compound of Formula I. For example, an amino group on an oligomer may be reacted with a carboxylic acid or an activated carboxylic acid derivative on the intermediate, or vice versa, to produce an amide linkage. Alternatively, reaction of an amine on an oligomer with an activated carbonate (e.g. succinimidyl or benzotriazyl carbonate) on the intermediate, or vice versa, forms a carbamate linkage. Reaction of an amine on an oligomer with an isocyanate (R—N=C=O) on an intermediate, or vice versa, forms a urea linkage (R—NH—(C=O)—NH—R'). Further, reaction of an alcohol (alkoxide) group on an oligomer with an alkyl halide, or halide group within an intermediate, or vice versa, forms an ether linkage. In yet another approach, an intermediate having an aldehyde function is coupled to an oligomer amino group by reductive amination, resulting in formation of a secondary amine linkage between the oligomer and the compound (or intermediate thereof) of the present invention.

Accordingly, each "POLY" (oligomer) is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where in certain embodiments, alkyl is methyl; α-hydroxy acid, such as lactic acid or glycolic acid; phosphazene, oxazoline, amino acids, carbohydrates such as monosaccharides, saccharide or mannitol; and N-acryloylmorpholine. In certain embodiments, monomer types include alkylene oxide, olefinic alcohol, hydroxyalkyl methacrylamide or methacrylate, N-acryloylmorpholine, and α-hydroxy acid. In certain embodiments, each oligomer is, independently, a co-oligomer of two monomer types selected from this group, or, in certain embodiments, is a homo-oligomer of one monomer type selected from this group.

The two monomer types in a co-oligomer may be of the same monomer type, for example, two alkylene oxides, such as ethylene oxide and propylene oxide. In certain embodiments, the oligomer is a homo-oligomer of ethylene oxide. Usually, although not necessarily, the terminus (or termini) of the oligomer that is not covalently attached to a compound (or intermediate thereof) of the present invention is capped to render it unreactive. Alternatively, the terminus may include a reactive group. When the terminus is a reactive group, the reactive group is either selected such that it is unreactive under the conditions of formation of the final oligomer or during covalent attachment of the oligomer to a compound (or intermediate thereof) of the present invention, or it is protected as necessary. One common end-functional group is hydroxyl or —OH, particularly for oligoethylene oxides.

The water-soluble oligomer (e.g., "POLY" in the structures provided herein) can have any of a number of different geometries. For example, it can be linear, branched, or forked. Most typically, the water-soluble oligomer is linear or is branched, for example, having one branch point. Although much of the discussion herein is focused upon poly(ethylene oxide) as an illustrative oligomer, the discussion and structures presented herein can be readily extended to encompass any of the water-soluble oligomers described above.

The molecular weight of the water-soluble oligomer, excluding the linker portion, in certain embodiments is generally relatively low. For example, the molecular weight of the water-soluble oligomer is typically below about 2200 Daltons, and more typically at around 1500 Daltons or below. In certain other embodiments, the molecular weight of the water-soluble oligomer may be below 800 Daltons.

In certain embodiments, exemplary values of the molecular weight of the water-soluble oligomer include less than or equal to about 500 Daltons, or less than or equal to about 420 Daltons, or less than or equal to about 370 Daltons, or less than or equal to about 370 Daltons, or less than or equal to about 325 Daltons, less than or equal to about 280 Daltons, less than or equal to about 235 Daltons, or less than or equal to about 200 Daltons, less than or equal to about 175 Daltons, or less than or equal to about 150 Daltons, or less than or equal to about 135 Daltons, less than or equal to about 90 Daltons, or less than or equal to about 60 Daltons, or even less than or equal to about 45 Daltons.

In certain embodiments, exemplary values of the molecular weight of the water-soluble oligomer, excluding the linker portion, include: below about 1500 Daltons; below about 1450 Daltons; below about 1400 Daltons; below about 1350 Daltons; below about 1300 Daltons; below about 1250 Daltons; below about 1200 Daltons; below about 1150 Daltons; below about 1100 Daltons; below about 1050 Daltons; below about 1000 Daltons; below about 950 Daltons; below about 900 Daltons; below about 850 Daltons; below about 800 Daltons; below about 750 Daltons; below about 700 Daltons; below about 650 Daltons; below about 600 Daltons; below about 550 Daltons; below about 500 Daltons; below about 450 Daltons; below about 400 Daltons; and below about 350 Daltons; but in each case above about 250 Daltons.

In certain embodiments, the number of monomers in the water-soluble oligomer falls within one or more of the following inclusive ranges: between 1 and 30 (i.e., is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30); between 1 and 25 (i.e., is selected from 1, 2, 3, 4, 5, 6, 7, 8, 9, 10, 11, 12, 13, 14, 15, 16, 17, 18, 19, 20, 21, 22, 23, 24, and 25); between 1 and 20 (i.e., is selected from 1, 2, 3, 4, 5, 6, 7, 8, 9, 10, 11, 12, 13, 14, 15, 16, 17, 18, 19, and 20); between 1 and 15 (is selected from 1, 2, 3, 4, 5, 6, 7, 8, 9, 10, 11, 12, 13, 14, 15); between 1 and 10 (i.e., is selected from 1, 2, 3, 4, 5, 6, 7, 8, 9, and 10); between 10 and 25 (i.e., is selected from 10, 11, 12, 13, 14, 15, 16, 17, 18, 19, 20, 21, 22, 23, 24, and 25); and between 15 and 20 (i.e., is selected from 15, 16, 17, 18, 19, and 20). In certain instances, the number of monomers in series in the oligomer (and the corresponding compound) is one of 1, 2, 3, 4, 5, 6, 7, 8, 9, 10, 11, 12, 13, 14, 15, 16, 17, 18, 19, 20, 21, 22, 23, 24, or 25. Thus, for example, when the water-soluble oligomer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, or 25. In certain embodiments, the number of monomers in the water-soluble oligomer falls within one or more of the following inclusive ranges: between 1 and 5 (i.e., is selected from 1, 2, 3, 4, and 5); between 1 and 4 (i.e., can be 1, 2, 3, or 4); between 1 and 3 (i.e., selected from 1, 2, or 3); between 1 and 2 (i.e., can be 1 or 2); between 2 and 5 (i.e., can be selected from 2, 3, 4, and 5); between 2 and 4 (i.e., is selected from 2, 3, and 4); between 2 and 3 (i.e., is either 2 or 3); between 3 and 5 (i.e., is either 3, 4 or 5); between 3 and 4 (i.e., is 3 or 4); and between 4 and 5 (i.e., is 4 or 5). In a specific instance, the number of monomers in series in the oligomer (and the corresponding compound) is selected from 1, 2, 3, 4, or 5. Thus, for example, when the water-soluble oligomer includes $CH_3$—$(OCH_2CH_2)_n$—, "n" is an integer that can be 1, 2, 3, 4, or 5.

When the water-soluble oligomer is attached to the synthetic intermediate of a compound of Formula I (in contrast to the step-wise addition of one or more monomers to effectively "grow" the oligomer onto the compound of Formula I or synthetic intermediate therof), the composition containing an activated form of the water-soluble oligomer may be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and in certain embodiments, is 1.001 or less, and in certain embodiments is 1.0005 or less. In certain embodiments, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

In certain embodiment, the water-soluble oligomer is obtained from a composition that is unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble oligomers can be prepared as described in Chen and Baker, *J. Org. Chem.* 6870-6873 (1999), WO 02/098949, and U.S. Patent Application Publication 2005/0136031.

As stated above, the water-soluble oligomer includes at least one functional group prior to reaction with the synthetic intermediate of a compound of Formula I. The functional group typically comprises an electrophilic or nucleophilic group for covalent attachment to the intermediate, depending upon the reactive group contained within the intermediate. Examples of nucleophilic groups that may be present in either the oligomer or the intermediate include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most intermediates will possess a free hydroxyl, amino, thio, aldehyde, ketone, or carboxyl group for reaction with the functional group on the oligomer.

Examples of electrophilic functional groups that may be present in either the oligomer or the synthetic intermediate of a compound of Formula I include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

It is possible, for example, to react a synthetic intermediate of a compound of Formula I bearing a carboxyl group by coupling it to an amino-terminated oligomeric ethylene glycol, to provide a synthetic intermediate for further modification or a compounds of Formula I wherein X comprises an amide. This can be performed, for example, by combining the carboxyl group-bearing intermediate with the amino-terminated oligomeric ethylene glycol in the presence of a coupling reagent, (such as dicyclohexylcarbodiimide or "DCC") in an anhydrous organic solvent. Similarly, the above reaction may take place between a synthetic intermediate of a compound of Formula I bearing an amino group and a carboxyl-terminated oligomeric ethylene glycol.

Further, it is possible to react a synthetic intermediate of a compound of Formula I bearing a hydroxyl group with an oligomeric ethylene glycol halide to result in a synthetic intermediate for further modification or a compound of Formula I wherein X comprises an ether (—O—). This can be performed, for example, by using sodium hydride to deprotonate the hydroxyl group followed by reaction with a halide-terminated oligomeric ethylene glycol. Similarly, the above reaction may take place between a synthetic intermediate of a compound of Formula I bearing a halo group and an oligomeric ethylene glycol bearing a hydroxyl group.

In another example, it is possible to convert a ketone of a synthetic intermediate of a compound of Formula I bearing a ketone group to a hydroxyl group by first reducing the ketone group to form the corresponding hydroxyl group. Thereafter, the synthetic intermediate may be reacted now bearing a hydroxyl group may be reacted as described herein.

In still another instance, it is possible to react a synthetic intermediate of a compound of Formula I bearing an amine group. In one approach, the amine group-bearing synthetic intermediate and an carbonyl-bearing oligomer are dissolved in a suitable buffer after which a suitable reducing agent (e.g., NaCNBH$_3$) is added. Following reduction, the result is an amine linkage formed between the amine group of the amine group-containing synthetic intermediate and the carbonyl carbon of the aldehyde-bearing oligomer. Similarly, the reaction may take place where the synthetic intermediate bears a carbonyl group and the oligomer bears and amine.

In another approach for preparing a compound of the present invention, where the synthetic intermediate bears an amine group, a carboxylic acid-bearing oligomer and the amine group-bearing intermdiate are combined, typically in the presence of a coupling reagent (e.g., DCC). The result is an amide linkage formed between the amine group of the amine group-containing synthetic intermediate and the carbonyl of the carboxylic acid-bearing oligomer. Similarly the above reaction may take place when the synthetic intermediate bears an carboxyl group and the oligomer bears an amine group.

The compounds of the present invention are understood to have activity as agonists of the kappa opioid receptor. The ability of each compound disclosed herein to act as kappa opioid agonists may be determined using methods known to those of skill in the art and as disclosed herein. The activity of compounds as kappa agonist can be assessed with in-vitro binding and functional assays in kappa opioid receptor expressing cell lines/membranes and compared to known kappa agonists.

Approaches for evaluating analgesic activity of a compound of the present invention in vivo include a "writhing test." Briefly, the compound to be tested is administered [by, for example, injection (e.g., subcutaneous injection)] to the mouse. Thereafter, a 0.5% acetic acid solution is administered (i.p.) to a mouse and the numbers of writhing responses are counted for twenty minutes. Antinociception is quantified as reduction in the number of writhes respective to vehicle.

Beyond acting as kappa opioid agonists, the present compounds are intended to act primarily on kappa opioid receptors in the peripheral nervous system rather than those receptors in the central nervous system. As recited above, each compound of Formula I includes at least one —X-POLY group. It is believed that the POLY portion of the compound of Formula I acts to reduce the rate and/or extent to which the compound of Formula I crosses into the central nervous system. The propensity of a compound of the present invention to cross the blood-brain barrier may be measured by methods known to those of skill in the art and those described herein.

With respect to the blood-brain barrier ("BBB"), this barrier consists of a continuous layer of unique endothelial cells joined by tight junctions. The cerebral capillaries, which comprise more than 95% of the total surface area of the BBB, represent the principal route for the entry of most solutes and drugs into the central nervous system.

As will be understood by one of skill in the art, molecular size, lipophilicity, and P-glycoprotein ("PgP") interaction are among the primary parameters affecting the intrinsic BBB permeability properties of a given molecule. That is to say, these factors, when taken in combination, play a significant role in determining whether a given molecule passes through the BBB. Other factors (e.g., other active transport mechanisms) may also play a role in ultimately determining whether a given molecule will pass through the BBB.

With respect to molecular size, the molecular size plays a significant role in determining whether a given molecule will pass through the BBB. Relatively very large molecules, for example a molecule having a molecular weight of 5,000 Daltons, will not cross the BBB, whereas relatively small molecules are more likely to cross the BBB. Other factors, however, also play a role in BBB crossing. Antipyrine and atenolol are both small molecule drugs; antipyrine readily crosses the BBB, whereas passage of atenolol is very limited, or effectively non-existent. Antipyrine is an industry standard for a high BBB permeation; atenolol is an industry standard for low permeation of the BBB. See, e.g., Summerfield et al., *J Pharmacol Exp Ther* 322:205-213 (2007).

Lipophilicity is also a factor in BBB permeation. Lipophilicity may be expressed as log P (partition coefficient) or in some instances log D (distribution coefficient). The log P (or log D) for a given molecule can be readily assessed by one of skill in the art. The value for log P may be a negative number (more hydrophilic molecules) or a positive number (more hydrophobic molecules). As used herein when referring to log P, "more negative" means moving in the direction, on the log P scale, from positive to negative log P (e.g., a log P of 2.0 is "more negative" than a log P of 4.0, a log P of -2.0 is "more negative" than a log P of -1.0). Molecules having a negative log P (hydrophilic molecules) generally do not permeate the BBB.

Permeability across the BBB is also dependent on the influence of transporters, such as P-glycoprotein, or PgP, an ATP-dependent efflux transporter highly expressed at the BBB. One of skill in the art can readily determine whether a compound is a substrate for PgP using in vitro methods. Compounds which are substrates for PgP in vitro likely will not permeate the BBB in vivo. Conversely, poor substrates for PgP, as assessed in vitro, are generally likely to display in vivo permeability of the BBB, provided the compound meets other criteria as discussed herein and as known to one of skill in the art. See, e.g., Tsuji, *NeuroRx* 2:54-62 (2005) and Rubin and Staddon, *Annu. Rev. Neurosci.* 22:11-28 (1999).

Even in the context of multiple variables (e.g., molecular size, lipophilicity, transporter influences, linkage type), it is possible to anazlyze a particular compounds ability to cross the BBB using methods known to those of skill in the art.

For any given compound whose degree of BBB crossing ability is not readily known, such BBB crossing ability can be determined using a suitable animal model such as an in situ rat brain perfusion ("RBP") model. Briefly, the RBP technique involves cannulation of the carotid artery followed by perfusion with a compound solution under controlled conditions, followed by a wash out phase to remove compound remaining in the vascular space. More specifically, in the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl et al. (2000) *J. Med. Chem.* 43:3714-3717 and Kelder et al. (1999) *Pharm. Res.* 16:1514-1519.

The compounds of the present invention are expected to have varying degrees of activity against the kappa agonist receptor as well as varying degrees to which they cross the BBB. While the compounds of the present invention have activity against the kappa opioid receptor, they are believed to also have some degree of exclusion from the central nervous system based on the presence of the X-POLY group in each compound.

Brain PK studies may also be conducted to measure the extent of brain entry in-vivo drug concentrations at enter the CNS at various time post-dose. In brief, rodents are administered with the test article (oral, subcutaneous, or other). At various times post dose terminal blood is collected. Then the rodent is transcardially perfused with cold isotonic saline to remove as much blood from the tissues and brain are extracted. Both plasma and brain are measured for drug content with LC/MS/MS.

The locomotor activity (LMA) model may be conducted to measure changes in activity following test article administration, which may be used to assess the CNS effects of the drug. In brief, at a predetermined time post-dose, rats are placed into observation chambers which are equipped with infrared photocells that can sense motion in the x, y, and z planes. Activity is measured as the number of photobeam breaks in a given plane (horizontal or vertical) or total distance traveled.

In further embodiments, the invention provides for compositions comprising the compounds disclosed herein and a pharmaceutically acceptable excipient or carrier. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the compound or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the compound in the composition will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, in certain embodiments from about 5%-98% by weight, in certain embodiments from about 15-95% by weight of the excipient, and in certain embodiments concentrations less than 30% by weight.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. In certain embodiments, preparations are in a form suitable for oral administration such as a tablet, caplet, capsule, gel cap, troche, dispersion, suspension, solution, elixir, syrup, lozenge, transdermal patch, spray, suppository, and powder. Oral dosage forms are preferred for those compounds that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the compounds described herein. In addition to the compound, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the compound-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compound can also be administered through the skin using conventional transdermal patch or other transdermal delivery system, wherein the compound is contained within a laminated structure that serves as a drug delivery device to be affixed to the skin. In such a structure, the compound is contained in a layer, or "reservoir," underlying an upper backing layer. The laminated structure can contain a single reservoir, or it can contain multiple reservoirs.

The compound can also be formulated into a suppository for rectal administration. With respect to suppositories, the compound is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a compound provided herein to a patient suffering from a condition that is responsive to treatment with the compound such as pain. The method comprises administering, generally orally, a therapeutically effective amount of the compound (in certain embodiments provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intraarterial, intraperitoneal, intracardiac, intrathecal, and intramuscular injection, as well as infusion injections.

The method of administering may be used to treat any condition that can be remedied or prevented by administration of a kappa opioid agonist. Most commonly, the compounds provided herein are administered for the management of pain, including visceral pain, chronic pelvic pain and interstitial cystitis. Kappa agonists have also been used to treat irritable bowel syndrome. Those of ordinary skill in the art appreciate which conditions a specific compound can effectively treat. The actual dose to be administered will vary depend upon the age, weight, and general condition of the subject as well as the severity of the condition being treated, the judgment of the health care professional, and compound being administered. Therapeutically effective amounts are known to those skilled in the art and/or are described in the pertinent reference texts and literature. Generally, a therapeutically effective amount will range from about 0.001 mg to 1000 mg, in certain embodiments in doses from 0.01 mg/day to 750 mg/day, and in certain embodiments in doses from 0.10 mg/day to 500 mg/day.

The unit dosage of any given compound (in certain embodiments, provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are hereby incorporated by reference in their entireties.

It is to be understood that while the invention has been described in conjunction with certain and specific embodiments, the foregoing description as well as the examples that follow are intended to illustrate and not limit the scope of the invention. Other aspects, advantages and modifications within the scope of the invention will be apparent to those skilled in the art to which the invention pertains.

EXAMPLES

All chemical reagents referred to in the appended examples are commercially available unless otherwise indicated. The preparation of PEG-mers is described in, for example, U.S. Patent Application Publication No. 2005/0136031.

Example 1

Preparation of 2-(3, 4-dichlorophenyl)-N-{(1S)-2-[(3S)-3-(2-methoxyethoxy)pyrrolidin-1-yl]-1-phenylethyl}-N-methylacetamide, hydrochloride salt (1)

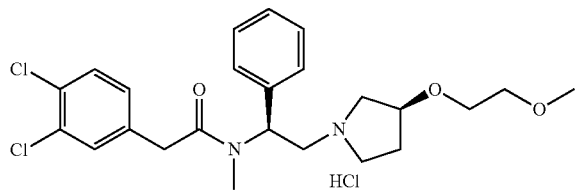

1

2-(3, 4-dichlorophenyl)-N-{(1S)-2-[(3S)-3-(2-methoxyethoxy)pyrrolidin-1-yl]-1-phenylethyl}-N-methylacetamide, hydrochloride salt (1) was prepared according to the following steps.

Step 1: Preparation of 2-(3,4-Dichlorophenyl)-N-{(1S)-2-((3S)-3-hydroxypyrrolidin-1-yl)-1-phenylethyl}-N-methylacetamide, hydrochloride salt (3)

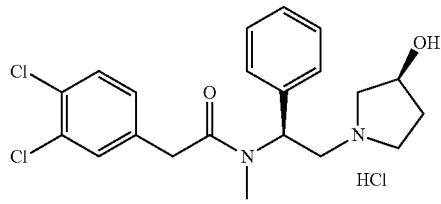 [SMILES: CN(C(=O)Cc1ccc(Cl)c(Cl)c1)[C@H](CN1CC[C@H](O)C1)c1ccccc1 ; Cl]

(3S)-1-[(2S)-2-(Methylamino)-2-phenylethyl] pyrrolidin-3-ol (2) (Ghosh, A. et. al., Chemical Communications (2002), #15, 1644) (0.70 g, 2.39 mmol), 2-(3,4-dichlorophenyl) acetic acid (0.45 g, 2.17 mmol), and N,N-diisopropylethylamine (0.56 g, 4.34 mmol) were dissolved in 20 mL of acetonitrile. The mixture was stirred for ten minutes at room temperature and then cooled to 0° C. O-(Benzotriazol-1-yl)-N,N,N',N'-tetramethyluronium tetrafluoroborate (TBTU) (0.84 g, 2.61 mmol) was added into the solution. The reaction mixture was stirred for 16 hours and then was concentrated. The residue was dissolved in ethyl acetate (50 mL) and was washed with saturated sodium bicarbonate (2×30 mL), brine (30 mL) and was dried over sodium sulfate. Evaporation of the solvent and purification of the residue by flash chromatography yielded 2-(3,4-dichlorophenyl)-N-{(1S)-2-((3S)-3-hydroxypyrrolidin-1-yl)-1-phenylethyl}-N-methylacetamide (3) (0.86 g, 97% yield). $^1$H NMR (500 MHz, CDCl$_3$): δ 7.45-7.25 (m, 7H), 7.15 (m, 1H), 6.10 (m, 0.85H), 5.05 (m, 0.15H), 4.30 (m, 1H), 3.75 (m, 2H), 3.20 (t, 1H), 3.05 (m, 1 H), 2.80 (m, 2H), 2.62 (s, 3H), 2.64 (m, 1H), 2.38 (m, 1H), 2.15 (m, 1H), 1.73 (m, 1H); MS (EI) for C$_{21}$H$_{24}$Cl$_2$N$_2$O$_2$: 407 (MH$^+$). The free base (20 mg) was dissolved in 1 mL of acetonitrile. To the solution was added 0.2 mL of 1N hydrochloride. The mixture was lyophilized to afford product as hydrochloride salt.

Step 2: Preparation of 2-(3, 4-Dichlorophenyl)-N-{(1S)-2-[(3S)-3-(2-methoxyethoxy)pyrrolidin-1-yl]-1-phenylethyl}-N-methylacetamide, hydrochloride salt (1)

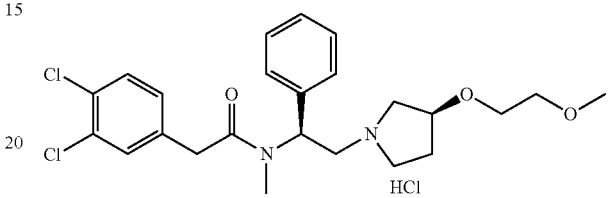

2-(3,4-Dichlorophenyl)-N-{(1S)-2-((3S)-3-hydroxypyrrolidin-1-yl)-1-phenylethyl}-N-methylacetamide (0.060 g, 0.15 mmol) was dissolved in 5 mL of N,N-dimethylformamide and sodium hydride (0.017 g of 60% in mineral oil, 0.44 mmol) was added into the solution. 1-bromo-2-methoxyethane (0.061 g, 0.44 mmol) in 1 mL of N,N-dimethylformamide was added under stirring. The reaction mixture was stirred at room temperature for 3 hours. 150 mL of dichloromethane was added into the reaction mixture. The solution was washed with water (100 mL×3) and was dried over sodium sulfate. Evaporation of the solvent and purification of the residue by flash chromatography yielded 2-(3, 4-dichlorophenyl)-N-{(1S)-2-[(3S)-3-(2-methoxyethoxy)pyrrolidin-1-yl]-1-phenylethyl}-N-methylacetamide (1) (0.020 g, 29% yield). The free base (18 mg) was dissolved in 1 mL of acetonitrile. To the solution was added 0.2 mL of 1N hydrochloride. The mixture was lyophilized to afford product as hydrochloride salt (3). $^1$H NMR (500 MHz, HCl salt in MeOD): δ 7.50 (m, 2H), 7.31 (m, 3H), 7.26 (m, 1H), 7.21 (m, 2H), 6.35 (d, 1H), 4.62 (d, 1H), 4.25 (m, 2H), 4.10-3.95 (m, 1H), 3.85 (m, 2H), 3.70-3.50 (m, 1H), 3.45 (m, 2H), 3.35 (m, 1H), 3.32 (s, 3H), 3.25 (m, 1H), 2.60 (d, 3H), 2.45-2.20 (m, 2H), 2.10 (m, 1H), 1.96 (m, 1H); MS (EI) for C$_{24}$H$_{30}$Cl$_2$N$_2$O$_3$: 465 (MH$^+$).

The example described above may be modified to introduce oligomers of various lengths as disclosed herein.

Example 2

Preparation of 2-(3, 4-Dichlorophenyl)-N-{(1S)-2-[(3S)-3-(2-(2-(2-methoxyethoxy) ethoxy]ethoxy) pyrrolidin-1-yl)-1-phenylethyl}-N-methylacetamide, hydrochloride salt (4)

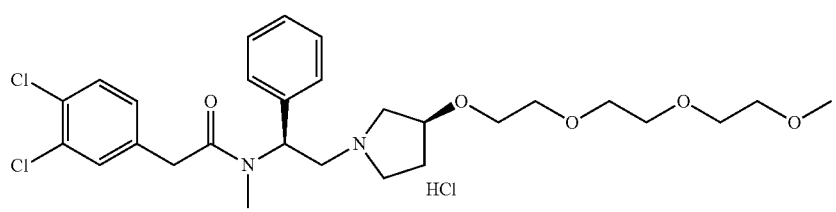

4

Step 1: Preparation of (S)-3-(2-(2-(2-methoxyethoxy)ethoxy)ethoxy)pyrrolidine

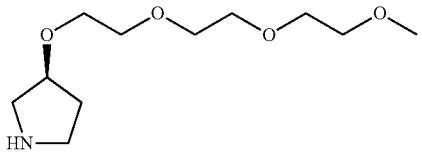

(S)-tert-Butyl-3-hydroxypyrrolidine-1-carboxylate (6.0 g, 32.04 mmol) was dissolved in THF (120 mL). The mixture was cooled to 0° C., NaH (1.54 g, 60% in mineral oil, 38.45 mmol) was added and reaction mixture was stirred for 30 min. 1-Bromo-2-(2-(2-methoxyethoxy)ethoxy)ethane (10.91 g, 48.06 mmol) dissolved in THF (25 mL) was added to the above mixture while maintaining the temperature of reaction at 0° C. The reaction mixture was stirred for additional 1 hour at 0° C. and allowed to warm to 22-25° C. and stirred for 18 hours at that temperature. The above mixture was concentrated under reduced pressure. The resulting residue was dissolved in DCM (120 mL) and the resulting solution was washed with water (50 mL×2). The organic layer was dried over anhydrous sodium sulfate and concentrated under vacuum to get a thick oil which was dissolved in DCM/TFA (2:1) (25 mL) and stirred for 4 hours at 22-25° C. and then concentrated under vacuum. The residue was dissolved in water (35 mL) and pH of mixture was adjusted to 9 by adding sodium carbonate. The solution was saturated with sodium chloride and extracted with DCM (50 mL×3). The organic phase was dried over anhydrous sodium sulfate and concentrated under reduced pressure and the crude product was purified by column chromatography yielded (S)-3-(2-(2-(2-methoxyethoxy)ethoxy)ethoxy)pyrrolidine (2.2 g, 29.5% yield) as an oil. $^1$H NMR (500 MHz, CDCl$_3$): δ 4.05 (m, 1H), 3.70-3.6 (m, 8H), 3.55 (m, 4H), 3.38 (s, 3H), 3.10 (m, 2H), 2.75 (m, 2H), 1.90 (m, 1H); MS (EI) for C$_{11}$H$_{23}$NO$_4$: 234 (MH$^+$).

Step 2: Preparation of benzyl ((S)-2-((S)-3-(2-(2-(2-methoxyethoxy)ethoxy)ethoxy) pyrrolidin-1-yl)-2-oxo-1-phenylethyl)carbamate

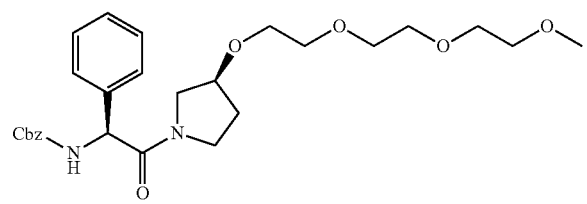 [SMILES: COCCOCCOCCO[C@H]1CCN(C(=O)[C@@H](NC(=O)OCc2ccccc2)c2ccccc2)C1]

(S)-3-(2-(2-(2-Methoxyethoxy)ethoxy)ethoxy)pyrrolidine (2.0 g, 8.57 mmol), (S)-2-(((benzyloxy)carbonyl)amino)-2-phenylacetic acid (2.44 g, 8.57 mmol) and DIPEA (3.32 g, 25.71 mmol) were dissolved in acetonitrile (40 mL). The above mixture was stirred for 15 min at 22-25° C. and then cooled to 0° C. O-(Benzotriazol-1-yl)-N,N,N',N'-tetramethyluronium tetrafluoroborate (TBTU) (3.30 g, 10.28 mmol) was added into the solution. The reaction mixture was stirred for 1 h at 0° C. and then 4 hours at room temperature. The reaction mixture was concentrated under reduced pressure. The resulting residue was dissolved in DCM (50 mL) and washed with brine (25 mL×2). The solution was dried over anhydrous sodium sulfate and concentrated. The obtained residue was then purified by column chromatography to yield benzyl ((S)-2-((S)-3-(2-(2-(2-methoxyethoxy)ethoxy)ethoxy)pyrrolidin-1-yl)-2-oxo-1-phenylethyl)carbamate (3.27 g, 76% yield). $^1$H NMR (500 MHz, CDCl$_3$): δ 7.43 (m, 2H), 7.34 (m, 8H), 6.40-6.25 (dd, 1H), 5.40 (m, 1 H), 5.23 (d, 1H), 5.04 (t, 1H), 4.08 (m, 1H), 3.70-3.50 (m, 12H), 3.42 (m, 2H), 3.41 (s, 3H), 3.21 (m. 2H), 2.12-1.80 (m, 2H); MS (EI) for C$_{27}$H$_{36}$N$_2$O$_7$: 501 (MH$^+$).

Step 3: Preparation of (S)-2-((S)-3-(2-(2-(2-methoxyethoxy)ethoxy)ethoxy)pyrrolidin-1-yl)-N-methyl-1-phenylethanamine

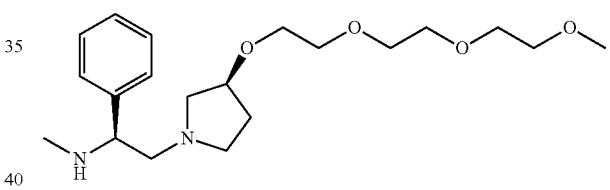

Benzyl ((S)-2-((S)-3-(2-(2-(2-methoxyethoxy)ethoxy)ethoxy)pyrrolidin-1-yl)-2-oxo-1-phenylethyl)carbamate (4.0 g, 8.0 mmol) was dissolved in THF (40 mL). The mixture was cooled to 0° C. LAH tablet (1.52 g, 40 mmol) was added to the above mixture and the mixture was stirred for 15 min at 0° C. and then heated to 65° C. and maintained at that temperature for four hours. A 3N aq. sodium carbonate solution was added cautiously until effervescence ceased. The solid was removed by filtration and was washed with DCM (100 mL). The filtrate was concentrated and the residue was dissolved in DCM (150 mL). The solution was washed with brine, dried over anhydrous sodium sulfate and concentrated under vacuum to obtain the crude product which was purified by column chromatography to yield (S)-2-((S)-3-(2-(2-(2-methoxyethoxy)ethoxy)ethoxy)pyrrolidin-1-yl)-N-methyl-1-phenylethanamine (1.35 g, 46% yield) as a thick oil. $^1$H NMR (500 MHz, CDCl$_3$): δ 7.35 (m, 4H), 7.25 (m, 1H), 4.05 (m, 1H), 3.67 (m, 8 H), 3.55 (m, 5H), 3.40 (s, 3H), 2.85 (m, 1H), 2.80 (m, 2H), 2.55 (m, 1H), 2.48 (m, 1H), 2.28 (s, 3H), 2.05 (m, 1H), 1.80 (m, 2H); MS (EI) for C$_{20}$H$_{34}$N$_2$O$_4$: 367 (MH$^+$).

Step 4: Preparation of 2-(3,4-dichlorophenyl)-N—((S)-2-((S)-3-(2-(2-(2-methoxyethoxy)ethoxy)ethoxy)pyrrolidin-1-yl)-1-phenylethyl)-N-methylacetamide, hydrochloride salt (4)

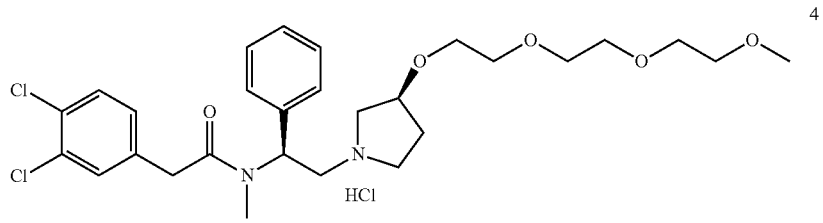 [SMILES: COCCOCCOCCO[C@H]1CCN(C[C@H](c2ccccc2)N(C)C(=O)Cc2ccc(Cl)c(Cl)c2)C1 ; Cl]

(S)-2-((S)-3-(2-(2-(2-Methoxyethoxy)ethoxy)ethoxy)pyrrolidin-1-yl)-N-methyl-1-phenylethanamine (3) (1.3 g, 3.54 mmol), 2-(3,4-dichlorophenyl)acetic acid (0.725 g, 3.54 mmol), and N,N-diisopropylethylamine (0.915 g, 7.08 mmol) were dissolved in acetonitrile (13 mL). The resulting mixture was stirred for 15 min at 22-25° C. and then cooled to 0° C. O-(Benzotriazol-1-yl)-N,N,N',N'-tetramethyluronium tetrafluoroborate (TBTU) (1.36 g, 4.25 mmol) was added into the solution. The reaction mixture was stirred for four hours at 22-25° C. and concentrated. The residue was dissolved in DCM (100 mL) and washed with water and dried over sodium sulfate. Evaporation of solvent and purification of the resulting residue by flash chromatography yielded 2-(3,4-dichlorophenyl)-N—((S)-2-((S)-3-(2-(2-(2-methoxyethoxy)ethoxy)ethoxy) pyrrolidin-1-yl)-1-phenylethyl)-N-methylacetamide (0.78 g, 40% yield). $^1$H NMR (500 MHz, CDCl$_3$): δ 7.40 (m, 2H), 7.32 (m, 2H), 7.25 (m, 2H), 7.20-7.10 (m, 2H), 6.10 (m, 1H), 4.05 (m, 1H), 3.78 (d, 1H), 3.65 (m, 8H), 3.55 (m, 4H), 3.40 (s, 3H), 3.15 (t, 1H), 3.05 (m, 1H), 2.85-2.70 (m, 2H), 2.70 (br, s, 3H), 2.50 (m, 2H), 2.05 (m, 1H), 1.80 (m, 1H); MS (EI) for C$_{28}$H$_{38}$Cl$_2$N$_2$O$_5$: 554 (MH$^+$). The free base was dissolved in 4M hydrochloride in 2-propanol. The mixture was concentrated to afford product as hydrochloride salt (4). The example described above may be modified to introduce oligomers of various lengths as disclosed herein.

Example 3

Preparation of (3S)-1-[(2S)-2-{[(3,4-Dichlorophenyl)acetyl](methyl)amino}-2-phenylethyl]pyrrolidin-3-yl {2-[2-(2-methoxyethoxy)ethoxy]ethyl}carbamate, hydrochloride salt (5)

2-(3,4-Dichlorophenyl)-N-{(1S)-2-((3S)-3-hydroxypyrrolidin-1-yl)-1-phenylethyl}-N-methylacetamide (3) (0.030 g, 0.074 mmol) and 4-nitrophenyl carbonochloride (0.017 g, 0.081 mmol) were dissolved in 3 mL of dichloromethane. N,N-diisopropylethylamine (0.018 g, 0.15 mmol) was added under stirring. The reaction mixture was stirred at room temperature for two hours. 2-(2-(2-methoxyethoxy)ethoxy)ethanamine (0.033 g, 0.20 mmol) was added. The reaction mixture was stirred at room temperature for 6 hours. 100 mL of dichloromethane was added into the reaction mixture. The resultant solution was washed with saturated sodium chloride (60 mL×3) and was dried over sodium sulfate. Evaporation of the solvent and purification of the residue by flash chromatography yielded (3S)-1-[(2S)-2-{[(3,4-Dichlorophenyl)acetyl](methyl)amino}-2-phenylethyl]pyrrolidin-3-yl {2-[2-(2-methoxyethoxy)ethoxy]ethyl}carbamate (0.023 g, 58% yield). $^1$H NMR (500 MHz, CDCl$_3$): δ 7.45-7.26 (m, 7H), 7.16 (m, 1H), 6.10 (m, 0.85H), 5.20 (m, 2H), 5.05 (m, 0.15H), 3.85-3.62 (m, 10H), 3.57 (m, 4H), 3.38 (s, 3H), 3.15 (t, 1H), 2.98 (m, 2H), 2.75 (m, 4H), 2.40 (m, 1H), 2.20 (m, 1H), 1.82 (m, 2H); MS (EI) for C$_{29}$H$_{39}$Cl$_2$N$_3$O$_6$: 596 (MH$^+$).

The free base (20 mg) was dissolved in 1 mL of acetonitrile. To the solution was added 0.2 mL of 1N hydrochloride. The mixture was lyophilized to afford product as hydrochloride salt (5).

The example described above may be modified to introduce oligomers of various lengths as disclosed herein.

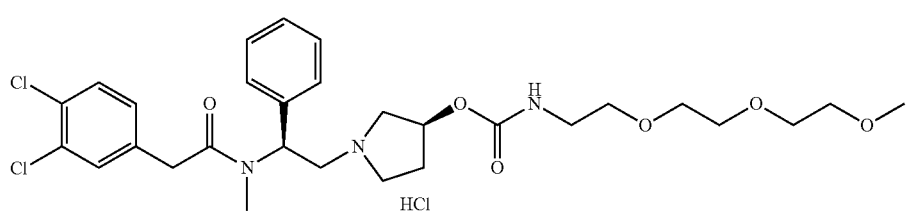

Example 4

(3S)-1-[(2S)-2-{[(3,4-Dichlorophenyl)acetyl]](methyl)amino}-2-phenylethyl]pyrrolidin-3-yl 2,5,8,11,14-pentaoxahexadecan-16-ylcarbamate, hydrochloride salt (6)

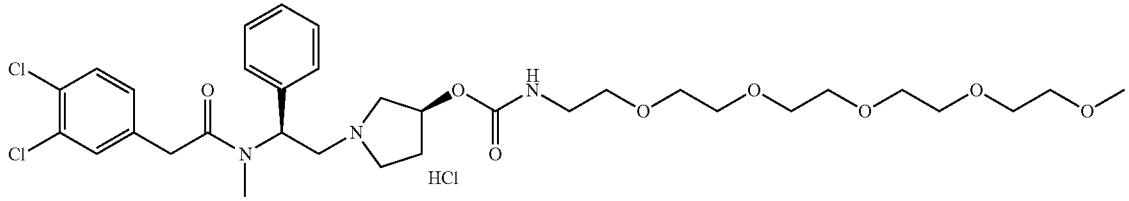

6

2-(3,4-Dichlorophenyl)-N-{(1S)-2-((3S)-3-hydroxypyrrolidin-1-yl)-1-phenylethyl}-N-methylacetamide (3) (0.035 g, 0.086 mmol) and 4-nitrophenyl carbonochloride (0.020 g, 0.10 mmol) were dissolved in 3 mL of dichloromethane. N,N-diisopropylethylamine (0.022 g, 0.172 mmol) was added under stirring. The reaction mixture was stirred at room temperature for 2 hours. 2,5,8,11,14-Pentaoxahexadecan-16-amine (0.060 g, 0.24 mmol) was added. The reaction mixture was stirred at room temperature overnight. Dichloromethane (100 mL) was added into the reaction mixture. The solution was washed with saturated sodium chloride (100 mL×3) and was dried over sodium sulfate. Evaporation of the solvent and purification of the residue by flash chromatography yielded (3S)-1-[(2S)-2-{[(3,4-dichlorophenyl)acetyl](methyl)amino}-2-phenylethyl]pyrrolidin-3-yl 2,5,8,11,14-pentaoxahexadecan-16-ylcarbamate (0.025 g, 47% yield). $^1$H NMR (500 MHz, DMSO-d6): δ 7.56 (m, 1H), 7.50 (s, 1H), 7.40-7.20 (m, 6H), 7.12 (m, 1H), 5.82 (m, 0.8H), 5.20 (m, 0.2 H), 4.95 (m, 1H), 3.92-3.65 (m, 2H), 3.50 (m, 16H), 3.48 (m, 4H), 3.24 (s, 3H), 3.10 (m, 3H), 2.90 (m, 1H), 2.75 (m, 4H), 2.42 (m, 1H), 2.20 (m, 1H), 1.65 (m, 1H); MS (EI) for $C_{33}H_{47}Cl_2N_3O_8$: 684 (MH$^+$).

The free base (22 mg) was dissolved in 1 mL of acetonitrile. To the solution was added 0.5 mL of 1N hydrochloride. The mixture was lyophilized to afford product as hydrochloride salt (6).

The example described above may be modified to introduce oligomers of various lengths as disclosed herein.

Example 5

2-(3,4-Dichlorophenyl)-N-methyl-N-{(1S)-2-[(3S)-3-(2,5,8,11,14-pentaoxahexadecan-16-yloxy)pyrrolidin-1-yl]-1-phenylethyl}acetamide, hydrochloride salt (7)

2-(3,4-Dichlorophenyl)-N-methyl-N-{(1S)-2-[(3S)-3-(2,5,8,11,14-pentaoxahexadecan-16-yloxy)pyrrolidin-1-yl]-1-phenylethyl}acetamide, hydrochloride salt (7) was prepared according to the following steps.

Step 1: Preparation of (3S)-3-(2,5,8,11,14-Pentaoxahexadecan-16-yloxy)pyrrolidine

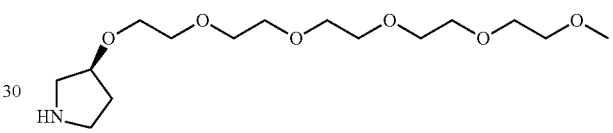

(S)—N-Boc-3-pyrrolidinol (1.0 g, 5.34 mmol) was dissolved in 10 mL of tetrahydrofuran. The resultant solution was cooled in an ice-bath and then sodium hydride (0.257 g of 60% in mineral oil, 6.41 mmol) was added. The mixture was stirred for five minutes before 16-bromo-2,5,8,11,14-pentaoxahexadecane (2.02 g, 6.41 mmol) in 5 mL of tetrahydrofuran was added. The reaction mixture was stirred at 0° C. for one hour and then overnight at room temperature. 150 mL of dichloromethane was added into the reaction mixture. The solution was washed with water (100 mL×3) and dried over sodium sulfate. An oil was obtained after removing solvent, which was dissolved in 10 mL of trifluoroacetic acid/dichloromethane (1:2). The mixture was stirred for 4 hours and then was concentrated. 5 mL of water was added into the mixture. The pH of the mixture was adjusted to 9 by adding sodium carbonate. The solution was saturated with sodium chloride and was extracted with dichloromethane (150 mL×3). The organic phase was dried over sodium sulfate. After removing solvent, an oil was obtained, which was purified by flash chromatography to afford (3S)-3-(2,5,8,11,14-Pentaoxahexadecan-16-yloxy)pyrrolidine (0.944 g, 56% yield). $^1$H NMR (500 MHz, CDCl$_3$): δ 4.24 (m, 1H), 3.69 (m, 15H), 3.66 (m, 6H), 3.52 (m, 1 H), 3.42 (m, 1H), 3.40 (s, 3H), 3.30 (m, 1H), 2.15 (m, 2H); MS (EI) for $C_{15}H_{31}NO_6$: 322 (MH$^+$).

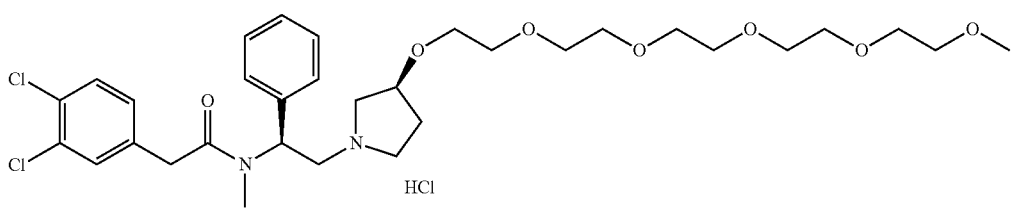

7

Step 2: Preparation of Benzyl {(1S)-2-oxo-2-[(3S)-3-(2,5,8,11,14-pentaoxahexadecan-16-yloxy)pyrrolidin-1-yl]-1-phenylethyl}carbamate

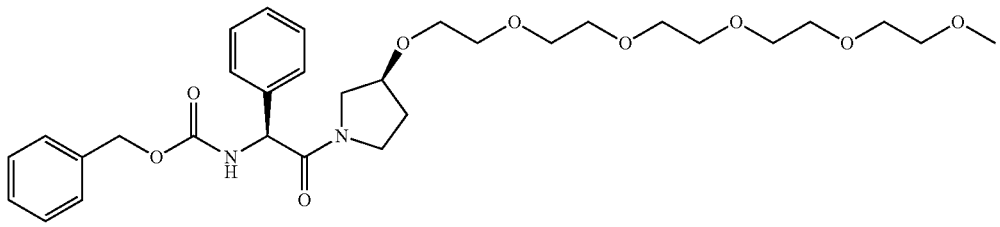 [SMILES: COCCOCCOCCOCCOCCO[C@H]1CCN(C(=O)[C@@H](NC(=O)OCc2ccccc2)c2ccccc2)C1]

Z-Phg-OH ((2S)-{[(Benzyloxy)carbonyl]amino}(phenyl) acetic acid) (1.0 g, 3.49 mmol), (3S)-3-(2,5,8,11,14-pentaoxahexadecan-16-yloxy)pyrrolidine (from step 1) (1.02 g, 3.17 mmol), and N,N-diisopropylethylamine (1.22 g, 9.52 mmol) were dissolved in 20 mL of acetonitrile. The mixture was stirred for 10 minutes at room temperature and then cooled to 0° C. O-(Benzotriazol-1-yl)-N,N,N',N'-tetramethyluronium tetrafluoroborate (TBTU) (1.22 g, 3.81 mmol) was added into the solution. The reaction mixture was stirred for 1 hour at 0° C. and then overnight at room temperature. 100 mL of dichloromethane was added into the reaction mixture, and the resultant solution was washed with 5% of sodium chloride (100 mL×3). The solution was dried over sodium sulfate and was concentrated. The purification of the residue by flash chromatography yielded benzyl {(1S)-2-oxo-2-[(3S)-3-(2,5,8,11,14-pentaoxahexadecan-16-yloxy) pyrrolidin-1-yl]-1-phenylethyl)}carbamate (1.1 g, 59% yield). $^1$H NMR (500 MHz, CDCl$_3$): δ 7.43 (m, 2H), 7.34 (m, 8H), 6.40-6.30 (dd, 1H), 5.40 (m, 1H), 5.23 (d, 1H), 5.04 (t, 1H), 4.08 (m, 1H), 3.70-3.50 (m, 20H), 3.42 (m, 2H), 3.41 (s, 3H), 3.21 (m. 2H), 2.12-1.80 (m, 2H); MS (EI) for C$_{31}$H$_{44}$N$_2$O$_9$: 589 (MH$^+$).

Step 3: Preparation of (1S)—N-Methyl-2-[(3S)-3-(2,5,8,11,14-pentaoxahexadecan-16-yloxy)pyrrolidin-1-yl]-1-phenylethanamine A solution of benzyl {(1S)-2-oxo-2-[(3S)-3-(2,5,8,11,14-pentaoxahexadecan-16-yloxy)pyrrolidin-1-yl]-1-phenylethyl}carbamate (from step 2) (0.95 g, 1.61 mmol) in tetrahydrofuran was added dropwise to a stirred 2.0 M solution of lithium aluminum hydride (4.0 mL, 8.0 mmol) at room temperature. The mixture was stirred for 30 minutes at room temperature and then was heated to 65° C. for four hours. After cooling down to room temperature, a 3N sodium carbonate solution was added into the reaction mixture carefully until effervescence ceased. The solid was filtered out and was washed with dichloromethane (100 mL). The filtrate was concentrated and the residue was dissolved in 150 mL of dichloromethane. The solution was washed with saturated sodium chloride solution and was dried over sodium sulfate. (1S)—N-Methyl-2-[(3S)-3-(2,5,8,11,14-pentaoxahexadecan-16-yloxy)pyrrolidin-1-yl]-1-phenylethanamine (0.60 g, 82% yield) was obtained after removing solvent. $^1$H NMR (500 MHz, CDCl$_3$): δ 7.39 (m, 2H), 7.35 (m, 3H), 4.08 (m, 1H), 3.67 (m, 16 H), 3.18 (m, 5H), 3.40 (s, 3H), 2.90 (m, 1H), 2.80 (m, 2H), 2.55 (m, 1H), 2.48 (m, 1H), 2.30 (s. 3H), 2.10 (m, 3H), 1.82 (m, 1H); MS (EI) for C$_{24}$H$_{42}$N$_2$O$_6$: 455 (MH$^+$).

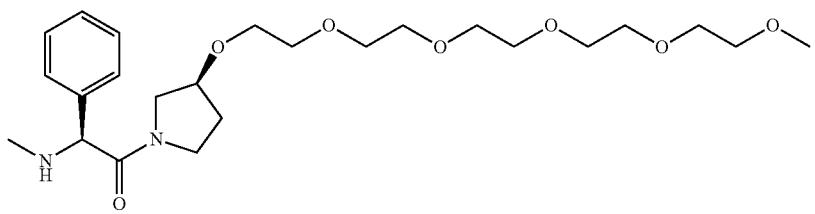

Step 4: Preparation of 2-(3,4-Dichlorophenyl)-N-methyl-N-{(1S)-2-[(3S)-3-(2,5,8,11,14-pentaoxahexadecan-16-yloxy)pyrrolidin-1-yl]-1-phenylethyl}acetamide, hydrochloride salt (7)

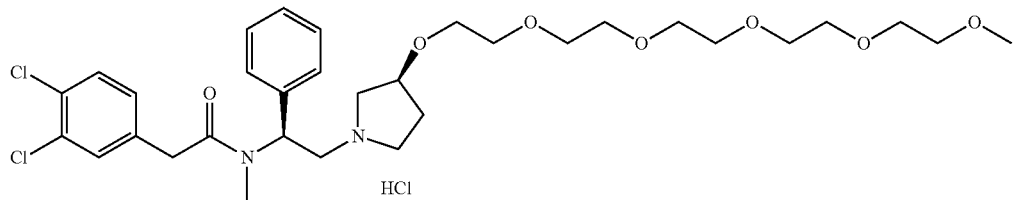 [SMILES: COCCOCCOCCOCCOCCO[C@H]1CCN(C[C@H](c2ccccc2)N(C)C(=O)Cc2ccc(Cl)c(Cl)c2)C1 ; Cl]

(1S)—N-Methyl-2-[(3S)-3-(2,5,8,11,14-pentaoxahexadecan-16-yloxy)pyrrolidin-1-yl]-1-phenylethanamine (from step 3) (0.100 g, 0.22 mmol), 2-(3,4-dichlorophenyl)acetic acid (0.045 g, 0.22 mmol), and N,N-diisopropylethylamine (0.056 g, 0.44 mmol) were dissolved in 3 mL of acetonitrile. The mixture was stirred for 10 minutes at room temperature and then cooled to 0° C. O-(Benzotriazol-1-yl)-N,N,N',N'-tetramethyluronium tetrafluoroborate (TBTU) (0.085 g, 0.26 mmol) was added into the solution. The reaction mixture was stirred for 4 hours at room temperature and was concentrated. The residue was dissolved in dichloromethane (100 mL), was washed with water and was dried over sodium sulfate. Evaporation of the solvent and purification of the residue by flash chromatography yielded 2-(3,4-dichlorophenyl)-N-methyl-N-{(1S)-2-[(3S)-3-(2,5,8,11,14-pentaoxahexadecan-16-yloxy)pyrrolidin-1-yl]-1-phenylethyl}acetamide (0.090 g, 64% yield). $^1$H NMR (500 MHz, CDCl$_3$): δ 7.40 (m, 2H), 7.32 (m, 2H), 7.30 (m, 3H), 7.15 (m, 1H), 6.10 (m, 0.83H), 5.02 (m, 0.17H), 4.05 (m, 1H), 3.78 (d, 1H), 3.65 (m, 17H), 3.55 (m, 4H), 3.39 (s, 3H), 3.16 (t, 1H), 3.05 (m, 1H), 2.85 (m, 1H), 2.70 (m, 4H), 2.50 (m, 2H), 2.05 (m, 1H), 1.80 (m, 1H); MS (EI) for $C_{32}H_{46}Cl_2N_2O_7$: 641 (MH$^+$).

The free base (85 mg) was dissolved in 1 mL of acetonitrile. To the solution was added 0.5 mL of 1N hydrochloride. The mixture was lyophilized to afford product as hydrochloride salt (7).

The example described above may be modified to introduce oligomers of various lengths as disclosed herein.

Example 6

Preparation of N-Methyl-N-{(1S)-2-[(3S)-3-(2,5,8,11,14-pentaoxahexadecan-16-yloxy)pyrrolidin-1-yl]-1-phenylethyl}-N²-phenylglycinamide, hydrochloride salt (8)

(1S)—N-Methyl-2-[(3S)-3-(2,5,8,11,14-pentaoxahexadecan-16-yloxy)pyrrolidin-1-yl]-1-phenylethanamine (from example 5, step 3) (0.070 g, 0.154 mmol), 2-(phenylamino)acetic acid (0.023 g, 0.154 mmol), and N,N-diisopropylethylamine (0.038 g, 0.308 mmol) were dissolved in 3 mL of acetonitrile. The mixture was stirred for 10 minutes at room temperature and then cooled to 0° C. O-(Benzotriazol-1-yl)-N,N,N',N'-tetramethyluronium tetrafluoroborate (TBTU) (0.059 g, 0.185 mmol) was added into the solution. The reaction mixture was stirred for 4 hours at room temperature and was concentrated. The residue was dissolved in dichloromethane (100 mL), was washed with water and was dried over sodium sulfate. Evaporation of the solvent and purification of the residue by flash chromatography yielded N-methyl-N-{(1S)-2-[(3S)-3-(2,5,8,11,14-pentaoxahexadecan-16-yloxy)pyrrolidin-1-yl]-1-phenylethyl}-N²-phenylglycinamide (0.050 g, 55% yield). $^1$H NMR (500 MHz, CDCl$_3$): δ 7.34 (m, 5H), 7.20 (m, 2H), 6.75 (m, 1H), 6.65 (m, 2H), 6.09 (m, 1H), 5.02 (m, 1H), 4.05 (m, 1H), 3.90 (m, 2H), 3.60 (m, 20H), 3.40 (s, 3H), 3.20 (m, 1H), 3.05 (m, 1H), 2.85 (m, 2H), 2.78 (s, 3H), 2.55 (m, 1H), 2.15 (br., 1H), 2.05 (m, 1H), 1.80 (m, 1H); MS (EI) for $C_{32}H_{49}N_3O_7$: 588 (MH$^+$).

The free base (22 mg) was dissolved in 1 mL of acetonitrile. To the solution was added 0.2 mL of 1N hydrochloride. The mixture was lyophilized to afford product as hydrochloride salt (8).

The example described above may be modified to introduce oligomers of various lengths as disclosed herein.

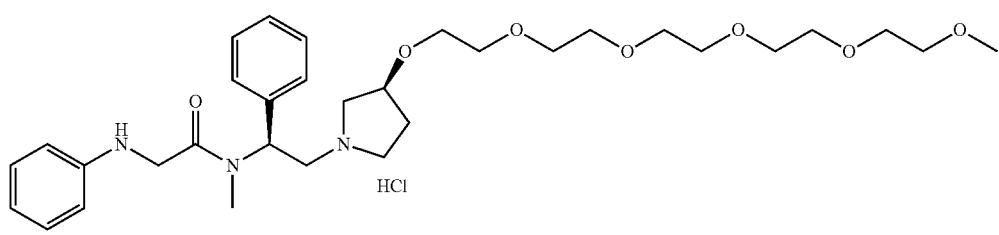

Example 7

Preparation of N-Methyl-N-{(1S)-2-[(3S)-3-(2,5,8,11,14-pentaoxahexadecan-16-yloxy)pyrrolidin-1-yl]-1-phenylethyl}-2,2-diphenylacetamide, hydrochloride salt (9)

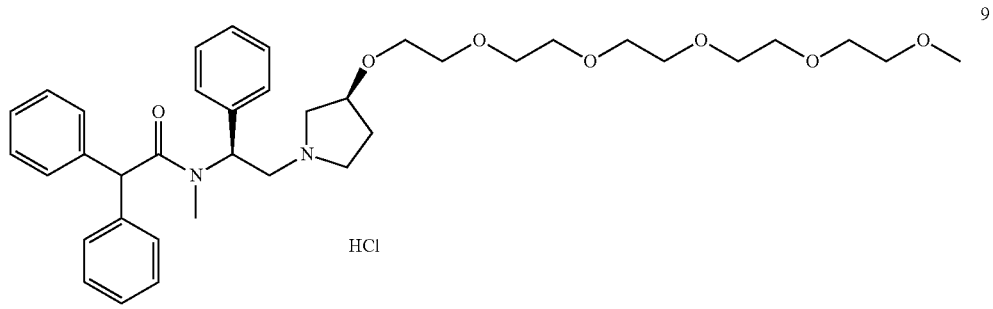 [SMILES: COCCOCCOCCOCCOCCO[C@H]1CCN(C[C@H](c2ccccc2)N(C)C(=O)C(c2ccccc2)c2ccccc2)C1 ; Cl]

9

(1S)—N-Methyl-2-[(3S)-3-(2,5,8,11,14-pentaoxahexadecan-16-yloxy)pyrrolidin-1-yl]-1-phenylethanamine (from example 5, step 3) (0.100 g, 0.22 mmol), 2,2-diphenylacetyl chloride (0.051 g, 0.22 mmol), and N,N-diisopropylethylamine (0.056 g, 0.44 mmol) were dissolved in 10 mL of dichloromethane. The mixture was stirred for 2 hours at room temperature and then 100 mL dichloromethane was added into the mixture. The resultant solution was washed with water and was dried over sodium sulfate. The solvent was removed and the residue was purified by flash chromatography. N-Methyl-N-{(1S)-2-[(3S)-3-(2,5,8,11,14-pentaoxahexadecan-16-yloxy)pyrrolidin-1-yl]-1-phenylethyl}-2,2-diphenylacetamide was obtained (0.100 g, 70% yield). $^1$H NMR (500 MHz, CDCl$_3$): δ 7.31 (m, 15H), 7.20 (d, 0.5H), 7.05 (d, 0.5H), 6.18 (m, 0.77H), 5.47 (s, 0.23H). 5.30 (s, 0.77H), 5.12 (m, 0.23H), 4.08 (m, 0.77H), 3.95 (m, 0.23H), 3.65 (m, 16H), 3.55 (m, 4H), 3.40 (s, 3H), 3.14 (m, 1H), 2.85 (m, 1H), 2.75 (m, 1H), 2.70 (s, 3H), 2.52 (m, 1H), 2.08 (m, 2H), 1.82 (m, 1H); MS (EI) for $C_{38}H_{52}N_2O_7$: 649 (MH$^+$).

The free base (95 mg) was dissolved in 1 mL of acetonitrile. To the solution was added 0.5 mL of 1N hydrochloride. The mixture was lyophilized to afford product as hydrochloride salt (9).

The example described above may be modified to introduce oligomers of various lengths as disclosed herein.

Example 8

Preparation of 2-(3,4-Dichlorophenyl)-N-{(1S)-2-[ethyl(2-methoxyethyl)amino]-1-phenylethyl}-N-methylacetamide, hydrochloride salt (10)

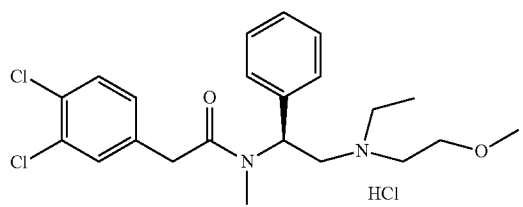

10

2-(3,4-Dichlorophenyl)-N-{(1S)-2-[ethyl(2-methoxyethyl)amino]-1-phenylethyl}-N-methylacetamide, hydrochloride salt (10) was prepared according to the following steps.

Step 1: Preparation of (1S)—N$^2$-Ethyl-N$^2$-(2-methoxyethyl)-N$^1$-methyl-1-phenylethane-1,2-diamine

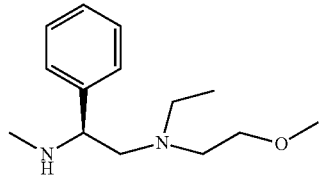

Boc-Phg-OH ((2S)-[(tert-Butoxycarbonyl)amino](phenyl)acetic acid) (0.5 g, 1.99 mmol), N-ethyl-2-methoxyethanamine (0.205 g, 1.99 mmol), and DPTS [1:1 salt of 4-(dimethylamino)pyridine and p-tolunesulfonic acid] (0.308 g, 1.0 mmol) were dissolved in 20 mL of dichloromethane. N, N'-Diisopropylcarbodiimide (0.376 g, 2.98 mmol) was added into the solution. The mixture was stirred for 1 hour. 150 mL of ethyl acetate was added into the reaction mixture. The resultant solution was washed with water (100 mL×3) and was dried over sodium sulfate. Evaporation of the solvent provided a residue which was dissolved in tetrahydrofuran. The tetrahydrofuran solution was added dropwise, over a period of 30 minutes, to a stirred suspension of lithium aluminum hydride (2.0 M, 3 mL, 6.0 mmol) at 0° C. The mixture was stirred for 16 hours at room temperature and then a 3N sodium carbonate solution was added carefully until effervescence ceased. The mixture was filtered through celite and the filtrate was concentrated. The residue was purified by flash chromatography. 1S)—N$^2$-Ethyl-N$^2$-(2-methoxyethyl)-N$^1$-methyl-1-phenylethane-1,2-diamine. (0.261 g, 56% yield) was obtained. $^1$H NMR (500 MHz, CDCl$_3$): δ 7.38 (m, 2H), 7.34 (m, 2H), 7.26 (m, 1H), 4.74 (br., 1H), 3.60 (m, 1H), 3.45 (m, 2H), 3.37 (s, 3H), 2.75 (m, 2H), 2.62 (m, 3H), 2.55 (m, 1H), 2.30 (s, 3H), 1.05 (m, 3H); MS (EI) for $C_{14}H_{24}N_2O$: 237 (MH$^+$).

Step 2: Preparation of 2-(3,4-Dichlorophenyl)-N-{(1S)-2-[ethyl(2-methoxyethyl)amino]-1-phenylethyl}-N-methylacetamide, hydrochloride salt (10)

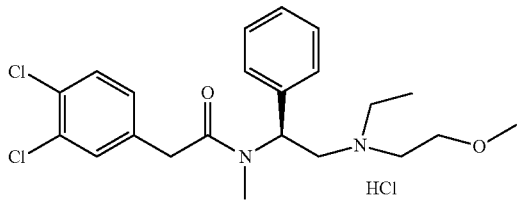

(1S)—N²-Ethyl-N²-(2-methoxyethyl)-N¹-methyl-1-phenylethane-1,2-diamine (Step 1) (0.080 g, 0.34 mmol), 2-(3,4-dichlorophenyl)acetic acid (0.069 g, 0.34 mmol), and N,N-diisopropylethylamine (0.040 g, 0.34 mmol) were dissolved in 10 mL of acetonitrile, and then O-(Benzotriazol-1-yl)-N,N,N',N'-tetramethyluronium tetrafluoroborate (TBTU) (0.109 g, 0.34 mmol) was added into the solution. The reaction mixture was stirred for 2 hours and then dichloromethane (100 mL) was added. The resultant solution was washed with water (100 mL×2). The organic phase was dried over sodium sulfate and was concentrated. The residue was purified by flash chromatography. 2-(3,4-Dichlorophenyl)-N-{(1S)-2-[ethyl(2-methoxyethyl)amino]-1-phenylethyl}-N-methylacetamide was obtained (0.050 g, 35% yield). $^1$H NMR (500 MHz, CDCl$_3$): δ 7.44-7.11 (m, 8H), 6.11 (m, 1H), 3.75 (m, 2H), 3.44 (m, 2H), 3.05 (m, 1H), 2.93 (m, 1H), 2.85 (m, 1H), 2.80 (m, 4H), 2.78 (m, 1H), 2.74 (m, 2H), 2.65 (m, 2H), 1.01 (m, 3H); MS (EI) for C$_{22}$H$_{28}$Cl$_2$N$_2$O$_2$: 423 (MH$^+$).

The free base (20 mg) was dissolved in 1 mL of acetonitrile. To the solution was added 0.2 mL of 1N hydrochloride. The mixture was lyophilized to afford product as hydrochloride salt (10).

The example described above may be modified to introduce oligomers of various lengths as disclosed herein.

Example 9

Preparation of N-[(1S)-2-[(3S)-3-Hydroxypyrrolidin-1-yl]-1-(3-{[(2-methoxyethoxy)acetyl]amino}phenyl)ethyl]-N-methyl-2,2-diphenylacetamide, hydrochloride salt (11)

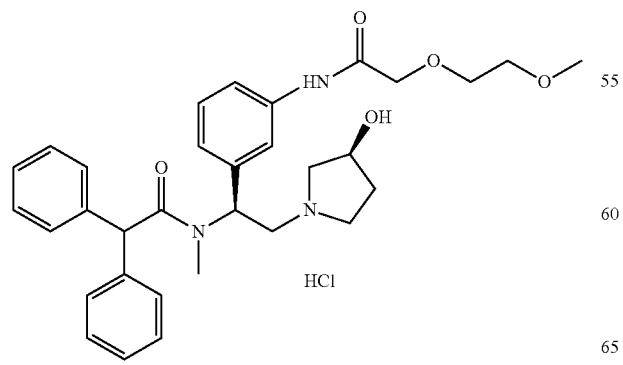

N-[(1S)-2-[(3S)-3-Hydroxypyrrolidin-1-yl]-1-(3-{[(2-methoxyethoxy)acetyl]amino}phenyl)ethyl]-N-methyl-2,2-diphenylacetamide was prepared according to the following steps.

Step 1: Preparation of ((3S)-1-[(2S)-2-[(Diphenylacetyl)(methyl)amino]-2-(3-nitrophenyl)ethyl]pyrrolidin-3-yl diphenylacetate

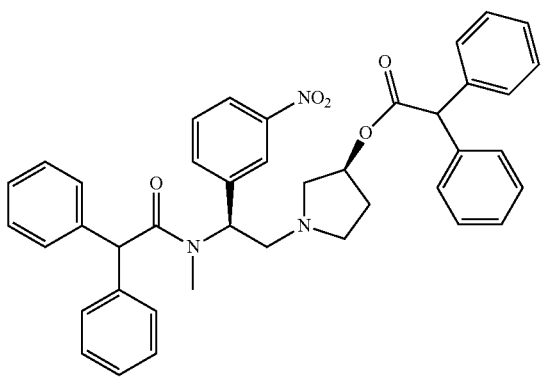 [SMILES: CN(C(=O)C(c1ccccc1)c1ccccc1)[C@H](CN1CC[C@H](OC(=O)C(c2ccccc2)c2ccccc2)C1)c1cccc([N+](=O)[O-])c1]

(3S)-1-[(2S)-2-(Methylamino)-2-(3-nitrophenyl)ethylpyrrolidin-3-ol (0.400 g, 1.21 mmol (prepared according to Ghosh, A., Chemical Communications, no. 15, p. 1644 (2002)), 2,2-diphenylacetyl chloride (0.618 g, 2.41 mmol), and N,N-diisopropylethylamine (0.463 g, 3.62 mmol)) were dissolved in 40 mL of dichloromethane. The mixture was stirred for 2 hours at room temperature and then 100 mL dichloromethane was added into the mixture. The resultant solution was washed with water and was dried over sodium sulfate. The solvent was removed and the residue was purified by flash chromatography. ((3S)-1-[(2S)-2-[(Diphenylacetyl)(methyl)amino]-2-(3-nitrophenyl)ethyl]pyrrolidin-3-yl diphenylacetate (0.410 g, 52% yield) was obtained. MS (EI) for C$_{41}$H$_{39}$N$_3$O$_5$: 654 (MH$^+$).

Step 2: Preparation of (3S)-1-{(2S)-2-(3-Aminophenyl)-2-[(diphenylacetyl)(methyl)amino]ethyl}pyrrolidin-3-yl diphenylacetate

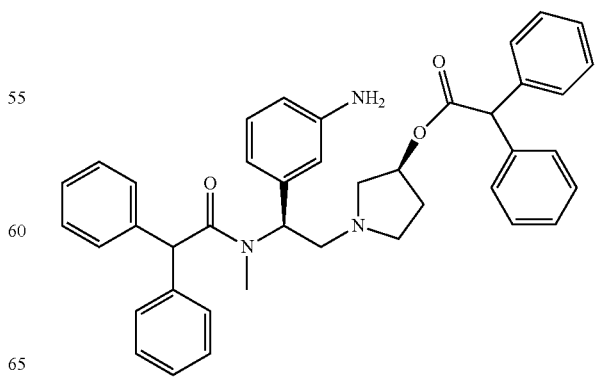

((3S)-1-[(2S)-2-[(Diphenylacetyl)(methyl)amino]-2-(3-nitrophenyl)ethyl]pyrrolidin-3-yl diphenylacetate (from step 1) (0.24 g, 0.37 mmol) was dissolved in 15 mL of tetrahydrofuran. The reduction reaction was performed by H-Cube (CatCart THS01131, 10% Pd/C, Flow rate 1 mL/Min). (3S)-1-{(2S)-2-(3-Aminophenyl)-2-[(diphenylacetyl)(methyl)amino]ethyl}pyrrolidin-3-yl diphenylacetate was obtained (0.2 g, 87% yield). $^1$H NMR (500 MHz, CDCl$_3$): δ 7.40-7.20 (m, 20H), 7.10 (m, 1H), 6.65 (m, 1H), 6.60 (m, 2H), 6.08 (m, 1H), 5.30 (m, 1H), 5.25 (s, 1H), 5.08 (s, 1H), 3.62 (br., 2H), 3.10 (t, 1H), 3.00 (m, 2H), 2.82 (m, 1H), 2.68 (s, 3H), 2.65 (m, 1H), 2.35 (m, 1H), 2.25 (m, 1H), 1.85 (m, 1H); MS (EI) for C$_{41}$H$_{41}$N$_3$O$_3$: 624 (MH$^+$).

Step 3: Preparation of N-[(1S)-2-[(3S)-3-Hydroxypyrrolidin-1-yl]-1-(3-{[(2-methoxyethoxy)acetyl]amino}phenyl)ethyl]-N-methyl-2,2-diphenylacetamide, hydrochloride salt (11)

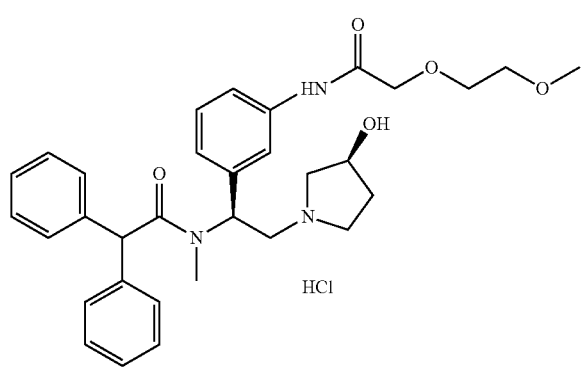 [SMILES: COCCOCC(=O)Nc1cccc([C@@H](CN2CC[C@H](O)C2)N(C)C(=O)C(c2ccccc2)c2ccccc2)c1 ; Cl]

(3S)-1-{(2S)-2-(3-Aminophenyl)-2-[(diphenylacetyl)(methyl)amino]ethyl}pyrrolidin-3-yl diphenylacetate (from step 2) (0.120 g, 0.192 mmol), 2-(2-methoxyethoxy)acetic acid (0.031 g, 0.231 mmol), and DPTS [1; 1 salt of 4-(dimethylamino)pyridine and p-tolunesulfonic acid](0.036 g, 0.115 mmol) were dissolved in 10 mL of dichloromethane. N,N-diisopropylcarbodiimide (0.073 g, 0.577 mmol) was added into the mixture. The reaction mixture was stirred for 2 hours. 100 mL of dichloromethane was added into the reaction mixture and the resultant solution was washed with water (100 mL×3). The solution was dried over sodium sulfate and was concentrated. The residue was dissolved in 6 mL of CH$_3$CN/0.5 N KOH (1:1). The mixture was stirred at 65° C. for 3 hours. The mixture was extracted with dichloromethane (50 mL×3). The dichloromethane solution was dried over sodium sulfate and was concentrated. The crude product was purified by flash chromatography. N-[(1S)-2-[(3S)-3-Hydroxypyrrolidin-1-yl]-1-(3-{[(2-methoxyethoxy)acetyl]amino}phenyl)ethyl]-N-methyl-2,2-diphenylacetamide (0.050 g, 49% yield) was obtained. $^1$H NMR (500 MHz, MeOD): δ 7.64-7.50 (m, 2H), 7.40-7.20 (m, 11H), 7.10 (m, 1H), 6.10 (m, 0.8H), 5.52 (s, 0.2H), 5.45 (s, 0.8H), 5.24 (m, 0.2H), 4.35 (br., 0.8H), 4.22 (br., 0.2H), 4.24 (m, 2H), 3.78 (m, 2H), 3.65 (m, 2H), 3.45 (s, 3H), 3.34 (s, 1H), 3.24 (t, 1H), 3.10 (m, 1H), 2.92-2.80 (m, 2H), 2.28 (s, 3H), 2.60 (m, 1H), 2.45 (m, 1H), 2.14 (m, 1H), 1.74 (m, 1H); MS (EI) for C$_{32}$H$_{39}$N$_3$O$_5$: 546 (MH$^+$).

The free base (25 mg) was dissolved in 1 mL of acetonitrile. To the solution was added 0.2 mL of 1N hydrochloride. The mixture was lyophilized to afford product as hydrochloride salt (11).

The example described above may be modified to introduce oligomers of various lengths as disclosed herein.

Example 10

Preparation of N-{3-[(1S)-1-[(Diphenylacetyl)(methyl)amino]-2-(pyrrolidin-1-yl)ethyl]phenyl}-2,5,8,11,14,17-hexaoxanonadecan-19-amide, hydrochloride salt (12)

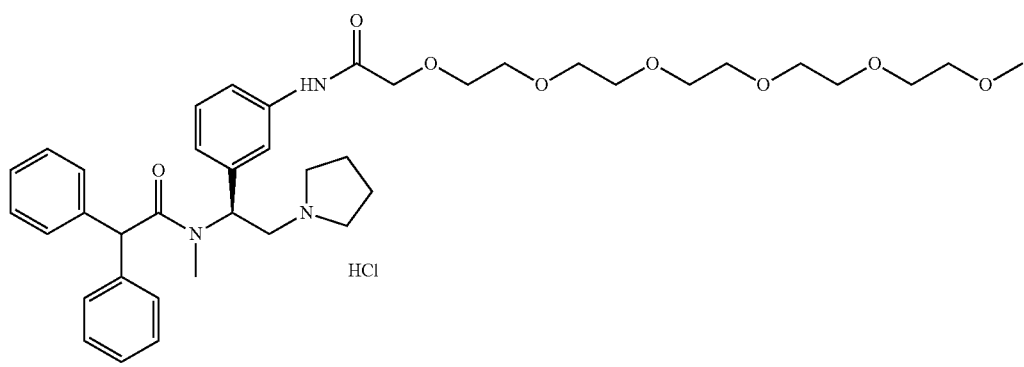

12

N-{3-[(1S)-1-[(Diphenylacetyl)(methyl)amino]-2-(pyrrolidin-1-yl)ethyl]phenyl}-2,5,8,11,14,17-hexaoxanonadecan-19-amide may be prepared according to the following steps.

Step 1: Preparation of (S)—N-Methyl-N-(1-(3-nitrophenyl)-2-(pyrrolidin-1-yl)ethyl)-2,2-diphenylacetamide

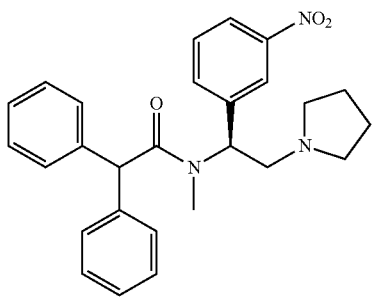 [SMILES: CN(C(=O)C(c1ccccc1)c1ccccc1)[C@H](CN1CCCC1)c1cccc([N+](=O)[O-])c1]

(S)-1-[2-(Methylamino)-2-(3/4-nitrophenyl)ethyl]pyrroldin (0.84 g, 3.37 mmol), (Portoghese, P., *Journal of Medicinal Chemistry*, (1994), vol. 37, pp. 4490-4498) was dissolved in anhydrous dichloromethane (14 mL). To the dark solution was added diisopropylethylamine (1.17 mL, 6.74 mmol) at 0° C. Diphenylacetyl chloride (0.95 g, 3.71 mmol) was dissolved in anhydrous dichloromethane (10 mL) and was added dropwise to the dark solution, maintaining the temperature below 5° C. The reaction mixture was allowed to equilibrate to room temperature. After approximately 17 hours at room temperature the mixture was partitioned between dichloromethane (35 mL) and saturated sodium chloride (50 mL). The aqueous layer was extracted with dichloromethane (3×15 mL). The combined organic portion was washed with saturated sodium bicarbonate (2×25 mL) and saturated sodium chloride (25 mL). The combined organic portion was dried over anhydrous sodium sulfate (approximately 1.70 g) and concentrated in vacuo. The residue was purified on a column of silica gel using dichloromethane/methanol (9:1) as eluent to give (S)—N-methyl-N-(1-(3-nitrophenyl)-2-(pyrrolidin-1-yl)ethyl)-2,2-diphenylacetamide (0.62 g, 42% yield), as a light-yellow oil. $^1$H NMR (500 MHz, CDCl$_3$): δ 8.13-7.23 (m, 14H), 6.17 (m, 1H), 5.25 (s, 1H), 3.09 (m, 1H), 2.86 (m, 1H), 2.75 (s, 3H), 2.72 (m, 2H), 2.52 (m, 2H), 1.77 (m, 4H); MS (EI) for C$_{27}$H$_{29}$N$_3$O$_3$: 444 (MH$^+$).

The compound was converted into the hydrochloride salt by dissolving the oil in acetonitrle and adding 1N hydrochloric acid. The solution was lyophilized to give the hydrochloride salt as a white powder.

Step 2: Preparation of (S)—N-Methyl-N-(1-(3-aminophenyl)-2-(pyrrolidin-1-yl)ethyl)-2,2-diphenylacetamide, dihydrochloride salt (51)

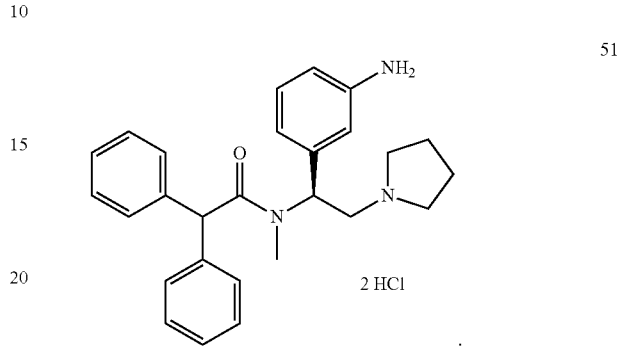

(S)—N-methyl-N-(1-(3-nitrophenyl)-2-(pyrrolidin-1-yl)ethyl)-2,2-diphenylacetamide (from step 1) (1.36 g, 3.07 mmol) was dissolved in ethyl acetate:ethanol (1:1, 30 mL each) and the reaction mixture was passed through a 10% Palladium/Carbon CatCart® cartridge (70 millimeters) in a continuous flow through the H-Cube™, in which hydrogen is generated in-situ from the electrolysis of water. The eluent was collected and was concentrated under reduced pressure to give a residue. The residue was purified on a column of silica gel using hexane/methanol (9:1) as eluent to give (S)—N-methyl-N-(1-(3-aminophenyl)-2-(pyrrolidin-1-yl)ethyl)-2,2-diphenylacetamide (0.47 g, 40% yield), as a light-yellow foam. $^1$H NMR (500 MHz, CDCl$_3$): δ 7.32-7.04 (m, 14H), 6.71 (m, 1H), 6.57 (m, 2H), 6.10 (m, 1H), 5.26 (s, 1H), 3.61-3.40 (m, 2H), 2.95-2.30 (m, 5H), 1.70 (m, 3H), 1.69 (m, 2H); MS (EI) for C$_{27}$H$_{31}$N$_3$O: 414 (MH$^+$).

The compound was converted into the dihydrochloride salt by dissolving the foam in acetonitrile and adding 1N hydrochloric acid. The solution was lyophilized to give the dihydrochloride salt (51) as a white powder.

Step 3: N-{3-[(1S)-1-[(Diphenylacetyl)(methyl)amino]-2-(pyrrolidin-1-yl)ethyl]phenyl}-2,5,8,11,14,17-hexaoxanonadecan-19-amide, hydrochloride salt (12)

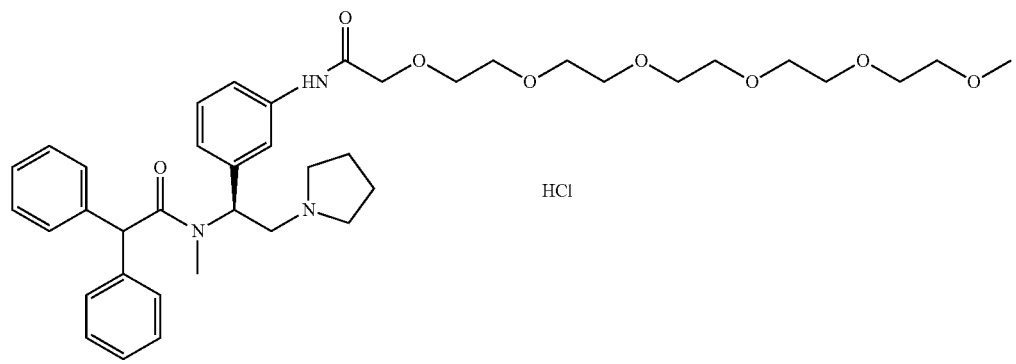 [SMILES: COCCOCCOCCOCCOCCOCC(=O)Nc1cccc([C@@H](CN2CCCC2)N(C)C(=O)C(c2ccccc2)c2ccccc2)c1 ; Cl]

(S)—N-methyl-N-(1-(3-aminophenyl)-2-(pyrrolidin-1-yl)ethyl)-2,2-diphenylacetamide (from step 2) (75 mg, 0.18 mmol) was dissolved in anhydrous dichloromethane (1 mL) and to the light-yellow solution was added diisopropylethylamine (0.06 mL, 0.36 mmol), N-(3-dimethylaminopropyl)-N'-ethylcarbodiimide hydrochloride (50 mg, 0.27 mmol) and 2, 5, 8, 11, 14, 17-hexaoxanonadecan-19-oic acid (80 mg, 0.27 mmol). The yellow reaction mixture was stirred under nitrogen at room temperature. After approximately 17 hours at room temperature, the reaction mixture was diluted with dichloromethane (25 mL) and partitioned with water (30 mL). The aqueous layer was extracted with dichloromethane (2×15 mL). The combined organic portion was washed with 1.0 N hydrochloric acid (35 mL), water (35 mL), saturated sodium bicarbonate (35 mL), and saturated sodium chloride (35 mL). The combined organic portion was dried over anhydrous sodium sulfate (approximately 0.20 g) and concentrated in vacuo. The residue was purified on a column of silica gel using dichloromethane/methanol (9:1) as eluent to give N-{3-[(1S)-1-[(diphenylacetyl)(methyl)amino]-2-(pyrrolidin-1-yl)ethyl]phenyl}-2,5,8,11,14,17-hexaoxanonadecan-19-amide (35 mg, 27% yield), as a light-yellow oil. $^1$H NMR (500 MHz, CDCl$_3$): δ 8.73 (bs, 1H), 7.53-7.06 (m, 14H), 6.15 (m, 1H), 5.25 (s, 1H), 4.11 (s, 2H), 3.76-3.54 (m, 21H), 3.38 (s, 3H), 2.75-2.60 (m, 5H), 2.50-2.42 (m, 3H), 1.75 (m, 4H); MS (EI) for C$_{40}$H$_{55}$N$_3$O$_8$: 706 (MH$^+$).

The compound was converted into the hydrochloride salt by dissolving the oil in acetonitrile and adding 1N hydrochloric acid. The solution was lyophilized to give the hydrochloride salt (12) as a white powder.

The example described above may be modified to introduce oligomers of various lengths as disclosed herein.

Example 11

Preparation of N-Methyl-2-[4-(2, 5, 8, 11, 14-pentaoxahexadecan-16-yloxy)phenyl]-N-[(1S)-1-phenyl-2-(pyrrolidin-1-yl)ethyl]acetamide, hydrochloride salt (13)

N-Methyl-2-[4-(2, 5, 8, 11, 14-pentaoxahexadecan-16-yloxy)phenyl]-N-[(1S)-1-phenyl-2-(pyrrolidin-1-yl)ethyl]acetamide was prepared according to the following steps.

Step 1: Preparation of 2-(4-Hydroxyphenyl)-N-methyl-N-[(1S)-1-phenyl-2-(pyrroldin-1-yl)ethyl acetamide, hydrochloride salt (52)

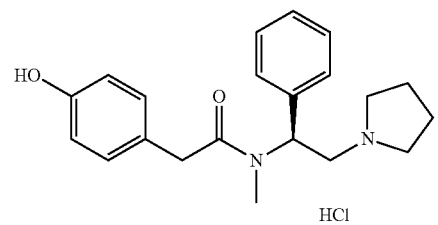

52

(1S)—N-Methyl-1-phenyl-2-pyrrolidin-1-yl)ethanamine (0.30 g, 1.46 mmol), (Singh, V. et. al., *Journal of Organic Chemistry* (1996), vol. 61, pp. 6108-6113) was dissolved in anhydrous acetonitrile (7 mL). The clear solution was stirred at 0° C., under nitrogen, followed by the addition of diisopropylethylamine (0.57 mL, 3.23 mmol), 2-(4-hydroxyphenyl)acetic acid (0.25 g, 1.61 mmol) and O-(benzotriazol-1-yl)-N,N,N',N'-tetramethyluronium tetrafluoroborate (0.39 g, 1.61 mmol). The clear reaction mixture was allowed to equilibrate to room temperature and stirred under nitrogen. After approximately 17 hours at room temperature the mixture was concentrated in vacuo. The residue was dissolved in ethyl acetate (8 mL) and was washed with saturated sodium bicarbonate (2×15 mL) and saturated sodium chloride (15 mL). The combined organic portion was dried over anhydrous sodium sulfate (approximately 0.60 g) and concentrated in vacuo. The residue was purified on a column of silica gel using dichloromethane/methanol (9:1) as eluent to give 2-(4-hydroxyphenyl)-N-methyl-N-[(1S)-1-phenyl-2-(pyrroldin-1-yl)ethyl acetamide (0.18 g, 36% yield), as a light-yellow oil. $^1$H NMR (500 MHz, CDCl$_3$): δ 7.37-7.02 (m, 9H), 6.67 (m, 2H), 6.15 (m, 1H), 3.76 (m, 2H), 2.77 (m, 6H), 2.52 (m, 2H), 1.75 (m, 4H); MS (EI) for C$_{21}$H$_{26}$N$_2$O$_2$: 339 (MH$^+$).

The compound was converted into the hydrochloride salt by dissolving the oil in acetonitrile and adding 1N hydrochloric acid. The solution was lyophilized to give the hydrochloride salt (52) as a white powder.

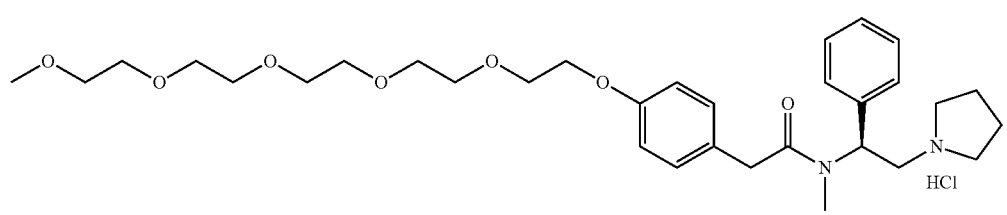

13

Step 2: Preparation of N-Methyl-2-[4-(2, 5, 8, 11, 14-pentaoxahexadecan-16-yloxy)phenyl]-N-[(1S)-1-phenyl-2-(pyrrolidin-1-yl)ethyl] acetamide, hydrochloride salt (13)

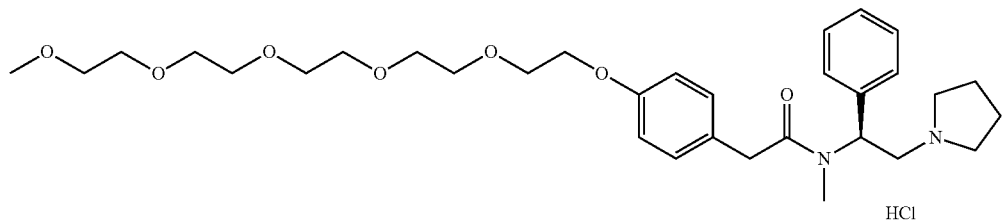 [SMILES: COCCOCCOCCOCCOCCOc1ccc(CC(=O)N(C)[C@H](CN2CCCC2)c2ccccc2)cc1 ; Cl]

2-(4-Hydroxyphenyl)-N-methyl-N-[(1S)-1-phenyl-2-(pyrroldin-1-yl)ethyl acetamide (from step 1) (0.10 g, 0.29 mmol) was dissolved in anhydrous acetone (10 mL) and to the clear solution was added potassium carbonate (0.10 g, 0.73 mmol), followed by 2, 5, 8, 11, 14-pentaoxahexadecan-16-yl methanesulfonate (0.10 g, 0.31 mmol). The light-yellow reaction mixture was stirred under nitrogen and heated to reflux. After approximately 17 hours the yellow reaction mixture was cooled to room temperature. The solvent was removed under reduced pressure and the residue was partitioned between water (10 mL) and dichloromethane (10 mL). The aqueous portion was extracted with dichloromethane (3×8 mL). The combined organic portion was washed with water (2×15 mL) and saturated sodium chloride (15 mL). The organic portion was dried over anhydrous sodium sulfate (approximately 0.25 g), filtered and concentrated under reduced pressure to give a yellow oil. The residue was purified on a column of silica gel using dichloromethane/methanol (9:1) as eluent to give N-methyl-2-[4-(2, 5, 8, 11,14-pentaoxahexadecan-16-yloxy)phenyl]-N-[(1S)-1-phenyl-2-(pyrrolidin-1-yl)ethyl] acetamide (89 mg, 53% yield), as a light-yellow oil. $^1$H NMR (500 MHz, CDCl$_3$): δ 7.29-7.18 (m, 7H), 6.84 (m, 2H), 6.12 (m, 1H), 4.10 (m, 2H), 3.84 (m, 2H), 3.66 (m, 3H), 3.56-3.54 (m, 15H), 3.37 (s, 3H), 3.14-2.48 (m, 9H), 1.76 (m, 4H); MS (EI) for C$_{32}$H$_{48}$N$_2$O$_7$: 573 (MH$^+$).

The compound was converted into the hydrochloride salt (13) by dissolving the oil in acetonitrile and adding 1N hydrochloric acid. The solution was lyophilized to give the hydrochloride salt as a white powder.

The example described above may be modified to introduce oligomers of various lengths as disclosed herein.

Example 12

Preparation of 2-(3,4-dichlorophenyl)-N-methyl-N-[(1S)-1-{3-[(methylsulfonyl)amino]phenyl}-2-(pyrrolidin-1-yl)ethyl]acetamide, hydrochloride salt (14)

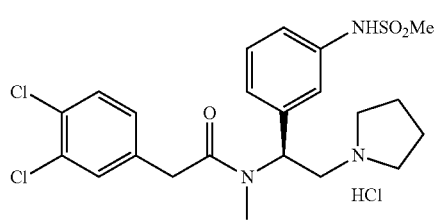

2-(3,4-Dichlorophenyl)-N-methyl-N-[(1S)-1-{3-[(methylsulfonyl)amino]phenyl})-2-(pyrrolidin-1-yl)ethyl]acetamide may be prepared according to the following steps.

Step 1: Preparation of 2-(3,4-dichlorophenyl)-N-methyl-N-[(1S)-1-(3-nitrophenyl)-2-(pyrrolidin-1-yl) ethyl]acetamide

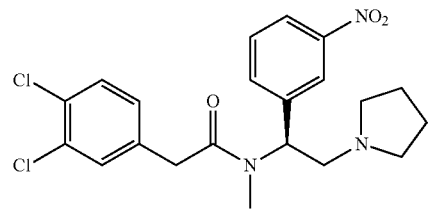

(S)-1-[2-(Methylamino)-2-(3/4-nitrophenyl)ethyl]pyrroldin (0.66 g, 2.65 mmol), (Portoghese, P. *Journal of Medicinal Chemistry*, 1994, 37, 4490-4498) was dissolved in anhydrous acetonitrile (14 mL). To the dark solution was added diisopropylethylamine (1.03 mL, 5.82 mmol) at 0° C., followed by 3, 4-dichlorophenylacetic acid (0.60 g, 2.91 mmol) and O-(benzotriazol-1-yl)-N,N,N',N'-tetramethyluronium tetrafluoroborate (0.96 g, 2.91 mmol). The reaction mixture was allowed to equilibrate to room temperature. After approximately 17 hours at room temperature the reaction mixture was concentrated under reduced pressure. The residue was taken up in ethyl acetate (15 mL) and washed with saturated sodium bicarbonate (2×25 mL) and saturated sodium chloride (25 mL). The combined organic portion was dried over anhydrous sodium sulfate and concentrated under reduced pressure. Purification by chromatography gave 2-(3, 4-dichlorophenyl)-N-methyl-N-[(1S)-1-(3-nitrophenyl)-2-(pyrrolidin-1-yl)ethyl acetamide (0.99 g, 86% yield), as a light-yellow oil. The compound was converted into the hydrochloride salt by dissolving the oil in acetonitrle and adding 1N hydrochloric acid. The solution was lyophilized to give the hydrochloride salt as a white powder. $^1$H NMR (500 MHz, CDCl$_3$): δ 8.13 (m, 2H), 7.66 (m, 1H), 7.51 (m, 1H), 7.37 (m, 2H), 7.15 (m, 1H), 6.11 (m, 1H), 3.77 (m, 2H), 3.13 (m, 1H), 2.80 (m, 1H), 2.69 (s, 3H), 2.60 (m, 2H), 1.76 (m, 4H); MS (EI) for C$_{21}$H$_{23}$Cl$_2$N$_3$O$_3$: 437 (MH$^+$).

Step 2: Preparation of N-[(1S)-1-(3-aminophenyl)-2-(pyrrolidin-1-yl)ethyl]-2-(3,4-dichlorophenyl)-N-methylacetamide

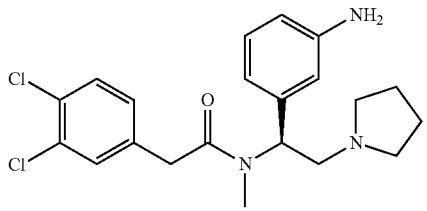 [SMILES: CN(C(=O)Cc1ccc(Cl)c(Cl)c1)[C@H](CN1CCCC1)c1cccc([N+](=O)[O-])c1]

2-(3, 4-dichlorophenyl)-N-methyl-N-[(1S)-1-(3-nitrophenyl)-2-(pyrrolidin-1-yl)ethyl acetamide (0.80 g, 1.77 mmol), hydrazine hydrate (1.36 g, 21.34 mmol) and Raney nickel slurry (1.0 mL) in 95% ethanol (89 mL) was heated to 55° C. After approximately two hours the reaction was complete as indicated by TLC. The reaction mixture was filtered through Celite, and the Raney nickel was washed with hot methanol. The combined filtrates were concentrated under reduced pressure to give 0.60 g (83%) of N-[(1S)-1-(3-aminophenyl)-2-(pyrrolidin-1-yl)ethyl]-2-(3,4-dichlorophenyl)-N-methylacetamide. $^1$H NMR (500 MHz, CDCl$_3$): δ 7.38 (m, 2H), 7.17 (m, 1H), 7.10 (m, 1H), 6.63 (m, 3H), 6.01 (m, 1H), 3.66-3.79 (m, 4H), 3.14 (m, 1H), 2.46-2.72 (m, 5H), 2.47 (m, 3H), 1.74 (m, 4H); MS (EI) for $C_{21}H_{25}Cl_2N_3O$: 406 (MH$^+$).

allowed to stir at 0° C., with the color turning orange. The reaction mixture was allowed to equilibrate to room temperature. After approximately 17 hours at room temperature, the reaction mixture was diluted with dichloromethane (25 mL) and then added water (30 mL). The aqueous portion was extracted with dichloromethane (2×15 mL). The combined organic portions were washed with 1N hydrochloric acid, water, saturated sodium bicarbonate, water and brine (35 mL each). The organic portion was dried over anhydrous sodium sulfate, filtered, concentrated and purified by chromatography to give 0.045 g (63%) of 2-(3,4-dichlorophenyl)-N-methyl-N-[(1S)-1-{3-[(methylsulfonyl)amino]phenyl}-2-(pyrrolidin-1-yl)ethyl]acetamide as a yellow oil. $^1$H NMR (500 MHz, CDCl$_3$): δ 7.07-7.34 (m, 7H), 6.06 (m, 1H), 3.79 (m, 1H), 3.70 (m, 1H), 3.23 (m, 1H), 2.88-3.10 (m, 6H), 2.76 (s, 3H), 2.58 (m, 2H), 1.79 (m, 5H); MS (EI) for $C_{22}H_{27}Cl_2N_3O_3S$: 484 (MH$^+$).

The compound was converted into the hydrochloride salt by dissolving the oil in acetonitrile and adding 1N hydrochloric acid. The solution was lyophilized to give the hydrochloride salt (14) as an off-white powder.

The example described above may be modified to introduce oligomers of various lengths as disclosed herein.

Example 13

Preparation of 2-(3,4-dichlorophenyl)-N-methyl-N-[(1S)-1-{3-[(2,5,8,11,14-pentaoxahexadecan-16-ylcarbamoyl)amino]phenyl}-2-(pyrrolidin-1-yl)ethyl]acetamide, hydrochloride salt (15)

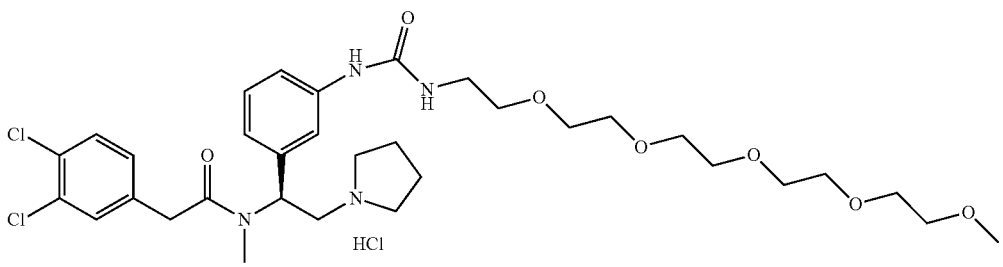

15

Step 3: 2-(3,4-Dichlorophenyl)-N-methyl-N-[(1S)-1-{3-[(methylsulfonyl)amino]phenyl}-2-(pyrrolidin-1-yl)ethyl]acetamide, hydrochloride salt (14)

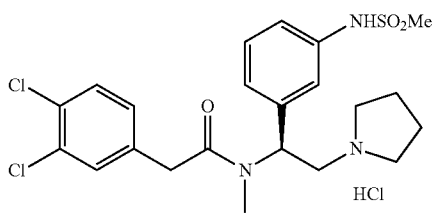

N-[(1S)-1-(3-Aminophenyl)-2-(pyrrolidin-1-yl)ethyl]-2-(3,4-dichlorophenyl)-N-methylacetamide (0.060 g, 0.15 mmol) was dissolved in dichloromethane (1.5 mL) and anhydrous pyridine (0.090 mL). To the cooled (0° C.) yellow solution there was added dropwise methanesulfonyl chloride (0.017 mL, 0.22 mmol). The yellow reaction mixture was To a solution of triphosgene (0.054 gm, 0.17 mmol) in anhydrous acetonitrile (3.5 mL), at −5° C., was added an acetonitrile (3.5 mL) solution of N-[(1S)-1-(3-aminophenyl)-2-(pyrrolidin-1-yl)ethyl]-2-(3,4-dichlorophenyl)-N-methylacetamide (0.12 gm, 0.29 mmol) and triethylamine (0.055 mL, 0.38 mmol) over a period often minutes. The mixture was stirred for an additional 20 minutes at 0° C., and then a dichloroethane (2.8 mL) solution of 2,5,8,11,14-pentaoxahexadecan-16-amine (0.096 gm, 0.38 mmol) and triethylamine (0.055 mL, 0.38 mmol) was added, maintaining the temperature less than 5° C. The reaction mixture was allowed to equilibrate to room temperature overnight. After 20 hours the mixture was diluted with dichloromethane (40 mL) and transferred to a separatory funnel with water (35 mL). The aqueous portion was extracted with dichloromethane (3×25 mL). The combined organic portions were washed with water (2×40 mL) and saturated sodium chloride (50 mL). The organic layer was dried over anhydrous sodium sulfate, filtered and concentrated under reduced pressure to a residue. Purification by chromatography was carried out to give 0.074 gm (37%) of 2-(3,4-dichlorophenyl)-N-methyl-N-[(1S)-1-{3-[(2,5,8,11,14-pentaoxahexadecan-16-ylcarbamoyl)amino]phenyl}-2-(pyrrolidin-1-yl)ethyl]acetamide as a yellow oil. $^1$H NMR (500 MHz, CDCl$_3$): δ 8.83 (m, 1H), 7.59-6.79 (m, 7H), 6.30 (m, 1H), 6.06 (m, 1H), 4.10 (m, 3H), 3.80 (m, 1H), 3.78-3.40 (m, 22H), 3.22 (m, 4H), 3.15 (m, 2H), 2.80 (m, 3H), 1.98 (m, 3H); MS (EI) for C$_{33}$H$_{48}$Cl$_2$N$_4$O$_7$: 683 (MH$^+$).

The compound was converted into the hydrochloride salt (15) by dissolving the oil in acetonitrile and adding 1N hydrochloric acid. The solution was lyophilized to give the hydrochloride salt as an off-white powder.

The example described above may be modified to introduce oligomers of various lengths as disclosed herein.

Example 14

Preparation of 2,2-Bis(4-chlorophenyl)-N-methyl-N-[(1S)-1-{3-[(2,5,8,11,14-pentaoxahexadecan-16-ylcarbamoyl)amino]phenyl}-2-(pyrrolidin-1-yl)ethyl]acetamide, hydrochloride salt. (16)

(S)-1-[2-(Methylamino)-2-(3/4-nitrophenyl)ethyl]pyrroldin (1.02 g, 4.09 mmol), (Portoghese, P. *Journal of Medicinal Chemistry*, 1994, 37, 4490-4498) was dissolved in anhydrous acetonitrile (20 mL). To the solution was added diisopropylethylamine (1.48 mL, 8.39 mmol) at 0° C. Diphenylacetyl chloride (1.03 g, 4.50 mmol) was taken up in anhydrous dichloromethane (10 mL) and added dropwise to the solution. The reaction mixture was allowed to equilibrate to room temperature. After approximately 17 hours at room temperature the reaction mixture was concentrated under reduced pressure. The residue was partitioned between dichloromethane (15 mL) and water (15 mL). The aqueous layer was extracted with dichloromethane (3×15 mL). The combined organic portion was washed with saturated sodium bicarbonate (2×25 mL) and saturated sodium chloride (25 mL). The combined organic portion was dried over anhydrous sodium sulfate and concentrated in vacuo. The residue was purified on a column of silica gel using dichloromethane/methanol (9:1) as eluent to give 1.38 g (76%) of 2,2-bis(4-chloro-phenyl)-N-methyl-N-[(1S)-1-(3-

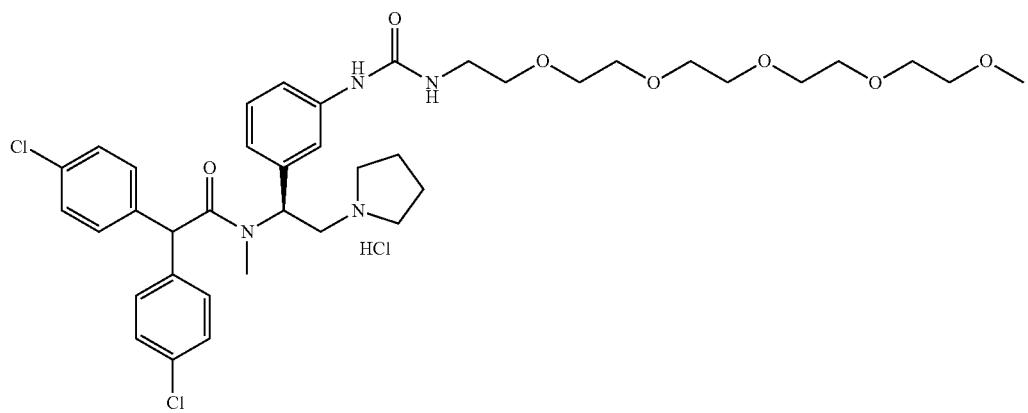

16

2,2-Bis(4-chlorophenyl)-N-methyl-N-[(1S)-1-{3-[(2,5,8,11,14-pentaoxahexadecan-16-ylcarbamoyl)amino]phenyl}-2-(pyrrolidin-1-yl)ethyl]acetamide may be prepared according to the following steps.

Step 1: Preparation of 2,2-bis(4-chlorophenyl)-N-methyl-N-[(1S)-1-(3-nitrophenyl)-2-(pyrrolidin-1-yl)ethyl]acetamide

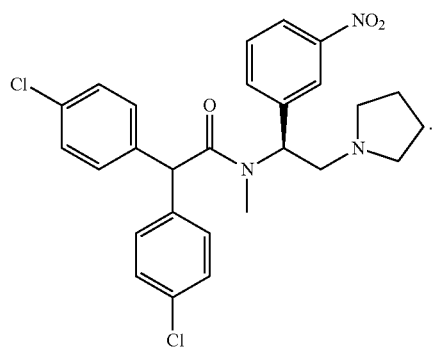 [SMILES: CN(C(=O)C(c1ccc(Cl)cc1)c1ccc(Cl)cc1)[C@H](CN1CCCC1)c1cccc([N+](=O)[O-])c1 ; "."]

nitrophenyl)-2-(pyrrolidin-1-yl)ethyl]acetamide as a yellow oil. MS (EI) for C$_{27}$H$_{27}$Cl$_2$N$_3$O$_3$: 512 (MH$^+$).

Step 2: Preparation of N-[(1S)-1-(3-aminophenyl)-2-(pyrrolidin-1-yl)ethyl]-2,2-bis(4-chlorophenyl)-N-methylacetamide

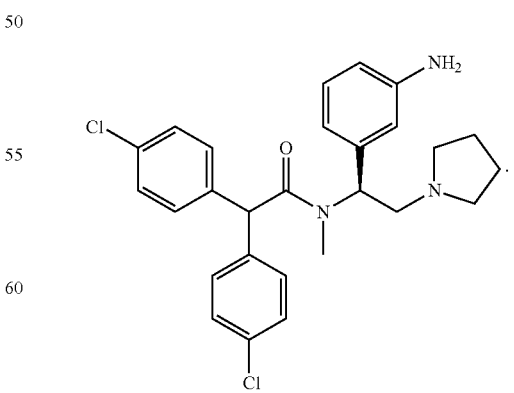

2,2-Bis(4-chlorophenyl)-N-methyl-N-[(1S)-1-(3-nitrophenyl)-2-(pyrrolidin-1-yl)ethyl]acetamide (0.60 g, 1.35 mmol) in ethyl acetate:ethanol (1:1; 13.5 mL each; 0.05 M) was pumped through the 10% Pd/C filled CatCart™ column in an H-Cube™ reactor operated at 20° C. and at a flow rate of 1.0 mL/min. The solvent was concentrated under reduced pressure to give 0.34 g (60%) of N-[(1S)-1-(3-aminophenyl)-2-(pyrrolidin-1-yl)ethyl]-2,2-bis(4-chlorophenyl)-N-methylacetamide as a light-yellow oil. MS (EI) for $C_{27}H_{29}Cl_2N_3O$: 482 (MH$^+$).

Step 3: Preparation of 2,2-bis(4-chlorophenyl)-N-methyl-N-[(1S)-1-{3-[(2, 5,8,11,14-pentaoxahexadecan-16-ylcarbamoyl)amino]phenyl}-2-(pyrrolidin-1-yl)ethyl]acetamide, hydrochloride salt (16)

(3×25 mL). The combined organic portion was washed with water (2×40 mL) and saturated sodium chloride (50 mL). The organic portion was dried over anhydrous sodium sulfate, filtered and concentrated under reduced pressure and purified by chromatography to give 0.034 gm (43%) of 2,2-bis(4-chlorophenyl)-N-methyl-N-[(1S)-1-{3-[(2,5,8,11,14-pentaoxahexadecan-16-ylcarbamoyl)amino]phenyl}-2-(pyrrolidin-1-yl)ethyl]acetamide as a yellow oil. $^1$H NMR (500 MHz, CDCl$_3$): δ 7.42 (m, 1H), 7.21-7.08 (m, 12H), 6.78 (m, 1H), 3.54-3.39 (m, 20H), 3.24-3.18 (m, 10H), 3.20 (m, 2H), 2.77 (m, 3H), 1.85 (m, 3H); MS (EI) for $C_{39}H_{52}Cl_2N_4O_7$: 759 (MH$^+$).

The compound was converted into the hydrochloride salt (16) by dissolving the oil in acetonitrile and adding 1N

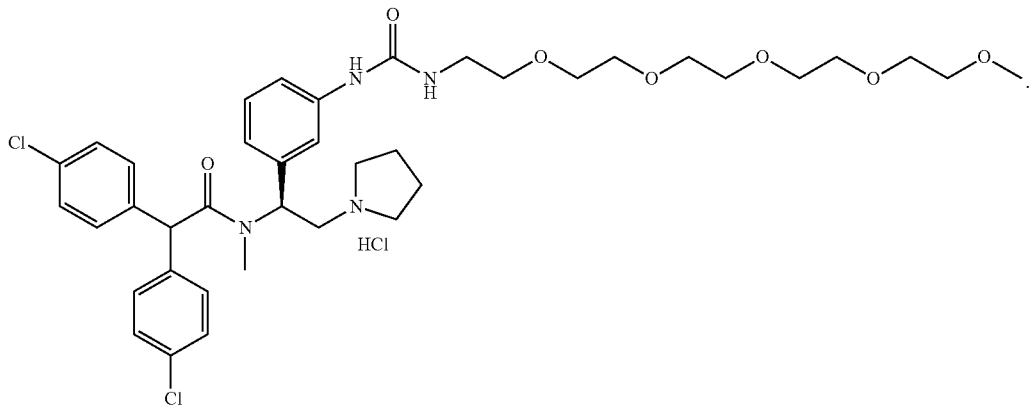 [SMILES: COCCOCCOCCOCCOCCNC(=O)Nc1cccc([C@@H](CN2CCCC2)N(C)C(=O)C(c2ccc(Cl)cc2)c2ccc(Cl)cc2)c1 ; Cl]

To a solution of triphosgene (0.054 gm, 0.17 mmol) in anhydrous acetonitrile (3.5 mL), at −5° C., was added an acetonitrile (3.5 mL) solution of N-[(1S)-1-(3-aminophenyl)-2-(pyrrolidin-1-yl)ethyl]-2,2-bis(4-chlorophenyl)-N-methylacetamide (0.12 gm, 0.29 mmol) and triethylamine (0.055 mL, 0.38 mmol) over a period often minutes. The mixture was stirred for an additional 20 minutes at 0° C., and then a dichloroethane (2.8 mL) solution of 2,5,8,11,14-pentaoxahexa-decan-16-amine (0.096 gm, 0.38 mmol) and triethylamine (0.055 mL, 0.38 mmol) was added, maintaining the temperature less than 5° C. The reaction mixture was allowed to equilibrate to room temperature overnight. After 20 hours the mixture was diluted with dichloromethane (40 mL) and transferred to a separatory funnel with water (35 mL). The aqueous layer was extracted with dichloromethane hydrochloric acid. The solution was lyophilized to give the hydrochloride salt as an off-white powder.

The example described above may be modified to introduce oligomers of various lengths as disclosed herein.

Example 15

Preparation of 2-(3,4-dichlorophenyl)-N-[(1S)-2-[(3S)-3-{2-[2-(2-methoxyethoxy)ethoxy]ethoxy}pyrrolidin-1-yl]-1-{3-[(methylsulfonyl)amino]phenyl}ethyl]-N-methylacetamide, hydrochloride salt. (17)

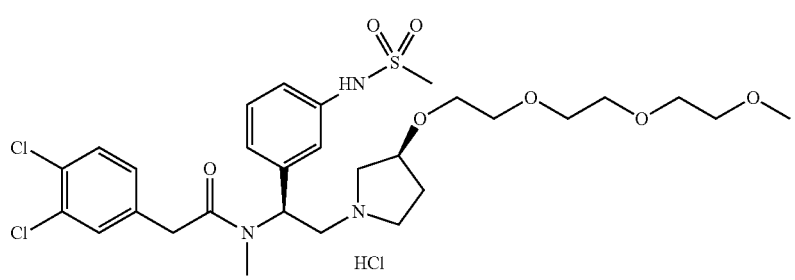

2-(3,4-Dichlorophenyl)-N-[(1S)-2-[(3S)-3-{2-[2-(2-methoxyethoxy)ethoxy]ethoxy}pyrrolidin-1-yl]-1-{3-[(methylsulfonyl)amino]phenyl}ethyl]-N-methylacetamide may be prepared according to the following steps.

Step 1: Preparation of tert-butyl (3S)-3-{2-[2-(2-methoxyethoxy)ethoxy]ethoxy}pyrrolidine-1-carboxylate

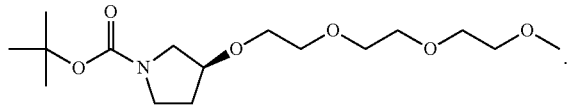 [SMILES: COCCOCCOCCO[C@H]1CCN(C(=O)OC(C)(C)C)C1]

(S)-Tert-butyl 3-hydroxypyrrolidine-1-carboxylate (1.0 g, 5.18 mmol) was taken up in tetrahydrofuran (30 mL) and then added to 60% sodium hydride (0.41 g, 10.3 mmol) and stirred for 30 minutes at room temperature. To the cloudy solution was added 1-bromo-2-(2-(2-methoxyethoxy)ethoxy)ethane (2.35 g, 10.3 mmol) in tetrahydrofuran (28 mL) and the temperature was stirred under nitrogen at room temperature. After approximately 17 hours at room temperature, the cloudy reaction mixture was concentrated under reduced pressure. The residue was diluted with methyl tert-butyl ether (100 mL) and transferred to a separatory funnel and then washed with saturated sodium chloride (2×150 mL), and dried over anhydrous sodium sulfate. The organic portion was filtered and concentrated under reduced pressure to give a light-yellow oil which was purified by chromatography to give 0.82 g (48%) of tert-butyl (3S)-3-{2-[2-(2-methoxyethoxy)ethoxy]ethoxy}pyrrolidine-1-carboxylate as a light-yellow oil. $^1$H NMR (500 MHz, DMSO-d6): δ 4.03 (m, 1H), 3.51-3.41 (m, 12H), 3.33-3.23 (m, 3H), 3.18 (m, 1H), 1.89 (m, 1H), 1.39 (s, 9H).

Step 2: Preparation of (3S)-3-{2-[2-(2-methoxyethoxy)ethoxy]ethoxy}pyrrolidine

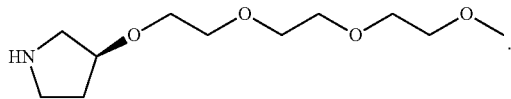 [SMILES: COCCOCCOCCO[C@H]1CCNC1]

Anhydrous hydrochloric acid (4 M hydrochloric acid in dioxane; 3.3 mL) was added to (S)-tert-butyl 3-(2-(2-(2-methoxyethoxy)ethoxy)ethoxy)pyrrolidine-1-carboxylate (0.80 g, 2.39 mmol) in dichloromethane (4 mL) at 0° C. The light-yellow reaction mixture was equilibrated to room temperature and stirred for two hours. The mixture was concentrated under reduced pressure, and the residual hydrochloric acid was removed by taking up in chloroform and evaporating the solvent. The light-brown residue was dried under high vacuum for three hours to give 0.64 g (quant.) of (3S)-3-{2-[2-(2-methoxyethoxy)ethoxy]ethoxy}pyrrolidine as a clear oil. $^1$H NMR (500 MHz, DMSO-d6): δ 9.10 (m, 1H), 4.21 (m, 1H), 3.54-3.41 (m, 10H), 3.34 (s, 3H), 3.23-3.17 (m, 8H), 2.02 (m, 1H), 1.92 (s, 1H); MS (EI) for $C_{11}H_{23}NO_4$: 234 (MH$^+$).

Step 3: Preparation of benzyl {(1S)-2-[(3S)-3-{2-[2-(2-methoxyethoxy)-ethoxy]ethoxy}-pyrrolidin-1-yl]-2-oxo-1-phenylethyl}carbamate

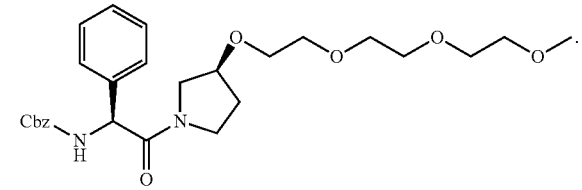 [SMILES: COCCOCCOCCO[C@H]1CCN(C(=O)[C@@H](NC(=O)OCc2ccccc2)c2ccccc2)C1]

A solution of (2S)-{[(benzyloxy)carbonyl]amino}(phenyl)acetic acid (0.71 g, 2.48 mmol), (3S)-3-{2-[2-(2-methoxyethoxy)ethoxy]ethoxy}pyrrolidine (0.67 g, 2.48 mmol) and diisopropylethyl amine (1.33 mL, 7.45 mmol) in anhydrous acetonitrile (16 mL) was stirred at room temperature for 15 minutes and then cooled to 0° C. O-(benzotriazol-1-yl)-N,N,N',N'-tetramethyluronium tetrafluoroborate (0.72 g, 2.98 mmol) was added and the light-brown reaction mixture was stirred at 0° C. for one hour, and then equilibrated to room temperature. After approximately 17 hours at room temperature the orange mixture was concentrated under reduced pressure. The residue was purified by chromatography to give 0.93 g (75%) of benzyl {(1S)-2-[(3S)-3-{2-[2-(2-methoxyethoxy)-ethoxy]ethoxy}-pyrrolidin-1-yl]-2-oxo-1-phenylethyl}carbamate as a clear oil. MS (EI) for $C_{27}H_{36}N_2O_7$: 501 (MH$^+$).

Step 4: Preparation of (1S)-2-[(3S)-3-{2-[2-(2-methoxyethoxy)ethoxy]ethoxy}pyrrolidin-1-yl]-N-methyl-1-phenylethanamine

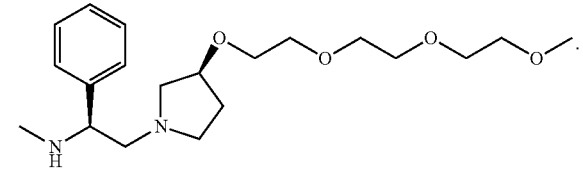

Benzyl {(1S)-2-[(3S)-3-{2-[2-(2-methoxyethoxy)-ethoxy]ethoxy}-pyrrolidin-1-yl]-2-oxo-1-phenylethyl)}carbamate (0.77 g, 1.53 mmol) was dissolved in anhydrous tetrahydrofuran (15 mL) and cooled to 0° C. To this solution was added lithium aluminum hydride (2 M in tetrahydrofuran, 1.53 mL, 3.08 mmol) carefully. The cloudy reaction mixture was then heated under reflux (oil bath at 70° C.) for two hours. The cloudy reaction mixture was allowed to equilibrate to room temperature. After approximately 18 hours at room temperature the cloudy mixture was cooled with an ice bath. The excess lithium aluminum hydride was quenched with two drops of ethyl acetate. The reaction mixture was treated with water (52 μL), followed by 4N NaOH (52 L). After five minutes water (154 μL) was added and stirred for 15 minutes. A white precipitate was filtered off and the filtrate was dried over anhydrous sodium sulfate, and then filtered and concentrated under reduced pressure. The residue was purified by chromatography to give 0.34 g (60%) of benzyl {(1S)-2-[(3S)-3-{2-[2-(2-methoxyethoxy)-ethoxy]ethoxy}-pyrrolidin-1-yl]-2-oxo-1- phenylethyl}carbamate as a light-yellow semi-solid. MS (EI) for $C_{20}H_{34}N_2O_4$: 367 (MH+).

Step 5: Preparation of (1S)-2-[(3S)-3-{2-[2-(2-methoxyethoxy)ethoxy]ethoxy}pyrrolidin-1-yl]-N-methyl-1-(3-nitrophenyl)ethanamine

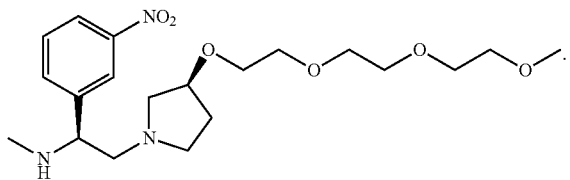

To an ice-cold solution of benzyl {(1S)-2-[(3S)-3-{2-[2-(2-methoxyethoxy)-ethoxy]ethoxy}-pyrrolidin-1-yl]-2-oxo-1-phenylethyl}carbamate (0.60 gm, 2.94 mmol) in concentrated sulfuric acid (11 mL) was added 70% nitric acid (0.28 mL, 4.41 mmol) with vigorous stirring. The stirring with ice-cooling continued for 45 minutes and the reaction mixture was made basic by careful addition of 4N sodium hydroxide and water with stirring and ice-cooling. The reaction mixture was partitioned between ethyl acetate (45 mL) and water (60 mL). The aqueous layer was extracted with ethyl acetate (3×20 mL). The organic portion was washed with water and saturated sodium chloride (60 mL each) and dried over anhydrous sodium sulfate to give 0.25 g (67%) of (1S)-2-[(3S)-3-{2-[2-(2-methoxyethoxy)ethoxy]ethoxy}pyrrolidin-1-yl]-N-methyl-1-(3-nitrophenyl)ethanamine as a light yellow oil. MS (EI) for $C_{20}H_{33}N_3O_6$: 412 (MH+).

Step 6: Preparation of 2-(3,4-dichlorophenyl)-N-[(1S)-2-[(3S)-3-{2-[2-(2-methoxyethoxy)ethoxy]ethoxy}pyrrolidin-1-yl]-1-(3-nitrophenyl)ethyl]-N-methylacetamide

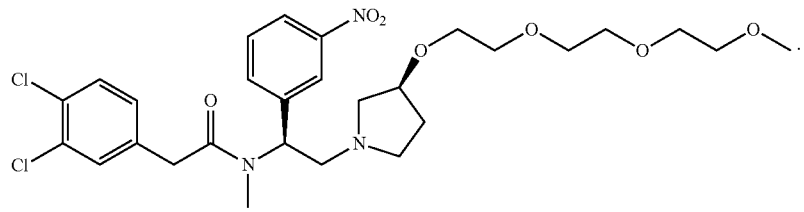 [SMILES: COCCOCCOCCO[C@H]1CCN(C[C@H](c2cccc([N+](=O)[O-])c2)N(C)C(=O)Cc2ccc(Cl)c(Cl)c2)C1]

To a stirring solution of (1S)-2-[(3S)-3-{2-[2-(2-methoxyethoxy)ethoxy]ethoxy}pyrrolidin-1-yl]-N-methyl-1-(3-nitrophenyl)ethanamine (0.66 gm, 2.65 mmol) in dry acetonitrile (13.2 mL; 0.20M) at 0° C. under nitrogen was added diisopropylethylamine (1.03 mL, 5.82 mmol), 3,4-dichlorophenylacetic acid (0.60 gm, 2.91 mmol) and O-(benzotriazol-1-yl)-N,N,N',N'-tetramethyluronium tetrafluoroborate (0.96 gm, 2.91 mmol). The dark reaction mixture was allowed to equilibrate to room temperature, and stirred under nitrogen. After approximately 17 hours at room temperature, the dark mixture was concentrated under reduced pressure. The dark oil was taken up in ethyl acetate and washed with saturated sodium bicarbonate and saturated sodium chloride. The organic portion was filtered and concentrated under reduced pressure. The residue was purified by chromatography to give 0.15 g (42%) of 2-(3,4-dichlorophenyl)-N-[(1S)-2-[(3S)-3-{2-[2-(2-methoxyethoxy)ethoxy]ethoxy}pyrrolidin-1-yl]-1-(3-nitrophenyl)ethyl]-N-methylacetamide as a light-yellow oil. MS (EI) for $C_{28}H_{37}Cl_2N_3O_7$: 598 (MH+).

Step 7: Preparation of 2-(3,4-dichlorophenyl)-N-[(1S)-2-[(3S)-3-{2-[2-(2-methoxyethoxy)ethoxy]ethoxy}pyrrolidin-1-yl]-1-(3-aminophenyl)ethyl]-N-methylacetamide

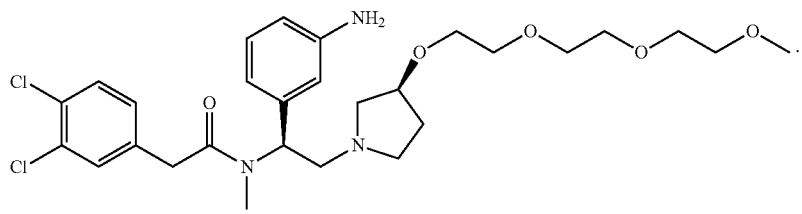

To a three-neck, 100 mL round bottom flask equipped with a condenser, thermometer, and magnetic stirrer was added (3,4-dichlorophenyl)-N-[(1S)-2-[(3S)-3-{2-[2-(2-methoxyethoxy)ethoxy]ethoxy}pyrrolidin-1-yl]-1-(3-nitrophenyl)ethyl]-N-methylacetamide compound (0.15 g, 0.25 mmol) in 9 mL absolute ethanol. To the light-yellow solution was added hydrazine hydrate (0.19 g, 3.05 mmol) and Raney nickel slurry (13 drops) and heated to 55° C. (oil bath temp at 64° C.). The light-yellow reaction turned clear and after approximately two hours at 55° C. the reaction was complete as indicated by LC-MS. The reaction mixture was filtered through Celite, and the Raney nickel was washed with hot methanol. The combined filtrates were concentrated under reduced pressure to give a light-yellow oil. Purification by chromatography gave 0.12 g (82%) of 2-(3,4-dichlorophenyl)-N-[(1S)-2-[(3S)-3-{2-[2-(2-methoxyethoxy)ethoxy]ethoxy}pyrrolidin-1-yl]-1-(3-aminophenyl)ethyl]-N-methylacetamide as a clear oil. MS (EI) for $C_{28}H_{39}Cl_2N_3O_5$: 568 (MH+).

Step 8: Preparation of 2-(3,4-dichlorophenyl)-N-[(1S)-2-[(3S)-3-{2-[2-(2-methoxyethoxy)ethoxy]ethoxy}pyrrolidin-1-yl]-1-{3-[(methylsulfonyl)amino]phenyl}ethyl]-N-methylacetamide, hydrochloride salt (17)

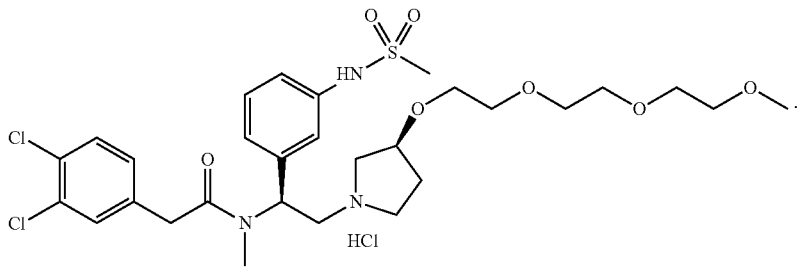 [SMILES: COCCOCCOCCO[C@H]1CCN(C[C@H](c2cccc(NS(C)(=O)=O)c2)N(C)C(=O)Cc2ccc(Cl)c(Cl)c2)C1 ; Cl]

2-(3,4-Dichlorophenyl)-N-[(1S)-2-[(3S)-3-{2-[2-(2-methoxyethoxy)ethoxy]ethoxy}pyrrolidin-1-yl]-1-(3-aminophenyl)ethyl]-N-methylacetamide (0.11 g, 0.20 mmol) was dissolved in dichloromethane (4 mL) and anhydrous pyridine (0.12 mL, 1.55 mmol). To the cooled (0° C.) clear solution there was added dropwise methanesulfonyl chloride (0.024 mL, 0.31 mmol), maintaining the temperature less than 10° C. The yellow reaction mixture was allowed to stir at 0° C., with the color turning orange. The reaction mixture was allowed to equilibrate to room temperature. After approximately 17 hours at room temperature the reaction mixture was diluted with dichloromethane (10 mL) and partitioned with water (15 mL). The organic portion was extracted with dichloromethane (3×5 mL). The organic portion was washed with saturated sodium chloride. The organic portion was filtered and concentrated under reduced pressure. Purification by chromatography gave 0.085 g (63%) of product as a clear oil. $^1$H NMR (500 MHz, CDCl$_3$): δ 7.32-6.98 (m, 7H), 5.95 (m, 1H), 3.96 (m, 1H), 3.63-3.45 (m, 16H), 3.30 (s, 3H), 2.97 (m, 1H), 2.93 (s, 3H), 2.75-2.40 (m, 6H), 1.97 (m, 1H), 1.71 (m, 2H); MS (EI) for C$_{29}$H$_{41}$Cl$_2$N$_3$O$_7$S: 646 (MH$^+$).

The compound was converted into the hydrochloride salt (17) by dissolving the oil in acetonitrile and adding 1N hydrochloric acid. The solution was lyophilized to give the hydrochloride salt as an off-white powder.

The example described above may be modified to introduce oligomers of various lengths as disclosed herein.

Example 16

Preparation of 2-(3,4-dichlorophenyl)-N-[(1S)-1-(3-{[(2-methoxyethyl)sulfonyl]amino}phenyl)-2-(pyrrolidin-1-yl)ethyl]-N-methylacetamide, hydrochloride salt. (18)

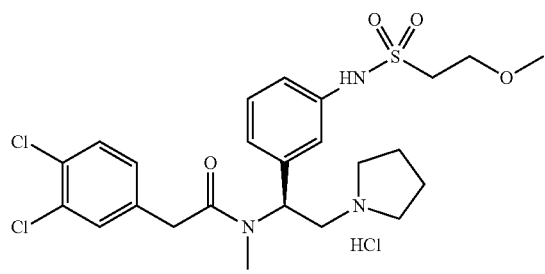

N-[(1S)-1-(3-Aminophenyl)-2-(pyrrolidin-1-yl)ethyl]-2-(3,4-dichloro-phenyl)-N-methylacetamide (0.10 g, 0.24 mmol) was dissolved in dichloromethane (2.5 mL) and anhydrous pyridine (0.15 mL). To the cooled (0° C.) yellow solution there was added dropwise 2-methoxyethanesulfonyl chloride (0.050 g, 0.31 mmol). The yellow reaction mixture was allowed to stir at 0° C., with the color turning orange. The reaction mixture was allowed to equilibrate to room temperature. The orange mixture was diluted with dichloromethane (15 mL) and partitioned with water (15 mL). The aqueous layer was extracted with dichloromethane (3×5 mL) and washed with saturated sodium chloride (2×15 mL). The organic portion was dried over anhydrous sodium sulfate, filtered and concentrated to an orange residue. Purification by chromatography gave 0.072 g (55%) of 2-(3,4-dichlorophenyl)-N-[(1S)-1-(3-{[(2-methoxyethyl)sulfonyl]amino}phenyl)-2-(pyrrolidin-1-yl)ethyl]-N-methylacetamide as a light-yellow oil. $^1$H NMR (500 MHz, CDCl$_3$): δ 7.37-7.14 (m, 7H), 6.05 (m, 1H), 3.81-3.71 (m, 4H), 3.41 (s, 3H), 3.21 (m, 2H), 3.14 (m, 1H), 2.80 (m, 3H), 2.69 (s, 3H), 2.49 (m, 3H), 1.75 (m, 4H); MS (EI) for C$_{29}$H$_{41}$Cl$_2$N$_3$O$_7$S: 646 (MH$^+$).

The compound was converted into the hydrochloride salt (18) by dissolving the oil in acetonitrile and adding 1N hydrochloric acid. The solution was lyophilized to give the hydrochloride salt as an off-white powder.

The example described above may be modified to introduce oligomers of various lengths (at the methoxyethyl substituent) as disclosed herein.

Example 17

Preparation of 2-(3,4-dichlorophenyl)-N-methyl-N-{(1S)-2-(pyrrolidin-1-yl)-1-[3-(({[2-(2,2,2-trifluoroethoxy)ethyl]sulfonyl}amino)phenyl]ethyl}acetamide, hydrochloride salt. (19)

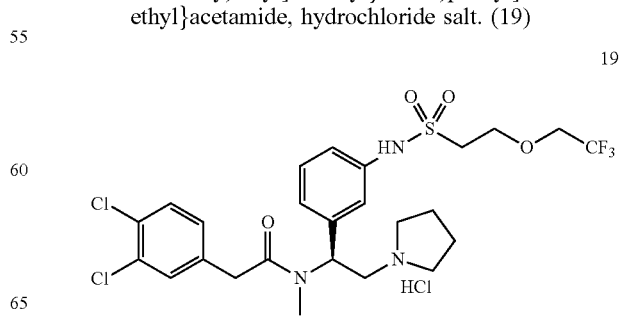

N-[(1S)-1-(3-Aminophenyl)-2-(pyrrolidin-1-yl)ethyl]-2-(3,4-dichloro-phenyl)-N-methylacetamide (0.048 g, 0.12 mmol) was dissolved in dichloromethane (2 mL) and anhydrous pyridine (0.072 mL, 0.88 mmol). To the cooled (0° C.) clear solution there was added dropwise 2-(2,2,2-trifluoroethoxy)ethanesulfonyl chloride (0.070 g, 0.29 mmol), maintaining the temperature less than 10° C. The yellow reaction mixture was allowed to stir at 0° C., with the color turning orange. The reaction mixture was allowed to equilibrate to room temperature. After approximately 17 hours at room temperature the orange mixture was diluted with dichloromethane (15 mL) and partitioned with water (15 mL). The aqueous layer was extracted with dichloromethane (3×5 mL) and washed with saturated sodium chloride (2×15 mL). The organic portion was dried over anhydrous sodium sulfate, filtered and concentrated to an orange residue. Purification by chromatography gave 0.039 g (55%) of 2-(3,4-dichlorophenyl)-N-methyl-N-{(1S)-2-(pyrrolidin-1-yl)-1-[3-({[2-(2,2,2-trifluoroethoxy)ethyl]sulfonyl}amino)phenyl]ethyl}acetamide as a clear oil. $^1$H NMR (500 MHz, CDCl$_3$): δ 7.29-7.07 (m, 7H), 5.96 (m, 1H), 3.98 (m, 2H), 3.82 (m, 2H), 3.69 (m, 2H), 3.21 (m, 2H), 3.10 (m, 1H), 2.63 (m, 5H), 2.42 (m, 4H), 1.68 (m, 4H); MS (EI) for $C_{25}H_{30}Cl_2F_3N_3O_4S$: 596 (MH$^+$).

The compound was converted into the hydrochloride salt (19) by dissolving the oil in acetonitrile and adding 1N hydrochloric acid. The solution was lyophilized to give the hydrochloride salt as an off-white powder.

The example described above may be modified to introduce oligomers of various lengths (at the trifluoroethoxyethyl substituent) as disclosed herein.

Example 18

Preparation of 2-(3,4-dichlorophenyl)-N-[(1S)-1-[3-({[2-(2-methoxyethoxy)ethyl]sulfonyl}amino)phenyl]-2-(pyrrolidin-1-yl)ethyl]-N-methylacetamide, hydrochloride salt. (20)

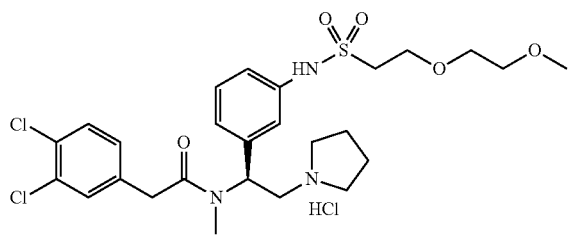 [SMILES: COCCOCCS(=O)(=O)Nc1cccc([C@@H](CN2CCCC2)N(C)C(=O)Cc2ccc(Cl)c(Cl)c2)c1 ; Cl]

N-[(1S)-1-(3-Aminophenyl)-2-(pyrrolidin-1-yl)ethyl]-2-(3,4-dichloro-phenyl)-N-methylacetamide (0.052 g, 0.12 mmol) was dissolved in dichloromethane (2.5 mL) and anhydrous pyridine (0.078 mL, 0.96 mmol). To the cooled (0° C.) clear solution there was added dropwise 2-(2-methoxyethoxy)ethanesulfonyl chloride (0.082 g, 0.38 mmol), maintaining the temperature less than 10° C. The yellow reaction mixture was allowed to stir at 0° C., with the color turning orange. The reaction mixture was allowed to equilibrate to room temperature. After approximately 17 hours at room temperature the orange mixture was diluted with dichloromethane (15 mL) and partitioned with water (15 mL). The aqueous layer was extracted with dichloromethane (3×5 mL) and washed with saturated sodium chloride (2×15 mL). The organic portion was dried over anhydrous sodium sulfate, filtered and concentrated to an orange residue. Purification by chromatography gave 31 mg (42%) of 2-(3,4-dichlorophenyl)-N-[(1S)-1-[3-({[2-(2-methoxyethoxy)ethyl]sulfonyl}amino)phenyl]-2-(pyrrolidin-1-yl)ethyl]-N-methylacetamide as a clear oil. $^1$H NMR (500 MHz, CDCl$_3$): δ 7.31-7.07 (m, 7H), 6.01 (m, 1H), 3.87 (m, 2H), 3.70-3.58 (m, 6H), 3.37 (s, 3H), 3.20-3.05 (m, 2H), 2.68 (m, 4H), 2.46 (m, 2H), 1.68 (m, 4H), 1.58 (m, 4H); MS (EI) for $C_{26}H_{35}Cl_2N_3O_5S$: 572 (MH$^+$).

The compound was converted into the hydrochloride salt (20) by dissolving the oil in acetonitrile and adding 1N hydrochloric acid. The solution was lyophilized to give the hydrochloride salt as an off-white powder.

The example described above may be modified to introduce oligomers of various lengths as disclosed herein.

Example 19

Preparation of N-[(1S)-1-{3-[({2-[2-(2-butoxyethoxy)ethoxy]ethyl}sulfonyl)amino]phenyl}-2-(pyrrolidin-1-yl)ethyl]-2-(3,4-dichlorophenyl)-N-methylacetamide, hydrochloride salt. (21)

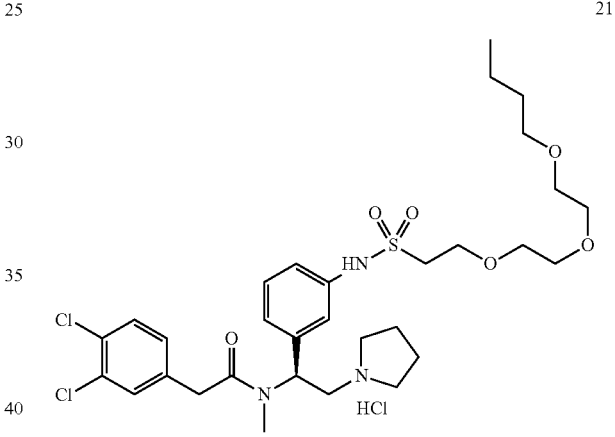

N-[(1S)-1-(3-Aminophenyl)-2-(pyrrolidin-1-yl)ethyl]-2-(3,4-dichloro-phenyl)-N-methylacetamide (0.048 g, 0.11 mmol) was dissolved in dichloromethane (2 mL) and anhydrous pyridine (0.072 mL, 0.88 mmol). To the cooled (0° C.) clear solution there was added dropwise 2-[2-(2-butoxyethoxy)ethoxy]ethanesulfonyl chloride (0.042 g, 0.17 mmol), maintaining the temperature less than 10° C. The yellow reaction mixture was allowed to stir at 0° C., with the color turning orange. The reaction mixture was allowed to equilibrate to room temperature. After approximately 17 hours at room temperature the orange mixture was diluted with dichloromethane (15 mL) and partitioned with water (15 mL). The aqueous layer was extracted with dichloromethane (3×5 mL) and washed with saturated sodium chloride (2×15 mL). The organic portion was dried over anhydrous sodium sulfate, filtered and concentrated to an orange residue. Purification by chromatography gave 0.026 mg (54%) of N-[(1S)-1-{3-[({2-[2-(2-butoxyethoxy)ethoxy]ethyl}sulfonyl)amino]phenyl}-2-(pyrrolidin-1-yl)ethyl]-2-(3,4-dichlorophenyl)-N-methylacetamide as a clear oil. $^1$H NMR (500 MHz, CDCl$_3$): δ 7.32-7.07 (m, 7H), 6.00 (m, 1H), 3.87 (m, 2H), 3.84-3.62 (m, 10H), 3.50 (m, 2H), 3.28 (m, 2H), 3.27 (m, 2H), 2.92 (m, 2H), 2.76 (m, 4H), 2.43 (m, 2H), 1.67 (m, 4H), 1.33 (m, 2H), 1.18 (m, 2H), 0.73 (m, 3H); MS (EI) for $C_{31}H_{45}Cl_2N_3O_6S$: 658 (MH$^+$).

The compound was converted into the hydrochloride salt (21) by dissolving the oil in acetonitrile and adding 1N hydrochloric acid. The solution was lyophilized to give the hydrochloride salt as an off-white powder.

The example described above may be modified to introduce oligomers of various lengths as disclosed herein.

Example 20

Preparation of 2-(3,4-dichlorophenyl)-N-[(1S)-1-(3-{[(4-hydroxy-1,1-dioxidotetrahydrothiophen-3-yl)sulfonyl]amino}phenyl)-2-(pyrrolidin-1-yl)ethyl]-N-methylacetamide, hydrochloride salt. (20)

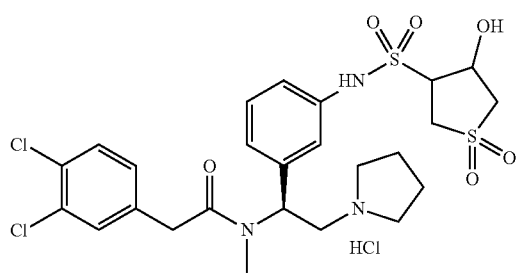

N-[(1S)-1-(3-Aminophenyl)-2-(pyrrolidin-1-yl)ethyl]-2-(3,4-dichloro-phenyl)-N-methylacetamide (0.038 g, 0.0.094 mmol) was dissolved in dichloromethane (1.8 mL) and anhydrous pyridine (0.057 mL, 0.70 mmol). To the cooled (0° C.) clear solution there was added dropwise 4-hydroxytetrahydrothiophene-3-sulfonyl chloride 1,1-dioxide (0.069 g, 0.28 mmol), maintaining the temperature less than 10° C. The yellow reaction mixture was allowed to stir at 0° C., with the color turning orange. The reaction mixture was allowed to equilibrate to room temperature. After approximately 17 hours at room temperature the orange mixture was diluted with dichloromethane (15 mL) and partitioned with water (15 mL). The aqueous layer was extracted with dichloromethane (3×5 mL) and washed with saturated sodium chloride (2×15 mL). The organic portion was dried over anhydrous sodium sulfate, filtered and concentrated to an orange residue. Purification by chromatography gave 26 mg (46%) of 2-(3,4-dichlorophenyl)-N-[(1S)-1-(3-{[(4-hydroxy-1,1-dioxidotetrahydrothiophen-3-yl)sulfonyl]amino}phenyl)-2-(pyrrolidin-1-yl)ethyl]-N-methylacetamide as a clear oil. $^1$H NMR (500 MHz, CDCl$_3$): δ 7.32-6.95 (m, 7H), 5.89 (m, 1H), 4.82 (m, 2H), 3.90-3.41 (m, 4H), 3.40-2.85 (m, 6H), 2.81-2.49 (m, 6H), 1.75 (m, 4H), 1.15 (m, 1H); MS (EI) for C$_{25}$H$_{31}$Cl$_2$N$_3$O$_6$S$_2$: 604 (MH$^+$).

The compound was converted into the hydrochloride salt (20) by dissolving the oil in acetonitrile and adding 1N hydrochloric acid. The solution was lyophilized to give the hydrochloride salt as an off-white powder.

Example 21

Preparation of 2-(3,4-difluorophenyl)-N-methyl-N-[(1S)-1-phenyl-2-(pyrrolidin-1-yl)ethyl]acetamide, hydrochloride salt. (23)

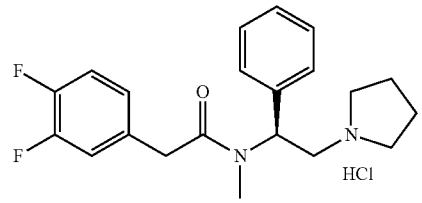

(1S)—N-Methyl-1-phenyl-2-pyrrolidin-1-yl)ethanamine (0.060 g, 0.29 mmol), (Singh, V. et. al., *Journal of Organic Chemistry* (1996), vol. 61, pp. 6108-6113) was dissolved in anhydrous acetonitrile (1.5 mL). The clear solution was stirred at 0° C., under nitrogen, followed by the addition of diisopropylethylamine (0.11 mL, 0.64 mmol), (3,4-difluorophenyl)acetic acid (0.057 g, 0.32 mmol) and O-(benzotriazol-1-yl)-N,N,N',N'-tetramethyluronium tetrafluoroborate (0.078 g, 0.32 mmol). The clear reaction mixture was allowed to equilibrate to room temperature and stirred under nitrogen. After approximately 17 hours at room temperature the mixture was concentrated in vacuo. The residue was dissolved in ethyl acetate (2 mL) and was washed with saturated sodium bicarbonate (2×10 mL) and saturated sodium chloride (10 mL). The combined organic portion was dried over anhydrous sodium sulfate and concentrated in vacuo. The residue was purified on a column of silica gel using dichloromethane/methanol (9:1) as eluent to give 45 mg (43%) of 2-(3,4-difluorophenyl)-N-methyl-N-[(1S)-1-phenyl-2-(pyrrolidin-1-yl)ethyl]acetamide as a light-yellow oil. $^1$H NMR (500 MHz, CDCl$_3$): δ 7.36-7.03 (m, 8H), 6.14 (m, 1H), 3.81 (m, 2H), 3.78 (m, 1H), 3.21 (m, 1H), 2.82-2.72 (m, 3H), 2.50 (m, 2H), 1.77 (m, 3H), 1.60 (m, 3H); MS (EI) for C$_{21}$H$_{24}$F$_2$N$_2$O: 359 (MH$^+$).

The compound was converted into the hydrochloride salt (23) by dissolving the oil in acetonitrile and adding 1N hydrochloric acid. The solution was lyophilized to give the hydrochloride salt as a white powder.

Example 22

Preparation of ({(3S)-1-[(2S)-2-{[(3,4-dichlorophenyl)acetyl](methyl)amino}-2-phenylethyl]pyrrolidin-3-yl}oxy)acetic acid, hydrochloride salt. (24)

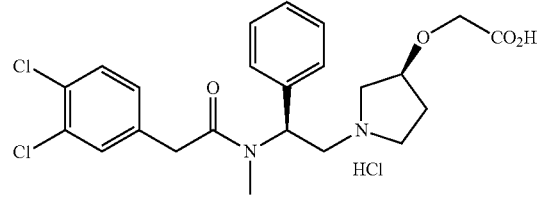 [SMILES: CN(C(=O)Cc1ccc(Cl)c(Cl)c1)[C@H](CN1CC[C@H](OCC(=O)O)C1)c1ccccc1 ; Cl]

({(3S)-1-[(2S)-2-{[(3,4-Dichlorophenyl)acetyl](methyl)amino}-2-phenylethyl]pyrrolidin-3-yl}oxy)acetic acid may be prepared according to the following steps.

Step 1: Preparation of (2-hydroxy-1-phenyl-ethyl)-methyl-carbamic acid tert-butyl ester

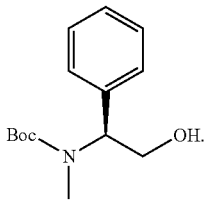

To a solution of lithium aluminum hydride (1.3 g) in tetrahydrofuran at 0° C. was added a solution of tert-butoxycarbonylamino-phenyl-acetic acid (2 g, 7.96 mmol) in tetrahydrofuran (40 mL) drop wise. The mixture was stirred at room temperature for 15 minutes, before heating in a 78° C. oil bath overnight. The mixture was then cooled in ice water bath, 6 mL 15% sodium hydroxide aqueous solution was added slowly. Tetrahydrofuran (25 mL) was added to dilute the mixture. After stirring at room temperature for thirty minutes, the mixture was filtered and washed with ethyl acetate. The filtrate was concentrated and taken into a mixture of dioxane/water (20 mL). 1 N sodium hydroxide was added (10 mL). Di-tert-butyl dicarbonate (1.7 g) was added. The mixture was stirred at room temperature for four hours. It was then concentrated and re-dissolved in ethyl acetate. After washing with water and brine, it was dried over sodium sulfate (anhydrous), filtered and concentrated to afford (2-hydroxy-1-phenyl-ethyl)-methyl-carbamic acid tert-butyl ester (1.4 g). The crude material was stored in freezer and used without further purification. LC-MS (ESI, MH+): 252.1.

Step 2: Preparation of {1-[2-(tert-butoxycarbonyl-methyl-amino)-2-phenyl-ethyl]-pyrrolidin-3-yloxy}-acetic acid ethyl ester

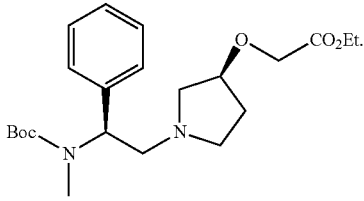 [SMILES: CCOC(=O)CO[C@H]1CCN(C[C@H](c2ccccc2)N(C)C(=O)OC(C)(C)C)C1]

(2-Hydroxy-1-phenyl-ethyl)-methyl-carbamic acid tert-butyl ester (700 mg, 2.8 mmol) was dissolved in dichloromethane (8 mL) and cooled in ice water bath. Dess Martin reagent (Oakwood, 621 mg, 2.8 mmol) was added in small portions. The mixture was stirred at room temperature for ninety minutes. LC/MS analysis showed >90% conversion. Sodium bicarbonate (aq. Sat. 10 mL) was then added, followed by aqueous sodium thiosulfate solution (3 mL) and dichloromethane (15 mL). The mixture was stirred at room temperature for 15 minutes. Layers were separated and the dichloromethane layer was dried over anhydrous sodium sulfate, filtered and concentrated to give the crude aldehyde (700 mg). LC-MS (ESI, MH+): 250.2. This material was used immediately in the next step. Freshly prepared crude aldehyde (700 mg, 2.81 mmol) was dissolved in dichloromethane (25 mL) and stirred under nitrogen atmosphere. The reaction was cooled in ice bath and ethyl-(S)-pyrrolidine-3-yloxy-acetate hydrochloride salt (875 mg, 3.55 mmol (the preparation of which is described in Example 28) in dichloromethane (5 mL) was added, followed by diisopropylethylamine (0.62 mL) and sodium triacetoxyborohydride (1.1 g, 5.2 mmol). The mixture was stirred overnight at room temperature. Dichloromethane (60 mL) was added and the solution was washed with 10% sodium bicarbonate, brine, dried over sodium sulfate and concentrated to give 1.2 g of crude {1-[2-(tert-Butoxycarbonyl-methyl-amino)-2-phenyl-ethyl]-pyrrolidin-3-yloxy}-acetic acid ethyl ester. LC-MS (ESI, MH+): 407.5.

Step 3/4: Preparation of crude [1-(2-{[2-(3,4-dichloro-phenyl)-acetyl]-methyl-amino}-2-phenyl-ethyl)-pyrrolidin-3-yloxy]-acetic acid ethyl ester

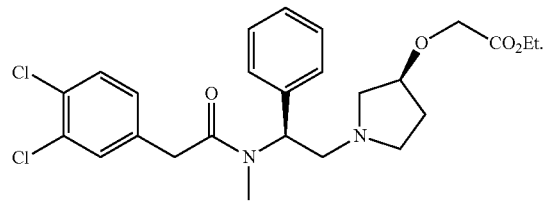 [SMILES: CCOC(=O)CO[C@H]1CCN(C[C@H](c2ccccc2)N(C)C(=O)Cc2ccc(Cl)c(Cl)c2)C1]

Crude {1-[2-(tert-Butoxycarbonyl-methyl-amino)-2-phenyl-ethyl]-pyrrolidin-3-yloxy}-acetic acid ethyl ester (1.2 g) was dissolved in dichloromethane/trifluoroacetic acid (5 mL each). The mixture was stirred at room temperature for one hour. LCMS show the reaction was completed. The mixture was then concentrated. The crude amine was dissolved in dimethylformamide (10 mL) under nitrogen atmosphere. 3,4-Dichlorophenyl acetic acid (590 mg, 2.88 mmol) was added, followed by diisopropylethylamine (2.8 mL, 16.0 mmol). The reaction mixture was cooled in an ice bath. HATU (1.0 g, 2.88 mmol) was added in one portion. The reaction was continued at room temperature for two hours. LCMS showed major product (M+H: 493.3). Ice water (20.0 mL) was added and the reaction mixture was extracted with ether (30.0 mL×2). The combined organic layer was washed with brine, dried over sodium sulfate and concentrated to give 1.0 g crude [1-(2-{[2-(3,4-Dichloro-phenyl)-acetyl]-methyl-amino}-2-phenyl-ethyl)-pyrrolidin-3-yloxy]-acetic acid ethyl ester.

Step 5: Preparation of [1-(2-{[2-(3,4-dichloro-phenyl)-acetyl]-methyl-amino}-2-phenyl-ethyl)-pyrrolidin-3-yloxy]-acetic acid as hydrochloride salt

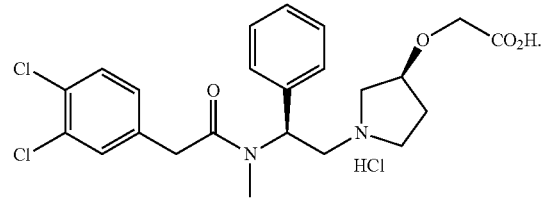 [SMILES: CN(C(=O)Cc1ccc(Cl)c(Cl)c1)[C@H](CN1CC[C@H](OCC(=O)O)C1)c1ccccc1 ; Cl]

Crude [1-(2-{[2-(3,4-Dichloro-phenyl)-acetyl]-methyl-amino}-2-phenyl-ethyl)-pyrrolidin-3-yloxy]-acetic acid ethyl ester (1 g, 2.03 mmol) was dissolved in 20 mL tetrahydrofuran. 3.5 mL of 2N lithium hydroxide was added. The mixture was stirred at room temperature for one hour. Aqueous hydrochloric acid (5 mL, 2%) was then added to adjust the pH to 3. Ethyl acetate (30 mL) was added and the mixture was washed with brine, dried over sodium sulfate and concentrated. The crude residue was purified by reverse phase high pressure liquid chromatography. The crude residue was purified by reverse phase high pressure liquid chromatography. The residue was diluted with 0.1 N hydrochloride and lyophilized to give 200 mg [1-(2-{[2-(3,4-Dichloro-phenyl)-acetyl]-methyl-amino}-2-phenyl-ethyl)-pyrrolidin-3-yloxy]-acetic acid as hydrochloride salt. $^1$H NMR (500 MHz, DMSO-d6): δ 10.85 (bs, 1H), 7.62-7.26 (m, 8H), 6.17 (m, 1H), 4.35 (m, 2H), 4.15-4.01 (m, 3H), 3.89-3.25 (m, 5H), 3.17 (m, 2H), 2.78 (m, 2H), 2.40-1.95 (2H); MS (EI) for $C_{23}H_{26}Cl_2N_2O_4$: 465.4 (MH$^+$).

Example 23

2-(3,4-Dichlorophenyl)-N-{(1S)-2-[(3S)-3-(2-hydroxyethoxy)pyrrolidin-1-yl]-1-phenylethyl}-N-methylacetamide, hydrochloride salt. (25)

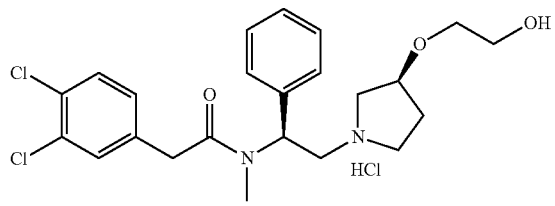

25

Using a synthetic approach similar to the one employed in Example 22, 2-(3,4-dichlorophenyl)-N-{(1S)-2-[(3S)-3-(2-hydroxyethoxy)pyrrolidin-1-yl]-1-phenylethyl}-N-methylacetamide, hydrochloride salt (25) was prepared. $^1$H NMR (500 MHz, CDCl$_3$): δ 7.50-7.17 (m, 8H), 6.45 (m, 1H), 4.14-3.98 (m, 5H), 3.75-3.52 (m, 4H), 3.34-3.15 (m, 4H), 2.87 (m, 3H), 2.40 (m, 1H), 2.25 (m, 2H); MS (EI) for $C_{23}H_{28}Cl_2N_2O_3$: 451.3 (MH$^+$).

The example described above may be modified to introduce oligomers of various lengths (at the 2-hydroxyethoxy substituent) as disclosed herein.

Example 24

2-(3,4-Dichlorophenyl)-N-[(1S)-2-{(3S)-3-[2-(2-hydroxyethoxy)ethoxy]pyrrolidin-1-yl)}-1-phenyl-ethyl]-N-methylacetamide, hydrochloride salt. (26)

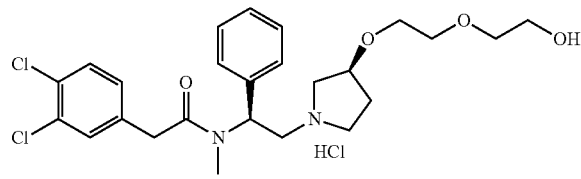

26

Using a synthetic approach similar to the one employed in Example 22, 2-(3,4-dichlorophenyl)-N-[(1S)-2-{(3S)-3-[2-(2-hydroxyethoxy)ethoxy]pyrrolidin-1-yl}-1-phenylethyl]-N-methylacetamide, hydrochloride salt (26) was prepared. $^1$H NMR (500 MHz, DMSO-d6): δ 7.57-7.24 (m, 8H), 6.13 (m, 1H), 4.30 (m, 2H), 4.12 (m, 2H), 3.90-3.35 (m, 12H), 2.77 (m, 3H), 2.31 (m, 2H), 2.06 (m, 2H); MS (EI) for $C_{25}H_{32}Cl_2N_2O_4$: 495.4 (MH$^+$).

The example described above may be modified to introduce oligomers of various lengths as disclosed herein.

Example 25

2-(3,4-Dichlorophenyl)-N-{(1S)-2-[(3S)-3-{2-[2-(2-hydroxyethoxy)ethoxy]ethoxy}pyrrolidin-1-yl]-1-phenylethyl}-N-methylacetamide, hydrochloride salt. (27)

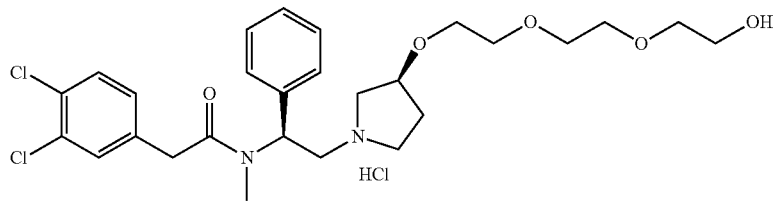

27

Using a synthetic approach similar to the one employed in Example 22, 2-(3,4-dichlorophenyl)-N-{(1S)-2-[(3S)-3-{2-[2-(2-hydroxyethoxy)ethoxy]ethoxy}pyrrolidin-1-yl]-1-phenylethyl}-N-methylacetamide, hydrochloride salt (27) was prepared. $^1$H NMR (500 MHz, DMSO-d6): δ 7.60-7.23 (m, 8H), 6.14 (m, 1H), 4.33-4.01 (m, 4H), 3.83 (m, 1H), 3.51-3.36 (m, 15H), 2.77 (m, 3H), 2.34 (m, 1H), 2.16 (m, 2H), 2.10 (m, 1H), 1.95 (m, 1H); MS (EI) for $C_{27}H_{36}Cl_2N_2O_5$: 538.2 (MH$^+$).

The example described above may be modified to introduce oligomers of various lengths as disclosed herein.

Example 26

[2-({(3S)-1-[(2S)-2-{[(3,4-Dichlorophenyl)acetyl] (methyl)amino}-2-phenylethyl]pyrrolidin-3-yl}oxy) ethoxy]acetic acid, hydrochloride salt. (28)

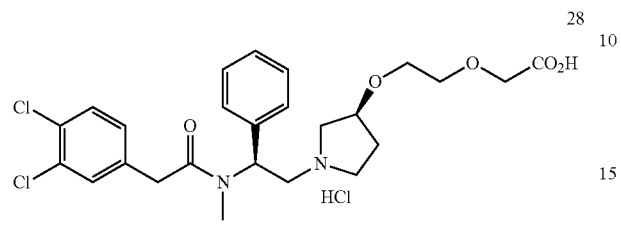

Using a synthetic approach similar to the one employed in Example 22, [2-({(3S)-1-[(2S)-2-{[(3,4-dichlorophenyl) acetyl](methyl)amino}-2-phenylethyl]pyrrolidin-3-yl}oxy) ethoxy]acetic acid, hydrochloride salt (28) was prepared. $^1$H NMR (500 MHz, DMSO-d6): δ 7.61-7.22 (m, 8H), 6.15 (m, 1H), 4.35-4.23 (m, 2H), 4.10-3.84 (m, 2H), 3.65-3.27 (m, 10H), 2.77 (m, 3H), 2.35 (m, 1H), 2.20-1.90 (m, 3H); MS (EI) for $C_{25}H_{30}Cl_2N_2O_5$: 509.5 (MH$^+$).

The example described above may be modified to introduce oligomers of various lengths as disclosed herein.

Example 27

{2-[2-({(3S)-1-[(2S)-2-{[(3,4-Dichlorophenyl) acetyl](methyl)amino}-2-phenylethyl]pyrrolidin-3-yl}oxy)ethoxy]ethoxy}acetic acid, hydrochloride salt. (29)

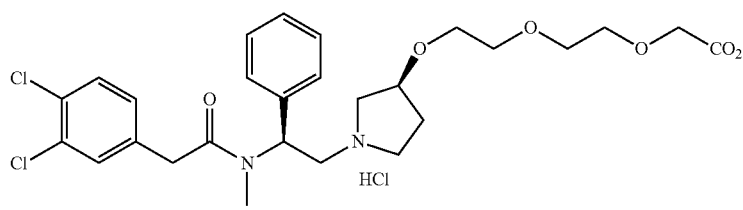

Using a synthetic approach similar to the one employed in Example 22, {2-[2-({(3S)-1-[(2S)-2-{[(3,4-dichlorophenyl) acetyl](methyl)amino}-2-phenylethyl]pyrrolidin-3-yl}oxy) ethoxy]ethoxy}acetic acid, hydrochloride salt (29) was prepared. $^1$H NMR (500 MHz, DMSO-d6): δ 7.62-7.23 (m, 8H), 6.15 (m, 1H), 4.33-4.25 (m, 2H), 4.13-3.85 (m, 2H), 3.98-3.29 (m, 15H), 2.75 (m, 3H), 2.37 (m, 1H), 2.15 (m, 1H), 1.97 (m, 1H); MS (EI) for $C_{27}H_{34}Cl_2N_2O_6$: 553.3 (MH$^+$).

The example described above may be modified to introduce oligomers of various lengths as disclosed herein.

Example 28

Preparation of Pyrrolidine-Based Compounds Potentially Useful in Synthetic Approaches Preparation of (S)-3-methoxycarbonylmethoxy-pyrrolidine-1-carboxylic acid benzyl ester

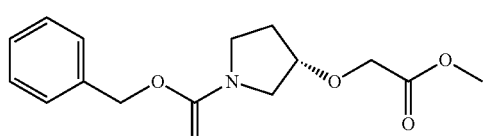

(S)-3-Methoxycarbonylmethoxy-pyrrolidine-1-carboxylic acid benzyl ester

To a stirred solution of cbz-(S)-pyrrolidin-3-ol (5.4 g, 24 mmol, 1 eq) in anhydrous tetrahydrofuran (100 mL) at 0° C., sodium hydride (60% in oil, 2.4 g, 60 mmol, 2.5 eq) was added and the solution was stirred at room temperature for thirty minutes. Methyl bromoacetate (7.3 g, 4.4 mL, 48 mmol, 2 eq) was added to the solution and then further stirred at room temperature for three hours, by which time LC-MS analysis revealed the formation of a new product. Saturated aqueous ammonium chloride solution (10 mL) was added to the mixture and the mixture was extracted with ether (3×30 mL). The combined organic layers were washed with saturated sodium bicarbonate solution (30 mL), brine (30 mL), dried over magnesium sulfate and concentrated in vacuo. The residue was purified by column chromatography on silica gel using a gradient of solvents, hexane:ethyl acetate from 5-50% ethyl acetate to give the desired product (6.6 g, 94.3%) as light brown oil. LC-MS (ESI, MH$^+$): 294.1. $^1$H NMR (250 MHz, CDCl$_3$) δ 7.6-7.1 (5H, m), 5.15 (2H, s), 4.25-4.05 (3H, m), 3.85-3.4 (7H, m), 2.2-1.7 (4 H, m).

Preparation of (S)-3-(2-methoxycarbonylmethoxyethoxy)-pyrrolidine-1-carboxylic acid benzyl ester

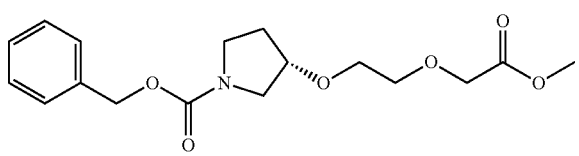 [SMILES: COC(=O)COCCO[C@H]1CCN(C(=O)OCc2ccccc2)C1]

(S)-3-(2-Methoxycarbonylmethoxy-ethoxy)-pyrrolidine-1-carboxylic acid benzyl ester To a stirred solution of (S)-3-(2-hydroxy-ethoxy)-pyrrolidine-1-carbooxylic acid benzyl ester (9 g, 34 mmol, 1 eq) in anhydrous tetrahydrofuran (100 mL) at 0° C., sodium hydride (60% in oil, 2.0 g, 51 mmol, 1.5 eq) was added and the solution was stirred at room temperature for 30 minutes. Methyl bromoacetate (6.3 g, 3.8 mL, 41 mmol, 1.2 eq) was added to the solution and then further stirred at room temperature for three hours, by which time LC-MS analysis indicated that no starting material left. Saturated aqueous ammonium chloride solution (60 mL) was added to the mixture and the mixture was extracted with ether (3×60 mL). The combined organic layers were washed with saturated sodium bicarbonate solution (50 mL), brine (50 mL), dried over magnesium sulfate and concentrated in vacuo. The residue was purified by column chromatography on silica gel using a gradient of solvents, hexane:ethyl acetate from 10-60% ethyl acetate to give(S)-3-(2-Methoxycarbonylmethoxy-ethoxy)-pyrrolidine-1-carboxylic acid benzyl ester as light brown oil (9 g, 78.3%). LC-MS: 338.2 (M$^+$+1), 675.3 (2 M$^+$+1), 692.5 (2M$^+$+hydrogenO).

Preparation of (S)-3-[2-(2-ethoxycarbonylmethoxy-ethoxy)-ethoxy]-pyrrolidine-1-carboxylic acid benzyl ester

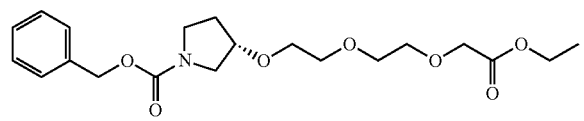 [SMILES: CCOC(=O)COCCOCCO[C@H]1CCN(C(=O)OCc2ccccc2)C1]

(S)-3-[2-(2-Ethoxycarbonylmethoxy-ethoxy)-ethoxy]-pyrrolidine-1-carboxylic acid benzyl ester To a stirred solution of (S)-3-[2-(2-hydroxy-ethoxy)-ethoxy]-pyrrolidine-1-carboxylic acid benzyl ester (2.4 g, 7.7 mmol, 1 eq) in anhydrous tetrahydrofuran (30 mL) at 0° C., sodium hydride (60% in oil, 468 mg, 11.7 mmol, 1.5 eq) was added and the solution was stirred at room temperature for thirty minutes. Ethyl bromoacetate (1.54 g, 1.02 mL, 9.2 mmol, 1.2 eq) was added to the solution and then further stirred at room temperature for three hours, by which time LC-MS analysis indicated that no starting material left. Saturated aqueous ammonium chloride solution (60 mL) was added to the mixture and the mixture was extracted with ether (3×60 mL). The combined organic layers were washed with saturated sodium bicarbonate solution (50 mL), brine (50 mL), dried over magnesium sulfate and concentrated in vacuo. The residue was purified by column chromatography on silica gel using a gradient of solvents, hexane:ethyl acetate from 10-60% ethyl acetate to give the desired product (S)-3-[2-(2-Ethoxycarbonylmethoxy-ethoxy)-ethoxy]-pyrrolidine-1-carboxylic acid benzyl ester (2.4 g, 80%) as light brown oil. LC-MS: 396.3 (M$^+$+1), 413.4 (M$^+$+hydrogenO).

Preparation of (S)-3-{2-[2-(2-benzyloxy-ethoxy)-ethoxy]-ethoxy}-pyrrolidine-1-carboxylic acid benzyl ester

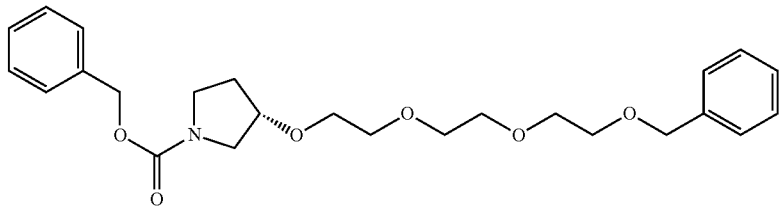 [SMILES: O=C(OCc1ccccc1)N1CC[C@H](OCCOCCOCCOCc2ccccc2)C1]

(S)-3-{2-[2-(2-Benzyloxy-ethoxy)-ethoxy]-ethoxy}-pyrrolidine-1-carboxylic acid benzyl ester To a solution of (S)-3-hydroxy-pyrrolidine-1-carboxylic acid benzyl ester (3.5 g, 15 mmol, 1.2 eq) in 60 mL of anhydrous tetrahydrofuran, NaH (60% in oil, 800 mg, 20 mmol) was added and the solution was stirred at room temperature for thirty minutes. Toluene-4-sulfonic acid 2-[2-benzyolxy-ethoxy)-ethoxy] ethyl ester (5 g, 13 mmol 1 eq) was then added. The mixture was heated at 50° C. overnight. LC-MS analysis revealed the formation of a new product. Saturated aqueous ammonium chloride solution (10 mL) was added to the mixture and the aqueous layer was extracted with ether (4×15 mL). The combined organic layers were washed with saturated sodium bicarbonate solution (4×10 mL), brine (4×10 mL), dried over magnesium sulfate and concentrated in vacuo. The residue was purified by column chromatography on silica gel using a gradient of hexane/ethyl acetate (10-60% ethyl acetate) to give (S)-3-{2-[2-(2-Benzyloxy-ethoxy)-ethoxy]-ethoxy}-pyrrolidine-1-carboxylic acid benzyl ester (4 g, 69.6%) as light brown oil.

Preparation of (S)-3-[2-(2-hydroxy-ethoxy)-ethoxy]-pyrrolidine-1-carboxylic acid benzyl ester

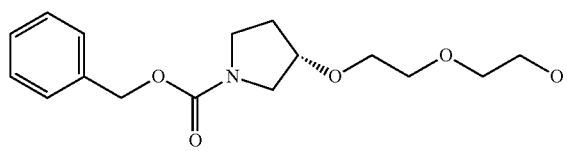 [SMILES: O=C(OCc1ccccc1)N1CC[C@H](OCCOCCO)C1]

S)-3-[2-(2-Hydroxy-ethoxy)-ethoxy]-pyrrolidine-1-carboxylic acid benzyl ester To a stirred solution of (S)-3-(2-Methoxycarbonyl-methoxy-ethoxy)-pyrrolidine-1-carboxylic acid benzyl ester (3.1 g, 9.2 mmol, 1 eq) in anhydrous tetrahydrofuran (100 mL) at 0° C., lithium aluminum hydride (240 mg, 11 mmol, 1.2 eq) was added and allowed to warm to room temperature and stirred overnight. The reaction was quenched by the portion wise addition of sodium sulfate decahydrate (20 g) and stirred for several hours. The heterogeneous mixture was filtered and washing the solid with tetrahydrofuran and the filtrate was concentrated under reduced pressure to give compound (S)-3-[2-(2-hydroxy-ethoxy)-ethoxy]-pyrrolidine-1-carboxylic acid benzyl ester (2.4 g, 88.9%) as oil which was used subsequently in next step. LC-MS: 310.3 ($M^+$+1), 619.6 (2 $M^+$+1), 636.7 (2$M^+$+hydrogenO).

Preparation of 2-{2-[2-((S)-pyrrolidin-3-yloxy)-ethoxy]-ethoxy}-ethanol

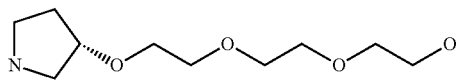 [SMILES: OCCOCCOCCO[C@H]1CCNC1]

2-{2-[2-((S)-Pyrrolidin-3-yloxy)-ethoxy]-ethoxy}-ethanol (S)-3-{2-[2-(2-Benzyloxy-ethoxy)-ethoxy]-ethoxy}-pyrrolidine-1-carboxylic acid benzyl ester (2.4 g) was dissolved in 40 mL of ethanol in a hydrogenation flask, 0.8 g of Pd/C (10%) was added. The mixture was hydrogenated on a Parr shaker (50 psi) for 24 hours. The mixture was purged with nitrogen and filtered through a celite pad washed with more ethanol. The filtrate was concentrated and concentrated. The crude product was purified by reverse phase prep HPLC to give pure product 650 mg (48%). LC-MS: 220.0 ($M^+$+1), 439.5 (2$M^+$+1).

Example 29

Preparation of N-[(1S)-1-{3-[({2-[2-(2-Butoxyethoxy)ethoxy]ethyl}sulfonyl)amino]phenyl}-2-(pyrrolidin-1-yl)ethyl]-N-methyl-2-(pyridin-2-yl)acetamide, dihydrochloride salt. (30)

N-[(1S)-1-{3-[({2-[2-(2-Butoxyethoxy)ethoxy]ethyl}sulfonyl)amino]phenyl}-2-(pyrrolidin-1-yl)ethyl]-N-methyl-2-(pyridin-2-yl)acetamide may be prepared according to the following steps.

Step 1: Preparation of N-Methyl-N-[(1S)-1-(3-nitrophenyl)-2-(pyrrolidin-1-yl)ethyl]-2-(pyridin-2-yl)acetamide

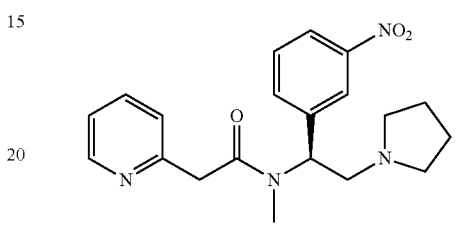

(S)-1-[2-(Methylamino)-2-(3/4-nitrophenyl)ethyl]pyrrolidin (0.25 g, 1.00 mmol), (Portoghese, P. *Journal of Medicinal Chemistry*, 1994, 37, 4490-4498) was dissolved in anhydrous acetonitrile (5 mL). To the yellow solution was added diisopropylethylamine (0.55 mL, 3.11 mmol) at 0° C., followed by pyridin-2-ylacetic acid (0.19 g, 1.10 mmol) and O-(benzotriazol-1-yl)-N,N,N',N'-tetramethyluronium tetrafluoroborate (0.26 g, 1.10 mmol). The reaction mixture was allowed to equilibrate to room temperature. After approximately 17 hours at room temperature the reaction mixture was concentrated under reduced pressure. The residue was taken up in ethyl acetate (15 mL) and washed with saturated sodium bicarbonate (2×25 mL) and saturated sodium chloride (25 mL). The combined organic portion was dried over anhydrous sodium sulfate (approximately 1.70 g) and concentrated in vacuo. The residue was purified on a column of silica gel using dichloromethane/methanol (9:1) as eluent to give 0.18 g (49%) of N-methyl-N-[(1S)-1-(3-nitrophenyl)-2-(pyrrolidin-1-yl)ethyl]-2-(pyridin-2-yl)acetamide as a clear oil. MS (EI) for $C_{20}H_{24}N_4O_3$: 369 (MH$^+$).

30

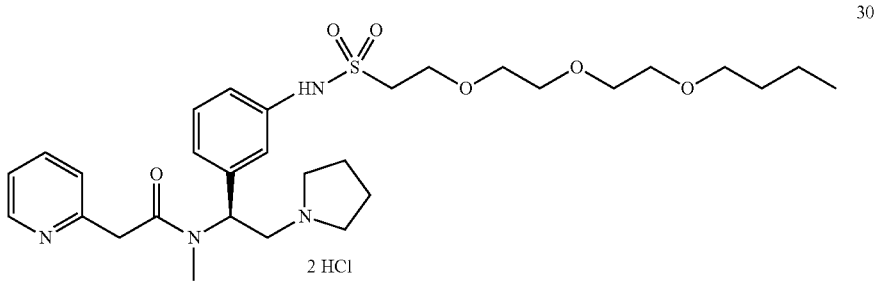 [SMILES: CCCCOCCOCCOCCS(=O)(=O)Nc1cccc([C@@H](CN2CCCC2)N(C)C(=O)Cc2ccccn2)c1]

Step 2: Preparation of N-[(1S)-1-(3-aminophenyl)-2-(pyrrolidin-1-yl)ethyl]-N-methyl-2-(pyridin-2-yl)acetamide

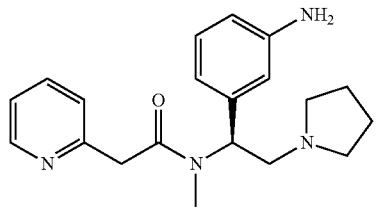 [SMILES: CN(C(=O)Cc1ccccn1)[C@H](CN1CCCC1)c1cccc(N)c1]

A mixture of N-methyl-N-[(1S)-1-(3-nitrophenyl)-2-(pyrrolidin-1-yl)ethyl]-2-(pyridin-2-yl)acetamide (0.13 g, 0.35 mmol), hydrazine hydrate (0.27 g, 4.23 mmol) and Raney Ni slurry (0.57 mL) in 95% ethanol (17.5 mL) was heated to 55° C. After approximately two hours at 55° C. the reaction was complete as indicated by TLC. The reaction mixture was filtered through Celite, and the Raney Ni was washed with hot methanol. The filtrate was concentrated under reduced pressure to give a brown residue. Purification by chromatography gave 0.11 g (92%) of N-[(1S)-1-(3-aminophenyl)-2-(pyrrolidin-1-yl)ethyl]-N-methyl-2-(pyridin-2-yl)acetamide as a light-yellow oil. MS (EI) for $C_{20}H_{26}N_4O$: 339 (MH$^+$).

Step 3: Preparation of N-[(1S)-1-{3-[({2-[2-(2-butoxyethoxy)ethoxy]ethyl}sulfonyl)amino]phenyl}-2-(pyrrolidin-1-yl)ethyl]-N-methyl-2-(pyridin-2-yl)acetamide, dihydrochloride salt (30)

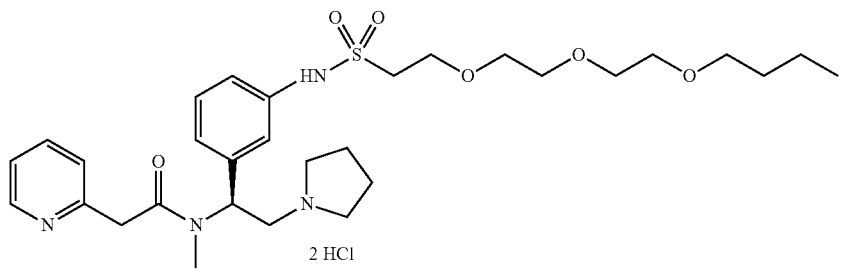 [SMILES: CCCCOCCOCCOCCS(=O)(=O)Nc1cccc([C@@H](CN2CCCC2)N(C)C(=O)Cc2ccccn2)c1]

N-[(1S)-1-(3-Aminophenyl)-2-(pyrrolidin-1-yl)ethyl]-N-methyl-2-(pyridin-2-yl)acetamide (0.11 g, 0.32 mmol) was dissolved in dichloromethane (6.5 mL) and anhydrous pyridine (0.19 mL, 2.43 mmol). To the cooled (0° C.) clear solution there was added dropwise 2-[2-(2-butoxyethoxy)ethoxy]ethanesulfonyl chloride (0.24 g, 0.81 mmol), maintaining the temperature less than 10° C. The yellow reaction mixture was allowed to stir at 0° C., with the color turning orange. After approximately 17 hours at room temperature the orange mixture was diluted with dichloromethane (15 mL) and partitioned with water (15 mL). The aqueous layer was extracted with dichloromethane (3×5 mL) and washed with saturated sodium chloride (2×15 mL). The organic portion was dried over anhydrous sodium sulfate, filtered and concentrated to an orange residue. Purification by chromatography gave 0.11 g (57%) of N-[(1S)-1-{3-[({2-[2-(2-butoxyethoxy)ethoxy]ethyl}sulfonyl)amino]phenyl}-2-(pyrrolidin-1-yl)ethyl]-N-methyl-2-(pyridin-2-yl)acetamide as a clear oil.

The compound was converted into the dihydrochloride salt by dissolving the oil in acetonitrile and adding 1N hydrochloric acid. The solution was lyophilized to give the hydrochloride salt as an off-white powder.

The example described above may be modified to introduce oligomers of various lengths as disclosed herein.

Example 30

Preparation of N-[(1S)-2-Amino-1-phenylethyl]-2-(3,4-dichlorophenyl)-N-methylacetamide, hydrochloride salt. (31)

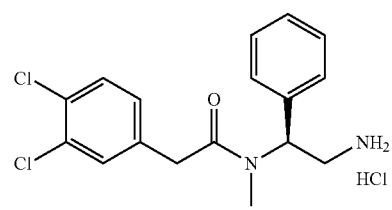

N-[(1S)-2-Amino-1-phenylethyl]-2-(3,4-dichlorophenyl)-N-methylacetamide may be prepared according to the following steps.

Step 1: Preparation of benzyl [(1S)-2-amino-2-oxo-1-phenylethyl]carbamate

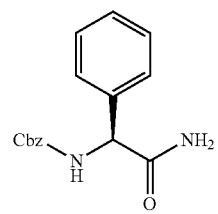 [SMILES: NC(=O)[C@@H](NC(=O)OCc1ccccc1)c1ccccc1]

A solution of (2S)-{[(benzyloxy)carbonyl]amino}(phenyl)acetic acid (2 g, 7.01 mmol), N-methylmorpholine (780 mg, 7.71 mmol) in tetrahydrofuran (32 mL) was cooled to −10° C. Ethyl chloroformate (837 mg, 7.71 mmol) was added and the solution was stirred for one hour at room temperature. The reaction mixture was cooled to −10° C. and aqueous ammonium hydroxide (28%) (524 μl, 7.71 mmol) was added. The mixture was stirred for three hours at −10° C. The solvent was removed under reduced pressure and the residue was dissolved in ethyl acetate. The organic portion, after being washed with saturated sodium bicarbonate solution, water and saturated sodium chloride, was dried over anhydrous sodium sulfate and concentrated under reduced pressure. The residue was crystallized from ethyl acetate-hexane to give 1.7 g (85%) of benzyl [(1S)-2-amino-2-oxo-1-phenylethyl]carbamate as a white solid.

Step 2: Preparation of (1S)—N'-methyl-1-phenylethane-1,2-diamine

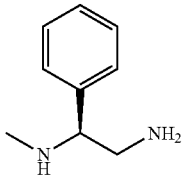

Benzyl [(1S)-2-amino-2-oxo-1-phenylethyl]carbamate (1.7 g, 5.97 mmol) was dissolved in tetrahydrofuran (34 mL). The solution was cooled to 0° C. and lithium aluminum hydride (1.13 g, 29.89 mmol) was added. The mixture was stirred for 15 minutes at 0° C., followed by 16 hours stirring at 65° C. The reaction mixture was cooled to 0° C. and 3N aqueous sodium carbonate (100 mL) was added carefully until effervescence ceased. The precipitated solid was filtered and washed with ethyl acetate (100 mL). The filtrate was concentrated and the residue was dissolved in ethyl acetate (150 mL). The product was extracted into 1N aqueous hydrochloric acid (2×10 mL) and washed with tert-butyl methyl ether (3×15 mL). The pH of the aqueous portion was adjusted to 9, and the product was extracted into ethyl acetate. The organic portion was washed with saturated sodium chloride, dried over anhydrous sodium sulfate and concentrated under reduced pressure. The residue was purified by chromatography to give 265 mg (30%) of (1S)—N'-methyl-1-phenylethane-1,2-diamine.

Step 3: Preparation of tert-butyl [(2S)-2-(methylamino)-2-phenylethyl]carbamate

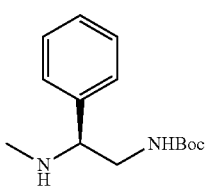 [SMILES: CN[C@H](CNC(=O)OC(C)(C)C)c1ccccc1]

To a solution of (1S)—N-methyl-1-phenylethane-1,2-diamine (258 mg, 1.717 mmol) in dichloromethane (4 mL) at room temperature, was added a solution of di-tert-butyl dicarbonate (337 mg, 1.54 mmol) in dichloromethane (1 mL). The reaction mixture was stirred for two hours and concentrated under reduced pressure. The residue was purified by chromatography to give 260 mg (61%) of tert-butyl [(2S)-2-(methylamino)-2-phenylethyl]carbamate.

Step 4: Preparation of tert-butyl [(2S)-2-{[(3,4-dichlorophenyl)acetyl](methyl) amino}-2-phenylethyl] carbamate

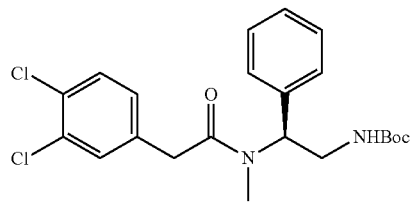 [SMILES: CN(C(=O)Cc1ccc(Cl)c(Cl)c1)[C@H](CNC(=O)OC(C)(C)C)c1ccccc1]

To a solution of tert-butyl [(2S)-2-(methylamino)-2-phenylethyl]carbamate (254 mg, 1.01 mmol) in acetonitrile (4 mL) was added 3,4-dichlorophenyl acetic acid (229 mg, 1.11 mmol), 1-hydroxybenzotriazole hydrate (164 mg, 1.21 mmol), diisopropylethyl amine (265 μl, 1.52 mmol) and N-(3-dimethylaminopropyl)-N'-ethylcarbodiimide hydrochloride (292 mg, 1.522 mmol) at room temperature. The mixture was stirred for two hours and the solvent was removed under reduced pressure. The residue was dissolved in dichloromethane (15 mL), and washed with 10% aqueous sodium carbonate (4×15 mL), 10% aqueous ammonium chloride (4×15 mL), and saturated sodium chloride (15 mL). The organic portion was dried over anhydrous sodium sulfate and concentrated under reduced pressure. The residue was purified by chromatography to give 280 mg (63%) of tert-butyl [(2S)-2-{[(3,4-dichlorophenyl)acetyl](methyl) amino}-2-phenylethyl]carbamate.

Step 5: Preparation of N-[(1S)-2-amino-1-phenylethyl]-2-(3,4-dichlorophenyl)-N-methylacetamide, hydrochloride salt (31)

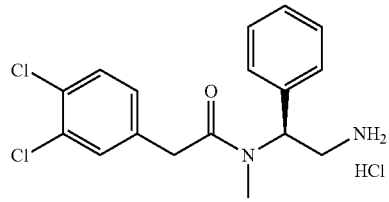 [SMILES: CN(C(=O)Cc1ccc(Cl)c(Cl)c1)[C@H](CN)c1ccccc1 ; Cl]

To a solution of tert-butyl [(2S)-2-{[(3,4-dichlorophenyl)acetyl](methyl)amino}-2-phenylethyl]carbamate (256 mg, 0.585 mmol) in isopropyl alcohol (2 mL) was added 4M hydrochloric acid in isopropyl alcohol (2 mL). The reaction mixture was stirred for two hours at room temperature and was concentrated under reduced pressure to give 195 mg (99%) of N-[(1S)-2-amino-1-phenylethyl]-2-(3,4-dichlorophenyl)-N-methylacetamide hydrochloride as a white solid. $^1$H NMR (500 MHz, DMSO-d6): δ 7.90 (bs, 3H), 7.2-7.6 (m, 8H), 5.95 (dd, 1H), 3.8 (quartet, 2H), 3.55 (dd, 2H), 2.75 (s, 3H); MS (EI): 337.09 (free base).

Example 31

Preparation of 2-(3,4-Dichlorophenyl)-N-{(1S)-2-[(3R,4R)-3,4-dihydroxypyrrolidin-1-yl]-1-phenylethyl}-N-methylacetamide, hydrochloride salt (32)

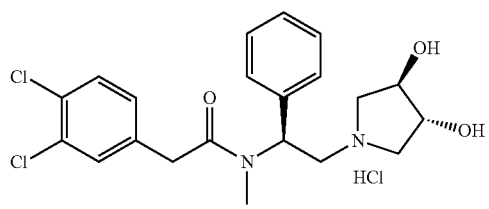

32

2-(3,4-Dichlorophenyl)-N-{(1S)-2-[(3R,4R)-3,4-dihydroxypyrrolidin-1-yl]-1-phenylethyl}-N-methylacetamide hydrochloride salt was prepared according to the following steps.

Step 1: Preparation of benzyl {(1S)-2-[(3R,4R)-3,4-dihydroxypyrrolidin-1-yl]-1-phenylethyl)}carbamate

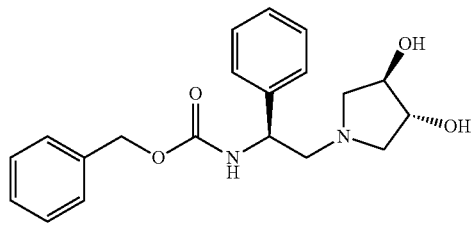 [SMILES: O=C(N[C@H](CN1C[C@@H](O)[C@H](O)C1)c1ccccc1)OCc1ccccc1]

(S)-2-(((Benzyloxy)carbonyl)amino)-2-phenylacetic acid (250 mg, 0.87 mmol), (3R,4R)-pyrrolidine-3,4-diol (90 mg, 0.87 mmol), and N,N-diisopropylethylamine (0.30 mL, 1.75 mmol) were dissolved in 18 mL of tetrahydrofuran. The mixture was stirred for ten minutes at room temperature and then O-(benzotriazol-1-yl)-N,N,N',N'-tetramethyluronium tetrafluoroborate (TBTU) (448 mg, 1.4 mmol) was added into the solution. The reaction mixture was stirred for three hours and then concentrated under reduced pressure. The resulting residue was dissolved in methylene chloride (50 mL) and washed with brine (25 mL×2). The organic phase was separated and dried over anhydrous sodium sulfate and concentrated. The obtained residue was then purified by flash chromatography to yield benzyl {(1S)-2-[(3R,4R)-3,4-dihydroxypyrrolidin-1-yl]-1-phenylethyl}carbamate (250 mg, 0.68 mmol, yield 77%). $^1$H NMR (500 MHz, CDCl$_3$): δ 7.36 (m, 2H), 7.34 (m, 8H), 6.24-6.22 (d, 1H), 5.39 (m, 1 H), 5.10 (d, 1H), 5.03 (d, 1H), 4.20 (m, 1H), 4.10 (m, 1H), 3.89 (m, 1H), 3.67 (m, 3H), 3.11 (m. 2H); MS (EI) for C$_{20}$H$_{24}$N$_2$O$_4$: 371 (MH$^+$).

Preparation of (3R,4R)-1-[(2S)-2-(Methylamino)-2-phenylethyl]pyrrolidine-3,4-diol

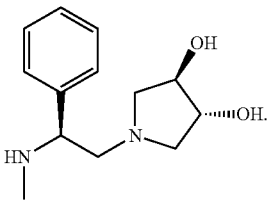 [SMILES: CN[C@H](CN1C[C@@H](O)[C@H](O)C1)c1ccccc1]

Step 2: Benzyl {(1S)-2-[(3R,4R)-3,4-dihydroxypyrrolidin-1-yl]-1-phenylethyl}carbamate (250 mg, 0.68 mmol) was dissolved in tetrahydrofuran (5 mL). The mixture was cooled to 0° C. Lithium aluminum hydride solution in tetrahydrofuran (1M, 2.7 mL, 2.7 mmol) was added to the above mixture and the solution was stirred for 15 minutes at 0° C. and then heated to 65° C. and maintained at that temperature for 14 hours. Sodium sulfate decahydrate was added cautiously until effervescence ceased. The solid was removed by filtration and was washed with methylene chloride (10 mL). The solution was dried over anhydrous sodium sulfate and concentrated under vacuum to obtain the crude product which was used for next step without further purification.

Preparation of 2-(3,4-Dichlorophenyl)-N-{(1S)-2-[(3R,4R)-3,4-dihydroxypyrrolidin-1-yl]-1-phenylethyl}-N-methylacetamide hydrochloride (32)

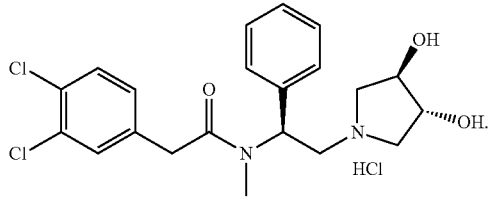 [SMILES: CN(C(=O)Cc1ccc(Cl)c(Cl)c1)[C@H](CN1C[C@@H](O)[C@H](O)C1)c1ccccc1 ; Cl]

(3R,4R)-1-[(2S)-2-(Methylamino)-2-phenylethyl]pyrrolidine-3,4-diol (150 mg, 0.64 mmol), 2-(3,4-dichlorophenyl) acetic acid (131 mg, 0.64 mmol), and N,N-diisopropylethylamine (0.23 ml, 1.28 mmol) were dissolved in methylene chloride (5 mL). The resulting mixture was stirred for 15 minutes at room temperature and then cooled to 0° C. O-(Benzotriazol-1-yl)-N,N,N'N'-tetramethyluronium tetrafluoroborate (TBTU) (227 mg, 0.89 mmol) was added into the solution. The reaction mixture was stirred for 18 hours at room temperature. The solution was added in methylene chloride (50 mL) and washed with water and dried over sodium sulfate. Evaporation of solvent and purification of the resulting residue by flash chromatography gave product as free base, which was then dissolved in 1M hydrochloride in acetonitrile to afford product as hydrochloride salt 2-(3, 4-Dichlorophenyl)-N-{(1S)-2-[(3R,4R)-3,4-dihydroxypyrrolidin-1-yl]-1-phenylethyl}-N-methylacetamide hydrochloride (32) (40 mg, 0.094 mmol, 14% yield for two steps). $^1$H NMR (500 MHz, MeOD): δ 7.43 (m, 2H), 7.40 (m, 3H), 7.30 (m, 2H), 7.25 (m, 1H), 6.31 (m, 1H), 4.28 (d, 2H), 4.17 (m, 1 H), 3.90-3.74 (m, 4H), 3.74 (m, 1H), 3.61 (m, 1H), 3.48 (d, 1H), 2.81 (s, 3H); MS (EI) for C$_{21}$H$_{24}$Cl$_2$N$_2$O$_3$: 423 (MH$^+$).

Example 32

Preparation of 2-(3,4-Dichlorophenyl)-N-{(1S)-2-[(3S)-3-{2-[2-(2-methoxyethoxy)ethoxy]ethoxy}pyrrolidin-1-yl]-1-[4-(trifluoromethyl)phenyl]ethyl}-N-methylacetamide, hydrochloride salt (33)

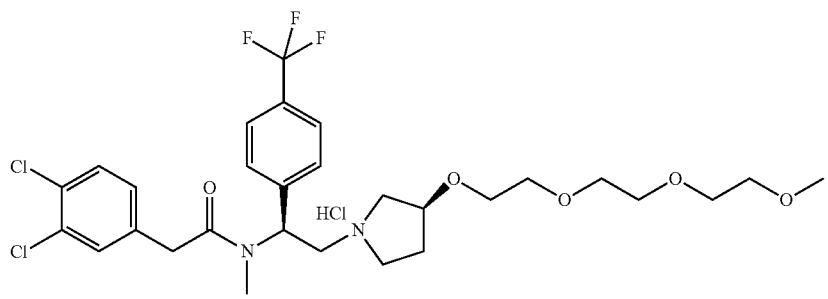

33

2-(3,4-Dichlorophenyl)-N-{(1S)-2-[(3S)-3-{2-[2-(2-methoxyethoxy)ethoxy]ethoxy}pyrrolidin-1-yl]-1-[4-(trifluoromethyl)phenyl]ethyl}-N-methylacetamide hydrochloride was prepared according to the following steps.

Step 1: Preparation of (2S)-[(tert-butoxycarbonyl)amino][4-(trifluoromethyl)phenyl]acetic acid

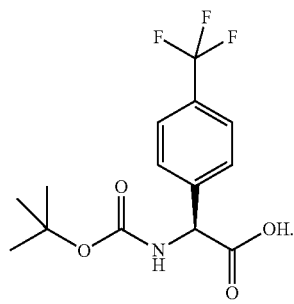 [SMILES: CC(C)(C)OC(=O)N[C@H](C(=O)O)c1ccc(C(F)(F)F)cc1]

4-(Trifluoromethyl)-L-phenylglycine (250 mg, 1.14 mmol) and sodium bicarbonate (168 mg, 2 mmol) were added in a mixture of 10 mL of dioxane and 10 mL water. Boc anhydride (300 mg, 1.37 mg) was added into the solution. The mixture was stirred at room temperature for 18 hours. 2N HCl solution was added to adjust to pH 5. The resulting solution was added to methylene chloride (50 mL) and washed with brine (25 mL×2). The organic phase was separated and dried over anhydrous sodium sulfate and concentrated. The obtained residue was then purified by flash chromatography to yield (2S)-[(tert-butoxycarbonyl)amino][4-(trifluoromethyl)phenyl]acetic acid (340 mg, 1.07 mmol, 93%). $^1$H NMR (500 MHz, CDCl$_3$): δ 8.25 (s, 1H), 7.64 (d, 2H), 7.58 (d, 2H), 5.22 (d, 1H), 3.73 (s, 1H), 1.24 (s, 9H).

Step 2: Preparation of tert-butyl {(1S)-2-[(3S)-3-{2-[2-(2-methoxyethoxy)ethoxy]ethoxy}pyrrolidin-1-yl]-2-oxo-1-[4-(trifluoromethyl)phenyl]ethyl}carbamate

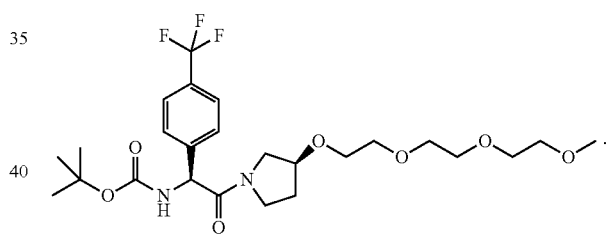

(2S)-[(tert-Butoxycarbonyl)amino][4-(trifluoromethyl)phenyl]acetic acid (293 mg, 1.02 mmol), (S)-3-(2-(2-(2-methoxyethoxy)ethoxy)ethoxy)pyrrolidine (210 mg, 0.90 mmol), and N,N-diisopropylethylamine (0.31 mL, 1.80 mmol) were dissolved in 18 mL of tetrahydrofuran. The mixture was stirred for 10 minutes at room temperature and then O-(benzotriazol-1-yl)-N,N,N',N'-tetramethyluronium tetrafluoroborate (TBTU) (376 mg, 1.17 mmol) was added into the solution and the solution was stirred for three hours. The reaction mixture was concentrated under reduced pressure. The resulting residue was dissolved in methylene chloride (50 mL) and washed with brine (25 mL×2). The solution was dried over anhydrous sodium sulfate and concentrated. The obtained residue was then purified by flash chromatography to yield tert-butyl {(1S)-2-[(3S)-3-{2-[2-(2-methoxyethoxy)ethoxy]ethoxy}pyrrolidin-1-yl]-2-oxo-1-[4-(trifluoromethyl)phenyl]ethyl}carbamate (380 mg, 0.71 mmol, yield 79%). $^1$H NMR (500 MHz, CDCl$_3$): δ 7.62 (m, 2H), 7.55 (m, 2H), 6.12 (dd, 1H), 5.40 (t, 1H), 4.07 (m, 1H), 3.77 (m, 1H), 3.70-3.55 (m, 12H), 3.44 (m, 2H), 3.38 (s, 3H), 2.17-1.76 (m, 2H), 1.41 (d, 9H); MS (EI) for $C_{25}H_{37}F_3N_2O_7$: 535 (MH$^+$).

Step 3: Preparation of 2-(3,4-dichlorophenyl)-N-{(1S)-2-[(3S)-3-{2-[2-(2-methoxyethoxy)ethoxy]ethoxy}pyrrolidin-1-yl]-1-[4-(trifluoromethyl)phenyl]ethyl)}-N-methylacetamide hydrochloride salt (33)

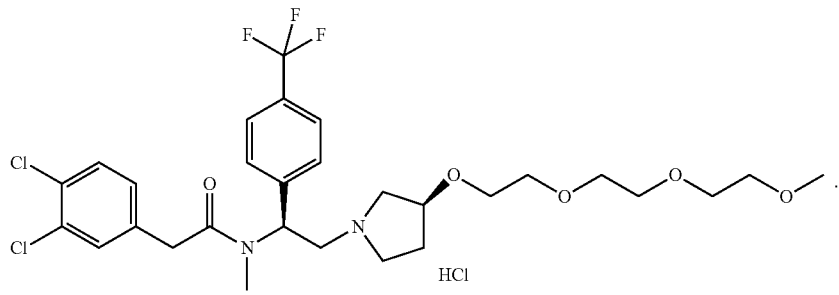 [SMILES: COCCOCCOCCO[C@H]1CCN(C[C@H](c2ccc(C(F)(F)F)cc2)N(C)C(=O)Cc2ccc(Cl)c(Cl)c2)C1 ; Cl]

A solution of tert-butyl {(1S)-2-[(3S)-3-{2-[2-(2-methoxyethoxy)ethoxy]ethoxy}pyrrolidin-1-yl]-2-oxo-1-[4-(trifluoromethyl)phenyl]ethyl}carbamate (380 mg, 0.71 mmol) in tetrahydrofuran (10 mL) was added dropwise to a stirred 1.0 M solution of lithium aluminum hydride (2.84 mL, 2.84 mmol) at room temperature. The mixture was stirred for thirty minutes at room temperature and then was heated to 65° C. for 14 hours. After cooling down to room temperature, sodium sulfate decahydrate was added cautiously until effervescence ceased. The solid was removed by filtration and was washed with methylene chloride (20 mL). The solution was dried over anhydrous sodium sulfate and concentrated under vacuum to obtain the crude product, which was used for next step without further purification. The above obtained crude, 2-(3,4-dichlorophenyl)acetic acid (0.127 g, 0.62 mmol), and N,N-diisopropylethylamine (0.22 g, 1.24 mmol) were dissolved in 3 mL of acetonitrile. The mixture was stirred for 10 minutes at room temperature and then cooled to 0° C. O-(Benzotriazol-1-yl)-N,N,N',N'-tetramethyluronium tetrafluoroborate (TBTU) (0.222 g, 0.87 mmol) was added into the solution. The reaction mixture was stirred for four hours at room temperature and was concentrated. The residue was dissolved in methylene chloride (20 mL), was washed with brine (20 mL). The organic phase was separated and dried over sodium sulfate. Evaporation of the solvent and purification of the residue by flash chromatography yielded 2-(3,4-Dichlorophenyl)-N-{(1S)-2-[(3S)-3-{2-[2-(2-methoxyethoxy)ethoxy]ethoxy}pyrrolidin-1-yl]-1-[4-(trifluoromethyl)phenyl]ethyl}-N-methylacetamide (0.080 g, 0.129 mmol, 20% yield). The free base as dissolved in acetonitrile. To the solution was added 1N hydrochloride. The mixture was lyophilized to afford product as the hydrochloride salt (33). $^1$H NMR (500 MHz, CDCl$_3$): δ 7.60 (d, 2H), 7.43 (d, 2H), 7.42 (d, 1H), 7.29 (s, 1H), 7.18 (d, 1H), 6.12 (m, 1H), 4.06 (m, 1H), 3.81 (m, 1H), 3.72-3.53 (m, 12H), 3.39 (s, 3H), 3.15 (m, 1H), 3.03 (m, 1H), 2.87 (m, 1H), 2.78 (m, 1H), 2.74 (s, 1H), 2.54 (m, 1H), 2.08 (m, 2H), 1.86 (m, 1H); MS (EI) for C$_{29}$H$_{37}$Cl$_2$F$_3$N$_2$O$_5$: 621 (MH$^+$).

The example described above may be modified to introduce oligomers of various lengths as disclosed herein.

Example 33

Preparation of (S)—N-(1-(4-(2,5,8,11,14-pentaoxahexadecan-16-yloxy)phenyl)-2-(pyrrolidin-1-yl)ethyl)-2-(3,4-dichlorophenyl)-N-methylacetamide, hydrochloride salt (34)

Using the procedure outlined in the schematic below, the named compound was prepared.

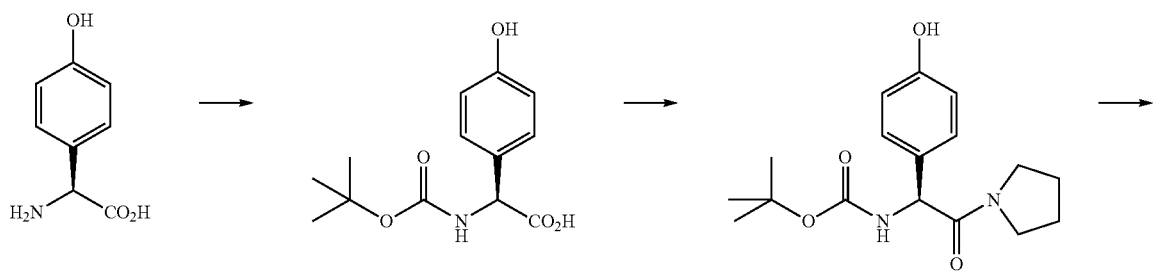

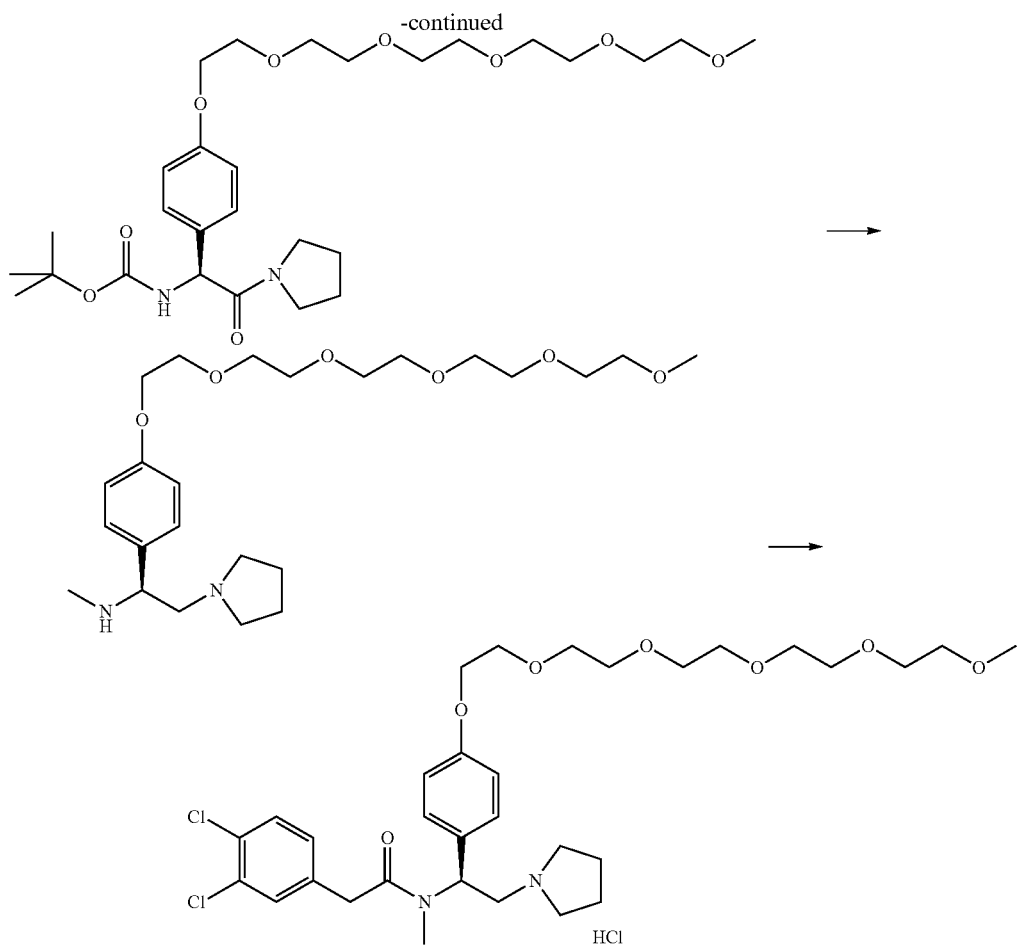

Step 1: Preparation of (S)-2-((tert-butoxycarbonyl)amino)-2-(4-hydroxyphenyl)acetic acid

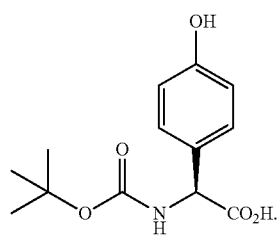 [SMILES: CC(C)(C)OC(=O)N[C@H](C(=O)O)c1ccc(O)cc1]

4-Hydroxy-L-phenylglycine (4.00 g, 23.93 mmol) and sodium bicarbonate (6.04 g, 71.80 mmol) was dissolved in water/tetrahydrofuran (70 mL/70 mL). The solution was cooled in an ice-bath and then di-tert-butyl dicarbonate (7.83 g, 35.90 mmol) was added into the solution. After stirring at room temperature overnight the mixture was washed with ether (50 mL). The aqueous portion was acidified to pH 4 with 2N HCl and extracted with dichloromethane (3×100 mL). The organic portion was washed with saturated sodium chloride (60 mL) and dried over anhydrous sodium sulfate. The organic portion was filtered, concentrated, and dried under high vacuum to give 6.35 g product as a white solid (yield: 99%). $^1$H NMR (500 MHz, CD$_3$OD): δ 7.22 (d, 2H), 6.77 (d, 2H), 5.07 (br, 1H), 1.45 (s, 9H); MS (EI) for C$_{13}$H$_{17}$NO$_5$: 266 (MH$^-$).

Step 2: Preparation of (S)-tert-butyl (1-(4-hydroxyphenyl)-2-oxo-2-(pyrrolidin-1-yl)ethyl)carbamate

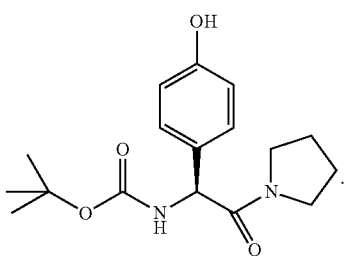 [SMILES: CC(C)(C)OC(=O)N[C@H](C(=O)N1CCCC1)c1ccc(O)cc1]

(S)-2-((Tert-butoxycarbonyl)amino)-2-(4-hydroxyphenyl)acetic acid (0.50 g, 1.87 mmol) and N,N-diisopropylethylamine (0.72 g, 5.61 mmol) were dissolved in 20 mL of dichloromethane. O-(Benzotriazol-1-yl)-N,N,N',N'-tetramethyluronium tetrafluoroborate (0.72 g, 2.25 mmol) and pyrrolidine (0.16 g, 2.25 mmol) in 10 mL of dichloromethane were added into the solution. The reaction mixture was stirred for 16 hours. Dichloromethane (100 mL) was added into the reaction mixture, and the resulted solution was washed with saturated sodium chloride solution (50 mL×2). The solution was dried over sodium sulfate and concentrated. The crude product was purified by flash chromatography and 0.36 g of product was obtained (yield: 60%). $^1$H NMR (500 MHz, CDCl$_3$): δ 7.19 (d, 2H), 6.82 (d, 2H), 5.92 (d, 1H), 5.28 (m, 1H), 3.50 (m, 2 H), 3.40 (m, 1H), 3.06 (m, 1H), 1.80 (m, 4H), 1.36 (s. 9H); MS (EI) for C$_{17}$H$_{24}$N$_2$O$_4$: 321 (MH$^+$).

Step 3: Preparation of (S)-tert-butyl (1-(4-(2,5,8,11,14-pentaoxahexadecan-16-yloxy)phenyl)-2-oxo-2-(pyrrolidin-1-yl)ethyl)carbamate

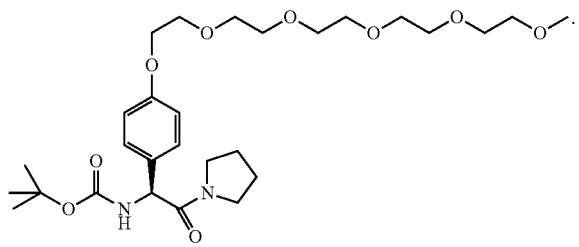 [SMILES: COCCOCCOCCOCCOCCOc1ccc([C@H](NC(=O)OC(C)(C)C)C(=O)N2CCCC2)cc1]

A solution of (S)-tert-butyl (1-(4-hydroxyphenyl)-2-oxo-2-(pyrrolidin-1-yl)ethyl)carbamate (0.30 g, 0.94 mmol) and 16-bromo-2,5,8,11,14-pentaoxahexadecane (0.59 g, 1.87 mmol) in acetone (20 mL) was added sodium carbonate (0.39 g, 2.81 mmol). The mixture was stirred at 70° C. and reaction was completed after six hours. The reaction mixture was cooled to room temperature and 150 mL of dichloromethane was added. The solution was washed with water (150 mL×2). Organic phase was dried over sodium sulfate and was then concentrated under reduced pressure. The residue was purified by column chromatography to provide product (0.51 g, yield: 98%). $^1$H NMR (500 MHz, CDCl$_3$): δ 7.32 (d, 2H), 6.88 (d, 2H), 6.02 (d, 1H), 5.31 (m, 1H), 4.12 (m, 2H), 3.87 (m, 2H), 3.74 (m, 2H), 3.72 (m, 10 H), 3.55 (m, 4H), 3.52 (m, 2H), 3.44 (m, 2H), 3.40 (s, 3H), 3.05 (m, 1H), 1.80 (m, 4H)' 1.41 (s, 9H); MS (EI) for C$_{28}$H$_{46}$N$_2$O$_9$: 555 (MH$^+$).

Step 4: Preparation of (S)-1-(4-(2,5,8,11,14-pentaoxahexadecan-16-yloxy)phenyl)-N-methyl-2-(pyrrolidin-1-yl)ethanamine

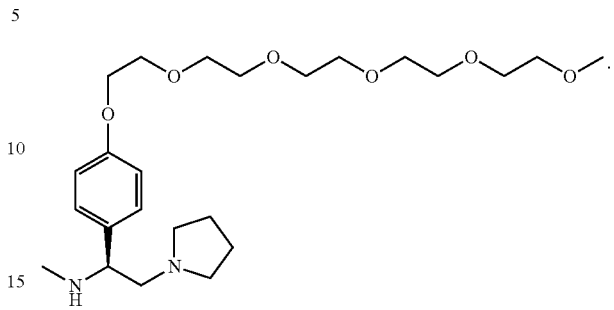

(S)-tert-butyl (1-(4-(2,5,8,11,14-pentaoxahexadecan-16-yloxy)phenyl)-2-oxo-2-(pyrrolidin-1-yl)ethyl)carbamate (0.50 g, 0.90 mmol) in tetrahydrofuran (10 mL) was added dropwise to a stirred 2.0 M solution of lithium aluminum hydride (3 mL, 6.0 mmol) at room temperature. The mixture was stirred for thirty minutes at room temperature and then was heated to 65° C. for four hours. A 3N solution of sodium carbonate was added cautiously until effervescence ceased. The solid was filtered out and washed with dichloromethane (100 mL). The filtrate was concentrated and the residue was dissolved in 150 mL of dichloromethane. The resulted solution was washed with saturated sodium chloride solution (100 mL) and dried over sodium sulfate. The product was obtained after removing solvent (0.33 g, yield 81%). $^1$H NMR (500 MHz, CDCl$_3$): δ 7.27 (d, 2H), 6.89 (d, 2H), 4.13 (m, 2H), 3.85 (m, 2H), 3.75 (m, 2H), 3.68 (m, 10H), 3.60 (m, 1H), 3.55 (m, 4 H), 3.40 (s, 3H), 2.62 (m, 2H), 2.46 (m, 2H), 2.30 (s, 3H), 2.28 (m, 1H), 2.10 (m, 2H)' 1.80 (m, 4H); MS (EI) for C$_{24}$H$_{42}$N$_2$O$_6$: 455 (MH$^+$).

Step 5: Preparation of (S)—N-(1-(4-(2,5,8,11,14-pentaoxahexadecan-16-yloxy)phenyl)-2-(pyrrolidin-1-yl)ethyl)-2-(3,4-dichlorophenyl)-N-methylacetamide, hydrochloride salt (34)

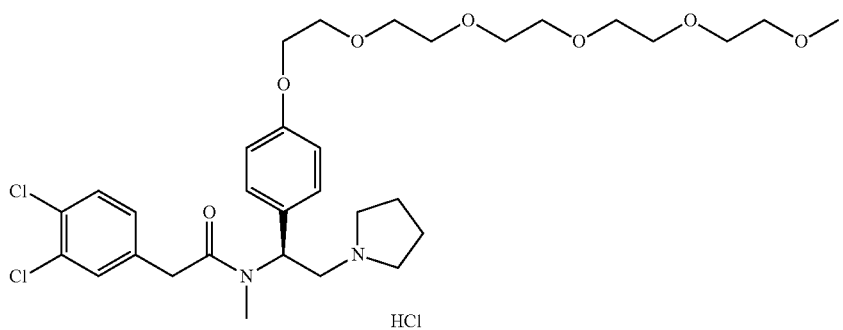 [SMILES: COCCOCCOCCOCCOCCOc1ccc([C@@H](CN2CCCC2)N(C)C(=O)Cc2ccc(Cl)c(Cl)c2)cc1 ; Cl]

(S)-1-(4-(2,5,8,11,14-Pentaoxahexadecan-16-yloxy)phenyl)-N-methyl-2-(pyrrolidin-1-yl)ethanamine (0.33 g, 0.73 mmol), 2-(3,4-dichlorophenyl)acetic acid (0.15 g, 0.73 mmol), and N,N-diisopropylethylamine (0.19 g, 1.47 mmol) were dissolved in 5 mL of acetonitrile. The mixture was stirred for ten minutes at room temperature and then cooled to 0° C. O-(Benzotriazol-1-yl)-N,N,N',N'-tetramethyluronium tetrafluoroborate (0.28 g, 0.88 mmol) was added into the solution. The reaction mixture was stirred for four hours at room temperature. Dichloromethane (150 mL) was added into the solution and the solution was washed with water and dried over sodium sulfate. Evaporation of the solvent and purification of the residue by flash chromatography yielded the target compound (0.22 g, yield: 47%). The free base was dissolved in acetonitrile. To the solution was added 1N hydrochloride. The mixture was lyophilized to afford product as hydrochloride salt. $^1$H NMR (500 MHz, CDCl$_3$): δ 7.35 (d, 2H), 7.18 (d, 2H), 7.10 (m, 1H), 6.85 (d, 2H), 6.04 (m, 0.82H), 4.98 (m, 0.18H), 4.10 (m, 2H), 3.84 (m, 2H), 3.70 (m, 3H), 3.66 (m, 14H), 3.52 (m, 2H), 3.35 (s, 3 H), 3.20 (m, 1H), 2.75 (m, 2H), 2.65 (s, 3H), 2.50 (br., 2H), 1.75 (m, 4H); MS (EI) for C$_{32}$H$_{46}$Cl$_2$N$_2$O$_7$: 641 (MH$^+$).

The example described above may be modified to introduce oligomers of various lengths as disclosed herein.

Example 34

Preparation of (S)—N-(1-(4-(2,5,8,11,14-pentaoxa-hexadecan-16-ylamino)phenyl)-2-(pyrrolidin-1-yl) ethyl)-2-(3,4-dichlorophenyl)-N-methylacetamide, dihydrochloride salt (35)

Using the procedure outlined in the schematic below, the named compound was prepared.

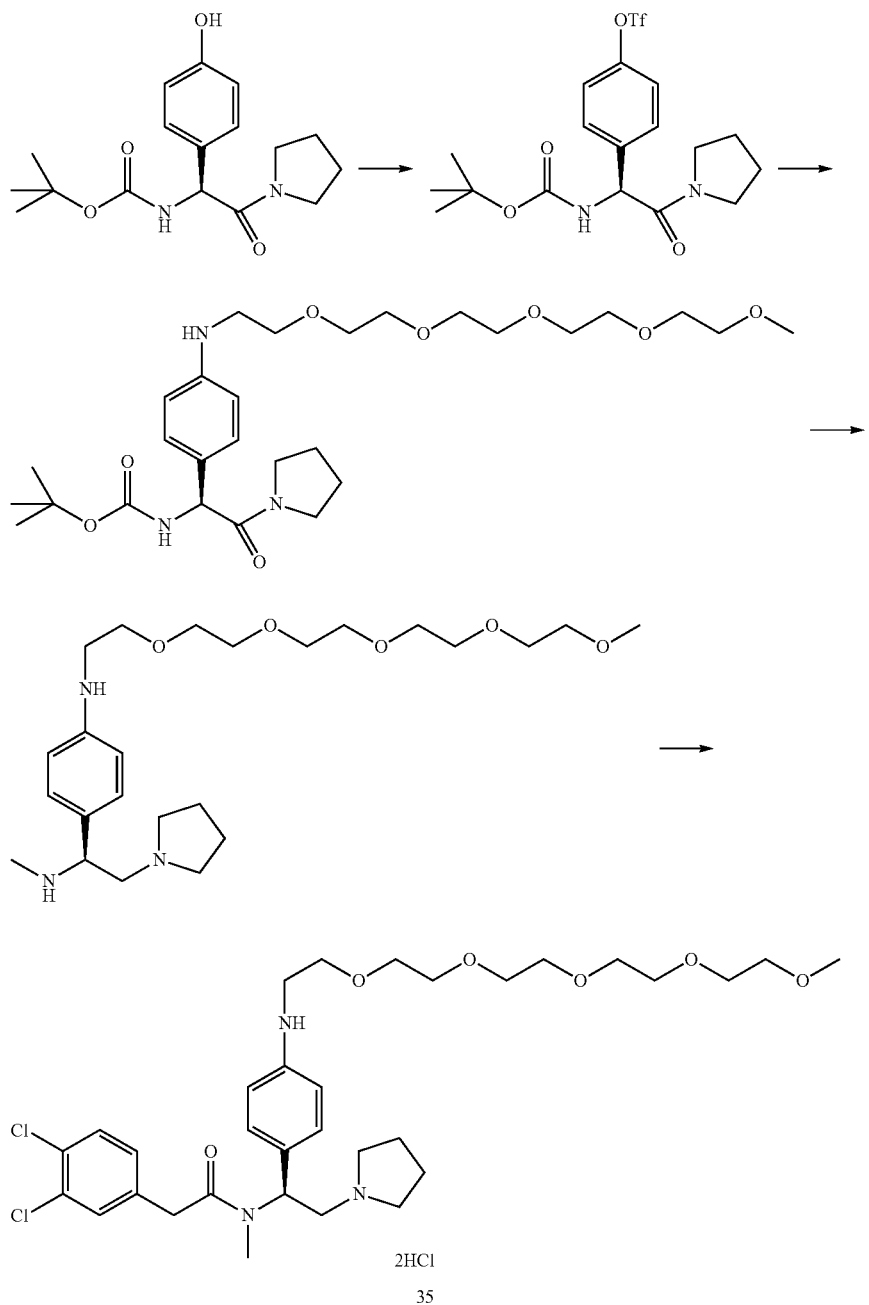

Step 1: Preparation of (S)-4-(1-((tert-butoxycarbonyl)amino)-2-oxo-2-(pyrrolidin-1-yl)ethyl)phenyl trifluoromethanesulfonate

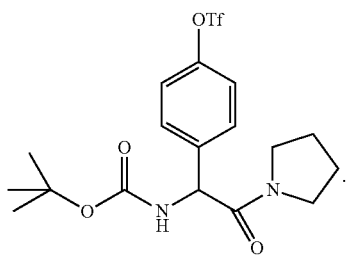 [SMILES: CC(C)(C)OC(=O)NC(C(=O)N1CCCC1)c1ccc(OS(=O)(=O)C(F)(F)F)cc1]

(S)-Tert-butyl (1-(4-hydroxyphenyl)-2-oxo-2-(pyrrolidin-1-yl)ethyl)carbamate (0.40 g, 1.25 mmol) and caesium carbonate (0.61 g, 1.87 mmol) were dissolved in tetrahydrofuran. Then, 1,1,1-trifluoro-N-phenyl-N-((trifluoromethyl)sulfonyl)methanesulfonamide (0.67 g, 1.87 mmol) was added to the mixture and the reaction was stirred under nitrogen at 70° C. for five hours. The tetrahydrofuran was removed by rotavap. To the residue was added dichloromethane (100 mL), followed by 100 mL of water. The organic phase was washed with brine and dried over sodium sulfate. The solvent was removed and the crude product was purified by flash chromatography yielded the target compound (0.45 g, yield: 79%). $^1$H NMR (500 MHz, CDCl$_3$): δ 7.49 (d, 2H), 7.23 (d, 2H), 6.13 (d, 1H), 5.40 (d, 1H), 3.56 (m, 2H), 3.42 (m, 1H), 3.04 (m, 1H), 1.80 (m, 4 H), 1.39 (s, 9H); MS (EI) for $C_{18}H_{23}F_3N_2O_6S$: 453 (MH$^+$).

Step 2: Preparation of (S)-tert-butyl (1-(4-(2,5,8,11,14-pentaoxahexadecan-16-ylamino)phenyl)-2-oxo-2-(pyrrolidin-1-yl)ethyl)carbamate

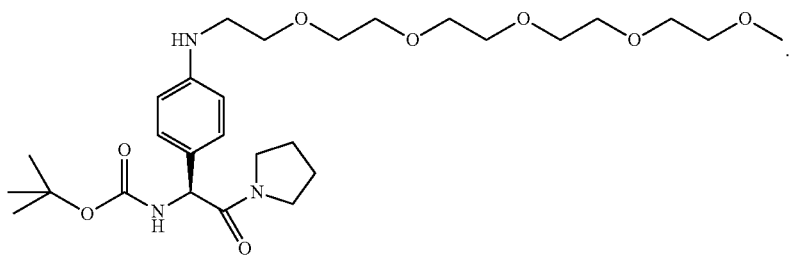 [SMILES: COCCOCCOCCOCCOCCNc1ccc([C@H](NC(=O)OC(C)(C)C)C(=O)N2CCCC2)cc1]

(S)-4-(1-((Tert-butoxycarbonyl)amino)-2-oxo-2-(pyrrolidin-1-yl)ethyl)phenyl trifluoromethanesulfonate (0.20 g, 0.44 mmol) and 2,5,8,11,14-pentaoxahexadecan-16-amine (0.36 g, 1.44 mmol) were dissolved in anhydrous toluene (10 mL). Caesium carbonate (0.47 g, 1.44 mmol), di-tert-butyl (2',4',6'-triisopropyl-3,6-dimethoxy-[1,1'-biphenyl]-2-yl) phosphine (0.048 g, 0.096 mmol), and diacetoxypalladium (0.011 g, 0.049 mmol) were added. The starting material was purged with nitrogen. The mixture was slight yellow after a few minutes. The mixture was stirred at 90° C. for five hours. Water (10 mL) and 2 mL of saturated sodium chloride solution were added into the reaction mixture. The mixture was extracted with dichloromethane (3×40 mL). The combined organic solution was dried over sodium sulfate and then concentrated. The residue was purified with flash column chromatography (0.13 g, yield 49%). $^1$H NMR (500 MHz, CDCl$_3$): δ 7.13 (d, 2H), 6.53 (d, 2H), 5.90 (d, 1H), 5.20 (m, 1H), 3.60 (m, 15H), 3.52 (m, 5H), 3.45 (m, 1H), 3.32 (m, 3H), 3.24 (m, 2H), 3.05 (m, 1H), 1.75 (m, 5 H), 1.35 (s, 9H); MS (EI) for $C_{28}H_{47}N_3O_8$: 554 (MH$^+$).

Step 3: Preparation of (S)—N-(4-(1-(methylamino)-2-(pyrrolidin-1-yl)ethyl)phenyl)-2, 5,8,11,14-pentaoxahexadecan-16-amine

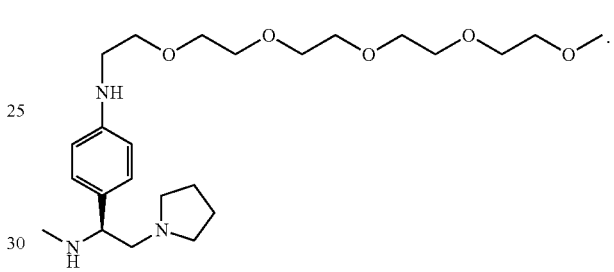

(S)-Tert-butyl (1-(4-(2, 5,8,11,14-pentaoxahexadecan-16-ylamino)phenyl)-2-oxo-2-(pyrrolidin-1-yl) ethyl)carbamate (0.15 g, 0.26 mmol) in tetrahydrofuran (3 mL) was added dropwise to a stirred 2.0 M solution of lithium aluminum hydride (1 mL, 2.0 mmol). The mixture was stirred for thirty minutes at room temperature and then was heated to 65° C. for four hours. A 3N solution of sodium carbonate was added cautiously until effervescence ceased. The solid was filtered out and washed with dichloromethane (100 mL). The filtrate was concentrated and the residue was dissolved in 150 mL of dichloromethane. The resulting solution was dried over sodium sulfate. The product was obtained after removing solvent (0.10 g, yield 84%). $^1$H NMR (500 MHz, CDCl$_3$): δ 7.27 (m, 2H), 6.58 (m, 2H), 3.65 (m, 16H), 3.51 (m, 2H), 3.50 (m, 1H), 3.35 (s, 3H), 3.30 (m, 2H), 3.12 (m, 2H), 2.85 (m, 1H), 2.60 (m, 2H), 2.40 (m, 2H), 2.25 (m, 3H), 1.75 (m, 4H); MS (EI) for $C_{24}H_{43}N_3O_5$: 454 (MH$^+$).

Step 4: Preparation of (S)—N-(1-(4-(2,5,8,11,14-pentaoxahexadecan-16-ylamino)phenyl)-2-(pyrrolidin-1-yl)ethyl)-2-(3,4-dichlorophenyl)-N-methylacetamide, dihydrochloride salt (35)

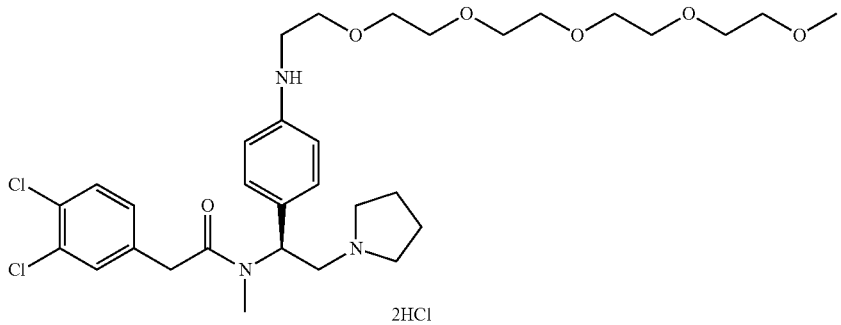

2HCl (S)—N-(4-(1-(Methylamino)-2-(pyrrolidin-1-yl)ethyl)phenyl)-2,5,8,11,14-pentaoxahexadecan-16-amine (0.10 g, 0.22 mmol), 2-(3,4-dichlorophenyl)acetic acid (0.041 g, 0.20 mmol), and N,N-diisopropylethylamine (0.056 g, 0.44 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.085 g, 0.27 mmol) was added into the solution. The reaction mixture was stirred for four hours at 0° C. Dichloromethane (100 mL) was added into the solution and the solution was washed with water and dried over sodium sulfate. Evaporation of the solvent and purification of the residue by flash chromatography yielded the target compound (0.040 g, yield: 28%). The free base was dissolved in acetonitrile. To the solution was added 1N hydrochloride. The mixture was lyophilized to afford product as the dihydrochloride salt (35). $^1$H NMR (500 MHz, CDCl$_3$): δ 7.35 (d, 2H), 7.18 (d, 2H), 7.10 (m, 1H), 6.58 (d, 2H), 6.05 (m, 0.8H), 4.96 (m, 0.2H), 4.25 (br. 1H). 3.82 (m, 1H), 3.66 (m, 17H), 3.55 (m, 2H), 3.40 (s, 3H), 3.30 (m, 2H), 2.95 (m, 1H), 2.78 (m, 2H), 2.70 (m, 3H), 2.50 (m, 2H), 1.80 (m, 4H); MS (EI) for C$_{32}$H$_{47}$Cl$_2$N$_3$O$_6$: 640 (MH$^+$).

The example described above may be modified to introduce oligomers of various lengths as disclosed herein.

Example 35

Preparation of (S)-2-(3,4-dichlorophenyl)-N-(1-(4-(2-hydroxyethoxy)phenyl)-2-(pyrrolidin-1-yl)ethyl)-N-methylacetamide, hydrochloride salt (36)

Using the procedure outlined in the schematic below, the named compound was prepared.

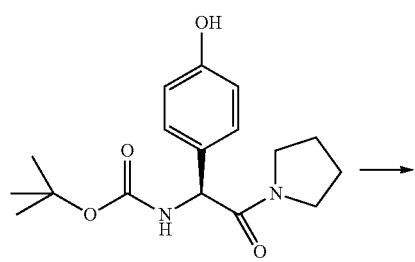

-continued

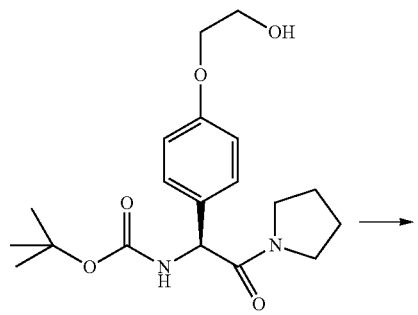

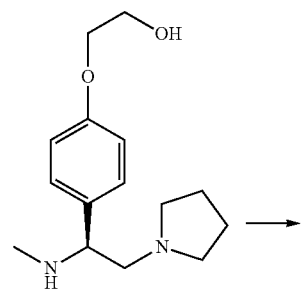

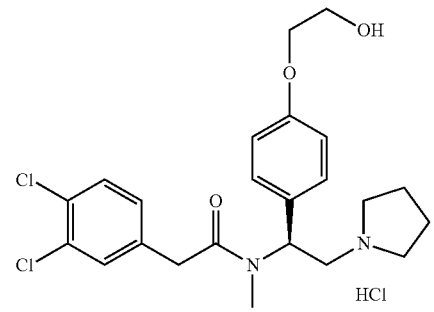

36

Step 1: Preparation of (S)-tert-butyl (1-(4-(2-hydroxyethoxy)phenyl)-2-oxo-2-(pyrrolidin-1-yl)ethyl) carbamate

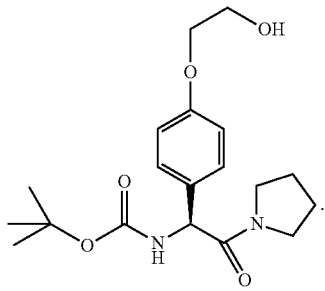 [SMILES: CC(C)(C)OC(=O)N[C@H](C(=O)N1CCCC1)c1ccc(OCCO)cc1]

A solution of (S)-tert-butyl (1-(4-hydroxyphenyl)-2-oxo-2-(pyrrolidin-1-yl)ethyl)carbamate (0.30 g, 0.94 mmol) and 2-bromoethanol (0.37 g, 2.81 mmol) in acetone (15 mL) was added potassium carbonate (0.39 g, 2.81 mmol). The mixture was stirred at 70° C. for six hours. 2-Bromoethanol (0.5 g) and 0.4 g of potassium carbonate were added. The mixture was stirred overnight at 70° C. After this period, the reaction mixture was cooled to room temperature and 150 mL of dichloromethane was added. The solid was filtered out and solution was washed with brine (150 mL×2). The organic phase was dried over sodium sulfate and was then concentrated under reduced pressure. The residue was purified by column chromatography to provide product (0.27 g, yield: 80%). $^1$H NMR (500 MHz, CDCl$_3$): δ 7.30 (d, 2H), 6.85 (d, 2H), 6.05 (d, 1H), 5.30 (m, 1H), 4.05 (m, 2H), 3.95 (m, 2H), 3.52 (m, 2H), 3.40 (m, 1H), 3.06 (m, 1H), 1.80 (m, 5 H), 1.35 (s, 9H); MS (EI) for C$_{19}$H$_{28}$N$_2$O$_5$: 365 (MH$^+$).

Step 2: Preparation of (S)-2-(4-(1-(methylamino)-2-(pyrrolidin-1-yl)ethyl)phenoxy)ethanol

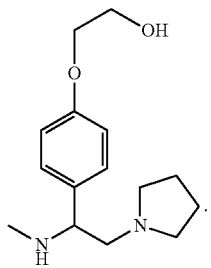 [SMILES: CNC(CN1CCCC1)c1ccc(OCCO)cc1]

(S)-Tert-butyl (1-(4-(2, 5,8,11,14-pentaoxahexadecan-16-ylamino)phenyl)-2-oxo-2-(pyrrolidin-1-yl) ethyl)carbamate (0.24 g, 0.66 mmol) was dissolved in tetrahydrofuran (5 mL). A 2.0 M solution of lithium aluminum hydride (2 mL, 4.0 mmol) was added into the solution at room temperature. The mixture was stirred for thirty minutes at room temperature and then was heated to 65° C. for four hours. A 3N solution of sodium carbonate was added cautiously until effervescence ceased. The solid was filtered out and washed with dichloromethane (100 mL). The filtrate was concentrated and the residue was dissolved in 150 mL of dichloromethane. The resulted solution was washed with sodium bicarbonate solution and dried over sodium sulfate. The product was obtained after removing solvent (0.66 g, yield 38%). $^1$H NMR (500 MHz, CDCl$_3$): δ 7.24 (d, 2H), 6.86 (d, 2H), 4.05 (m, 2H), 3.92 (m, 2H), 3.50 (m, 3H), 2.86 (t, 1H), 2.60 (m, 2H), 2.45 (m, 2H), 2.30 (s, 3H), 1.75 (m, 4H); MS (EI) for C$_{15}$H$_{24}$N$_2$O$_2$: 265 (MH$^+$).

Step 3: Preparation of: (S)-2-(3,4-dichlorophenyl)-N-(1-(4-(2-hydroxyethoxy)phenyl)-2-(pyrrolidin-1-yl)ethyl)-N-methylacetamide, hydrochloride salt (36)

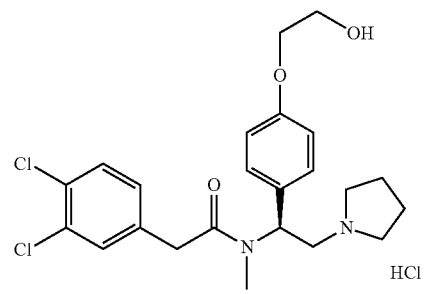 [SMILES: CN(C(=O)Cc1ccc(Cl)c(Cl)c1)[C@H](CN1CCCC1)c1ccc(OCCO)cc1 ; Cl]

(S)-2-(4-(1-(Methylamino)-2-(pyrrolidin-1-yl)ethyl)phenoxy)ethanol (0.066 g, 0.25 mmol), 3,4-dichlorophenylacetic acid (0.049 g, 0.237 mmol), and N,N-diisopropylethylamine (0.064 g, 0.50 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.096 g, 0.30 mmol) was added into the solution. The reaction mixture was stirred for four hours at 0° C. Dichloromethane (100 mL) was added into the solution and the solution was washed with water and dried over sodium sulfate. Evaporation of the solvent and purification of the residue by flash chromatography yielded the target compound (0.05 g, yield: 44%). The free base was dissolved in acetonitrile. To the solution was added 1N hydrochloride. The mixture was lyophilized to afford product as hydrochloride salt (36). $^1$H NMR (500 MHz, CDCl$_3$): δ 7.37 (m, 2H), 7.25 (m, 2H), 7.15 (m, 1H), 6.90 (m, 2H), 6.09 (m, 0.8H), 5.02 (m, 0.2H), 4.09 (m, 2H), 3.97 (m, 2H), 3.28 (m, 1H), 3.70 (m, 1H), 3.20 (br., 1H), 2.75 (m, 5H), 2.52 (m, 3H), 1.80 (m, 4H); MS (EI) for C$_{23}$H$_{28}$Cl$_2$N$_2$O$_3$: 451 (MH$^+$).

Example 36

Preparation of 2-(3,4-Dichlorophenyl)-N-{(1S)-1-[4-(2-hydroxyethoxy)phenyl]-2-[(3S)-3-{2-[2-(2-methoxyethoxy)ethoxy]ethoxy}pyrrolidin-1-yl] ethyl}-N-methylacetamide, hydrochloride (37)

Using the procedure outlined in the schematic below, the named compound was prepared.

119 120

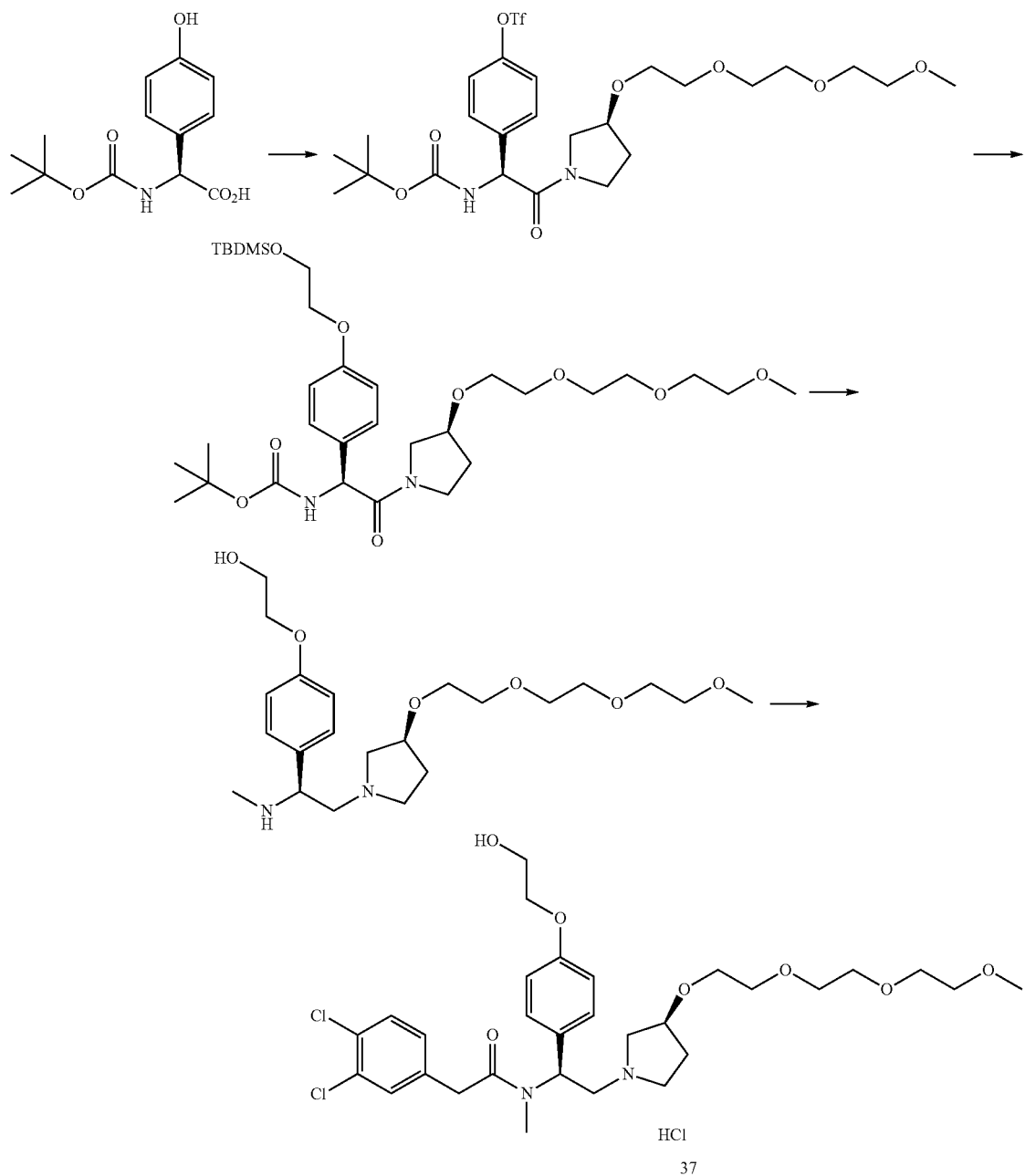

Step 1: Preparation of tert-butyl ((S)-1-(4-hydroxyphenyl)-2-((S)-3-(2-(2-(2-methoxyethoxy)ethoxy)ethoxy)pyrrolidin-1-yl)-2-oxoethyl)carbamate

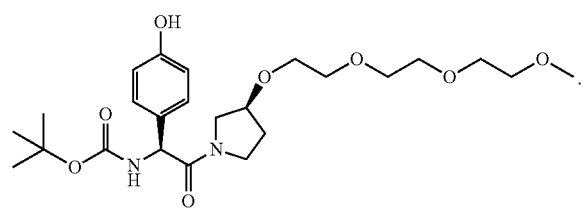 [SMILES: COCCOCCOCCO[C@H]1CCN(C(=O)[C@@H](NC(=O)OC(C)(C)C)c2ccc(O)cc2)C1]

(S)-3-(2-(2-(2-Methoxyethoxy)ethoxy)ethoxy)pyrrolidine HCl salt (0.505 g, 1.87 mmol) and N,N-diisopropylethylamine (0.84 g, 6.55 mmol) were dissolved in 20 mL of dichloromethane. (S)-2-((Tert-butoxycarbonyl)amino)-2-(4-hydroxyphenyl)acetic acid (0.50 g, 1.87 mmol) was added into the solution and the mixture was cooled in an ice-bath under stirring. O-(Benzotriazol-1-yl)-N,N,N',N'-tetramethyluronium tetrafluoroborate (0.72 g, 2.25 mmol) was added into the solution. The reaction mixture was stirred for four hours at room temperature. Dichloromethane (150 mL) was added into the mixture and resultant solution was washed with water (2×100 mL) and dried over sodium sulfate. The crude product was purified by flash chromatography and 0.72 g product was obtained (yield: 80%). $^1$H NMR (500 MHz, CDCl$_3$): δ 7.45 (m, 1H), 7.28 (m, 2H), 6.81 (m, 2H), 5.98 (m, 1H), 5.25 (m, 1H), 4.00 (m, 1H), 4.00 (m, 1H), 3.65 (m, 6H), 3.52 (m, 3H), 3.42 (s, 3H), 3.35 (m, 3H), 3.20 (m, 2H), 2.90 (m, 1H), 2.00 (m, 1H), 1.90 (m, 1H), 1.42 (s, 9H); MS (EI) for $C_{24}H_{38}N_2O_8$: 483 (MH$^+$).

Step 2: Preparation of tert-butyl ((S)-1-(4-(2-((tert-butyldimethylsilyl)oxy)ethoxy)phenyl)-2-((S)-3-(2-(2-(2-methoxyethoxy)ethoxy)ethoxy)pyrrolidin-1-yl)-2-oxoethyl)carbamate

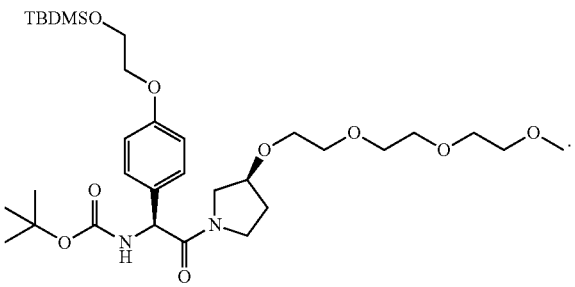 [SMILES: COCCOCCOCCO[C@H]1CCN(C(=O)[C@@H](NC(=O)OC(C)(C)C)c2ccc(OCCO[Si](C)(C)C(C)(C)C)cc2)C1]

A solution of tert-butyl ((S)-1-(4-hydroxyphenyl)-2-((S)-3-(2-(2-(2-methoxyethoxy)ethoxy)ethoxy)pyrrolidin-1-yl)-2-oxoethyl)carbamate (0.54 g, 1.12 mmol) and (2-bromoethoxy)(tert-butyl)dimethylsilane (1.34 g, 5.60 mmol) in acetone (20 mL) was added potassium carbonate (0.77 g, 5.60 mmol). The mixture was stirred at 70° C. for twenty hours. After this period, the reaction mixture was cooled to room temperature and 150 mL of dichloromethane was added. The solution was washed with water (150 mL×2). The organic phase was dried over sodium sulfate and was then concentrated under reduced pressure. The residue was purified by column chromatography (0.62 g, yield: 86%). $^1$H NMR (500 MHz, CDCl$_3$): δ 7.31 (m, 2H), 6.88 (d, 2H), 6.00 (dd, 1H), 5.30 (m, 1H), 4.08 (m, 3H), 3.96 (m, 2H), 3.85 (m, 2H), 3.62 (m, 10H), 3.45 (m, 2H), 3.40 (s, 3H), 3.25 (m, 1H), 2.10 (m, 1H), 1.95 (m, 1H), 1.80 (m, 1H), 1.40 (s, 9H), 0.90 (s, 9H), 0.10 (m, 6H); MS (EI) for $C_{32}H_{56}N_2O_9Si$; 641 (MH$^+$).

Step 3: Preparation of 2-(4-((S)-2-((S)-3-(2-(2-(2-methoxyethoxy)ethoxy)ethoxy)pyrrolidin-1-yl)-1-(methylamino)ethyl)phenoxy)ethanol

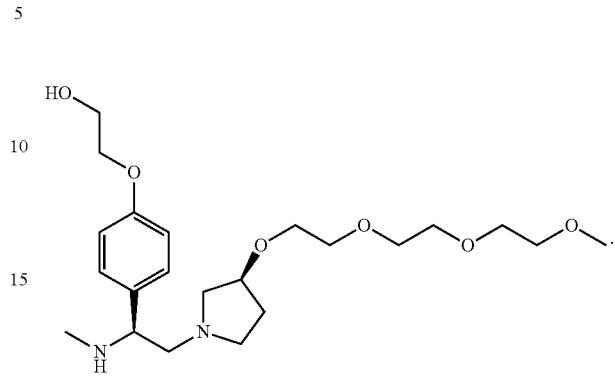

Tert-butyl ((S)-1-(4-(2-((tert-butyldimethylsilyl)oxy)ethoxy)phenyl)-2-((S)-3-(2-(2-(2-methoxyethoxy)ethoxy)ethoxy)pyrrolidin-1-yl)-2-oxoethyl)carbamate (0.52 g, 0.80 mmol) was dissolved in tetrahydrofuran (6 mL). A 2.0 M solution of lithium aluminum hydride (2.8 mL, 5.6 mmol) was added into the solution at room temperature. The mixture was stirred at 65° C. for four hours. A 3N solution of sodium carbonate was added cautiously until effervescence ceased. Dichloromethane (50 mL) was added into the mixture. The solid was filtered out and washed with dichloromethane (100 mL). The filtrate was washed with saturated sodium chloride solution and dried over sodium sulfate. The product was obtained after removing solvent (0.23 g, yield 60%). $^1$H NMR (500 MHz, CDCl$_3$): δ 7.25 (m, 2H), 6.88 (m, 2H), 4.06 (m, 3H), 3.95 (m, 2H), 3.65 (m, 9H), 3.55 (m, 5H), 3.40 (s, 3H), 3.30 (br., 2H), 2.82 (m, 3H), 2.55 (m, 1H), 2.44 (m, 1H), 2.30 (m, 1H), 2.06 (m, 1H), 1.80 (m, 1H); MS (EI) for $C_{22}H_{38}N_2O_6$; 427 (MH$^+$).

Step 4: Preparation of 2-(3,4-Dichlorophenyl)-N-{(1S)-1-[4-(2-hydroxyethoxy)phenyl]-2-[(3S)-3-{2-[2-(2-methoxyethoxy)ethoxy]ethoxy}pyrrolidin-1-yl]ethyl}-N-methylacetamide, hydrochloride salt (37)

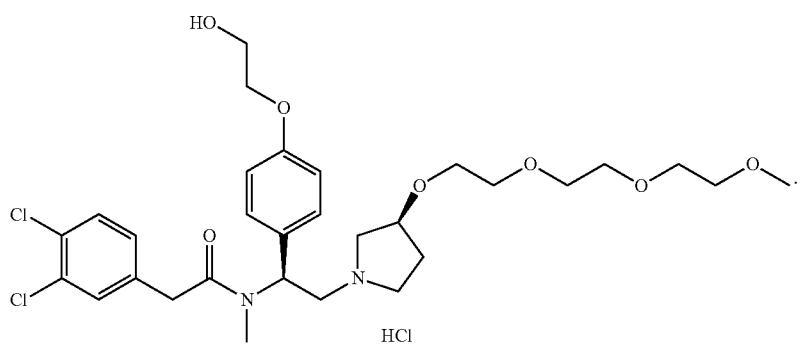 [SMILES: COCCOCCOCCO[C@H]1CCN(C[C@H](c2ccc(OCCO)cc2)N(C)C(=O)Cc2ccc(Cl)c(Cl)c2)C1 ; Cl]

2-(4-((S)-2-((S)-3-(2-(2-(2-methoxyethoxy)ethoxy)ethoxy)pyrrolidin-1-yl)-1-(methylamino)ethyl)phenoxy)ethanol (0.21 g of 80%, 0.39 mmol), 3,4-dichlorophenylacetic acid (0.081 g, 0.39 mmol), and N,N-diisopropylethylamine (0.10 g, 0.79 mmol) were dissolved in 5 mL of acetonitrile. The mixture was stirred for ten minutes at room temperature and then cooled to 0° C. O-(Benzotriazol-1-yl)-N,N,N',N'-tetramethyluronium tetrafluoroborate (0.15 g, 0.47 mmol) was added into the solution. The reaction mixture was stirred for one hour at 0° C. and then overnight. Dichloromethane (150 mL) was added into the solution and the solution was washed with water and dried over sodium sulfate. Evaporation of the solvent and purification of the residue by flash chromatography yielded product (0.20 g, yield: 83%). The free base was dissolved in acetonitrile. To the solution was added 1N hydrochloride. The mixture was lyophilized to afford product as hydrochloride salt (37). $^1$H NMR (500 MHz, CDCl$_3$): δ 7.36 (m, 2H), 7.18 (m, 2H), 7.05 (m, 1H), 6.82 (m, 2H), 6.00 (m, 0.83H), 4.96 (m, 0.17H), 4.02 (m, 3H), 3.90 (m, 1H), 3.76 (m, 1H), 3.65 (m, 9H), 3.55 (m, 4H), 3.45 (s, 3H), 3.14 (m, 1H), 3.00 (m, 1H), 2.80 (m, 3H), 2.65 (s, 3H), 2.62 (m, 1H), 2.50 (m, 2H), 2.00 (m, 1H), 1.80 (m, 1H); MS (EI) for C$_{30}$H$_{42}$Cl$_2$N$_2$O$_7$: 613 (MH$^+$).

The example described above may be modified to introduce oligomers of various lengths as disclosed herein.

Example 37

Preparation of 2-(3,4-dichlorophenyl)-N—((S)-1-(4-(2-hydroxyethoxy)phenyl)-2-((S)-3-hydroxypyrrolidin-1-yl)ethyl)-N-methylacetamide, hydrochloride salt (38)

Using the procedure outlined in the schematic below, the named compound was prepared.

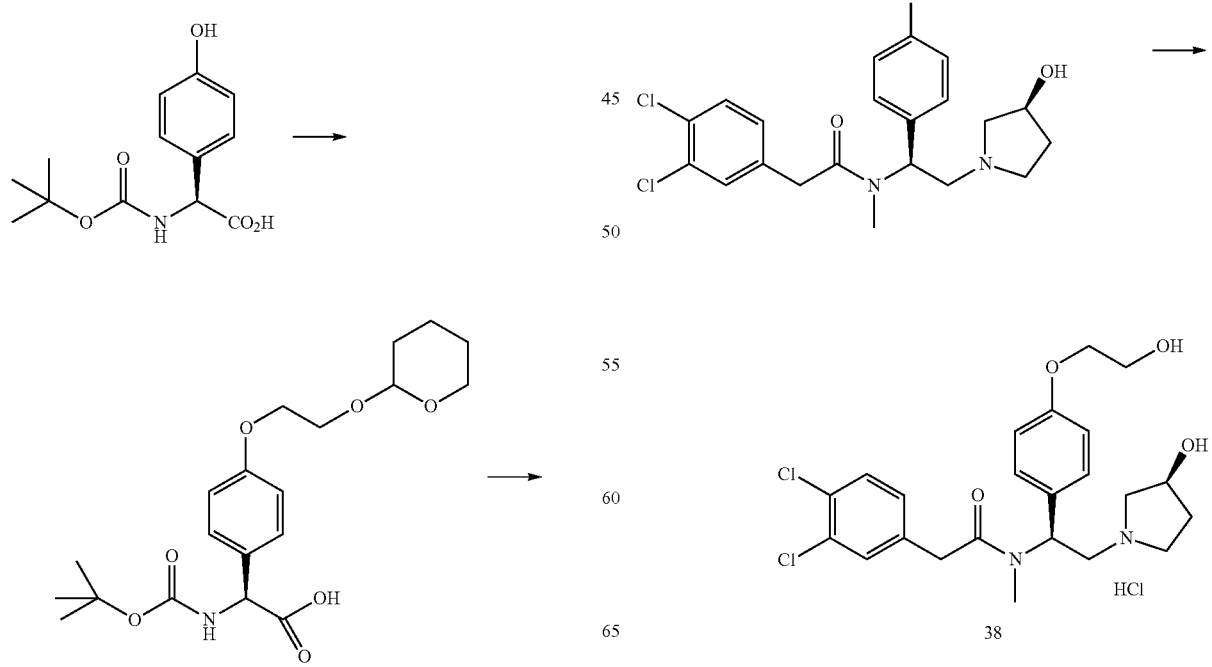

Step 1: Preparation of (2S)-2-((tert-butoxycarbonyl)amino)-2-(4-(2-((tetrahydro-2H-pyran-2-yl)oxy)ethoxy)phenyl)acetic acid

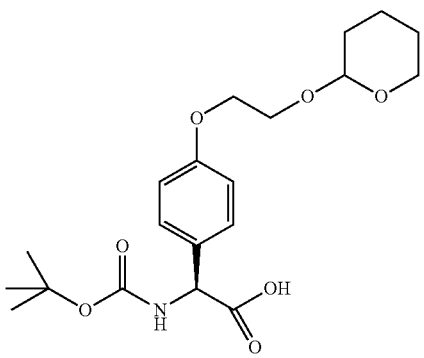

(S)-2-((Tert-butoxycarbonyl)amino)-2-(4-hydroxyphenyl)acetic acid (2.67 g, 10.0 mmol) was dissolved in 70 mL of dimethylformamide and the solution was cooled in an ice bath. Sodium hydride (0.88 g, 60% in mineral oil, 22.0 mmol) was added in portions. The mixture was stirred for thirty minutes before 2-(2-bromoethoxy)tetrahydro-2H-pyran (2.30 g, 11.0 mmol) in 30 mL of dimethylformamide was added portionally. The reaction mixture was stirred at room temperature for 17 hours. Sodium hydride (0.16 g) was added and reaction was continued for one hour and then diluted with ice/water. The mixture was extracted with ethyl acetate (100 mL×2). The aqueous layer was cooled in an ice bath and acidified using 1.5 M aqueous potassium hydrogen sulfate to pH 2-3. The resulting mixture was extracted with ethyl acetate (100 mL×2). The organic phase was washed with water, brine, and dried over sodium sulfate. The product (3.3 g) was obtained (yield: 84%). $^1$H NMR (500 MHz, CDCl$_3$): δ 7.32 (m, 2H), 6.92 (m, 2H), 5.55 (m, 0.5H), 5.28 (m, 0.5H), 4.74 (m, 1H), 4.15 (m, 2H), 4.05 (m, 1H), 3.90 (m, 1H), 3.85 (m, 1H), 3.55 (m, 1H), 1.85 (m, 1H), 1.75 (m, 1H), 1.60 (m, 5H), 1.45 (s, 5H), 1.28 (s, 4H); MS (EI) for C$_{20}$H$_{29}$NO$_7$; 394 (MH$^-$).

Step 2: Preparation of tert-butyl ((1S)-2-((S)-3-hydroxypyrrolidin-1-yl)-2-oxo-1-(4-(2-((tetrahydro-2H-pyran-2-yl)oxy)ethoxy)phenyl)ethyl)carbamate

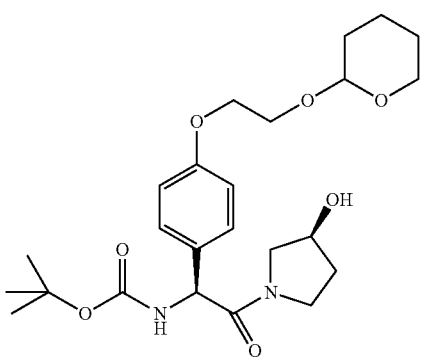

(2S)-2-((Tert-butoxycarbonyl)amino)-2-(4-(2-((tetrahydro-2H-pyran-2-yl)oxy)ethoxy)phenyl)acetic acid (3.20 g, 8.09 mmol), (s)-pyrrolidin-3-ol (0.78 g, 8.90 mmol), and N,N-diisopropylethylamine (2.07 g, 16.18 mmol) were dissolved in 18 mL of acetonitrile. The mixture was stirred for 10 min. at room temperature and then cooled to 0° C. O-(Benzotriazol-1-yl)-N,N,N',N'-tetramethyluronium tetrafluoroborate (3.12 g, 9.71 mmol) was added into the solution. The reaction mixture was stirred for two hours under an ice bath (15% starting materials remaining) and the reaction was continued at room temperature for four hours (no change). O-(Benzotriazol-1-yl)-N,N,N',N'-tetramethyluronium tetrafluoroborate (120 mg) was added and the reaction was completed after one hour. Dichloromethane (200 mL) was added into the reaction mixture, and the resulted solution was washed with water (200 mL×3). The solution was dried over sodium sulfate and concentrated. The product was obtained after dried under vacuum (3.40 g, yield: 90%). $^1$H NMR (500 MHz, CDCl$_3$): δ 7.30 (m, 2H), 6.90 (m, 2H), 5.96 (dd, 1H), 5.30 (dd, 1H), 4.70 (m, 1H), 4.45 (m, 1H), 4.15 (m, 1H), 4.05 (m, 1H), 3.90 (m, 1H), 3.80 (m, 1H), 3.70 (m, 2H), 3.55 (m, 2H), 3.35 (m, 0.5H), 3.10 (m, 0.5H), 1.96 (m, 1H), 1.85 (m, 2H), 1.75 (m, 1H), 1.60 (m, 2H), 1.55 (m, 3H), 1.40 (s, 9H); MS (EI) for C$_{24}$H$_{36}$N$_2$O$_7$; 465 (MH$^+$).

Step 3: Preparation of (3S)-1-((2S)-2-(methylamino)-2-(4-(2-((tetrahydro-2H-pyran-2-yl)oxy)ethoxy)phenyl)ethyl)pyrrolidin-3-ol

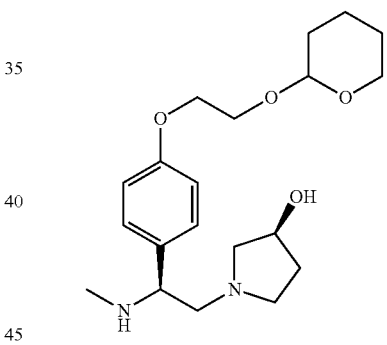

Tert-butyl ((1S)-2-((S)-3-hydroxypyrrolidin-1-yl)-2-oxo-1-(4-(2-((tetrahydro-2H-pyran-2-yl)oxy)ethoxy)phenyl)ethyl)carbamate (1.33 g, 2.85 mmol) was dissolved in tetrahydrofuran (20 mL). A 2.0 M solution of lithium aluminum hydride (8.0 mL, 16 mmol) was added into the solution at room temperature. The mixture was stirred at 65° C. for four hours. A 3N solution of sodium carbonate was added cautiously until effervescence ceased. Ethyl acetate (100 mL) was added into the mixture. The solid was filtered out and washed with ethyl acetate (100 mL). The filtrate was washed with saturated sodium chloride solution and dried over sodium sulfate. The product was obtained after removing solvent (0.84 g, yield: 71%). $^1$H NMR (500 MHz, CDCl$_3$): δ 7.28 (m, 2H), 6.92 (m, 2H), 4.74 (m, 1H), 4.34 (m, 1H), 4.16 (m, 2H), 4.06 (m, 1H), 3.92 (m, 1H), 3.84 (m, 1H), 3.55 (m, 2H), 3.02 (m, 1H), 2.85 (m, 1H), 2.65 (m, 2H), 2.30 (m, 3H), 2.20 (m, 2H), 1.80 (m, 4H), 1.60 (m, 5H); MS (EI) for C$_{20}$H$_{32}$N$_2$O$_4$; 365 (MH$^+$).

Step 4: Preparation of 2-(3,4-dichlorophenyl)-N—((S)-1-(4-(2-hydroxyethoxy)phenyl)-2-((S)-3-hydroxypyrrolidin-1-yl)ethyl)-N-methylacetamide, hydrochloride salt (38)

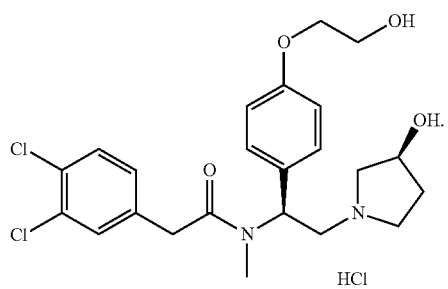 [SMILES: CN(C(=O)Cc1ccc(Cl)c(Cl)c1)[C@H](CN1CC[C@H](O)C1)c1ccc(OCCO)cc1 ; Cl]

(3S)-1-((2S)-2-(methylamino)-2-(4-(2-((tetrahydro-2H-pyran-2-yl)oxy)ethoxy)phenyl)ethyl)pyrrolidin-3-ol (0.092 g of 80%, 0.20 mmol), 3,4-dichlorophenylacetic acid (0.041 g, 0.20 mmol), and N,N-diisopropylethylamine (0.052 g, 0.40 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.078 g, 0.24 mmol) was added into the solution. The reaction mixture was stirred for three hours under an ice-bath. Dichloromethane (150 mL) was added into the solution and the resultant solution was washed with water and dried over sodium sulfate. Evaporation of the solvent and purification of the residue by flash chromatography yielded an oil (0.090 g, 0.16 mmol), which was dissolved in 10 mL of CH₃OH. p-Toluenesulfonic acid (0.056 g, 0.32 mmol) was added into the solution. The mixture was stirred for sixty minutes at room temperature. Dichloromethane (100 mL) was added into the solution and the solution was washed with sodium carbonate (10%), water and dried over sodium sulfate. Evaporation of the solvent and purification of the residue by flash chromatography yielded product as an oil (0.046 g, yield: 60%). The free base was dissolved in acetonitrile. To the solution was added 1N hydrochloride. The mixture was lyophilized to afford product as hydrochloride salt (38). $^1$H NMR (500 MHz, CDCl$_3$): δ 7.40 (m, 2H), 7.22, 7.05 (dd, 2H), 7.15 (m, 1H), 6.90 (m, 2H), 6.05 (m, 0.84H), 5.00 (m, 0.16H), 4.31 (m, 1H), 4.10 (m, 2H), 3.96 (m, 2H), 3.72 (m, 2H), 3.10 (m, 2H), 2.75 (m, 2H), 2.70 (s, 3H), 2.55 (m, 1H), 2.35 (m, 2H), 2.20 (m, 2H), 1.72 (m, 1H); MS (EI) for C$_{23}$H$_{28}$Cl$_2$N$_2$O$_4$: 467 (MH$^+$).

The example described above may be modified to introduce various substituted phenyl moieties (such as difluorophenyl, 4-trifluorophethyl) and heterocycles (such as pyridine, thoazole, benzofuran).

The example described above may be modified to introduce oligomers of various lengths (at the 2-hydroxyethoxy substituent) as disclosed herein.

Example 38

Preparation of (S)—N-(2-(4-(2,5,8,11,14-pentaoxahexadecan-16-yl)piperazin-1-yl)-1-phenylethyl)-2-(3,4-dichlorophenyl)-N-methylacetamide, dihydrochloride salt (39)

Using the procedure outlined in the schematic below, the named compound was prepared.

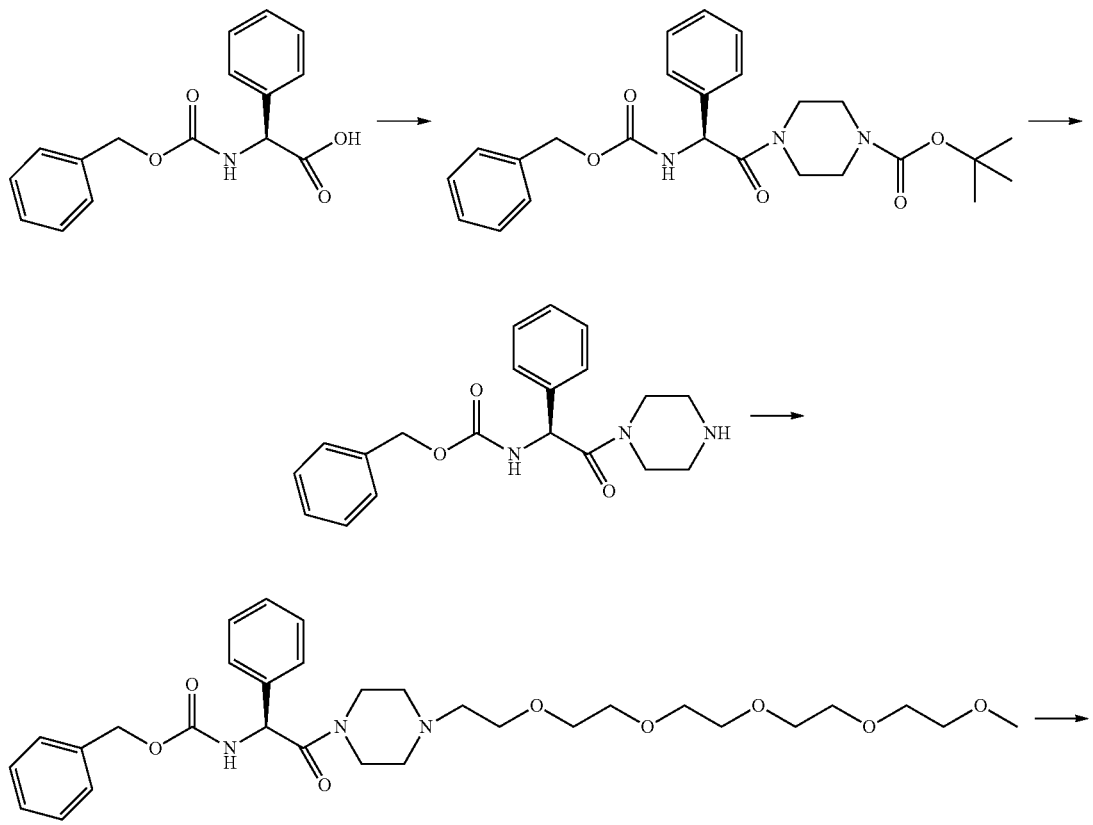

-continued

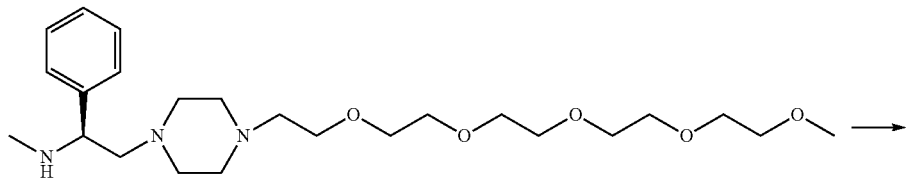

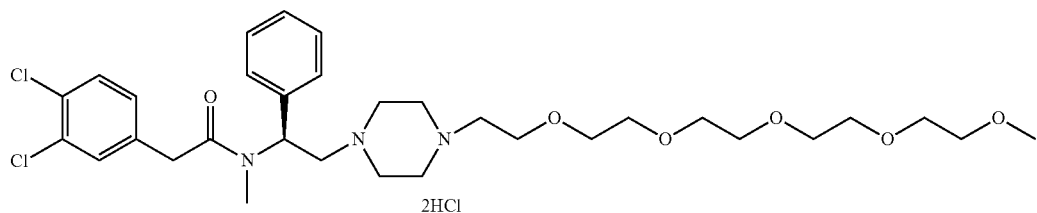

39

Step 1: Preparation of (S)-tert-butyl 4-(2-(((benzyloxy)carbonyl)amino)-2-phenylacetyl)piperazine-1-carboxylate

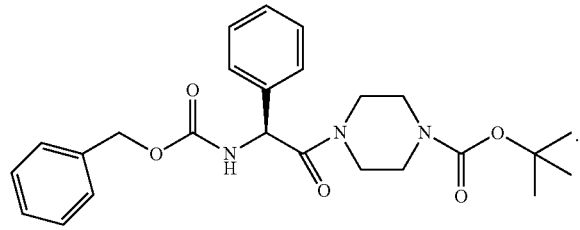 [SMILES: CC(C)(C)OC(=O)N1CCN(C(=O)[C@@H](NC(=O)OCc2ccccc2)c2ccccc2)CC1]

(S)-2-((Tert-butoxycarbonyl)amino)-2-phenylacetic acid (0.70 g, 2.45 mmol), 4-dimethylaminopyridine/p-toluenesulfonic acid (1:1 salt) (0.38 g, 1.23 mmol) and N,N'-diisopropylcarbodiimide (0.62 g, 4.91 mmol) were dissolved in 15 mL of dichloromethane. To the solution was added 1-Boc-piperazine (0.46 g, 2.45 mmol). The mixture was stirred for four hours at room temperature. Dichloromethane (200 mL) was added into the reaction mixture, and the resulted solution was washed with water (200 mL×3). The solution was dried over sodium sulfate and concentrated. The purification of the residue by flash chromatography yielded the target compound (0.9 g, yield: 81%). $^1$H NMR (500 MHz, CDCl$_3$): δ 7.38 (m, 10H), 6.38 (m, 1H), 5.60 (d, 1H), 5.65 (m, 1H), 5.03 (m, 1H), 3.70 (m, 1H), 3.50 (m, 2H), 3.30 (m, 4H), 2.72 (m, 1H), 1.42 (s. 9H); MS (EI) for C$_{25}$H$_{31}$N$_3$O$_5$: 398 [(M-Bu)H$^+$].

Step 2: Preparation of (S)-benzyl (2-(4-(2,5,8,11,14-pentaoxahexadecan-16-yl)piperazin-1-yl)-2-oxo-1-phenylethyl)carbamate

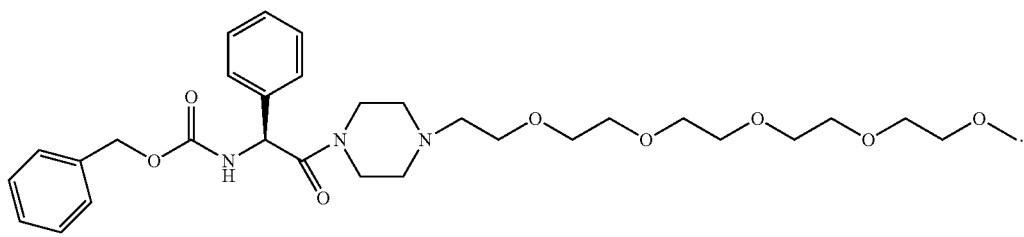 [SMILES: COCCOCCOCCOCCOCCN1CCN(C(=O)[C@@H](NC(=O)OCc2ccccc2)c2ccccc2)CC1]

(S)-Tert-butyl 4-(2-(((benzyloxy)carbonyl)amino)-2-phenylacetyl)piperazine-1-carboxylate (0.90 g, 1.98 mmol) was dissolved in 9 mL of dichloromethane, and then 3 mL of trifloroacetic acid was added. The mixture was stirred for 1.5 hours and then was adjusted to pH 10 with saturated sodium bicarbonate. The resulting solution was extracted with dichloromethane (200 mL×3). The organic solution was washed with brine, dried over sodium sulfate, and concentrated (0.66 g, yield: 94%). MS (EI) for $C_{20}H_{23}N_3O_3$: 354 (MH$^+$).

A solution of above product [(S)-benzyl (2-oxo-1-phenyl-2-(piperazin-1-yl)ethyl)carbamate] (0.19 g, 0.54 mmol) and 16-bromo-2,5,8,11,14-pentaoxahexadecane (0.51 g, 1.62 mmol) in acetonitrile (10 mL) was added potassium carbonate (0.22 g, 1.61 mmol). The mixture was stirred at 90° C. for four hours. The solution was washed with water (150 mL×2). The organic phase was dried over sodium sulfate and was then concentrated under reduced pressure. The residue was purified by column chromatography to provide product (0.20 g, yield: 63%). $^1$H NMR (500 MHz, CDCl$_3$): δ 7.32 (m, 10H), 6.42 (m, 1H), 5.58 (m, 1H), 5.10 (m, 1H), 5.00 (m, 1H), 3.60 (m, 19H), 3.40 (m, 1H), 3.35 (s, 3H), 3.25 (m, 1H), 2.50 (m, 4H), 2.35 (m, 2H), 1.80 (m. 1H); MS (EI) for $C_{31}H_{45}N_3O_8$: 588 (MH$^+$).

Step 3: Preparation of (S)-2-(4-(2,5,8,11,14-pentaoxahexadecan-16-yl)piperazin-1-yl)-N-methyl-1-phenylethanamine (S)-Benzyl (2-(4-(2, 5,8,11,14-pentaoxahexadecan-16-yl)piperazin-1-yl)-2-oxo-1-phenylethyl)carbamate (0.20 g, 0.33 mmol) in tetrahydrofuran (3 mL) was added dropwise to a stirred 2.0 M solution of lithium aluminum hydride (1.5 mL, 3.0 mmol) at room temperature. The mixture was stirred at 65° C. for four hours. A 3N solution of sodium carbonate was added cautiously until effervescence ceased. The solid was filtered out and washed with dichloromethane (100 mL). The filtrate was washed with water and then dried over sodium sulfate. The product was obtained after removing solvent (0.14 g, yield: 93%). $^1$H NMR (500 MHz, CDCl$_3$): δ 7.30 (m, 4H), 7.20 (m, 1H), 4.62 (s, 1H), 3.60 (m, 17H), 3.52 (m, 2H), 3.35 (s, 3H), 2.50 (m, 7H), 2.40 (m, 2H), 2.30 (m, 1H), 2.24 (s, 3H), 1.62 (m. 1H); MS (EI) for $C_{24}H_{43}N_3O_5$: 454 (MH$^+$).

Step 4: Preparation of (S)—N-(2-(4-(2,5,8,11,14-pentaoxahexadecan-16-yl)piperazin-1-yl)-1-phenylethyl)-2-(3,4-dichlorophenyl)-N-methylacetamide, dihydrochloride salt (39)

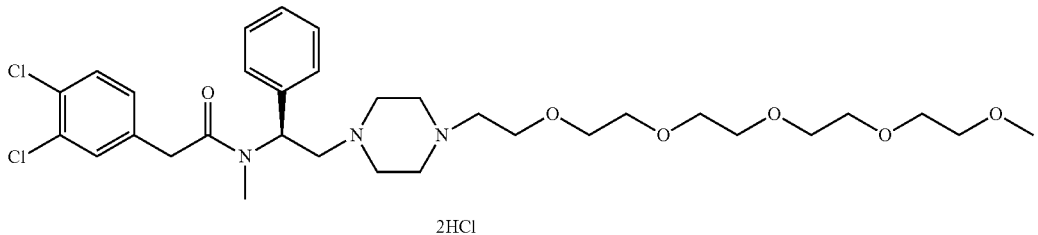

(S)-2-(4-(2,5,8,11,14-Pentaoxahexadecan-16-yl)piperazin-1-yl)-N-methyl-1-phenylethanamine (0.16 g, 0.35 mmol), 3,4-dichlorophenylacetic acid (0.080 g, 0.39 mmol), and N,N-diisopropylethylamine (0.090 g, 0.70 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.14 g, 0.42 mmol) was added into the solution. The reaction mixture was stirred overnight. Dichloromethane (100 mL) was added into the solution and washed with water and dried over sodium sulfate. Evaporation of the solvent and purification of the residue by flash chromatography yielded the target compound (0.12 g, yield: 93%). The free base was dissolved in acetonitrile. To the solution was added 1N hydrochloride. The mixture was lyophilized to afford the product as a dihydrochloride salt (39). $^1$H NMR (500 MHz, CDCl$_3$): δ 7.33 (m, 2H), 7.33, 7.10 (m, 5H), 7.18 (m, 1H), 6.13 (m, 0.82H), 5.00 (m, 0.18H), 3.75 (m, 1H), 3.65 (m, 18H), 3.52 (m, 2H), 3.35 (s, 3H), 2.90 (m, 1H), 2.80 (m, 2H), 2.70 (s, 3H), 2.60 (m, 2H), 2.43 (br., 6H); MS (EI) for $C_{32}H_{47}Cl_2N_2O_6$: 640 (MH$^+$).

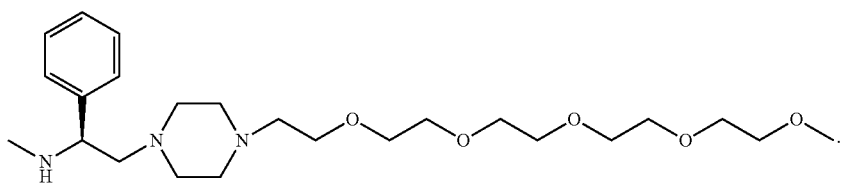

The example described above may be modified to introduce oligomers of various lengths as disclosed herein.

Example 39

Preparation of (S)-2-(3,4-dichlorophenyl)-N-(2-(3,3-difluoropyrrolidin-1-yl)-1-phenylethyl)-N-methylacetamide, hydrochloride salt (40)

Using the procedure outlined in the schematic below, the named compound was prepared.

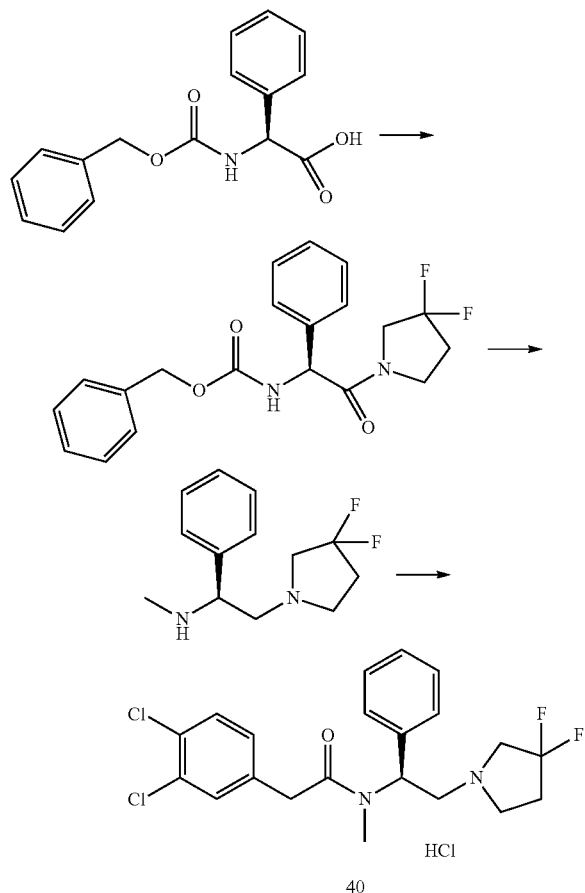

Step 1: Preparation of (S)-benzyl (2-(3,3-difluoropyrrolidin-1-yl)-2-oxo-1-phenylethyl)carbamate

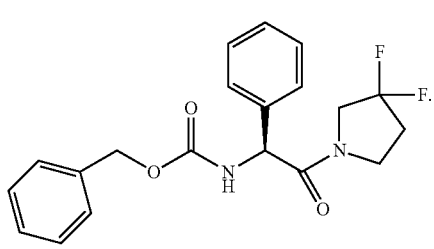 [SMILES: O=C(N[C@H](C(=O)N1CCC(F)(F)C1)c1ccccc1)OCc1ccccc1]

(S)-2-(((Benzyloxy)carbonyl)amino)-2-phenylacetic acid (0.48 g, 1.69 mmol) and 4-dimethylaminopyridine/p-toluenesulfonic acid (1:1 salt) (0.26 g, 0.85 mmol) were dissolved in 20 mL dichloromethane. N,N'-diisopropylcarbodiimide (0.43 g, 3.38 mmol) was added into the solution. Finally 3,3-difluoropyrrolidine HCl (0.25 g, 1.69 mmol) and N,N-diisopropylethylamine (0.432 g, 3.38 mmol) in 5 mL of dichloromethane were added. The mixture was stirred for two hours at room temperature. Dichloromethane (200 mL) was added into the reaction mixture, and the resulted solution was washed with water (200 mL×3). The solution was dried over sodium sulfate and concentrated. The purification twice of the residue by flash chromatography yielded the target compound (0.22 g, yield: 35%). $^1$H NMR (500 MHz, CDCl$_3$): δ 7.36 (m, 10H), 6.45 (m, 1H), 5.50 (m, 0.5H), 5.35 (m, 0.5H), 5.10 (m, 2H), 3.90 (m, 1H), 3.76 (m, 2H), 3.62 (m, 0.5H), 3.30 (m, 0.5H), 2.25 (m. 2H); MS (EI) for $C_{20}H_{20}F_2N_2O_3$: 375 (MH$^+$).

Step 2: Preparation of (S)-2-(3,3-difluoropyrrolidin-1-yl)-N-methyl-1-phenylethanamine

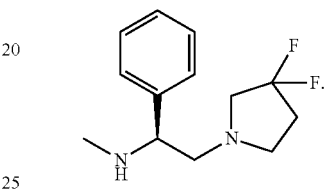

(S)-Benzyl (2-(3,3-difluoropyrrolidin-1-yl)-2-oxo-1-phenylethyl)carbamate (0.22 g, 0.59 mmol) in tetrahydrofuran (3 mL) was added dropwise to a stirred 2.0 M solution of lithium aluminum hydride (2 mL, 4.0 mmol) at room temperature. The mixture was stirred for thirty minutes at room temperature and then was heated to 65° C. for four hours. A 3N solution of sodium carbonate was added cautiously until effervescence ceased. The solid was filtered out and washed with dichloromethane (100 mL). The filtrate was concentrated and the residue was dissolved in 150 mL of dichloromethane. The resulted solution was washed with saturated sodium chloride solution (100 mL) and dried over sodium sulfate. The product was obtained after removing solvent (0.12 g, yield 85%). $^1$H NMR (500 MHz, CDCl$_3$): δ 7.35 (m, 5H), 3.54 (m, 1H), 3.10 (m, 2H), 2.82 (m, 3H), 2.75 (m. 1H), 2.40 (m. 1H), 2.30 (m, 1H), 2.28 (s, 3H); MS (EI) for $C_{13}H_{18}F_2N_2$: 241 (MH$^+$).

Step 3: Preparation of (S)-2-(3,4-dichlorophenyl)-N-(2-(3,3-difluoropyrrolidin-1-yl)-1-phenylethyl)-N-methylacetamide, hydrochloride salt (40)

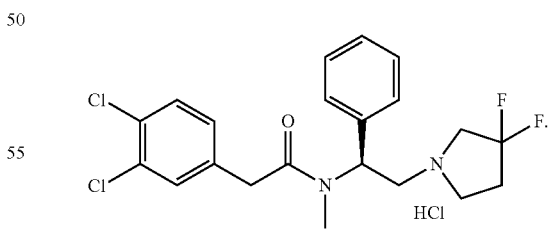

(S)-2-(3,3-Difluoropyrrolidin-1-yl)-N-methyl-1-phenylethanamine (0.059 g, 0.25 mmol), 3,4-dichlorophenylacetic acid (0.055 g, 0.27 mmol), and N,N-diisopropylethylamine (0.063 g, 0.491 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.095 g, 0.30 mmol) was added into the solution. The reaction mixture was stirred overnight. Dichloromethane (100 mL) was added into the solution and the solution was washed with water and dried over sodium sulfate. Evaporation of the solvent and purification of the residue by flash chromatography yielded the target compound (0.040 g, yield: 38%). The free base was dissolved in acetonitrile. To the solution was added 1N hydrochloride. The mixture was lyophilized to afford product as hydrochloride salt (40). $^1$H NMR (500 MHz, CDCl$_3$): δ 7.40 (m, 7H), 7.15 (m, 1H), 6.10 (m, 0.85H), 5.30 (m, 0.15H), 3.75 (m, 2H), 3.18 (m, 2H), 3.02 (m, 1H), 2.90 (m, 1H), 2.75 (m. 2H), 2.70 (s. 3H), 2.28 (m, 2H); MS (EI) for C$_{21}$H$_{22}$Cl$_2$F$_2$N$_2$O: 427 (MH$^+$).

Example 40

Preparation of N—((S)-2-((S)-3-(2,5,8,11,14-pentaoxahexadecan-16-yloxy)pyrrolidin-1-yl)-1-phenylethyl)-N-methyl-2-(2-nitrophenyl)acetamide, hydrochloride salt (41)

Using the procedure outlined in the schematic below, the named compound was prepared.

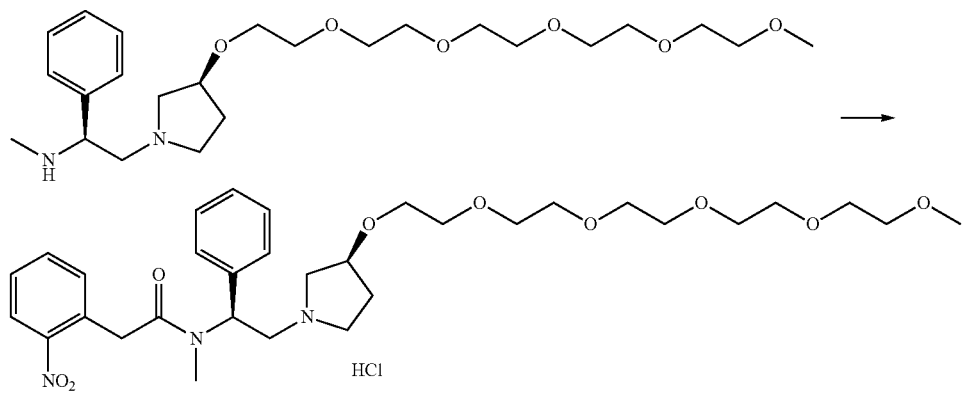

41

(S)-2-((S)-3-(2,5,8,11,14-Pentaoxahexadecan-16-yloxy) pyrrolidin-1-yl)-N-methyl-1-phenylethanamine (0.10 g, 0.22 mmol), 2-(3,4-dichlorophenyl)acetic acid (0.040 g, 0.22 mmol), and N,N-diisopropylethylamine (0.056 g, 0.44 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.085 g, 0.26 mmol) was added into the solution. The reaction mixture was stirred for four hours at room temperature and concentrated. The residue was dissolved in dichloromethane (100 mL) and the solution was washed with water and dried over sodium sulfate. Evaporation of the solvent and purification of the residue by flash chromatography yielded the target compound (0.09 g, yield: 66%). The free base was dissolved in acetonitrile. To the solution was added 1N hydrochloride. The mixture was lyophilized to afford product as hydrochloride salt (41). $^1$H NMR (500 MHz, CDCl$_3$): δ 8.10 (d, 1H), 7.60 (m, 1H), 7.45 (m, 2H), 7.35 (m, 5H), 6.05 (m, 0.82H), 5.18 (m, 0.18H), 4.10 (m, 3H), 3.60 (m, 20H), 3.38 (s, 3H), 3.16 (m, 1H), 3.05 (m, 1H), 2.85 (s, 3H), 2.80 (m, 2H), 2.55 (m, 2H), 2.10 (m, 1H), 1.82 (m, 1H); MS (EI) for C$_{32}$H$_{47}$N$_3$O$_9$: 618 (MH$^+$).

The example described above may be modified to introduce oligomers of various lengths as disclosed herein.

Example 41

Preparation of N—((S)-2-((S)-3-hydroxypyrrolidin-1-yl)-1-phenylethyl)-N-methyl-2-(2-nitrophenyl) acetamide, hydrochloride salt (42)

Using the procedure outlined in the schematic below, the named compound was prepared.

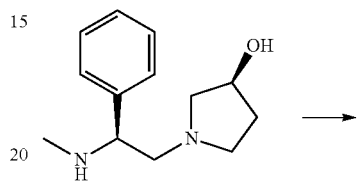

-continued

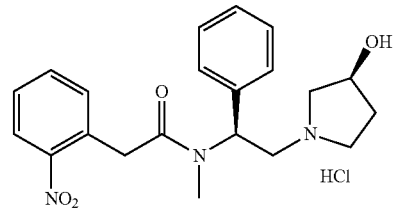

42

(S)-1-((S)-2-(Methylamino)-2-phenylethyl)pyrrolidin-3-ol (0.15 g, 0.68 mmol), 2-(2-nitrophenyl)acetic acid (0.12 g, 0.68 mmol), and N,N-diisopropylethylamine (0.17 g, 1.36 mmol) were dissolved in 5 mL of acetonitrile. The mixture was stirred for ten minutes at room temperature and then cooled to 0° C. O-(Benzotriazol-1-yl)-N,N,N',N'-tetramethyluronium tetrafluoroborate (0.26 g, 0.82 mmol) was added into the solution. The reaction mixture was stirred for four hours at room temperature and concentrated. The residue was dissolved in dichloromethane (100 mL) and the solution was washed with water and dried over sodium sulfate. Evaporation of the solvent and purification of the residue by flash chromatography yielded the target compound (0.13 g, yield: 50%). The free base was dissolved in acetonitrile. To the solution was added 1N hydrochloride. The mixture was lyophilized to afford product as hydrochloride salt (42). ¹H NMR (500 MHz, CDCl₃): δ 8.10 (m, 1H), 7.60 (m, 1H), 7.35 (m, 7H), 6.05 (m, 0.9H), 5.20 (m, 0.1H), 4.38 (d, 0.5H), 4.30 (m, 1H), 4.20 (d, 0.5H), 4.05 (d, 0.5H), 3.88 (d, 0.5H), 3.20 (m, 3H), 3.00 (m, 1H), 2.85 (s, 3H), 2.75 (m, 1H), 2.55 (m, 2H), 2.20 (m, 1H), 1.82 (m, 1H); MS (EI) for $C_{21}H_{25}N_3O_4$: 384 (MH⁺).

Example 42

Preparation of 2-(2-aminophenyl)-N—((S)-2-((S)-3-hydroxypyrrolidin-1-yl)-1-phenylethyl)-N-methylacetamide, dihydrochloride salt (43)

Using the procedure outlined in the schematic below, the named compound was prepared.

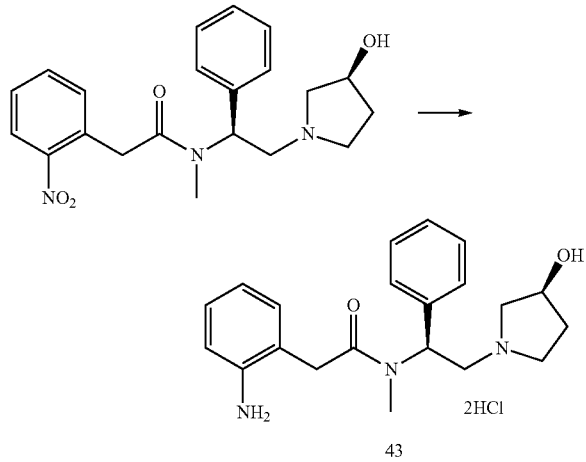

N—((S)-2-((S)-3-Hydroxypyrrolidin-1-yl)-1-phenylethyl)-N-methyl-2-(2-nitrophenyl)acetamide was dissolved in 10 mL of tetrahydrofuran. The reduction reaction was performed by H-Cube (CatCart THS01131, 10% Pd/C, Flow rate 1 mL/Min). The product was purified by biotage and 0.02 g of product was obtained (yield: 27%). The free base was dissolved in acetonitrile. To the solution was added 1N hydrochloride. The mixture was lyophilized to afford the product as a dihydrochloride salt (43). ¹H NMR (500 MHz, CDCl₃): δ 7.30 (m, 5H), 7.10 (m, 2H), 6.72 (m, 2H), 6.10 (m, 0.8H), 5.30 (s, 0.2H). 4.25 (m, 1H), 3.70 (m, 1H), 3.65 (m, 1H), 3.20 (m, 1H), 3.04 (m, 1H), 2.90 (m, 1H), 2.85 (s, 3H), 2.75 (m, 2H), 2.50 (m, 2H), 2.15 (m, 1H), 1.65 (m, 1H); MS (EI) for $C_{21}H_{27}N_3O_2$: 354 (MH⁺).

Example 43

Preparation of 2-(2,4-Difluorophenyl)-N-methyl-N-[(1S)-1-phenyl-2-(pyrrolidin-1-yl)ethyl]acetamide, hydrochloride salt (44)

Using the procedure outlined in the schematic below, the named compound was prepared.

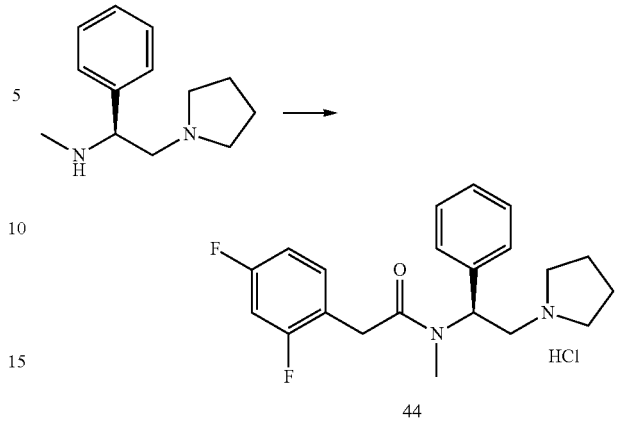

(S)—N-Methyl-1-phenyl-2-(pyrrolidin-1-yl)ethanamine (0.062 g, 0.30 mmol), 2-(2,4-difluorophenyl)acetic acid (0.052 g, 0.30 mmol), and N,N-diisopropylethylamine (0.078 g, 0.61 mmol) were dissolved in 2 mL of acetonitrile. The mixture was stirred for ten minutes at room temperature and then cooled to 0° C. O-(Benzotriazol-1-yl)-N,N,N',N'-tetramethyluronium tetrafluoroborate (0.12 g, 0.36 mmol) was added into the solution. The reaction mixture was stirred for two hours at 0° C. Dichloromethane (100 mL) was added into the solution and the solution was washed with water and dried over sodium sulfate. Evaporation of the solvent and purification of the residue by flash chromatography yielded product (0.078 g, yield 72%). The free base was dissolved in acetonitrile. To the solution was added 1N hydrochloride. The mixture was lyophilized to afford product as hydrochloride salt (44). ¹H NMR (HCl salt, 500 MHz, CDCl₃): δ 7.5 (m, 1H), 7.40 (m, 3H), 7.24 (m, 2H), 6.82 (m, 2H), 6.36 (d, 1H), 4.10 (m, 3H), 4.00 (t, 1H), 3.80 (d, 1H), 3.25 (m, 1H), 2.98 (s, 3H), 2.90 (m, 2H), 2.38 (m, 1H), 2.28 (m, 1H), 2.05 (m, 2H); MS (EI) for $C_{21}H_{24}F_2N_2O$: 359 (MH⁺).

Example 44

Preparation of N-Methyl-N-[(1S)-1-phenyl-2-(pyrrolidin-1-yl)ethyl]-2-(pyridine-2-yl)acetamide, dihydrochloride salt (45)

Using the procedure outlined in the schematic below, the named compound was prepared.

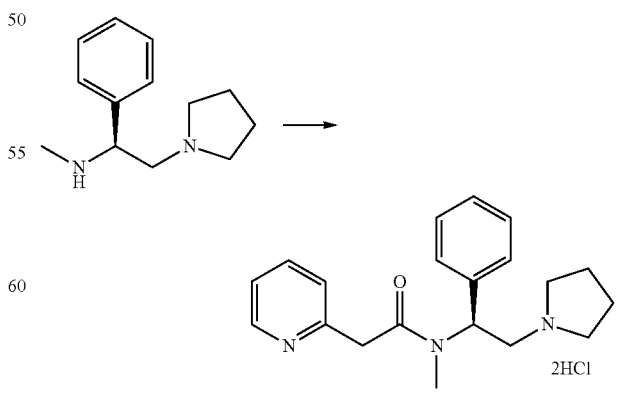

(S)—N-Methyl-1-phenyl-2-(pyrrolidin-1-yl)ethanamine (0.064 g, 0.31 mmol), 2-(pyridin-2-yl)acetic acid hydrochloride (0.054 g, 0.31 mmol), and N,N-diisopropylethylamine (0.080 g, 0.63 mmol) were dissolved in 2 mL of acetonitrile. The mixture was stirred for ten minutes at room temperature and then cooled to 0° C. O-(Benzotriazol-1-yl)-N,N,N',N'-tetramethyluronium tetrafluoroborate (0.12 g, 0.38 mmol) was added into the solution. The reaction mixture was stirred for two hours at 0° C. Dichloromethane (100 mL) was added into the solution and the solution was washed with water and dried over sodium sulfate. Evaporation of the solvent and purification of the residue by flash chromatography yielded product (0.063 g, yield 62%). The free base was dissolved in acetonitrile. To the solution was added 1N hydrochloride. The mixture was lyophilized to afford product as the dihydrochloride salt (45). $^1$H NMR (HCl salt, 500 MHz, CDCl$_3$): δ 8.62 (m, 1H), 8.50 (m, 1H), 8.35 (m, 1H), 7.80 (m, 1H), 7.45 (m, 2H), 7.39 (m, 1H), 7.30 (m, 2H), 6.35 (m, 1H), 4.95 (d, 1H), 4.74 (d, 1H), 4.10 (m, 2H), 3.96 (m, 1H), 3.40 (m, 1H), 3.00 (m, 2H), 2.94 (s, 3H), 2.35 (m, 1H), 2.25 (m, 1H), 2.05 (m, 2H); MS (EI) for C$_{20}$H$_{25}$N$_3$O: 324 (MH$^+$).

Example 45

Preparation of 2-(6-Chloropyridin-3-yl)-N-methyl-N-[(1S)-1-phenyl-2-(pyrrolidin-1-yl)ethyl]acetamide, dihydrochloride salt (46)

Using the procedure outlined in the schematic below, the named compound was prepared.

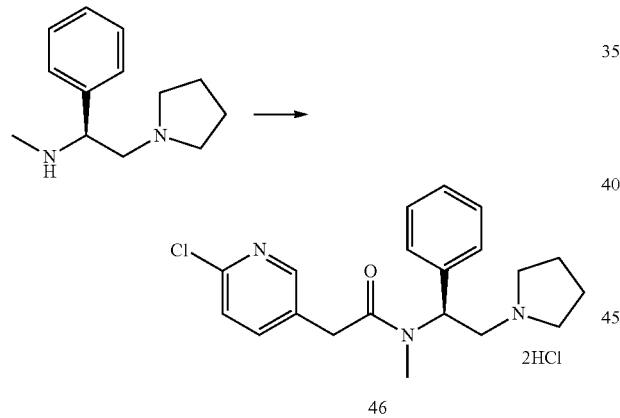

(S)—N-Methyl-1-phenyl-2-(pyrrolidin-1-yl)ethanamine (0.050 g, 0.25 mmol), 2-(6-chloropyridin-3-yl)acetic acid (0.042 mg, 0.25 mmol), and N,N-diisopropylethylamine (0.063 g, 0.49 mmol) were dissolved in 2 mL of acetonitrile. The mixture was stirred for ten minutes at room temperature and then cooled to 0° C. O-(Benzotriazol-1-yl)-N,N,N',N'-tetramethyluronium tetrafluoroborate (0.094 g, 0.29 mmol) was added into the solution. The reaction mixture was stirred for two hours at 0° C. Dichloromethane (100 mL) was added into the solution and the solution was washed with water and dried over sodium sulfate. Evaporation of the solvent and purification of the residue by flash chromatography yielded product (0.075 g, yield 86%). The free base was dissolved in acetonitrile. To the solution was added 1N hydrochloride. The mixture was lyophilized to afford the product as a dihydrochloride salt (46). $^1$H NMR (HCl salt, 500 MHz, CDCl$_3$): δ 8.72 (d, 1H), 8.60 (s, 1H), 7.64 (d, 1H), 7.40 (m, 3H), 7.24 (m, 2H), 6.35 (d, 1H), 4.66 (d, 1H), 4.10 (m, 3H), 3.70 (d, 1H), 3.35 (m, 1H), 3.05 (m, 2H), 2.94 (s, 3H), 2.38 (m, 1H), 2.25 (m, 1H), 2.10 (m, 2H); MS (EI) for C$_{20}$H$_{24}$ClN$_3$O: 358 (MH$^+$).

Example 46

Preparation of N—((S)-1-(3-aminophenyl)-2-((S)-3-hydroxypyrrolidin-1-yl)ethyl)-2-(3,4-dichlorophenyl)-N-methylacetamide, dihydrochloride salt (47)

Using the procedure outlined in the schematic below, the named compound was prepared.

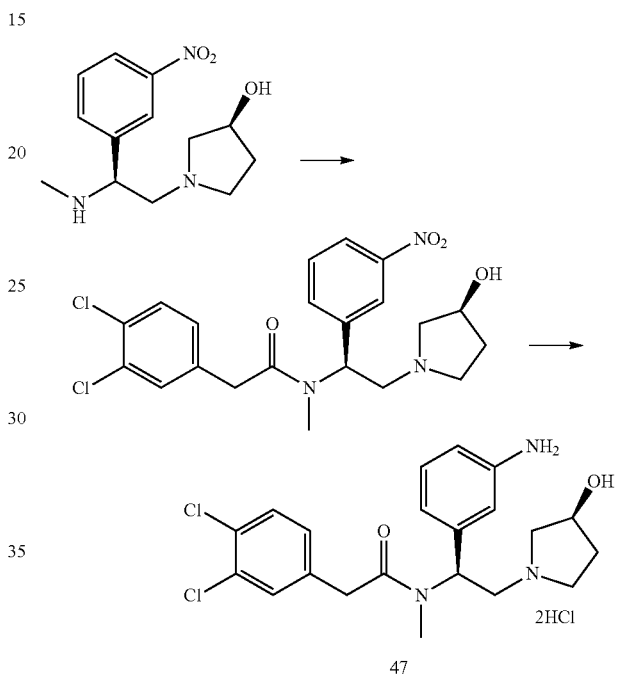

Step 1: Preparation of 2-(3,4-dichlorophenyl)-N—((S)-2-((S)-3-hydroxypyrrolidin-1-yl)-1-(3-nitrophenyl)ethyl)-N-methylacetamide (S)-1-((S)-2-(Methylamino)-2-(3-nitrophenyl)ethyl)pyrrolidin-3-ol (0.47 g, 1.77 mmol), 3,4-dichlorophenylacetic acid (0.31 g, 1.51 mmol), and N,N-diisopropylethylamine (0.45 g, 3.54 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.68 g, 2.13 mmol) was added into the solution. The reaction mixture was stirred for two hours at 0° C. Dichloromethane (100 mL) was added into the solution and the solution was washed with water and dried over sodium sulfate. Evaporation of the solvent and purification of the residue by flash chromatography yielded product (0.48 g, yield: 60%). $^1$H NMR (500 MHz, CDCl$_3$): δ 8.10 (m, 2H), 7.62 (m, 1H), 7.50 (m, 1H), 7.35 (m, 2H), 7.12 (m, 1H), 6.06 (m, 0.9H), 5.10 (m, 0.1H), 4.30 (m, 1H), 3.64 (m, 2H), 3.15 (m, 1H), 2.90 (m, 2H), 2.80 (m, 2H), 2.75 (s, 3H), 2.60 (m, 1H), 2.40 (m, 1H), 2.10 (m, 1H), 1.70 (m, 1H); MS (EI) for C$_{21}$H$_{23}$Cl$_2$N$_3$O$_4$: 452 (MH$^+$).

Step 2: Preparation of N—((S)-1-(3-aminophenyl)-2-((S)-3-hydroxypyrrolidin-1-yl)ethyl)-2-(3,4-dichlorophenyl)-N-methylacetamide, dihydrochloride salt (47)

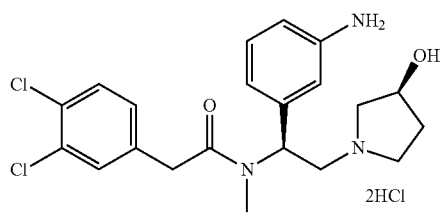 [SMILES: CN(C(=O)Cc1ccc(Cl)c(Cl)c1)[C@H](CN1CC[C@H](O)C1)c1cccc(N)c1]

To a three-neck, 100 mL round bottom flask equipped with a condenser, thermometer and magnetic stirrer was added 2-(3,4-dichlorophenyl)-N—((S)-2-((S)-3-hydroxypyrrolidin-1-yl)-1-(3-nitrophenyl)ethyl)-N-methylacetamide (0.42 g, 0.93 mmol) in 20 mL absolute ethanol. To the light-yellow solution was added hydrazine hydrate (0.72 g, 11.7 mmol) and Raney Ni slurry (40 drops) and heated to 55° C. The light-yellow reaction turned clear and after approximately two hours at 55° C. The reaction mixture was filtered through Celite, and the Raney Ni was washed with hot methanol. The combined filtrate was concentrated under reduced pressure to give the aniline product as oil (0.26 g, yield: 66%). The free base was dissolved in acetonitrile. To the solution was added 1N hydrochloride. The mixture was lyophilized to afford the product as a dihydrochloride salt (47) $^1$H NMR (500 MHz, CDCl$_3$): δ 7.40 (m, 2H), 7.14 (m, 2H), 6.15 (m, 1H), 6.10 (m, 2H), 6.00 (m, 0.86H), 4.92 (m, 0.14H), 4.30 (m, 1H), 3.70 (m, 4H), 3.15 (m, 2H), 2.20 (m, 5H), 2.32 (m, 1H), 2.15 (m, 1H), 1.74 (m, 1H); MS (EI) for C$_{21}$H$_{25}$Cl$_2$N$_3$O$_2$: 422 (MH$^+$).

Example 47

Preparation of N-(3-{(1S)-1-{[(3,4-Dichlorophenyl)acetyl](methyl)amino}-2-[(3S)-3-hydroxypyrrolidin-1-yl]ethyl}phenyl)-N$^2$-2,5,8,11,14,17,20,23-octaoxa-tetracosan-1-oylvalinamide, hydrochloride salt (48)

Using the procedure outlined in the schematic below, the named compound was prepared.

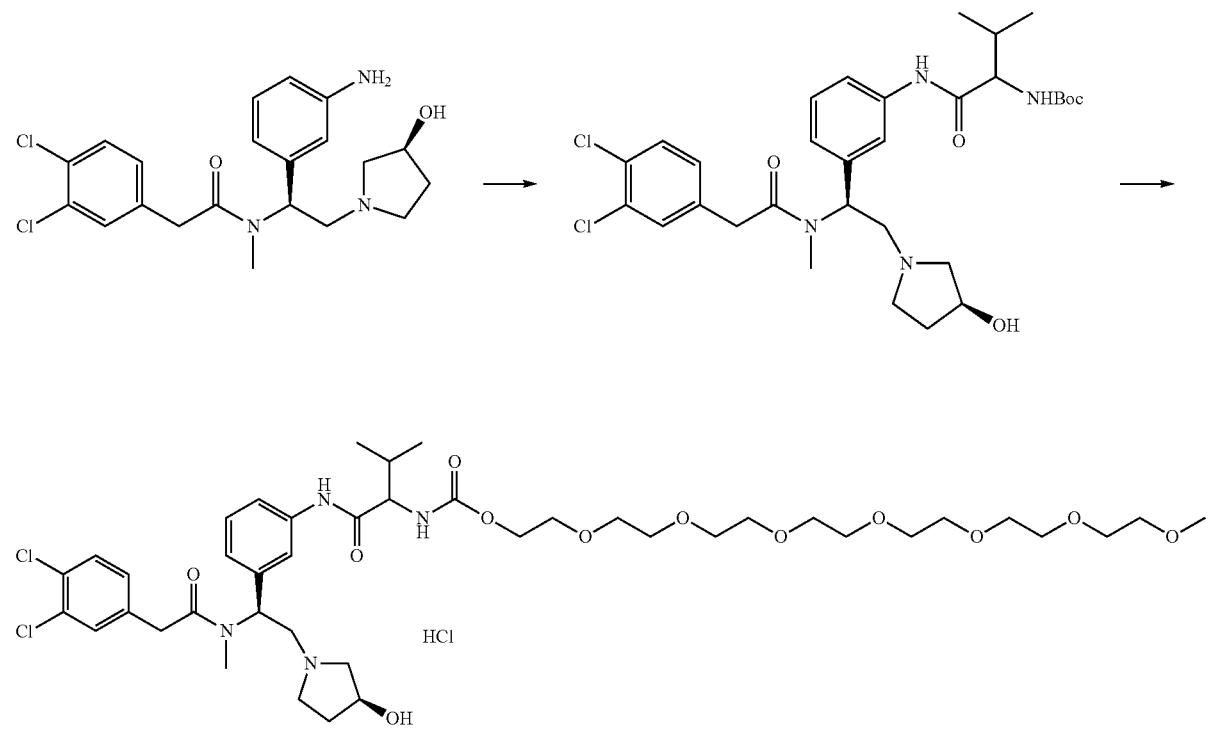

Step 1: Preparation of (3S)-1-((2S)-2-(3-(2-((tert-butoxycarbonyl)amino)-3-methylbutanamido)phenyl)-2-(2-(3,4-dichlorophenyl)-N-methylacetamido)ethyl)pyrrolidin-3-yl 2-((tert-butoxycarbonyl)amino)-3-methylbutanoate

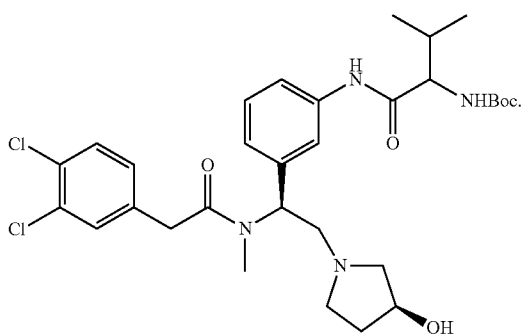 [SMILES: CC(C)C(NC(=O)OC(C)(C)C)C(=O)Nc1cccc([C@@H](CN2CC[C@H](O)C2)N(C)C(=O)Cc2ccc(Cl)c(Cl)c2)c1]

N—((S)-1-(3-Aminophenyl)-2-((S)-3-hydroxypyrrolidin-1-yl)ethyl)-2-(3,4-dichlorophenyl)-N-methylacetamide (0.15 g, 0.36 mmol), 2-((tert-butoxycarbonyl)amino)-3-methylbutanoic acid (0.17 g, 0.78 mmol), and 4-dimethylaminopyridine/p-toluenesulfonic acid (1:1 salt) (0.11 g, 0.36 mmol) were dissolved in 10 mL of dichloromethane. N,N'-diisopropylcarbodiimide (0.22 g, 1.77 mmol) was added into the mixture. The reaction mixture was stirred for three hours. Dichloromethane (100 mL) was added into the reaction mixture and the resulted solution was washed with water (100 mL×3). The solution was dried over sodium sulfate and concentrated. Product was obtained after purified by flash chromatography.

The above product [(3S)-1-((2S)-2-(3-(2-((tert-butoxycarbonyl)amino)-3-methylbutanamido)phenyl)-2-(2-(3,4-dichlorophenyl)-N-methylacetamido)ethyl)pyrrolidin-3-yl 2-((tert-butoxycarbonyl)amino)-3-methylbutanoate] was dissolved in 3 mL of acetonitrile, and then 3 mL of 0.5 N potassium hydroxide was added into the mixture. The reaction mixture was stirred for two hours at 65° C. Dichloromethane (100 mL) was added into the reaction mixture and the resulted solution was washed with water (100 mL×3). The solution was dried over sodium sulfate and concentrated. The crude product was purified by flash chromatography and 0.94 g (yield: 43%) product was obtained as white solid. $^1$H NMR (500 MHz, CDCl$_3$): δ 8.92 (m, 1H), 7.50 (m, 1H), 7.37 (m, 3H), 7.15 (m, 2H), 6.95 (m, 1H), 6.00 (m, 0.84H), 5.45 (m, 1H), 4.98 (m, 0.16H), 4.30 (m, 1H), 4.10 (m, 1H), 3.70 (m, 2H), 3.00 (m, 3H), 2.75 (m, 2H), 2.68 (s, 3H), 2.55 (m, 1H), 2.35 (m, 1H), 2.10 (m, 2H), 1.70 (m, 1H), 1.42 (s, 9H), 1.00 (m, 6H); MS (EI) for $C_{31}H_{42}Cl_2N_4O_5$: 621 (MH$^+$).

Step 2: Preparation of N-(3-{(1S)-1-{[(3,4-Dichlorophenyl)acetyl](methyl)amino}-2-[(3S)-3-hydroxypyrrolidin-1-yl]ethyl}phenyl)-N$^2$-2,5,8,11,14,17,20,23-octaoxatetracosan-1-oylvalinamide, hydrochloride salt (48)

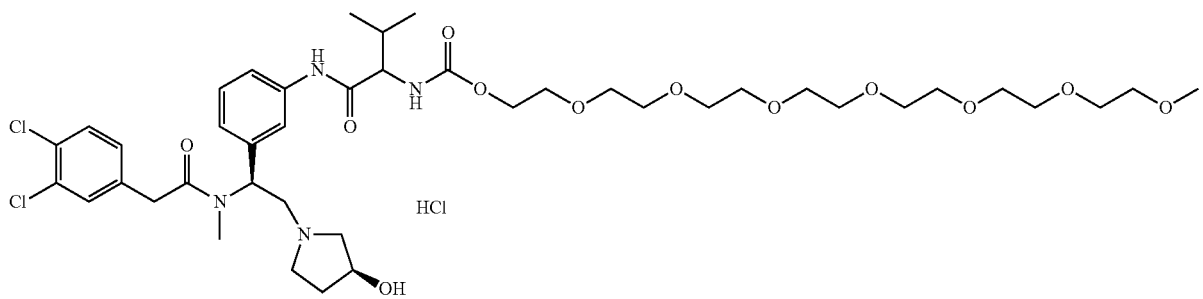

The product of step 1 [tert-butyl (1-((3-((S)-1-(2-(3,4-dichlorophenyl)-N-methylacetamido)-2-((S)-3-hydroxypyrrolidin-1-yl)ethyl)phenyl)amino)-3-methyl-1-oxobutan-2-yl)carbamate] (0.094 g, 0.21 mmol) was dissolved in 2 mL of dioxane, and then 2 mL of 4 N HCl in dioxane was added into the mixture. The reaction mixture was stirred for two hours. The solvent was removed and 0.079 g product was obtained as white solid, which was dissolved in 10 mL of dichloromethane. To the solution was added 2,5-dioxopyrrolidin-1-yl 2,5,8,11,14,17,20-heptaoxadocosan-22-yl carbonate (0.11 g, 1.5 mmol) and N,N-diisopropylethylamine (0.19 g, 1.5 mmol). The resulted solution was stirred at room temperature for three hours. A colorless oil was obtained after removing solvent. The crude product was purified by flash chromatography and 0.080 g of product was obtained after the purification (yield 60%). The free base was dissolved in acetonitrile. To the solution was added 1N hydrochloride. The mixture was lyophilized to afford product as hydrochloride salt (48). $^1$H NMR (500 MHz, CDCl$_3$): δ 9.00 (br., 1H), 7.55 (m, 1H), 7.40 (m, 1H), 7.35 (m, 2H), 7.22 (m, 1H), 7.15 (m, 1H), 6.90 (m, 1H), 6.12 (m, 1H), 5.30 (m, 1H), 4.40 (m, 1H), 4.20 (m, 3H), 3.88 (m, 1H), 3.60 (m, 28H), 3.46 (s, 3H), 3.10 (m, 2H), 2.75 (s, 3H), 2.20 (m, 3H), 1.90 (m, 1H), 1.60 (m, 1H), 1.00 (m, 6H); MS (EI) for C$_{42}$H$_{64}$Cl$_2$N$_4$O$_{12}$: 887 (MH$^+$).

The example described above may be modified to introduce oligomers of various lengths as disclosed herein.

Example 48

Preparation of 2,5,8,11,14,17,20-Heptaoxadocosan-22-yl {1-[(3-{(1S)-1-{[(3,4dichlorophenyl)acetyl] (methyl)amino}-2-[(3S)-3-hydroxypyrrolidin-1yl] ethyl}phenyl)carbamoyl]cyclopropyl}carbamate, hydrochloride salt (49)

Using the procedure outlined in the schematic below, the named compound was prepared.

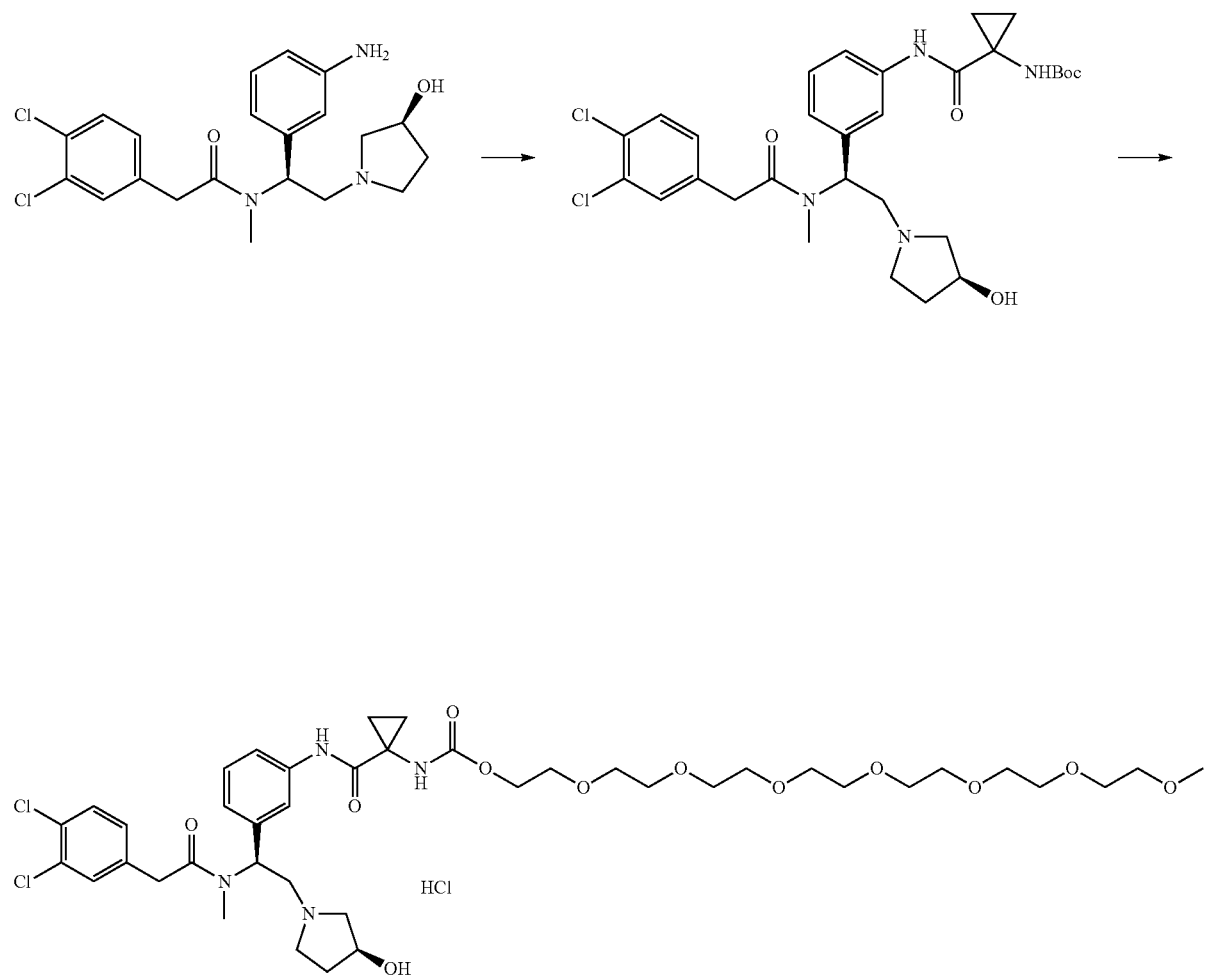

Step 1: Preparation of tert-butyl (1-((3-((S)-1-(2-(3,4-dichlorophenyl)-N-methylacetamido)-2-((S)-3-hydroxypyrrolidin-1-yl)ethyl)phenyl)carbamoyl)cyclopropyl)carbamate

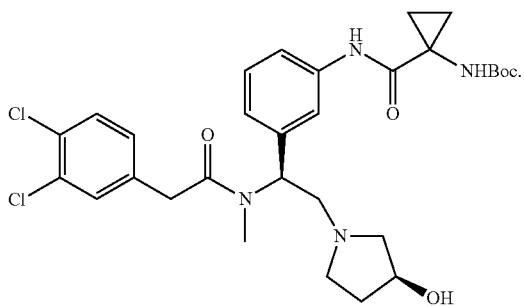 [SMILES: CN(C(=O)Cc1ccc(Cl)c(Cl)c1)[C@H](CN1CC[C@H](O)C1)c1cccc(NC(=O)C2(NC(=O)OC(C)(C)C)CC2)c1]

N—((S)-1-(3-Aminophenyl)-2-((S)-3-hydroxypyrrolidin-1-yl)ethyl)-2-(3,4-dichlorophenyl)-N-methylacetamide (0.10 g, 0.24 mmol), 1-((tert-butoxycarbonyl)amino)cyclopropanecarboxylic acid (0.11 g, 0.52 mmol), and 4-dimethylaminopyridine/p-toluenesulfonic acid (1:1 salt) (0.073 g, 0.24 mmol) were dissolved in 20 mL of dichloromethane. N,N'-Diisopropylcarbodiimide (0.15 g, 1.18 mmol) was added into the mixture. The reaction mixture was stirred for three hours. Dichloromethane (100 mL) was added into the reaction mixture and the resulted solution was washed with water (100 mL×3). The solution was dried over sodium sulfate and concentrated. Crude product was dissolved in 2 mL of acetonitrile and 2 mL of 0.5 N potassium hydroxide was added. The mixture was stirred at 65° C. for two hours. Dichloromethane (100 mL) was added into the reaction mixture and the resulted solution was washed with water (100 mL×3). The solution was dried over sodium sulfate and concentrated. The product was obtained after purified by flash chromatography (0.046 g, yield: 32%). $^1$H NMR (500 MHz, CDCl$_3$): δ 8.55 (br., 1H), 7.56 (m, 1H), 7.42 (m, 2H), 7.30 (m, 2H), 7.20 (m, 1H), 7.02 (m, 1H), 6.05 (m, 0.83H), 5.40 (m, 1H), 5.02 (m, 0.17H), 4.40 (m, 1H), 3.72 (m, 2H), 3.15 (m, 1H), 3.06 (m, 1H), 2.75 (m, 4H), 2.68 (m, 1H), 2.35 (m, 3H), 2.15 (m, 1H), 1.72 (m, 1H), 1.65 (m, 2H), 1.50 (s, 9H), 1.20 (m, 2H); MS (EI) for C$_{30}$H$_{38}$Cl$_2$N$_4$O$_5$: 605 (MH$^+$).

Step 2: Preparation of 2,5,8,11,14,17,20-Heptaoxadocosan-22-yl {1-[(3-{(1S)-1-{[(3,4dichlorophenyl)acetyl](methyl)amino}-2-[(3S)-3-hydroxypyrrolidin-1 yl]ethyl}phenyl)carbamoyl]cyclopropyl}carbamate, hydrochloride salt Tert-butyl (1-((3-((S)-1-(2-(3,4-dichlorophenyl)-N-methylacetamido)-2-((S)-3-hydroxypyrrolidin-1-yl)ethyl)phenyl)carbamoyl)cyclopropyl)carbamate (0.045 g, 0.074 mmol) was dissolved in 2 mL of dioxane and 2 mL 4 N HCl in dioxane was added. The mixture was stirred at 20° C. for two hours. The solvent was removed and the residue (35 mg, 0.069 mmol) was dissolved in 10 mL of dichloromethane. To the solution was added 2,5-dioxopyrrolidin-1-yl 2,5,8,11,14,17,20-heptaoxadocosan-22-yl carbonate (0.040 g, 0.083 mmol) and N,N-diisopropylethylamine (0.12 mL, 0.7 mmol). The resulted solution was stirred at room temperature for three hours. Dichloromethane (100 mL) was added into the reaction mixture. The resulted solution was washed with water (100 mL), 5% sodium bicarbonate (100 mL), and then water (100 mL) again. The organic phase was dried over sodium sulfate. A colorless oil was obtained after removing the solvent. The crude product was purified by biotage and 0.015 g of product was obtained after the purification (yield: 25%). The free base was dissolved in acetonitrile. To the solution was added 1N hydrochloride. The mixture was lyophilized to afford product as hydrochloride salt (49). $^1$H NMR (500 MHz, CDCl$_3$): δ 8.84 (br., 1H), 7.65 (s, 1H), 7.55 (br., 1H), 7.50 (m, 2H), 7.30 (m, 1H), 7.20 (m, 1H), 7.00 (m, 1H), 6.15 (br., 1H), 4.30 (br., 1H), 3.60 (m, 29H), 3.58 (m, 3H), 3.40 (s, 3H), 2.80 (br., 4H), 2.28 (br., 3H), 1.70 (m, 2H), 1.18 (m, 4H); MS (EI) for C$_{41}$H$_{60}$Cl$_2$N$_4$O$_{12}$: 871 (MH$^+$).

The example described above may be modified to introduce oligomers of various lengths as disclosed herein.

Example 49

Preparation of 2-(3,4-dichlorophenyl)-N-[(1S)-2-[(3S)-3-hydroxypyrrolidin-1-yl]-1-(3-{[(2-methoxyethoxy)acetyl]amino}phenyl)ethyl]-N-methylacetamidee, hydrochloride salt (50)

Using the procedure outlined in the schematic below, the named compound was prepared.

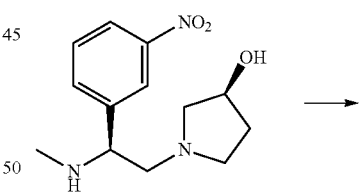

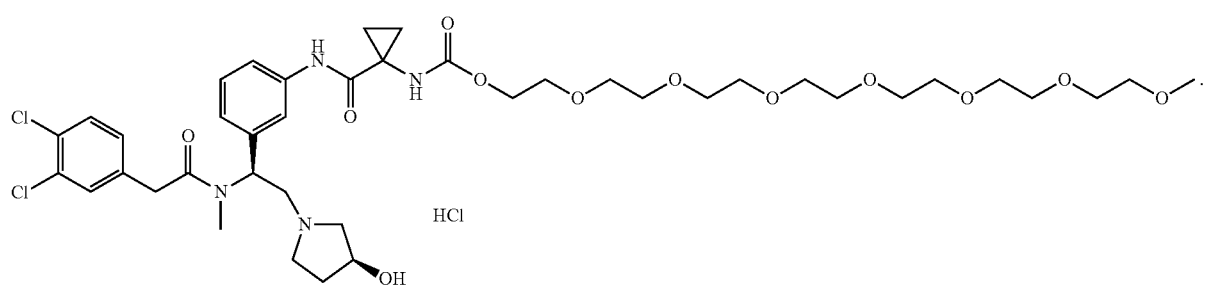 [SMILES: COCCOCCOCCOCCOCCOCCOCCOC(=O)NC1(C(=O)Nc2cccc([C@@H](CN3CC[C@H](O)C3)N(C)C(=O)Cc3ccc(Cl)c(Cl)c3)c2)CC1 ; Cl]

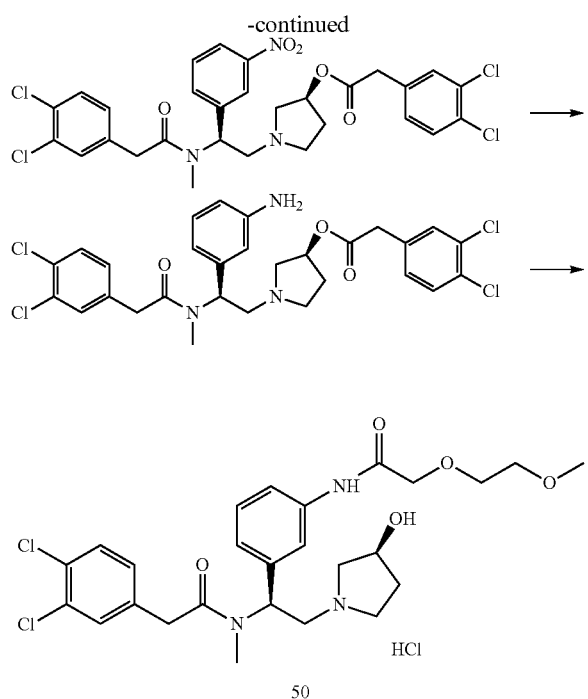

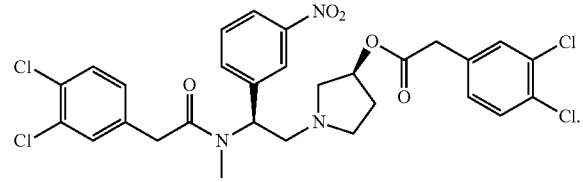 [SMILES: CN(C(=O)Cc1ccc(Cl)c(Cl)c1)[C@H](CN1CC[C@H](OC(=O)Cc2ccc(Cl)c(Cl)c2)C1)c1cccc([N+](=O)[O-])c1]

Step 1: Preparation of (S)-1-((S)-2-(2-(3,4-dichlorophenyl)-N-methylacetamido)-2-(3-nitrophenyl)ethyl) pyrrolidin-3-yl 2-(3,4-dichlorophenyl)acetate

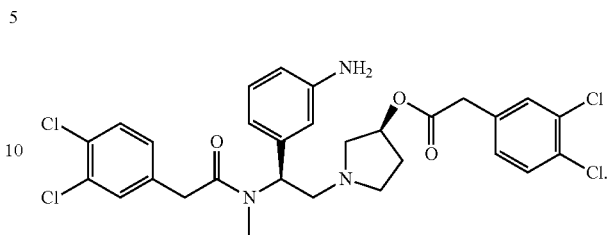

(S)-1-((S)-2-(methylamino)-2-(3-nitrophenyl)ethyl)pyrrolidin-3-ol (0.30 g, 1.13 mmol), 2-(3,4-dichlorophenyl) acetic acid (0.46 g, 2.26 mmol), and 4-dimethylaminopyridine/p-toluenesulfonic acid (1:1 salt) (0.35 g, 1.13 mmol) were dissolved in 20 mL of dichloromethane. N,N'-Diisopropylcarbodiimide (0.71 g, 5.65 mmol) was added into the mixture. The reaction mixture was stirred for three hours. Dichloromethane (100 mL) was added into the reaction mixture and the resulted solution was washed with water (100 mL×3). The solution was dried over sodium sulfate and concentrated. Crude product was purified by flash chromatography. 0.40 g of product (yield: 55%) was obtained. $^1$H NMR (500 MHz, CDCl$_3$): δ 8.15 (m, 2H), 7.65 (m, 1H), 7.54 (m, 1H), 7.40 (m, 4H), 7.13 (m, 2H), 6.10 (m, 1H), 5.20 (m, 1H), 3.75 (m, 2H), 3.55 (m, 1H), 3.12 (m, 1H), 2.95 (m, 2H), 2.85 (m, 2H), 2.75 (s, 3H), 2.66 (m, 1H), 2.45 (m, 1H), 2.21 (m, 1H), 1.72 (m, 1H); MS (EI) for C$_{29}$H$_{27}$Cl$_4$N$_3$O$_5$: 638 (MH$^+$).

Step 2: Preparation of (S)-1-((S)-2-(3-aminophenyl)-2-(2-(3,4-dichlorophenyl)-N-methylacetamido) ethyl)pyrrolidin-3-yl 2-(3,4-dichlorophenyl)acetate

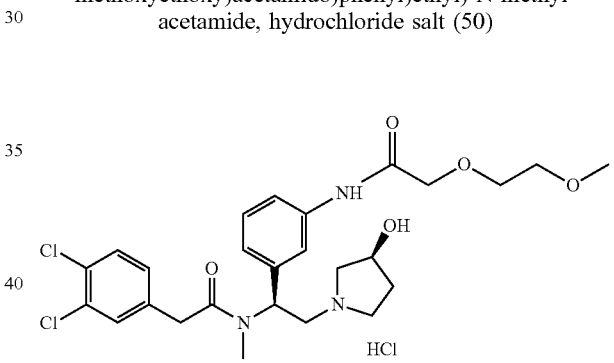

(S)-1-((S)-2-(N-methyl-2,2-diphenylacetamido)-2-(3-nitrophenyl)ethyl)pyrrolidin-3-yl 2,2-diphenylacetate (0.40 g, 0.63 mmol) was dissolved in 15 mL of tetrahydrofuran. The reduction reaction was performed by H-Cube. CatCart THS01131, 10% Pd/C, Flow rate 1 mL/Min. The product was purified by flash chromatography (0.32 g, yield: 84%). $^1$H NMR (500 MHz, CDCl$_3$): δ 7.40 (m, 4H), 7.15 (m, 3H), 6.65 (m, 3H), 6.00 (m, 0.82H), 5.20 (m, 1H), 4.95 (m, 0.18H), 3.72 (m, 4H), 3.12 (m, 1H), 2.95 (m, 2H), 2.72 (s, 3H), 2.58 (m, 2H), 2.40 (m, 1H), 2.22 (m, 1H), 1.80 (m, 1H); MS (EI) for C$_{29}$H$_{29}$Cl$_4$N$_3$O$_3$: 608 (MH$^+$).

Step 3: Preparation of 2-(3,4-dichlorophenyl)-N—((S)-2-((S)-3-hydroxypyrrolidin-1-yl)-1-(3-(2-(2-methoxyethoxy)acetamido)phenyl)ethyl)-N-methylacetamide, hydrochloride salt (50)

(S)-1-((S)-2-(3-Aminophenyl)-2-(2-(3,4-dichlorophenyl)-N-methylacetamido)ethyl)pyrrolidin-3-yl 2-(3,4-dichlorophenyl)acetate (0.12 g, 0.20 mmol), 2-(2-methoxyethoxy)acetic acid (0.032 g, 0.24 mmol), and 4-dimethylaminopyridine/p-toluenesulfonic acid (1:1 salt) (0.037 g, 0.12 mmol) were dissolved in 10 mL of dichloromethane. N,N-diisopropylcarbodiimide (0.1 mL) was added into the mixture. The reaction mixture was stirred for two hours. Dichloromethane (100 mL) was added into the reaction mixture and the resulted solution was washed with water (100 mL×3). The solution was dried over sodium sulfate and concentrated. Crude product was dissolved in 6 mL of acetonitrile/0.5 N potassium hydroxide (1:1). The mixture was stirred at 65° C. for three hours and then extracted with dichloromethane (50 mL×3). The organic solution was dried over sodium sulfate and concentrated. The crude product was purified by flash chromatography and 0.020 g (54%) product was obtained. The free base was dissolved in acetonitrile. To the solution was added 1N hydrochloride. The mixture was lyophilized to afford the product as a hydrochloride salt (50). $^1$H NMR (500 MHz, CDCl$_3$): δ 7.60 (m, 2H), 7.45 (m, 2H), 7.32 (m, 1H), 7.23 (m, 1H), 7.10 (m, 1H), 6.04 (m, 0.87H), 5.20 (m, 0.13H), 4.35 (m, 1H), 4.13 (s, 2H), 3.80 (m, 4H), 3.65 (m, 2H), 3.45 (s, 3H), 3.35 (m 2H), 3.10 (m, 1H), 2.95 (m, 1H), 2.72 (m, 4H), 2.68 (m, 1H), 2.55 (m, 1H), 2.12 (m, 1H), 1.75 (m, 1H); MS (EI) for $C_{26}H_{33}Cl_2N_3O_5$: 538 (MH$^+$).

The example described above may be modified to introduce oligomers of various lengths as disclosed herein.

Example 50

Preparation of 2-methoxy-N-methyl-2-phenyl-N—((S)-1-phenyl-2-(pyrrolidin-1-yl) ethyl) acetamide, hydrochloride salt (53)

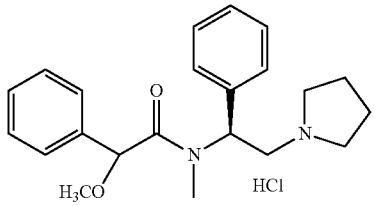

53

(S)—N-Methyl-1-phenyl-2-(pyrrolidin-1-yl)ethanamine (0.050 g, 0.245 mmol), 2-methoxy-2-phenylacetic acid (0.045 g, 0.270 mmol), and N,N-diisopropylethylamine (0.05 mL) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.078 g, 0.245 mmol) was added into the solution. The reaction mixture was stirred for 16 hours and then concentrated. The residue was dissolved in dichloromethane (50 mL) and washed with water (50 mL) and dried over sodium sulfate. Evaporation of the solvent and purification of the residue by flash chromatography yielded the target compound in base form (0.030 g, yield: 35%). The free base was dissolved in acetonitrile. To the solution was added 1N hydrochloride. The mixture was lyophilized to afford the product as the hydrochloride salt (53). $^1$H NMR (500 MHz, HCl salt in MeOD): δ 7.40 (m, 5H), 7.28 (m, 3H), 7.05 (m, 2H), 6.33 (m, 1H), 5.24 (s, 1H), 4.15 (m, 1H), 4.00 (br., 1H), 3.78 (m, 2H), 3.40 (s, 3H), 3.30 (br., 2H), 2.55 (s, 3H), 2.20 (m, 4H); MS (EI) for $C_{22}H_{28}N_2O_2$: 353.2 (MH$^+$).

Example 51

Preparation of N—((S)-2-((S)-3-hydroxypyrrolidin-1-yl)-1-phenylethyl)-N-methyl-2-(4-(trifluoromethyl) phenyl) acetamide, hydrochloride salt (54)

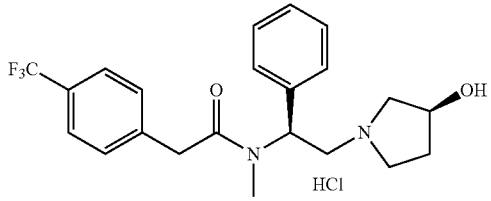

54

(S)-1-((S)-2-(Methylamino)-2-phenylethyl)pyrrolidin-3-ol dihydrochloride (0.050 g, 0.170 mmol), 2-(4-(trifluoromethyl)phenyl)acetic acid (0.032 g, 0.155 mmol), and N,N-diisopropylethylamine (0.2 mL) were dissolved in 3 mL of acetonitrile. The mixture was stirred for 10 min. at room temperature and then cooled to 0° C. O-(Benzotriazol-1-yl)-N,N,N',N'-tetramethyluronium tetrafluoroborate (0.060 g, 0.190 mmol) was added into the solution. The reaction mixture was stirred for 4 hours and then was concentrated. The residue was dissolved in dichloromethane (50 mL) and washed with saturated sodium bicarbonate (30 mL), brine (30 mL) and dried over sodium sulfate. Evaporation of the solvent and purification of the residue by flash chromatography yielded the target compound in base form (0.040 g, yield: 63%). The free base was dissolved in acetonitrile. To the solution was added 1N hydrochloride. The mixture was lyophilized to afford the product as the hydrochlorise salt (54). $^1$H NMR (500 MHz, CDCl$_3$): δ 7.60 (m, 2H), 7.45 (m, 2H), 7.32 (m, 4.6H), 7.12 (m, 0.4H), 6.14 (m, 0.84H), 5.05 (m, 0.16H), 4.30 (m, 1H), 3.85 (m, 2H), 3.20 (m, 1H), 3.12 (m, 1H), 2.78 (m, 2H), 2.74 (s, 3H), 2.67 (m, 1H), 2.32 (m, 2H), 2.25 (m, 1H), 1.72 (m, 1H); MS (EI) for $C_{22}H_{25}F_3N_2O_2$: 407.2 (MH$^+$).

Example 52

Preparation of 2-(3,4-dichlorophenyl)-N—((S)-2-((S)-3-((2-(2-(2-methoxyethoxy)ethoxy)ethyl)amino) pyrrolidin-1-yl)-1-phenylethyl)-N-methylacetamide dihydrochloride salt (55)

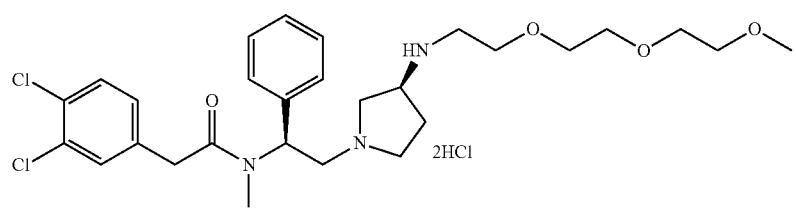

55

56

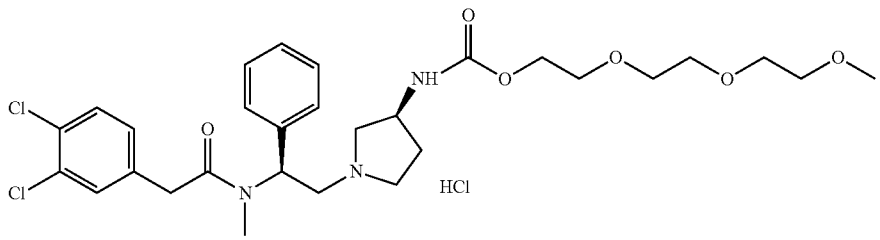

2-(3,4-Dichlorophenyl)-N—((S)-2-((S)-3-((2-(2-(2-methoxyethoxy)ethoxy)ethyl)amino) pyrrolidin-1-yl)-1-phenylethyl)-N-methylacetamide dihydrochloride salt (55) was synthesized according to the following steps.

Step 1: Preparation of (S)-2-(((benzyloxy)carbonyl)amino)-2-phenylacetic acid

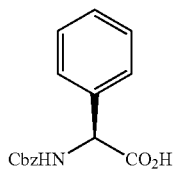 [SMILES: O=C(N[C@H](C(=O)O)c1ccccc1)OCc1ccccc1]

To a solution (S)-2-amino-2-phenylacetic acid (20 g, 0.132 mol) in water (500 mL) was added sodium carbonate (27.97 g, 0.264 mol) and sodium bicarbonate (11.1 g, 0.132 mol) at ambient temperature. The mixture was stirred to get a clear solution. Acetone (40 mL) was added and the resulting slightly turbid solution was cooled (in an ice water bath) to 15-20° C. Cbz-Cl (28.15 g, 0.165 mol) was added slowly, with stirring, and the reaction mixture allowed to warm to ambient temperature. After stirring for an additional three hours, the mixture was extracted with methyl tertbutyl ether (100 mL). The pH of aqueous layer was adjusted to 2 using aqueous HCl. The resulting oil was extracted into ethyl acetate (100 mL×2). The combined organic layer was washed with water and concentrated under vacuum to get (S)-2-(((benzyloxy)carbonyl)amino)-2-phenylacetic acid (30.2 g, 80% yield) as a white solid.

Step 2: Preparation of benzyl ((S)-2-((R)-3-hydroxypyrrolidin-1-yl)-2-oxo-1-phenylethyl) carbamate

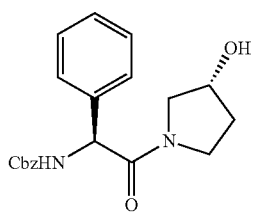 [SMILES: O=C(N[C@H](C(=O)N1CC[C@@H](O)C1)c1ccccc1)OCc1ccccc1]

(S)-2-(((Benzyloxy)carbonyl)amino)-2-phenylacetic acid (10.36 g, 36.3 mmol), (R)-pyrrolidin-3-ol (3.48 g, 39.93 mmol) and diisopropyl ethyl amine (14.0 g, 108.9 mmol) were dissolved in acetonitrile (80 mL). The mixture was stirred for fifteen minutes at 22-25° C. and then cooled to 0° C. O-(Benzotriazol-1-yl)-N,N,N',N'-tetramethyluronium tetrafluoroborate (TBTU) (14.0 g, 43.56 mmol) was added into the solution. The reaction mixture was stirred for one hour at 0° C. and then at four hours at ambient temperature. At the end of four hours, the reaction mixture was concentrated under reduced pressure. The residue was dissolved in dichloromethane (50 mL) and washed with brine (25 mL×2). The dichloromethane solution was dried over anhydrous sodium sulfate and concentrated. The obtained residue, when purified by column chromatography yielded ((S)-2-((R)-3-hydroxypyrrolidin-1-yl)-2-oxo-1-phenylethyl) carbamate (7.5 g, 58% yield).

Step 3: Preparation of (R)-1-((S)-2-(methylamino)-2-phenylethyl)pyrrolidin-3-ol

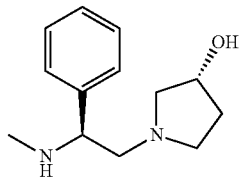 [SMILES: CN[C@H](CN1CC[C@@H](O)C1)c1ccccc1]

((S)-2-((R)-3-Hydroxypyrrolidin-1-yl)-2-oxo-1-phenylethyl) carbamate (7.0 g, 19.75 mmol) was dissolved in tetrahydrofuran (55 mL). The mixture was cooled to 0° C. and LAH (3.74 g, 98.75 mmol) was added. The mixture was stirred for fifteen minutes at 0° C., followed by sixteen hours of stirring at 65° C. The reaction mass was cooled to 0° C. and 3N aq. sodium carbonate solution (150 mL) was added (cautiously) until effervescence ceased. The precipitated solid was filtered and washed with ethyl acetate (100 mL). In the filtrate, the organic layer was separated, and from the organic layer the product was extracted into 1N aq. HCl (2×25 mL). The acidic aqueous layer was washed with methyl tertbutyl ether (3×15 mL). The pH of the aqueous layer was adjusted to 9, and the product was extracted into ethyl acetate. The organic layer was washed with brine, dried over anhydrous sodium sulfate and concentrated under vacuum to obtain the crude compound. The crude compound, upon purification using column chromatography, yielded (R)-1-((S)-2-(methylamino)-2-phenylethyl)pyrrolidin-3-ol (2.5 g, 58% yield).

Step 4: Preparation of 2-(3,4-dichlorophenyl)-N—((S)-2-((R)-3-hydroxypyrrolidin-1-yl)-1-phenylethyl)-N-methylacetamide

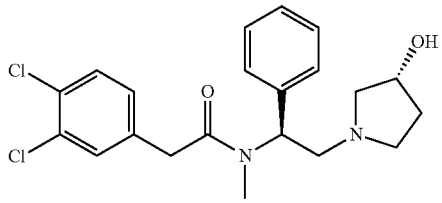 [SMILES: CN(C(=O)Cc1ccc(Cl)c(Cl)c1)[C@H](CN1CC[C@@H](O)C1)c1ccccc1]

To a solution of (R)-1-((S)-2-(methylamino)-2-phenylethyl)pyrrolidin-3-ol (2.5 mg, 11.35 mmol) in acetonitrile (40 mL) were added 3,4-dichlorophenyl acetic acid (2.56 g, 12.48 mmol), HOBt.H₂O (1.84 g, 13.62 mmol), diisopropyl ethyl amine (2.2 g, 17.02 mmol) and EDC.HCl (3.26 g, 17.02 mmol) at ambient temperature. The mixture was stirred for two hours and acetonitrile was distilled off. The crude compound, dissolved in dichloromethane (25 mL), was washed with 10% sodium carbonate (4×25 mL), 10% ammonium chloride (4×25 mL), and brine (25 mL). The organic layer was dried over anhydrous sodium sulfate and concentrated under vacuum. The resultant gummy mass, upon purification by column chromatography, yielded 2-(3,4-dichlorophenyl)-N—((S)-2-((R)-3-hydroxypyrrolidin-1-yl)-1-phenylethyl)-N-methylacetamide (2.9 g, 63% yield).

Step 5: Preparation of (R)-1-((S)-2-(2-(3,4-dichlorophenyl)-N-methylacetamido)-2-phenylethyl)pyrrolidin-3-yl methanesulfonate

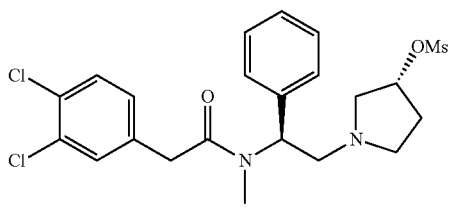 [SMILES: CN(C(=O)Cc1ccc(Cl)c(Cl)c1)[C@H](CN1CC[C@@H](OS(C)(=O)=O)C1)c1ccccc1]

To a solution of 2-(3,4-dichlorophenyl)-N—((S)-2-((R)-3-hydroxypyrrolidin-1-yl)-1-phenylethyl)-N-methylacetamide (0.5 g, 1.23 mmol) in dichloromethane (5 mL) were added triethyl amine (1.48 mmol) and MsCl (1.35 mmol) at ambient temperature. The mixture was stirred for two hours and quenched with water (10 mL). The organic layer was separated and washed with 5% aq. ammonium chloride (5 mL×2) followed by brine (5 mL). The organic layer was dried over anhydrous sodium sulfate and concentrated under vacuum to give (R)-1-((S)-2-(2-(3,4-dichlorophenyl)-N-methylacetamido)-2-phenylethyl)pyrrolidin-3-yl methanesulfonate (0.53 g, 90% yield) as light yellow color gum.

Step 6: Preparation of N—((S)-2-((S)-3-azidopyrrolidin-1-yl)-1-phenylethyl)-2-(3,4-dichlorophenyl)-N-methylacetamide

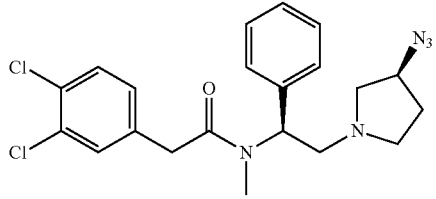 [SMILES: CN(C(=O)Cc1ccc(Cl)c(Cl)c1)[C@H](CN1CC[C@H](N=[N+]=[N-])C1)c1ccccc1]

To a solution of (R)-1-((S)-2-(2-(3,4-dichlorophenyl)-N-methylacetamido)-2-phenylethyl)pyrrolidin-3-yl methanesulfonate (0.5 g, 1.03 mmol) in DMF (5 mL) was added sodium azide (0.1 g, 1.54 mmol). The mixture was heated to 60° C. for three hours. After cooling down to ambient temperature, the mixture was concentrated under reduced pressure. To the residue, water (10 mL) was added and the product was extracted into dichloromethane (10 mL×2). The combined organic layer was washed with brine (20 mL) and concentrated under vacuum to afford N—((S)-2-((S)-3-azidopyrrolidin-1-yl)-1-phenylethyl)-2-(3,4-dichlorophenyl)-N-methylacetamide (0.39 g, 88% yield) as brown color gum.

Preparation of N—((S)-2-((S)-3-aminopyrrolidin-1-yl)-1-phenylethyl)-2-(3,4-dichlorophenyl)-N-methy acetamide

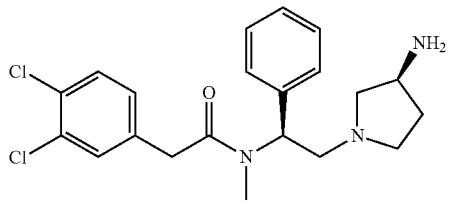 [SMILES: CN(C(=O)Cc1ccc(Cl)c(Cl)c1)[C@H](CN1CC[C@H](N)C1)c1ccccc1]

A solution of N—((S)-2-((S)-3-azidopyrrolidin-1-yl)-1-phenylethyl)-2-(3,4-dichlorophenyl)-N-methylacetamide (0.35 g, 0.81 mmol) and water (87 μL, 4.86 mmol) in tetrahydrofuran (3.5 mL) was cooled to 0° C. (in an ice-bath). PPh₃ (0.425 g, 1.62 mmol) was added into the mixture, as a solid, in small portions. After the addition, the mixture was slowly warmed to ambient temperature. It was then heated to 50° C. for five hours. At the end of five hours of stirring, the mixture was concentrated under vacuum and to it water (7 mL) and dichloromethane (10 mL) were charged. The layers were separated. The pH of the aqueous layer was adjusted with 1N HCl to 2, and then washed with dichloromethane (10 mL×2). The aqueous phase was then basified, with 6N NaOH, to pH 10. The basic aqueous layer was extracted with dichloromethane (10 mL×3), and the organic layers were combined. The combined organic layer was washed with brine (10 mL), dried over anhydrous sodium sulfate and concentrated under vacuum to give N—((S)-2-((S)-3-aminopyrrolidin-1-yl)-1-phenylethyl)-2-(3,4-dichlorophenyl)-N-methylacetamide (0.23 g, 70% yield) as light yellow color gum.

Step 8: Preparation of 2-(3,4-dichlorophenyl)-N—((S)-2-((S)-3-((2-(2-(2-methoxyethoxy)ethoxy)ethyl)amino) pyrrolidin-1-yl)-1-phenylethyl)-N-methylacetamide dihydrochloride salt (55)

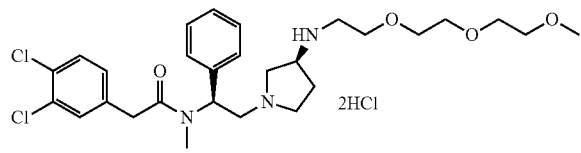

55

2HCl

To a solution of N—((S)-2-((S)-3-aminopyrrolidin-1-yl)-1-phenylethyl)-2-(3,4-dichlorophenyl)-N-methylacetamide (150 mg, 0.37 mmol) in acetonitrile (3 mL) was added mPEG₃-NH₂ (66 mg, 0.407 mmol) and potassium carbonate (153 mg, 1.11 mmol). The mixture was heated to 50° C. for 18 hours. After 18 hours, the mixture was concentrated under vacuum and the resulting crude was dissolved in ethyl acetate (10 mL). The organic layer, after washes with aq. ammonium chloride (10 mL), water (10 mL) and brine (10 mL), was dried over anhydrous sodium sulfate and concentrated under vacuum to give the crude compound. The crude compound post purification by column chromatography afforded 2-(3,4-dichlorophenyl)-N—((S)-2-((S)-3-((2-(2-(2-methoxyethoxy)ethoxy)ethyl)amino)pyrrolidin-1-yl)-1-phenylethyl)-N-methylacetamide as the free base (0.081 g, 40% yield). ¹H NMR (500 MHz, CDCl₃): δ 7.61 (m, 1H), 7.40-7.27 (m, 7H), 5.22 (m, 1H), 4.20 (t, 2H), 3.70-3.45 (m, 10H), 3.32 (s, 3H), 3.24 (m, 2H), 3.04 (m, 1H), 2.79-2.72 (m, 2H), 2.62 (s, 3H), 2.46-2.30 (m, 4H), 1.54-1.79 (m, 2H); MS (EI) for $C_{28}H_{39}Cl_2N_3O_4$: 553 (MH⁺). The free base was dissolved in 4M hydrochloride in 2-propanol. The mixture was concentrated to afford product as dihydrochloride salt (55).

The example described above may be modified to introduce oligomers of various lengths as disclosed herein.

Example 53

Preparation of 2-(2-(2-methoxyethoxy)ethoxy)ethyl ((S)-1-((S)-2-(2-(3,4-dichlorophenyl)-N-methylacetamido)-2-phenylethyl)pyrrolidin-3-yl)carbamate hydrochloride salt (56)

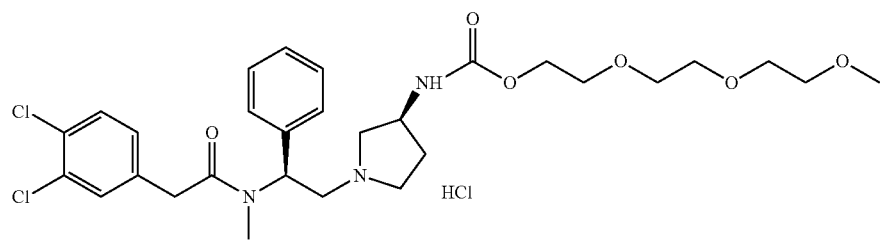 [SMILES: COCCOCCOCCOC(=O)N[C@H]1CCN(C[C@H](c2ccccc2)N(C)C(=O)Cc2ccc(Cl)c(Cl)c2)C1 ; Cl]

56

HCl 2-(2-(2-methoxyethoxy)ethoxy)ethyl ((S)-1-((S)-2-(2-(3,4-dichlorophenyl)-N-methylacetamido)-2-phenylethyl)pyrrolidin-3-yl)carbamate hydrochloride salt (56) was synthesized as described below.

Step 1: Preparation of 2-(2-(2-methoxyethoxy)ethoxy)ethyl ((S)-1-((S)-2-(2-(3,4-dichlorophenyl)-N-methylacetamido)-2-phenylethyl)pyrrolidin-3-yl) carbamate hydrochloride salt (56)

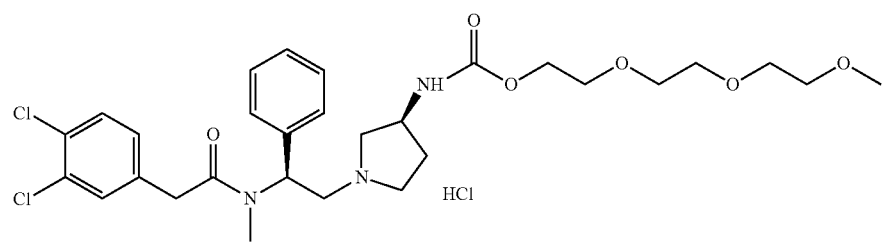

HCl

To a solution of N—((S)-2-((S)-3-aminopyrrolidin-1-yl)-1-phenylethyl)-2-(3,4-dichlorophenyl)-N-methylacetamide (prepared in accordance with Step 7 of Example 52) (200 mg, 0.492 mmol) in dichloromethane (3 mL) was added 2,5-dioxopyrrolidin-1-yl (2-(2-(2-methoxyethoxy)ethoxy)ethyl) carbonate (165 mg, 0.54 mmol) and triethyl amine (103 µL, 0.74 mmol) at ambient temperature. The mixture was stirred for 16 hours at the same temperature. After 16 hours, the mixture was washed with water (10 mL×2) and brine (10 mL). The organic layer was dried over anhydrous sodium sulfate and concentrated under vacuum to yield 2-(2-(2-methoxyethoxy)ethoxy)ethyl ((S)-1-((S)-2-(2-(3,4-dichlorophenyl)-N-methylacetamido)-2-phenylethyl)pyrrolidin-3-yl)carbamate free base (225 mg, 77% yield). $^1$H NMR (500 MHz, CDCl$_3$): δ 8.03 (br, s, 1H), 7.6-7.27 (m, 8H), 5.22 (m, 1H), 4.20 (t, 2H), 3.80-3.45 (m, 11H), 3.37 (m, 2H), 3.30 (s, 3H), 3.04 (m, 1H), 2.79 (m, 1H), 2.72 (s, 3H), 2.60-2.3 (m, 4H), 1.94-1.70 (m, 2H); MS (EI) for C$_{29}$H$_{39}$Cl$_2$N$_3$O$_6$: 597 (MH$^+$). The free base was dissolved in 4M hydrochloride in 2-propanol. The mixture was concentrated to afford the product as the hydrochloride salt (56).

The example described above may be modified to introduce oligomers of various lengths as disclosed herein.

Example 54

Preparation of (S)—N-(1-(3-((N-(2,5,8,11,14,17,20-heptaoxadocosan-22-yl)sulfamoyl)amino)phenyl)-2-(pyrrolidin-1-yl)ethyl)-2-(3,4-dichlorophenyl)-N-methylacetamide hydrochloride salt (57)

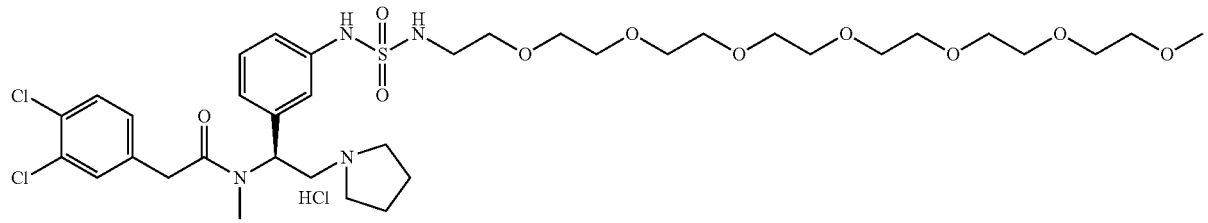 [SMILES: COCCOCCOCCOCCOCCOCCOCCNS(=O)(=O)Nc1cccc([C@@H](CN2CCCC2)N(C)C(=O)Cc2ccc(Cl)c(Cl)c2)c1 ; Cl]

(S)—N-(1-(3-((N-(2,5,8,11,14,17,20-heptaoxadocosan-22-yl)sulfamoyl)amino)phenyl)-2-(pyrrolidin-1-yl)ethyl)-2-(3,4-dichlorophenyl)-N-methylacetamide hydrochloride salt (57) was synthesized as given below.

Step 1: Preparation of 2,5,8,11,14,17,20-heptaoxadocosan-22-ylsulfamoyl chloride To a solution of mPEG$_7$-NH$_2$ (2.5 g, 7.36 mmol) in dichloromethane (25 mL) was added triethyl amine (2.15 µL, 15.5 mmol). The mixture was cooled to −78° C. A solution of sulfuryl chloride (1.2 mL, 14.72 mmol) in dichloromethane (12 mL) was slowly added to the above reaction mixture, making sure temperature of reaction mixture did not increase above −50 OC. After the addition, the reaction mixture was slowly warmed to ambient temperature and thereafter stirred for additional two hours. The reaction mixture was then quenched into ice-cold water and stirred for 15 minutes. The organic layer was separated, dried over anhydrous sodium sulfate, and concentrated under vacuum to give 2,5,8,11,14,17,20-heptaoxadocosan-22-ylsulfamoyl chloride (2.5 g, 77% yield) which was used directly for the next step.

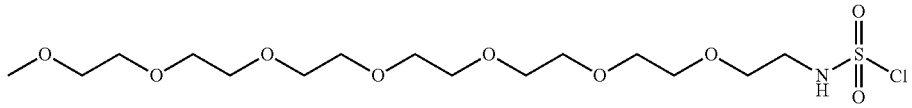 [SMILES: COCCOCCOCCOCCOCCOCCOCCNS(=O)(=O)Cl]

Step 2: Preparation of (S)—N-(1-(3-((N-(2,5,8,11,14,17,20-heptaoxadocosan-22-yl)sulfamoyl)amino)phenyl)-2-(pyrrolidin-1-yl)ethyl)-2-(3,4-dichlorophenyl)-N-methylacetamide hydrochloride salt (57)

present invention were tested as HCl salts) were evaluated using radioligand binding assays in membranes prepared from CHO-K1 cells expressing recombinant human kappa (KOR) or mu (MOR) opioid receptors.

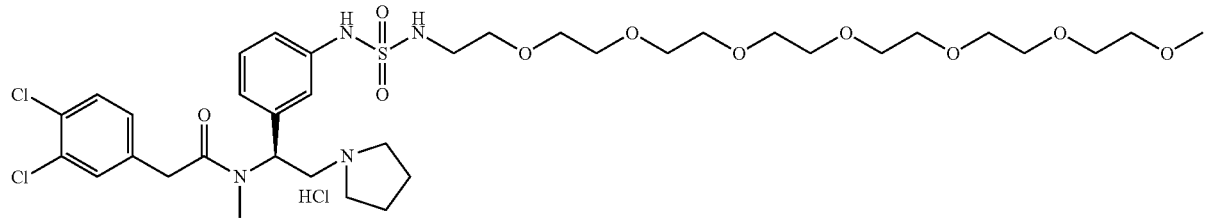 [SMILES: COCCOCCOCCOCCOCCOCCOCCNS(=O)(=O)Nc1cccc([C@@H](CN2CCCC2)N(C)C(=O)Cc2ccc(Cl)c(Cl)c2)c1 ; Cl]

To A solution of (S)—N-(1-(3-aminophenyl)-2-(pyrrolidin-1-yl)ethyl)-2-(3,4-dichlorophenyl)-N-methylacetamide (100 mg, 0.246 mmol), triethyl amine (106 µL, 0.738 mmol) in dichloromethane (2.5 mL) was cooled to 0° C. A mixture of 2,5,8,11,14,17,20-heptaoxadocosan-22-ylsulfamoyl chloride (0.215 g, 0.492 mmol) in dichloromethane (1 mL) was slowly added to the above mixture. After the addition, the reaction mixture was slowly warmed to ambient temperature and stirred for 18 hours. The reaction mixture was washed with water (10 mL), 5% aqueous ammonium chloride (10 mL) and brine (1 mL). The organic layer was dried over anhydrous sodium sulfate and concentrated under vacuum to give a crude product. The crude product was purified by column chromatography to yield (S)—N-(1-(3-((N-(2,5,8,11,14,17,20-heptaoxadocosan-22-yl)sulfamoyl)amino)phenyl)-2-(pyrrolidin-1-yl)ethyl)-2-(3,4-dichlorophenyl)-N-methylacetamide (85 mg, 43% yield) a light yellow gum, as free base. $^1$H NMR (500 MHz, CDCl$_3$): δ 7.74 (br, s 1H), 7.61 (m, 1H), 7.25-7.15 (m, 3H), 7.10-6.95 (m, 3H), 5.11 (m, 1H), 4.0 (br, s, 1H), 3.96 (t, 2H), 3.83-3.45 (m, 24H), 3.31 (s, 3H), 3.37 (s, 2H), 3.04 (m, 1H), 2.96 (t, 2H), 2.79 (m, 1H), 2.72 (s, 3H), 2.55-2.41 (m, 2H), 2.33-2.22 (m, 2H); MS (EI) for $C_{36}H_{56}Cl_2N_4O_{10}S$: 808 (MH$^+$). The free base was dissolved in 4M hydrochloride in 2-propanol. The mixture was concentrated to afford product as hydrochloride salt (57).

The example described above may be modified to introduce oligomers of various lengths as disclosed herein.

Example 55

Radioligand Competition Binding and cAMP Accumulation Assays

Radio Competition Binding Assay. The binding affinities of certain kappa agonist compounds (compounds of the Competition binding experiments were conducted by incubating membrane protein to equilibrium in triplicate in the presence of a fixed concentration of radioligand and increasing concentrations of test compound for evaluation of binding to KOR or single concentration (10 µM) of test compound for evaluation of binding to MOR in 101 µL final volume. The radioligands used were specific for each receptor type, and the assay conditions are described in Table 1. Following incubations, the membranes were rapidly filtered through GF/B filter plate (presoaked with 0.5% polyethyleneimine), washed five times with cold 50 mM Tris-HCl, pH 7.5, and the bound radioactivity was then measured by liquid scintillation counting. Non-specific binding was measured in the presence of excess ligand; this value was subtracted from the total binding to yield the specific binding at each test concentration. Assay conditions are reported in Table 1 below.

TABLE 1

| Receptor | Receptor Source | Membrane Protein | Radioligand | $K_d$ | Non-specific binding | Methods |
|---|---|---|---|---|---|---|
| Kappa Opioid | Human recombinant in CHO-K1 cells | 2.5 µg/well | [$^3$H] Diprenorphine (1 nM) | 0.3 nM | U-50488 (10 µM) | Reaction in 50 mM Tris-HCl (pH 7.5), 5 mM MgCl$_2$, 0.05% BSA at room temperature for 1 h with shaking |
| Mu Opioid | Human recombinant in CHO-K1 cells | 5 µg/well | [$^3$H] Naloxone (4 nM) | — | Naloxone (10 µM) | Reaction in 50 mM Tris-HCl (pH 7.5), 5 mM MgCl$_2$ at room temperature for 1 h with shaking |

For KOR binding, IC$_{50}$ (concentration of test compound required to inhibit 50% of specific binding) values were obtained from non-linear regression analysis of dose-response curves, using GraphPad's Prism 5.01 software, and were calculated for those compounds that showed >50% inhibition of specific binding at the highest concentration tested. K$_i$ (affinity of test compound) was obtained using the Cheng Prusoff correction using experimental K$_d$ (affinity of radioligand) values that were previously determined under these assay conditions. For MOR binding, compounds were tested at one concentration, 10 µM, to evaluate its ability to inhibit specific radioligand binding. The values are expressed as percent inhibition of specific binding and greater than 50% inhibition of binding was considered to be significant. Data are expressed as means of one experiment in triplicate determination and reported in Table 2.

cAMP Accumulation Assay. Inhibition of cAMP accumulation by select compounds was measured in forskolin-stimulated CHO-K1 cells stably expressing KOR. CHO-K1 cells stably expressing KOR were harvested using Invitrogen Cell Dissociation Buffer, and then centrifuged at 1200 rpm for five minutes. The supernatant was aspirated and cells were resuspended in assay buffer to a density of $4 \times 10^5$ cells/mL. Cells (25 μL) were added into a white half-area 96 well plate. Fourteen point serial dilutions of test compounds were done in assay buffer (PBS with 0.5 mM IBMX). One of ketazocine, ICI-199441, or asimadoline was used as a positive control for each assay. Compound (12.5 μL) was added to the cells in duplicate for each test concentration. The cells were then stimulated with 12.5 μL forskolin at a final concentration 20 M. Cells were incubated for 45 minutes in a 37° C., 5% $CO_2$ water jacketed incubator. CisBio HTRF cAMP assay reagent was used for cAMP quantitation. Two hours after substrate addition, signal at 665/615 nm was measured using the Perkin Elmer Victor X4 HTRF reader. Data analysis was carried out by use of GraphPad Prism, sigmoidal dose-response (variable slope) curve fitting. Certain compounds of the present invention (as HCl salts) were tested as described above. Data is reported in Table 2 below.

TABLE 2

| Compound Number | Kappa receptor binding | | Mu receptor % inhibition at single concentration | Mu receptor binding | Kappa receptor activity |
|---|---|---|---|---|---|
| (not example number) | IC50 (nM) | Ki (nM) | % inhibition @ 10 μM | IC50 (nM) | EC50 cAMP (nM) |
| ICI-199,441 | 0.35 | 0.08 | 96.3 | 136.6 | 0.05 |
| Asimadoline | 11.5 | 2.6 | 46.3 | 11560 | 0.41 |
| U50, 488H | 30.23 | 6.98 | 58.6 | 5829.00 | 1.24 |
| 1 | 7.5 | 1.7 | 79.1 | | 1.2 |
| 10 | 82.7 | 19.1 | 82.8 | | 3.1 |
| 3 | 0.13 | 0.03 | 99.8 | 10.6 | 0.03 |
| 4 | 8.9 | 2.1 | 82 | 20410 | 0.42 |
| 7 | 298.1 | 68.79 | 68.6 | 15620 | 9 |
| 5 | 1194 | 275.5 | 35.6 | | 75.7 |
| 6 | 1105 | 255 | 20.6 | 31240 | 56 |
| 9 | 8974 | 2071 | 36.9 | | 178 |
| 12 | 849.3 | 196 | 46.5 | 53340 | 36.12 |
| 8 | 1480 | 341.6 | 47.5 | | 74.71 |
| 13 | 1320 | 304.7 | 69.9 | | |
| 11 | 58.12 | 13.41 | 45.2 | | 5.02 |
| 14 | 0.34 | 0.08 | 99.3 | | 0.05 |
| 15 | 2.33 | 0.54 | 84.1 | | 0.42 |
| 16 | 62.75 | 14.48 | 27.1 | | 15.1 |
| 17 | 1568 | 361.9 | 81.9 | | 67.32 |
| 18 | 0.57 | 0.13 | 97.8 | | 0.09 |
| 19 | 0.69 | 0.16 | 99.1 | | 0.08 |
| 20 | 0.6 | 0.14 | 97.1 | | 0.15 |
| 21 | 0.18 | 0.04 | 96.5 | | 0.2 |
| 22 | 0.32 | 0.07 | 90.2 | | 0.03 |
| 23 | 2.28 | 0.3 | 75.0 | | 0.09 |
| 24 | 3592 | 468.5 | −7.9 | 158300 | 264.60 |
| 25 | 31.84 | 4.15 | 57.5 | 4512 | 4.07 |
| 26 | 1132 | 147.6 | 35.1 | 38680 | 14.35 |
| 27 | 106.1 | 13.84 | 50.4 | 9215 | 4.38 |
| 28 | 2100 | 273.9 | 4.9 | 73360 | 147.70 |
| 29 | 580 | 110.9 | 30.5 | 25940 | 41.22 |
| 30 | 463.6 | 60.47 | 85.5 | | 38.9 |
| 31 | 59.82 | 7.8 | 95.6 | 177.8 | 16.4 |
| 32 | 1.08 | 0.25 | 78.0 | | 0.18 |
| 33 | 1237 | 285.4 | 84.1 | | |
| 34 | 106.6 | 24.64 | 17.6 | | 13 |
| 35 | 24.68 | 5.7 | 30.6 | | 2.59 |
| 36 | 0.43 | 0.1 | 64.9 | | 0.029 |
| 37 | 98.14 | 22.64 | 57.8 | | 4.15 |
| 38 | 0.49 | 0.06 | 87.2 | | 0.03 |
| 39 | 18490 | 4268 | 9.6 | | 1955 |
| 40 | 34.59 | 7.98 | 55.6 | | 2.34 |
| 41 | 5195 | 1199 | 20.5 | | |
| 42 | 2.9 | 0.67 | 67.4 | | 0.47 |
| 43 | 10.53 | 2.43 | 47.3 | | 1.12 |
| 44 | 4.86 | 1.12 | 67.7 | | 0.93 |
| 45 | 48.55 | 11.2 | 50.4 | | 30.1 |
| 46 | 3.95 | 0.91 | 73.7 | | 0.92 |
| 47 | 0.23 | 0.05 | 101 | | 0.02 |
| 48 | 3.48 | 0.8 | 73.2 | | 0.43 |
| 49 | 1.61 | 0.37 | 78.1 | | 0.11 |
| 50 | 0.52 | 0.12 | 101 | | 0.06 |
| 51 | 62.17 | 14.35 | 54.5 | | 5.18 |
| 52 | 66.42 | 15.33 | 64.8 | | 13.1 |
| 53 | 12.22 | 2.82 | 88 | | 0.52 |
| 54 | 0.16 | 0.04 | 101.4 | | 0.009 |

Asimadoline, ICI-199,441 and U50,488 were assayed as known kappa opioid agonists. As is evident from Table 2, several of the tested compounds have affinity for the kappa opioid receptor. Further, for the compounds tested at the mu opioid receptor (where an IC50 was generated), there is a selectivity for the kappa opioid receptor over the mu receptor.

The data in Table 2 further indicates that the tested compounds were effective in reducing cAMP in cells following KOR binding, indicating that the compounds function as agonists at the kappa opioid receptor.

Example 56

Assessment of of Hepatic Clearance in Humans and Rats Using Hepatocytes

All test compounds were obtained from Nektar Therapeutics (San Francisco, Calif., USA). Human and rat cryopreserved hepatocytes were purchased from Xenotech LLC (Lenexa, Kans., USA). Doxepin, acetonitrile, and formic acid were purchased from Sigma-Aldrich (St. Louis, Mo., USA).

Test compounds were incubated with species-specific, thawed hepatocytes for up to 0, 30, 60, 90, and 120 minutes at 37° C., 5% $CO_2$, and 75% relative humidity. Incubations were carried out at a final hepatocyte concentration of 0.5 million viable cells/mL and a final test article concentration of 500 nM. Final DMSO concentration was 0.01% (v/v). At each sampling time, 100 μL incubations were terminated by addition of 100 μL of ice-cold acetonitrile containing 200 nM doxepin as an internal standard and 0.1% (v/v) formic acid. Samples were immediately placed in an ice bath until centrifugation at 4,000 g for 30 min at 4° C. Sample supernatant was collected and stored at −70° C. prior to LC/MS/MS analysis. The slope of the linear regression from natural log percentage remaining of test compounds versus incubation time relationships was used in calculation of in vitro intrinsic clearance. In vivo hepatic clearance (Table 3) of test compounds was predicted from in vitro intrinsic clearance using the well-stirred model.

The data in Table 3 show that hepatic clearance of all the compounds in humans is predicted to be moderate to high and to be similar to that in rats except for the test compounds 34, 35, and 36. For the test compounds 34, 35, and 36, higher hepatic clearance is predicted in humans than in rats.

TABLE 3

| Compound | In vitro Hepatocyte Clearance | | | |
|---|---|---|---|---|
| Number | Rat | | Human | |
| (not example number) | CL (mL/min/kg) | % hep Blood flow | CL (mL/min/kg) | % hep Blood flow |
| ICI-199,441 | 44.0 | 73.0 | 19.7 | 85.0 |
| Asimadoline | 51.0 | 85.0 | 18.2 | 79.0 |
| 1 | 50.1 | 83.0 | 19.0 | 82.0 |
| 10 | 49.72 | 83 | 20.62 | 89 |
| 3 | 51.0 | 85.0 | 20.7 | 89.0 |
| 4 | 49 | 82 | 19.4 | 84 |
| 5 | 49.1 | 82 | 20.44 | 88 |
| 6 | 48.82 | 81 | 20.05 | 86 |
| 19 | 26.8 | 45 | 11.7 | 50 |
| 34 | 15.4 | 26 | 16.4 | 71 |
| 35 | 26.5 | 44 | 15 | 65 |
| 36 | 14.3 | 24 | 16.5 | 71 |

Based on the data reported in Table 4, there is comparable in-vitro clearance in both rat and human liver hepatocytes across all the compounds relative to known kappa agonists (ICI-199,441 and Asimadoline), where higher clearance is predicted in the rat relative to human.

Prophetic Example 1

Preparation of 2-(3,4-dichlorophenyl)-N-{(1S)-1-(3-{[(2-hydroxypropyl)sulfonyl]amino}phenyl)-2-[(3R)-3-hydroxypyrrolidin-1-yl]ethyl}-N-methylacetamide, hydrochloride salt

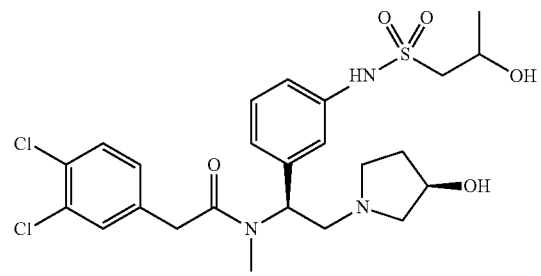 [SMILES: CC(O)CS(=O)(=O)Nc1cccc([C@@H](CN2CC[C@@H](O)C2)N(C)C(=O)Cc2ccc(Cl)c(Cl)c2)c1]

2-(3,4-Dichlorophenyl)-N-{(1S)-1-(3-{[(2-hydroxypropyl)sulfonyl]amino}phenyl)-2-[(3R)-3-hydroxypyrrolidin-1-yl]ethyl}-N-methylacetamide may be prepared according to the following steps.

Step 1: Preparation of N-{(1S)-1-(3-{[(2-{[tert-butyl(dimethyl)silyl]oxy}propyl) sulfonyl] amino}phenyl)-2-[(3R)-3-hydroxypyrrolidin-1-yl] ethyl}-2-(3,4-dichlorophenyl)-N-methylacetamide

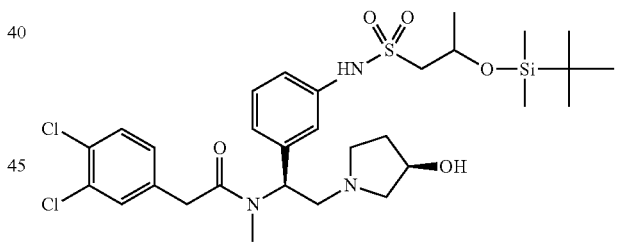

N-[(1S)-1-(3-Aminophenyl)-2-(pyrrolidin-1-yl)ethyl]-2-(3,4-dichloro-phenyl)-N-methylacetamide is dissolved in dichloromethane and anhydrous pyridine (7.5 equivalents). To the ice-cold solution is added 2-{[tert-butyl(dimethyl) silyl]oxy}propane-1-sulfonyl chloride (2.0 equivalents), dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives N-{(1S)-1-(3-{[(2-{[tert-butyl(dimethyl)silyl]oxy}propyl)sulfonyl]amino}phenyl)-2-[(3R)-3-hydroxypyrrolidin-1-yl] ethyl}-2-(3,4-dichlorophenyl)-N-methylacetamide.

Step 2: Preparation of 2-(3,4-dichlorophenyl)-N-{(1S)-1-(3-{[(2-hydroxypropyl)sulfonyl]amino}phenyl)-2-[(3R)-3-hydroxypyrrolidin-1-yl]ethyl}-N-methylacetamide, hydrochloride salt

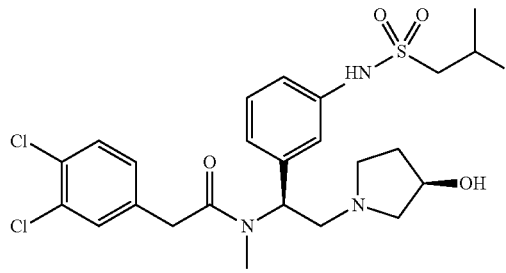

To a solution of N-{(1S)-1-(3-{[(2-{[tert-butyl(dimethyl)silyl]oxy}propyl) sulfonyl]amino}phenyl)-2-[(3R)-3-hydroxypyrrolidin-1-yl]ethyl}-2-(3,4-dichlorophenyl)-N-methylacetamide in tetrahydrofuran is added tetrabutylammonium fluoride (1.2 equivalents), and the resulting solution is stirred at room temperature for one hour. The solution is diluted with water, and the mixture is extracted three times with dichloromethane. The combined organic portions are dried over sodium sulfate, filtered, and concentrated under reduced pressure. The residue is purified by chromatography to give 2-(3,4-dichlorophenyl)-N-{(1S)-1-(3-{[(2-hydroxypropyl)sulfonyl]amino}phenyl)-2-[(3R)-3-hydroxypyrrolidin-1-yl]ethyl}-N-methylacetamide. The compound is converted into the hydrochloride salt by dissolving the oil in acetonitrile and adding 1N hydrochloric acid. The solution is lyophilized to give the hydrochloride salt.

Prophetic Example 2

Preparation of N-{(1S)-1-(3-{[(2-hydroxypropyl)sulfonyl]amino}phenyl)-2-[(3R)-3-hydroxypyrrolidin-1-yl]ethyl}-N-methyl-2,2-diphenylacetamide, hydrochloride salt

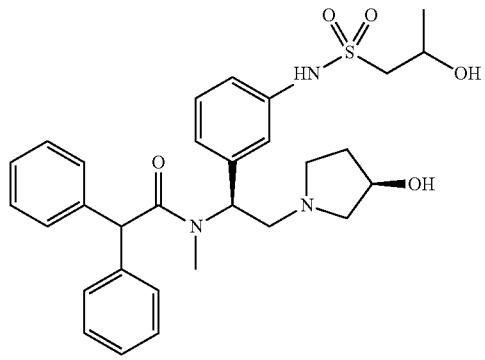 [SMILES: CC(O)CS(=O)(=O)Nc1cccc([C@@H](CN2CC[C@@H](O)C2)N(C)C(=O)C(c2ccccc2)c2ccccc2)c1]

N-{(1S)-1-(3-{[(2-Hydroxypropyl)sulfonyl]amino}phenyl)-2-[(3R)-3-hydroxypyrrolidin-1-yl]ethyl}-N-methyl-2,2-diphenylacetamide may be prepared according to the following steps.

Step 1: Preparation of N-{(1S)-1-(3-{[(2-{[tert-butyl(dimethyl)silyl]oxy}propyl)sulfonyl]amino}phenyl)-2-[(3R)-3-hydroxypyrrolidin-1-yl]ethyl}-N-methyl-2,2-diphenylacetamide

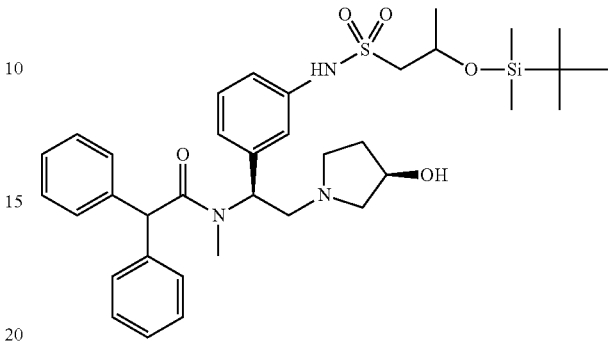

N-[(1S)-1-(3-Aminophenyl)-2-(pyrrolidin-1-yl)ethyl]-N-methyl-2,2-diphenylacetamide is dissolved in dichloromethane and anhydrous pyridine (7.5 equivalents). To the ice-cold solution is added 2-{[tert-butyl(dimethyl)silyl]oxy}propane-1-sulfonyl chloride (2.0 equivalents), dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous layer is extracted with dichloromethane and washed with saturated sodium chloride. The organic portion is dried over anhydrous sodium sulfate, filtered and concentrated to an orange residue. Purification by chromatography gives N-{(1S)-1-(3-{[(2-{[tert-butyl(dimethyl)silyl]oxy}propyl) sulfonyl]amino}phenyl)-2-[(3R)-3-hydroxypyrrolidin-1-yl]ethyl}-N-methyl-2,2-diphenylacetamide.

Step 2: Preparation of N-{(1S)-1-(3-{[(2-hydroxypropyl)sulfonyl]amino}phenyl)-2-[(3R)-3-hydroxypyrrolidin-1-yl]ethyl}-N-methyl-2,2-diphenylacetamide

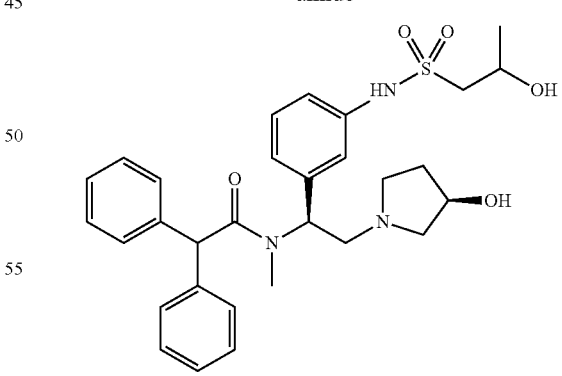

To a solution of N-{(1S)-1-(3-{[(2-{[tert-butyl(dimethyl)silyl]oxy}propyl) sulfonyl]amino}phenyl)-2-[(3R)-3-hydroxypyrrolidin-1-yl]ethyl}-N-methyl-2,2-diphenylacetamide in tetrahydrofuran is added tetrabutylammonium fluoride (1.2 equivalents), and the resulting solution is stirred at room temperature for one hour. The solution is diluted with water, and the mixture is extracted three times with dichloromethane. The combined organic portions are dried over sodium sulfate, filtered, and concentrated under reduced pressure. The residue is purified by chromatography to give N-{(1S)-1-(3-{[(2-hydroxypropyl)sulfonyl]amino}phenyl)-2-[(3R)-3-hydroxypyrrolidin-1-yl]ethyl}-N-methyl-2,2-diphenylacetamide. The compound is converted into the hydrochloride salt by dissolving the oil in acetonitrile and adding 1N hydrochloric acid. The solution is lyophilized to give the hydrochloride salt.

Prophetic Example 3

Preparation of 2-(3,4-dichlorophenyl)-N-{(1S)-2-[(3R)-3-hydroxypyrrolidin-1-yl]-1-[3-({[2-(2,2,2-trifluoroethoxy)ethyl]sulfonyl}amino)phenyl]ethyl}-N-methylacetamide, hydrochloride salt

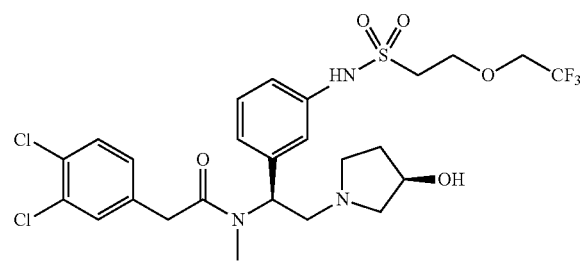 [SMILES: CN(C(=O)Cc1ccc(Cl)c(Cl)c1)[C@H](CN1CC[C@@H](O)C1)c1cccc(NS(=O)(=O)CCOCC(F)(F)F)c1]

N-{(1S)-1-(3-Aminophenyl)-2-[(3R)-3-hydroxypyrrolidin-1-yl]ethyl}-2-(3,4-dichlorophenyl)-N-methylacetamide is dissolved in dichloromethane and anhydrous pyridine (7.5 equivalents). To the ice-cold solution is added 2-(2,2,2-trifluoroethoxy)ethanesulfonyl chloride (2.0 equivalents), dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives 2-(3,4-dichlorophenyl)-N-{(1S)-2-[(3R)-3-hydroxypyrrolidin-1-yl]-1-[3-({[2-(2,2,2-trifluoroethoxy)ethyl]sulfonyl}amino)phenyl]ethyl}-N-methylacetamide.

The compound is converted into the hydrochloride salt by dissolving the oil in acetonitrile and adding 1N hydrochloric acid. The solution is lyophilized to give the hydrochloride salt.

Prophetic Example 4

Preparation of N-{(1S)-2-[(3R)-3-hydroxypyrrolidin-1-yl]-1-[3-({[2-(2,2,2-trifluoroethoxy)ethyl]sulfonyl}amino)phenyl]ethyl}-N-methyl-2,2-diphenylacetamide, hydrochloride salt

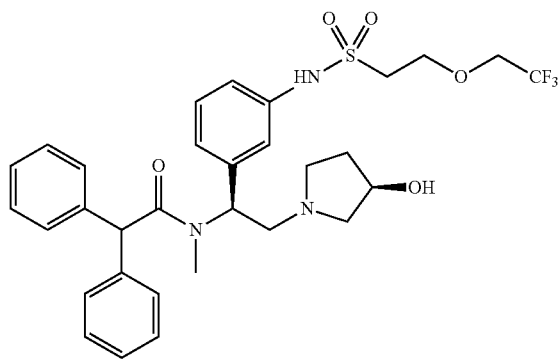 [SMILES: CN(C(=O)C(c1ccccc1)c1ccccc1)[C@H](CN1CC[C@@H](O)C1)c1cccc(NS(=O)(=O)CCOCC(F)(F)F)c1]

N-[(1S)-1-(3-Aminophenyl)-2-(pyrrolidin-1-yl)ethyl]-N-methyl-2,2-diphenylacetamide is dissolved in dichloromethane and anhydrous pyridine (7.5 equivalents). To the ice-cold solution is added 2-(2,2,2-trifluoroethoxy)ethanesulfonyl chloride (2.0 equivalents), dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous layer is extracted with dichloromethane and washed with saturated sodium chloride. The organic portion is dried over anhydrous sodium sulfate, filtered and concentrated to an orange residue. Purification by chromatography gives N-{(1S)-2-[(3R)-3-hydroxypyrrolidin-1-yl]-1-[3-({[2-(2,2,2-trifluoroethoxy)ethyl]sulfonyl}amino)phenyl]ethyl}-N-methyl-2,2-diphenylacetamide.

The compound is converted into the hydrochloride salt by dissolving the oil in acetonitrile and adding 1N hydrochloric acid. The solution is lyophilized to give the hydrochloride salt Prophetic Example 5

Preparation of N-{(1S)-1-(3-{[(4-cyanophenyl)sulfonyl]amino}phenyl)-2-[(3R)-3-hydroxypyrrolidin-1-yl]ethyl}-2-(3,4-dichlorophenyl)-N-methylacetamide, hydrochloride salt

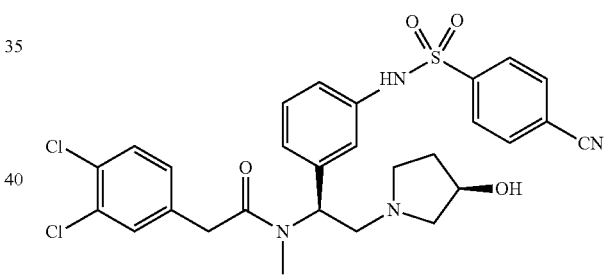

N-{(1S)-1-(3-Aminophenyl)-2-[(3R)-3-hydroxypyrrolidin-1-yl]ethyl}-2-(3,4-dichlorophenyl)-N-methylacetamide is dissolved in dichloromethane and anhydrous pyridine (7.5 equivalents). To the ice-cold solution is added 4-cyanobenzenesulfonyl chloride (2.0 equivalents) dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives N-{(1S)-1-(3-{[(4-cyanophenyl)sulfonyl]amino}phenyl)-2-[(3R)-3-hydroxypyrrolidin-1-yl]ethyl}-2-(3,4-dichlorophenyl)-N-methylacetamide.

The compound is converted into the hydrochloride salt by dissolving the oil in acetonitrile and adding 1N hydrochloric acid. The solution is lyophilized to give the hydrochloride salt.

Prophetic Example 6

Preparation of N-{(1S)-1-(3-{[(4-cyanophenyl)sulfonyl]amino}phenyl)-2-[(3R)-3-hydroxypyrrolidin-1-yl]ethyl}-N-methyl-2,2-diphenylacetamide, hydrochloride salt

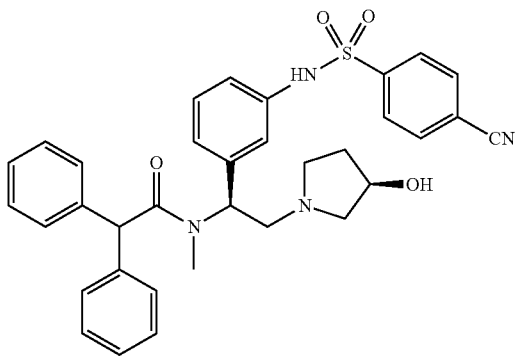 [SMILES: CN(C(=O)C(c1ccccc1)c1ccccc1)[C@H](CN1CC[C@@H](O)C1)c1cccc(NS(=O)(=O)c2ccc(C#N)cc2)c1]

N-[(1S)-1-(3-Aminophenyl)-2-(pyrrolidin-1-yl)ethyl]-N-methyl-2,2-diphenylacetamide is dissolved in dichloromethane and anhydrous pyridine (7.5 equivalents). To the ice-cold solution is added 4-cyanobenzenesulfonyl chloride (2.0 equivalents) dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives N-{(1S)-1-(3-{[(4-cyanophenyl)sulfonyl]amino}phenyl)-2-[(3R)-3-hydroxypyrrolidin-1-yl]ethyl}-N-methyl-2,2-diphenylacetamide.

The compound is converted into the hydrochloride salt by dissolving the oil in acetonitrile and adding 1N hydrochloric acid. The solution is lyophilized to give the hydrochloride salt.

Prophetic Example 7

Preparation of N-{(1S)-1-(3-{[(6-cyanopyridin-3-yl)sulfonyl]amino}phenyl)-2-[(3R)-3-hydroxypyrrolidin-1-yl]ethyl}-2-(3,4-dichlorophenyl)-N-methylacetamide, hydrochloride salt

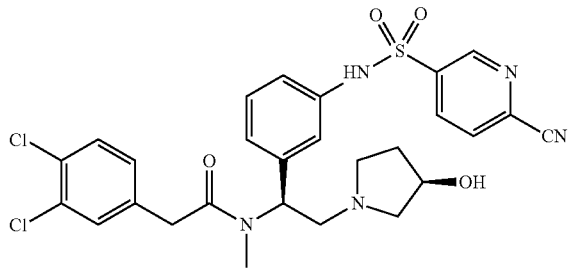 [SMILES: CN(C(=O)Cc1ccc(Cl)c(Cl)c1)[C@H](CN1CC[C@@H](O)C1)c1cccc(NS(=O)(=O)c2ccc(C#N)nc2)c1]

N-{(1S)-1-(3-Aminophenyl)-2-[(3R)-3-hydroxypyrrolidin-1-yl]ethyl}-2-(3,4-dichlorophenyl)-N-methylacetamide is dissolved in dichloromethane and anhydrous pyridine (7.5 equivalents). To the ice-cold solution is added 6-cyanopyridine-3-sulfonyl chloride (2.0 equivalents) dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives N-{(1S)-1-(3-{[(6-cyanopyridin-3-yl)sulfonyl]amino}phenyl)-2-[(3R)-3-hydroxypyrrolidin-1-yl]ethyl}-2-(3,4-dichlorophenyl)-N-methylacetamide.

The compound is converted into the hydrochloride salt by dissolving the oil in acetonitrile and adding 1N hydrochloric acid. The solution is lyophilized to give the hydrochloride salt.

Prophetic Example 8

Preparation of N-{(1S)-1-(3-{[(6-cyanopyridin-3-yl)sulfonyl]amino}phenyl)-2-[(3R)-3-hydroxypyrrolidin-1-yl]ethyl}-N-methyl-2,2-diphenylacetamide, hydrochloride salt

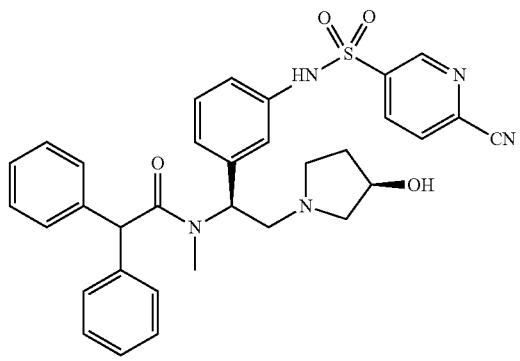 [SMILES: CN(C(=O)C(c1ccccc1)c1ccccc1)[C@H](CN1CC[C@@H](O)C1)c1cccc(NS(=O)(=O)c2ccc(C#N)nc2)c1]

N-[(1S)-1-(3-Aminophenyl)-2-(pyrrolidin-1-yl)ethyl]-N-methyl-2,2-diphenylacetamide is dissolved in dichloromethane and anhydrous pyridine (7.5 equivalents). To the ice-cold solution is added 6-cyanopyridine-3-sulfonyl chloride (2.0 equivalents) dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives N-{(1S)-1-(3-{[(6-cyanopyridin-3-yl)sulfonyl]amino}phenyl)-2-[(3R)-3-hydroxypyrrolidin-1-yl]ethyl}-N-methyl-2,2-diphenylacetamide.

The compound is converted into the hydrochloride salt by dissolving the oil in acetonitrile and adding 1N hydrochloric acid. The solution is lyophilized to give the hydrochloride salt.

Prophetic Example 9

Preparation of N-{(1S)-1-[3-({[4-cyano-3-(trifluoromethyl)phenyl]sulfonyl}amino)phenyl]-2-[(3R)-3-hydroxypyrrolidin-1-yl]ethyl}-2-(3,4-dichlorophenyl)-N-methylacetamide, hydrochloride salt

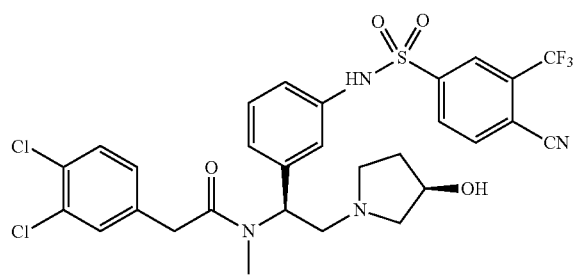 [SMILES: CN(C(=O)Cc1ccc(Cl)c(Cl)c1)[C@H](CN1CC[C@@H](O)C1)c1cccc(NS(=O)(=O)c2ccc(C#N)c(C(F)(F)F)c2)c1]

N-{(1S)-1-(3-Aminophenyl)-2-[(3R)-3-hydroxypyrrolidin-1-yl]ethyl}-2-(3,4-dichlorophenyl)-N-methylacetamide is dissolved in dichloromethane and anhydrous pyridine (7.5 equivalents). To the ice-cold solution is added 4-Cyano-3-(trifluoromethyl)benzenesulfonyl chloride (2.0 equivalents) dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives N-{(1S)-1-[3-({[4-cyano-3-(trifluoromethyl)phenyl]sulfonyl}amino)phenyl]-2-[(3R)-3-hydroxypyrrolidin-1-yl]ethyl}-2-(3,4-dichlorophenyl)-N-methylacetamide.

The compound is converted into the hydrochloride salt by dissolving the oil in acetonitrile and adding 1N hydrochloric acid. The solution is lyophilized to give the hydrochloride salt.

Prophetic Example 10

Preparation of N-{(1S)-1-[3-({[4-cyano-3-(trifluoromethyl)phenyl]sulfonyl}amino)phenyl]-2-[(3R)-3-hydroxypyrrolidin-1-yl]ethyl}-N-methyl-2,2-diphenylacetamide, hydrochloride salt

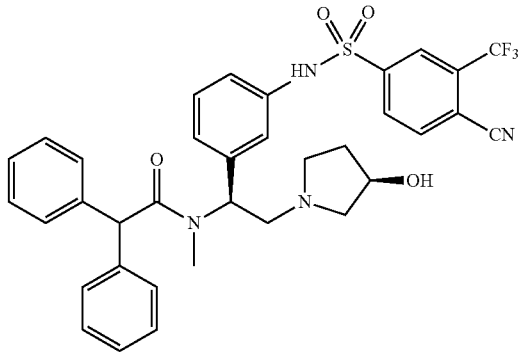 [SMILES: CN(C(=O)C(c1ccccc1)c1ccccc1)[C@H](CN1CC[C@@H](O)C1)c1cccc(NS(=O)(=O)c2ccc(C#N)c(C(F)(F)F)c2)c1]

N-[(1S)-1-(3-Aminophenyl)-2-(pyrrolidin-1-yl)ethyl]-N-methyl-2,2-diphenylacetamide is dissolved in dichloromethane and anhydrous pyridine (7.5 equivalents). To the ice-cold solution is added 4-Cyano-3-(trifluoromethyl)benzenesulfonyl chloride (2.0 equivalents) dropwise, maintaining the temperature less than 10° C. The yellow reaction mixture is allowed to stir at 0° C., with the color turning orange. The reaction mixture is allowed to equilibrate to room temperature. After approximately 17 hours at room temperature the orange mixture is diluted with dichloromethane and partitioned with water. The aqueous portion is extracted with dichloromethane and washed with saturated sodium chloride. The organic portion is dried over anhydrous sodium sulfate, filtered and concentrated to an orange residue. Purification by chromatography gives N-{(1S)-1-[3-({[4-cyano-3-(trifluoromethyl)phenyl]sulfonyl}amino)phenyl]-2-[(3R)-3-hydroxypyrrolidin-1-yl]ethyl}-N-methyl-2,2-diphenylacetamide.

The compound is converted into the hydrochloride salt by dissolving the oil in acetonitrile and adding 1N hydrochloric acid. The solution is lyophilized to give the hydrochloride salt.

Prophetic Example 11

Preparation of 2-(3,4-dichlorophenyl)-N-{(1S)-1-{3-[(2,5,8,11,14,17,20-heptaoxadocosan-22-ylcarbamoyl)amino]phenyl}-2-[(3R)-3-hydroxypyrrolidin-1-yl]ethyl}-N-methylacetamide, hydrochloride salt

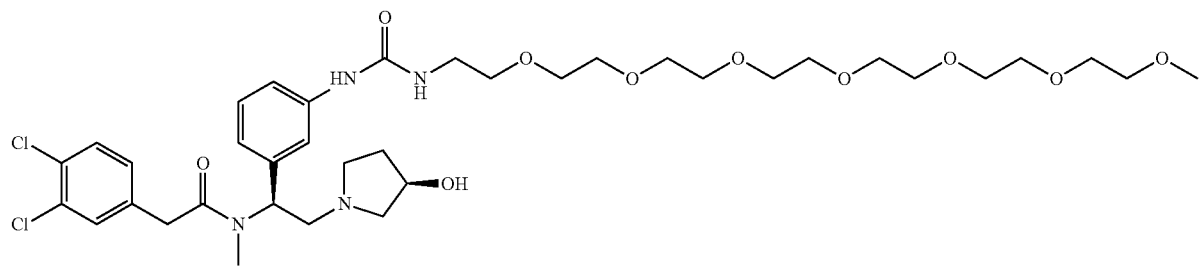 [SMILES: COCCOCCOCCOCCOCCOCCOCCNC(=O)Nc1cccc([C@@H](CN2CC[C@@H](O)C2)N(C)C(=O)Cc2ccc(Cl)c(Cl)c2)c1]

To a solution of triphosgene (0.50 equivalents) in anhydrous acetonitrile, at −5° C., is added an acetonitrile solution of N-{(1S)-1-(3-aminophenyl)-2-[(3R)-3-hydroxypyrrolidin-1-yl]ethyl}-2-(3,4-dichlorophenyl)-N-methylacetamide (1.0 equivalent) and triethylamine (1.30 equivalents) over a period of 10 minutes. The mixture is stirred for an additional 20 minutes at 0° C., and then a dichloroethane solution of 2,5,8,11,14,17,20-heptaoxadocosan-22-amine and triethylamine (1.30 equivalents) is added, maintaining the temperature less than 5° C. The reaction mixture is allowed to equilibrate to room temperature overnight. After approximately 17 hours the mixture is diluted with dichloromethane (40 mL) and partitioned with water. The aqueous portion is extracted with dichloromethane three times. The combined organic portions are washed with water and saturated sodium chloride. The organic portion is dried over anhydrous sodium sulfate, filtered and concentrated under reduced pressure to give a residue. Purification by chromatography gives 2-(3,4-dichlorophenyl)-N-{(1S)-1-{3-[(2,5,8,11,14,17,20-heptaoxadocosan-22-ylcarbamoyl)amino]phenyl}-2-[(3R)-3-hydroxypyrrolidin-1-yl]ethyl}-N-methylacetamide.

The compound is converted into the hydrochloride salt by dissolving the oil in acetonitrile and adding 1N hydrochloric acid. The solution is lyophilized to give the hydrochloride salt.

The prophetic example described above may be modified to introduce oligomers of various lengths as disclosed herein.

Prophetic Example 12

Preparation of N-{1-[4-(2-hydroxyethyl)phenyl]-2-[(3S)-3-hydroxypyrrolidin-1-yl]ethyl}-N-methyl-2,2-diphenylacetamide, hydrochloride salt

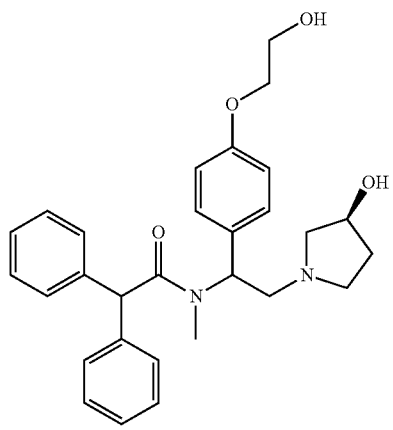 [SMILES: CN(C(=O)C(c1ccccc1)c1ccccc1)C(CN1CC[C@H](O)C1)c1ccc(OCCO)cc1]

N-{1-[4-(2-hydroxyethyl)phenyl]-2-[(3S)-3-hydroxypyrrolidin-1-yl]ethyl}-N-methyl-2,2-diphenylacetamide may be prepared according to the following steps.

Step 1: Preparation of N-(2-[(3S)-3-Hydroxypyrrolidin-1-yl]-1-{4-[2-(tetrahydro-2H-pyran-2-yloxy)ethoxy]phenyl}ethyl)-N-methyl-2,2-diphenylacetamide

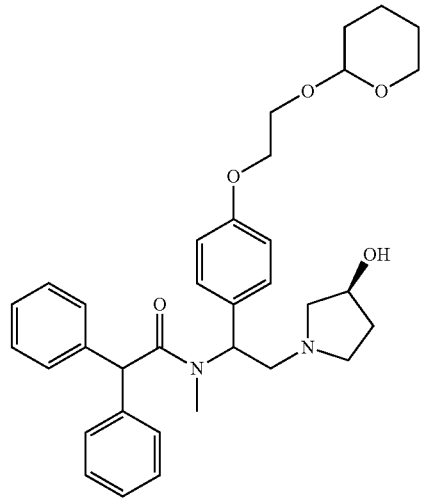 [SMILES: CN(C(=O)C(c1ccccc1)c1ccccc1)C(CN1CC[C@H](O)C1)c1ccc(OCCOC2CCCCO2)cc1]

(3S)-1-[(2S)-2-(Methylamino)-2-{4-[2-(tetrahydro-2H-pyran-2-yloxy)ethoxy]phenyl}ethyl]pyrrolidin-3-ol is dissolved in anhydrous dichloromethane. To the solution is added diisopropylethylamine (2.0 equivalents) at 0° C. Diphenylacetyl chloride (1.10 equivalents) is dissolved in anhydrous dichloromethane and is added dropwise to the above solution, maintaining the temperature below 5° C. The reaction mixture is allowed to equilibrate to room temperature. After approximately 17 hours at room temperature the mixture is partitioned between dichloromethane and water. The aqueous layer is extracted with dichloromethane three times. The combined organic portion is washed with saturated sodium bicarbonate, and saturated sodium chloride. The organic portion is dried over anhydrous sodium sulfate, filtered and concentrated under reduced pressure. The residue is purified by chromatography to give N-(2-[(3S)-3-hydroxypyrrolidin-1-yl]-1-{4-[2-(tetrahydro-2H-pyran-2-yloxy)ethoxy]phenyl}ethyl)-N-methyl-2,2-diphenylacetamide.

Step 2: Preparation of N-{1-[4-(2-hydroxyethyl)phenyl]-2-[(3S)-3-hydroxypyrrolidin-1-yl]ethyl}-N-methyl-2,2-diphenylacetamide, hydrochloride salt

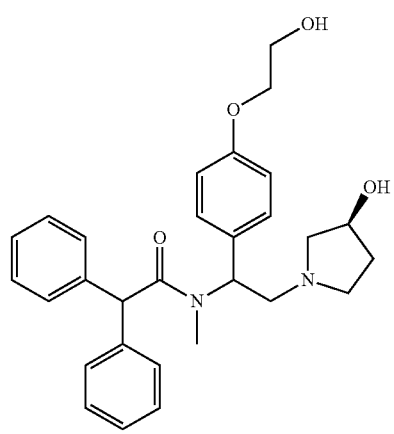 [SMILES: CN(C(=O)C(c1ccccc1)c1ccccc1)C(CN1CC[C@H](O)C1)c1ccc(OCCO)cc1]

N-(2-[(3S)-3-Hydroxypyrrolidin-1-yl]-1-{4-[2-(tetrahydro-2H-pyran-2-yloxy)ethoxy]phenyl}ethyl)-N-methyl-2,2-diphenylacetamide and 4-methylbenzenesulfonic acid (2.0 equivalents) are dissolved in methanol. The mixture is stirred for one hour at room temperature. After one hour the reaction mixture is diluted with dichloromethane and partitioned with water. The aqueous layer is extracted with dichloromethane three times. The combined organic portions are washed with aqueous sodium carbonate, water and saturated sodium chloride. The organic portion is dried over anhydrous sodium sulfate, filtered and concentrated under reduced pressure. The residue is purified by chromatography to give N-{1-[4-(2-hydroxyethyl)phenyl]-2-[(3S)-3-hydroxypyrrolidin-1-yl]ethyl}-N-methyl-2,2-diphenylacetamide.

The compound is converted into the hydrochloride salt by dissolving the oil in acetonitrile and adding 1N hydrochloric acid. The solution is lyophilized to give the hydrochloride salt.

The prophetic example described above may be modified to introduce oligomers of various lengths as disclosed herein.

Prophetic Example 13

Preparation of 2-(3,4-Dichlorophenyl)-N-{(1S)-1-[4-(2-hydroxyethoxy)phenyl]-2-[(3S)-3-(2-hydroxyethoxy)pyrrolidin-1-yl]ethyl}-N-methylacetamide Using the procedure outlined in the schematic below, the named compound can be prepared.

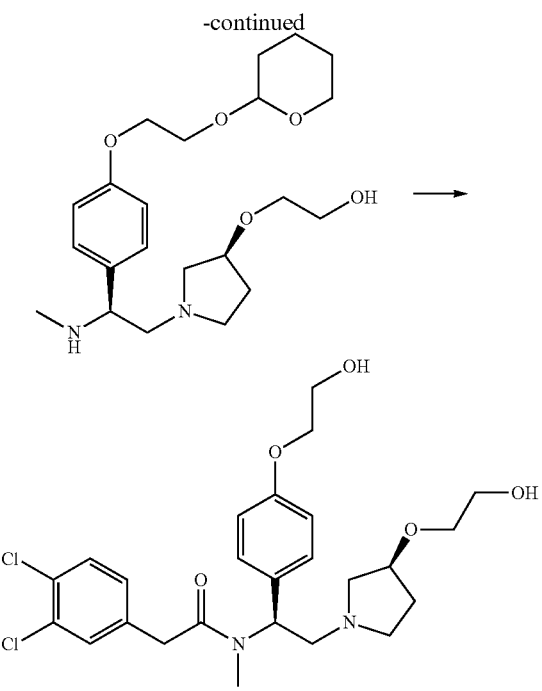

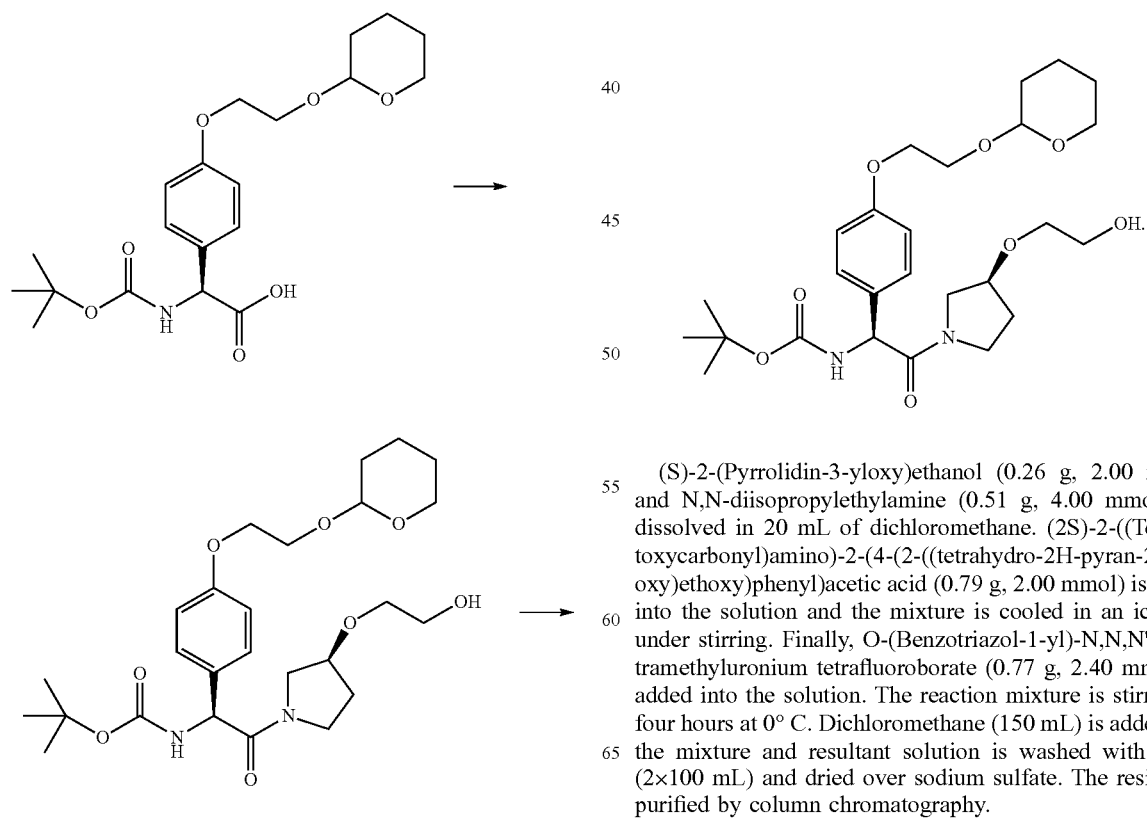

Step 1: Preparation of tert-butyl ((1S)-2-((S)-3-(2-hydroxyethoxy)pyrrolidin-1-yl)-2-oxo-1-(4-(2-((tetrahydro-2H-pyran-2-yl)oxy)ethoxy)phenyl)ethyl)carbamate.

(S)-2-(Pyrrolidin-3-yloxy)ethanol (0.26 g, 2.00 mmol) and N,N-diisopropylethylamine (0.51 g, 4.00 mmol) are dissolved in 20 mL of dichloromethane. (2S)-2-((Tert-butoxycarbonyl)amino)-2-(4-(2-((tetrahydro-2H-pyran-2-yl)oxy)ethoxy)phenyl)acetic acid (0.79 g, 2.00 mmol) is added into the solution and the mixture is cooled in an ice-bath under stirring. Finally, O-(Benzotriazol-1-yl)-N,N,N',N'-tetramethyluronium tetrafluoroborate (0.77 g, 2.40 mmol) is added into the solution. The reaction mixture is stirred for four hours at 0° C. Dichloromethane (150 mL) is added into the mixture and resultant solution is washed with water (2×100 mL) and dried over sodium sulfate. The residue is purified by column chromatography.

Step 2: Preparation of 2-(((3S)-1-((2S)-2-(methylamino)-2-(4-(2-((tetrahydro-2H-pyran-2-yl)oxy)ethoxy)phenyl)ethyl)pyrrolidin-3-yl)oxy)ethanol,

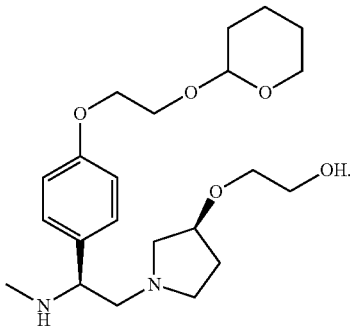 [SMILES: CN[C@H](CN1CC[C@H](OCCO)C1)c1ccc(OCCOC2CCCCO2)cc1]

Tert-butyl ((1S)-2-((S)-3-(2-hydroxyethoxy)pyrrolidin-1-yl)-2-oxo-1-(4-(2-((tetrahydro-2H-pyran-2-yl)oxy)ethoxy)phenyl)ethyl)carbamate (0.51 g, 1.00 mmol) is dissolved in tetrahydrofuran (6 mL). A 2.0 M solution of lithium aluminum hydride (2.8 mL, 5.6 mmol) is added into the solution at room temperature. The mixture is stirred at 65° C. for four hours. A 3N solution of sodium carbonate is added cautiously until effervescence ceased. Dichloromethane (50 mL) is added into the mixture. The solid is filtered out and washed with dichloromethane (100 mL). The filtrate is washed with saturated sodium chloride solution and dried over sodium sulfate. The product is obtained after removing solvent.

oxy)ethanol (0.082 g, 0.20 mmol), 3,4-dichlorophenylacetic acid (0.041 g, 0.20 mmol), and N,N-diisopropylethylamine (0.051 g, 0.40 mmol) are dissolved in 5 mL of acetonitrile. The mixture is stirred for ten minutes at room temperature and then cooled to 0° C. O-(Benzotriazol-1-yl)-N,N,N',N'-tetramethyluronium tetrafluoroborate (0.077 g, 0.24 mmol) is added into the solution. The reaction mixture is stirred for three hours under an ice-bath. Dichloromethane (150 mL) is added into the solution and the resultant solution is washed with water and dried over sodium sulfate. Evaporation of the solvent and purification of the residue by flash chromatography yield an oil, which is dissolved in 10 mL of methanol. p-Toluenesulfonic acid (0.056 g, 0.32 mmol) is added into the solution. The mixture is stirred for 60 minutes at room temperature. Dichloromethane (100 mL) is added into the solution and the solution is washed with sodium carbonate (10%), water and dried over sodium sulfate. Evaporation of the solvent and purification of the residue by flash chromatography yield product.

The third step of reaction described above may be modified to introduce various substituted phenyl (such as difluorophenyl, 4-trifluorophethyl) and heterocycles (such as pyridine, thoazole, benzofuran).

The prophetic example described above may be modified to introduce oligomers of various lengths as disclosed herein.

Prophetic Example 14

Preparation of (S)—N-(1-(3-(N-(2,5,8,11,14,17,20-heptaoxadocosan-22-yl)sulfamoyl)phenyl)-2-(pyrrolidin-1-yl)ethyl)-2-(3,4-dichlorophenyl)-N-methylacetamide hydrochloride

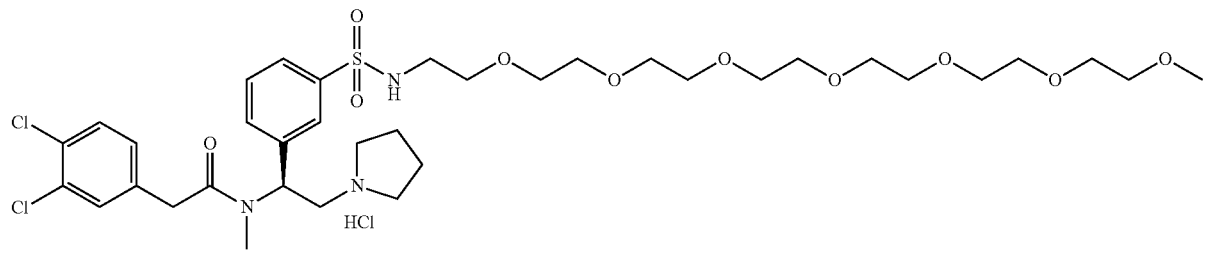

Step 3: Preparation 2-(3,4-dichlorophenyl)-N—((S)-1-(4-(2-hydroxyethoxy)phenyl)-2-((S)-3-(2-hydroxyethoxy)pyrrolidin-1-yl)ethyl)-N-methylacetamide (S)—N-(1-(3-(N-(2,5,8,11,14,17,20-Heptaoxadocosan-22-yl)sulfamoyl)phenyl)-2-(pyrrolidin-1-yl)ethyl)-2-(3,4-dichlorophenyl)-N-methylacetamide hydrochloride can be synthesized as per following procedures.

Step 1: Preparation of (S)-benzyl (2-oxo-1-phenyl-2-(pyrrolidin-1-yl)ethyl)carbamate

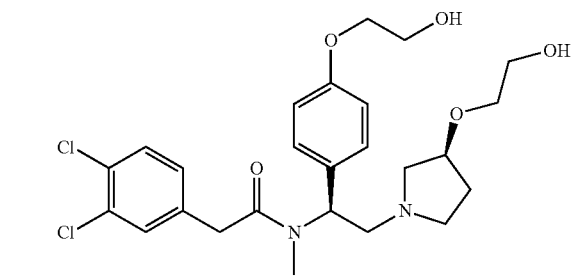 [SMILES: CN(C(=O)Cc1ccc(Cl)c(Cl)c1)[C@H](CN1CC[C@H](OCCO)C1)c1ccc(OCCO)cc1]

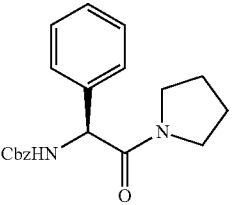 [SMILES: O=C(N[C@H](C(=O)N1CCCC1)c1ccccc1)OCc1ccccc1]

2-(((3S)-1-((2S)-2-(Methylamino)-2-(4-(2-((tetrahydro-2H-pyran-2-yl)oxy)ethoxy)phenyl)ethyl)pyrrolidin-3-yl)

To a stirred and cooled solution (0° C.) of (S)-2-(((Benzyloxy)carbonyl)amino)-2-phenylacetic acid (3 g, 10.51 mmol), pyrrolidine (0.822 g, 11.57 mmol) and diisopropyl ethyl amine (2.75 mL, 15.76 mmol) in acetonitrile (45 mL) is charged O-(benzotriazol-1-yl)-N,N,N',N'-tetramethyluronium tetrafluoroborate (TBTU) (5.06 g, 15.76 mmol). The solution is stirred for one hour at 0° C. and then for four hours at ambient temperature. A work up step comprising concentration of the reaction mixture, will give a crude product, which is dissolved in dichloromethane (50 mL). Following washes with brine (25 mL×2) and drying over anhydrous sodium sulfate, the dichloromethane layer is concentrated. The residue obtained is purified by column chromatography to afford (S)-benzyl (2-oxo-1-phenyl-2-(pyrrolidin-1-yl)ethyl)carbamate.

Step 2: Preparation of (S)—N-methyl-1-phenyl-2-(pyrrolidin-1-yl)ethanamine

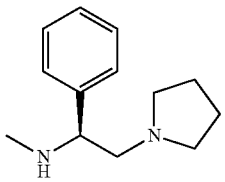

(S)-benzyl (2-oxo-1-phenyl-2-(pyrrolidin-1-yl)ethyl)carbamate (2.5 g, 7.4 mmol) is dissolved in tetrahydrofuran (25 mL) and the solution is cooled to 0° C. To the cooled solution, LAH (1.40 g, 37 mmol) is charged. After stirring the reaction for 15 minutes at 0° C., it is warmed to 65° C. and stirred for 16 hours. After cooling the reaction mass to 0° C., 3N aq. sodium carbonate solution (75 mL) is charged to it, until effervescence ceases. Precipitated solid is filtered and the organic layer is separated (in the filtrate). The product is extracted into 1N aq. HCl (25 mL×2), form the organic phase. The combine aqueous acidic layer is washed with methyl tertbutyl ether (15 mL×3). The pH of the aqueous layer is adjusted to 9, and the product is extracted into ethyl acetate (20 mL×2). The organic layer is washed with brine, dried over anhydrous sodium sulfate and concentrated under vacuum to afford the crude compound. The crude is purified using column chromatography to afford (S)—N-methyl-1-phenyl-2-(pyrrolidin-1-yl)ethanamine.

Step 3: Preparation of (S)-(9H-fluoren-9-yl)methyl methyl(1-phenyl-2-(pyrrolidin-1-yl)ethyl)carbamate

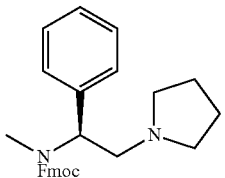

(S)—N-Methyl-1-phenyl-2-(pyrrolidin-1-yl)ethanamine (2.2 g, 10.76 mmol), diisopropyl ethyl amine (1.87 mL, 10.76 mmol) are dissolved in acetonitrile (20 mL), and the solution is cooled to 0° C. FMOC-Cl (2.78 g, 10.76 mmol) is charged to the cooled solution. After the addition, the mixture is warmed to ambient temperature, and the reaction is stirred for two hours. At the end of two hours, the reaction mixture is concentrated under reduced pressure and the crude mass is dissolved in ethyl acetate (20 mL). The ethyl acetate solution, after washes with water (10 mL×2) and brine (10 mL), is dried over anhydrous sodium sulfate. Concentration of the organic layer under vacuum would affords the crude compound. The crude is purified by column chromatography to afford (S)-(9H-fluoren-9-yl)methyl methyl(1-phenyl-2-(pyrrolidin-1-yl)ethyl)carbamate.

Step 4: Preparation of (S)-(9H-fluoren-9-yl)methyl (1-(3-(chlorosulfonyl)phenyl)-2-(pyrrolidin-1-yl)ethyl)(methyl)carbamate

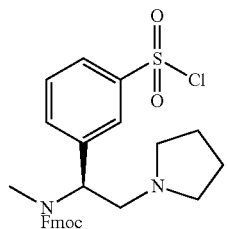

A solution of (S)-(9H-fluoren-9-yl)methyl methyl(1-phenyl-2-(pyrrolidin-1-yl)ethyl)carbamate (2.0 g, 4.67 mmol) in dichloromethane (20 mL) is cooled to −20° C. The cooled solution is charged with a solution of chlorosulfonic acid (0.655 g, 5.62 mmol) in dichloromethane (2 mL) at −20° C. (over 15 minutes). The contents are slowly warmed to ambient temperature and stirred for 16 hours at that temperature. The reaction mixture is quenched into a stirring mixture of dichloromethane (20 mL), crushed ice and water. The organic layer is separated, washed with brine, dried over anhydrous sodium sulfate and concentrated under vacuum to afford crude (S)-(9H-fluoren-9-yl)methyl (1-(3-(chlorosulfonyl)phenyl)-2-(pyrrolidin-1-yl)ethyl)(methyl) carbamate.

Step 5: Preparation of (S)-(9H-fluoren-9-yl)methyl (1-(3-(N-(2,5,8,11,14,17,20-heptaoxadocosan-22-yl)sulfamoyl)phenyl)-2-(pyrrolidin-1-yl)ethyl)(methyl) carbamate

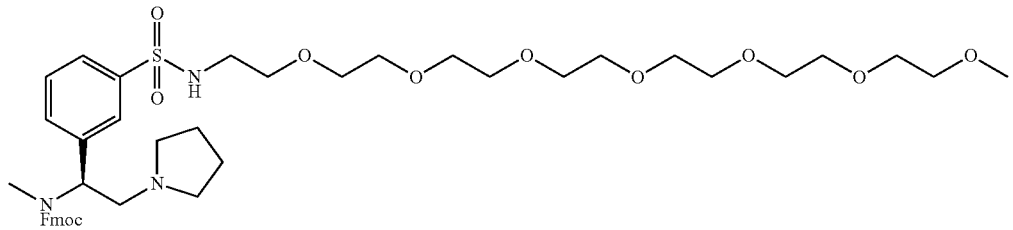

A mixture of (S)-(9H-fluoren-9-yl)methyl(1-(3-(chlorosulfonyl)phenyl)-2-(pyrrolidin-1-yl)ethyl)(methyl)carbamate (1.0 g, 1.90 mmol), TEA (0.32 mL, 2.28 mmol) in DCM (10 mL) is reacted with mPEG$_7$-NH$_2$ (0.65 g, 1.90 mmol) at ambient temperature. After five hours of stirring, the reaction mixture is washed with H$_2$O (10 mL×2) and brine (10 mL). The organic layer, post drying over anhydrous sodium sulfate, is concentrated under vacuum to afford the crude product. The crude product, upon purification using column chromatography affords (S)-(9H-fluoren-9-yl)methyl (1-(3-(N-(2,5,8,11,14,17,20-heptaoxadocosan-22-yl)sulfamoyl)phenyl)-2-(pyrrolidin-1-yl)ethyl)(methyl)carbamate.

Step 6: Preparation of (S)—N-(2,5,8,11,14,17,20-heptaoxadocosan-22-yl)-3-(1-(methylamino)-2-(pyrrolidin-1-yl)ethyl)benzenesulfonamide To a solution of (S)—N-(2,5,8,11,14,17,20-heptaoxadocosan-22-yl)-3-(1-(methylamino)-2-(pyrrolidin-1-yl)ethyl)benzenesulfonamide (200 mg, 0.33 mmol) in acetonitrile (5 mL), 3,4-dichlorophenyl acetic acid (75 mg, 0.363 mmol), HOBt.H$_2$O (53 mg, 0.396 mmol), DIPEA (115 μL, 0.66 mmol) and EDC.HCl (76 mg, 0.396 mmol), are charged at ambient temperature. The reaction mixture, after stirring for two hours, is concentrated under vacuum. The residue is dissolved in DCM (10 mL), and is washed with 10% sodium carbonate (10 mL×2), 10% NH$_4$Cl (10 mL×2), and brine (10 mL), respectively. The organic layer, after drying over anhydrous sodium sulfate, is concentrated under vacuum. The resultant gummy mass upon purification by column chromatography affords (S)—N-(1-(3-(N-(2,5,8,11,14,17,20-heptaoxadocosan-22-yl)sulfamoyl)phenyl)-2-(pyrrolidin-1-yl)ethyl)-2-(3,4-dichlorophenyl)-N-methylacetamide free base. The free base is dissolved in 4M hydrochloride in

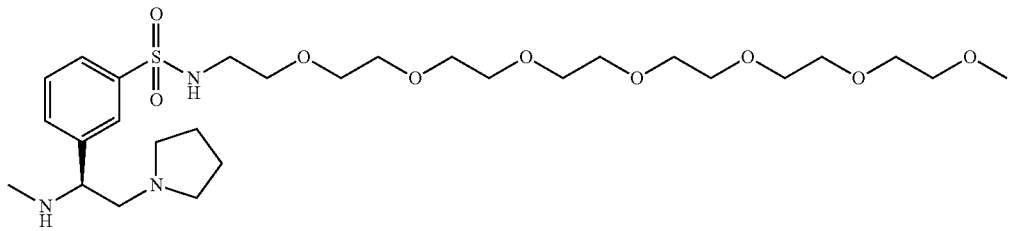

To a solution of (S)-(9H-fluoren-9-yl)methyl (1-(3-(N-(2,5,8,11,14,17,20-heptaoxadocosan-22-yl)sulfamoyl)phenyl)-2-(pyrrolidin-1-yl)ethyl)(methyl)carbamate (1.00 g, 1.20 mmol) in acetonitrile, TEA (0.34 mL, 2.4 mmol) is charged at ambient temperature. The mixture would is stirred for three hours. After three hours, the reaction mixture is concentrated under vacuum. The crude product, upon purification by column chromatography, afforts (S)—N-(2,5,8,11,14,17,20-heptaoxadocosan-22-yl)-3-(1-(methylamino)-2-(pyrrolidin-1-yl)ethyl)benzenesulfonamide.

Step 7: Preparation of (S)—N-(1-(3-(N-(2,5,8,11,14,17,20-heptaoxadocosan-22-yl)sulfamoyl)phenyl)-2-(pyrrolidin-1-yl)ethyl)-2-(3,4-dichlorophenyl)-N-methylacetamide hydrochloride 2-propanol and the mixture would be concentrated to afford product as hydrochloride salt.

The prophetic example described above may be modified to introduce oligomers of various lengths as disclosed herein.

Prophetic Example 15

Preparation of N-{(1S)-2-(Azetidin-1-yl)-1-[4-(2-hydroxyethoxy)phenyl]ethyl}-2-(3,4-dichlorophenyl)-N-methylacetamide Using the procedure outlined in the schematic below, the named compound can be prepared.

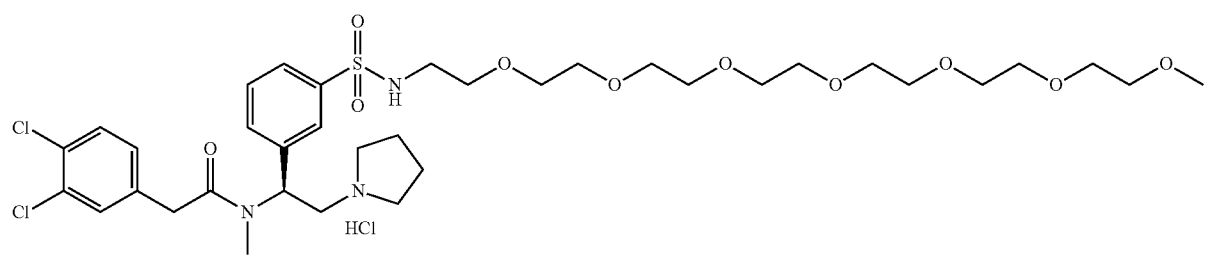 [SMILES: COCCOCCOCCOCCOCCOCCOCCNS(=O)(=O)c1cccc([C@@H](CN2CCCC2)N(C)C(=O)Cc2ccc(Cl)c(Cl)c2)c1 ; Cl]

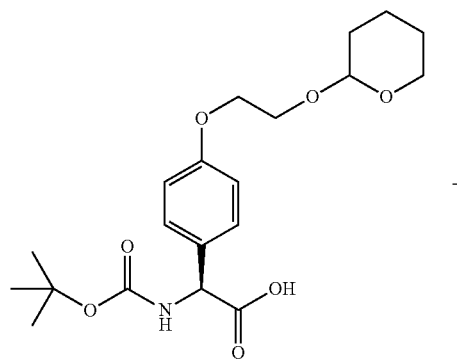

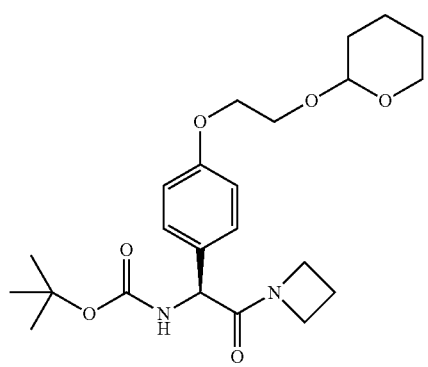 [SMILES: CC(C)(C)OC(=O)N[C@H](C(=O)N1CCC1)c1ccc(OCCOC2CCCCO2)cc1]

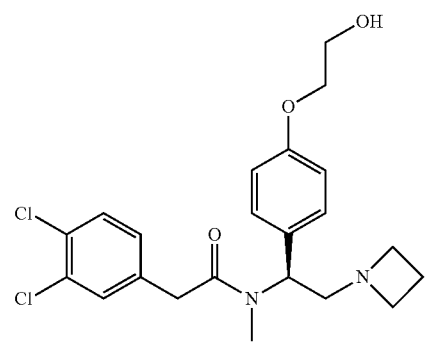 [SMILES: CN(C(=O)Cc1ccc(Cl)c(Cl)c1)[C@H](CN1CCC1)c1ccc(OCCO)cc1]

Step 1: Preparation of tert-Butyl [(1S)-2-(azetidin-1-yl)-2-oxo-1-{4-[2-(tetrahydro-2H-pyran-2-yloxy)ethoxy]phenyl}ethyl]carbamate Azetidine (0.057 g, 1.00 mmol) and N,N-diisopropylethylamine (0.256 g, 2.00 mmol) are dissolved in 20 mL of dichloromethane. (2S)-2-((tert-butoxycarbonyl)amino)-2-(4-(2-((tetrahydro-2H-pyran-2-yl)oxy)ethoxy)phenyl)acetic acid (0.395 g, 1.00 mmol) is added into the solution and the mixture is cooled in an ice-bath under stirring. Finally, O-(benzotriazol-1-yl)-N,N,N',N'-tetramethyluronium tetrafluoroborate (0.385 g, 1.20 mmol) is added into the solution. The reaction mixture is stirred for four hours at 0° C. Dichloromethane (150 mL) is added into the mixture and resultant solution is washed with water (2×100 mL) and dried over sodium sulfate. The residue is purified by column chromatography.

Step 2: Preparation of (1S)-2-(azetidin-1-yl)-N-methyl-1-(4-(2-((tetrahydro-2H-pyran-2 yl)oxy)ethoxy)phenyl)ethanamine Tert-butyl ((1S)-2-(azetidin-1-yl)-2-oxo-1-(4-(2-((tetrahydro-2H-pyran-2-yl)oxy)ethoxy)phenyl)ethyl)carbamate (0.20 g, 0.46 mmol) is dissolved in tetrahydrofuran (3 mL). A 2.0 M solution of lithium aluminum hydride ("LAM") (1.5 mL, 3.0 mmol) is added into the solution at room temperature. The mixture is stirred at 65° C. for four hours. A 3N solution of sodium carbonate is added cautiously until effervescence ceases. Dichloromethane (50 mL) is added into the mixture. The solid is filtered out and washed with dichloromethane (100 mL). The filtrate is washed with saturated sodium chloride solution and dried over sodium sulfate. The product is obtained after removing solvent.

Step 3: Preparation of N-{(1S)-2-(Azetidin-1-yl)-1-[4-(2-hydroxyethoxy)phenyl]ethyl}-2-(3,4-dichlorophenyl)-N-methylacetamide

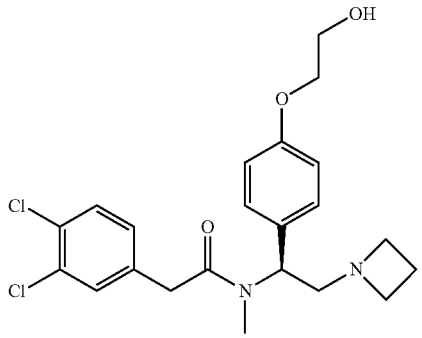

(1S)-2-(Azetidin-1-yl)-N-methyl-1-(4-(2-((tetrahydro-2H-pyran-2-yl)oxy)ethoxy)phenyl)ethanamine (0.20 g, 0.60 mmol), 3,4-dichlorophenylacetic acid (0.120 g, 0.60 mmol), and N,N-diisopropylethylamine (0.15 g, 1.20 mmol) are dissolved in 5 mL of acetonitrile. The mixture is stirred for ten minutes at room temperature and then cooled to 0° C. O-(Benzotriazol-1-yl)-N,N,N',N'-tetramethyluronium tetrafluoroborate (0.23 g, 0.72 mmol) is added into the solution. The reaction mixture is stirred for three hours under an ice-bath. Dichloromethane (150 mL) is added into the solution and the resultant solution is washed with water and dried over sodium sulfate. Evaporation of the solvent and purification of the residue by flash chromatography yield an oil, which is dissolved in 10 mL of methanol. P-Toluenesulfonic acid (0.20 g, 1.2 mmol) is added into the solution. The mixture is stirred for sixty minutes at room temperature. Dichloromethane (100 mL) is added into the solution and the solution is washed with sodium carbonate (10%), water and dried over sodium sulfate. Evaporation of the solvent and purification of the residue by flash chromatography yield product.

The example described above may be modified to introduce various substituted azetidines (such as azetidin-3-ol, azetidin-3-amine, and azetidin-3-one) and heterocycles to replace dichlorophenyl (such as pyridine, thoazole, benzofuran).

The prophetic example described above may be modified to introduce oligomers of various lengths as disclosed herein.

Prophetic Example 16

Preparation of 2-(3,4-dichlorophenyl)-N-methyl-N-{(1S)-1-phenyl-2-[(3S)-3-(2-{2-[2-(trifluoromethoxy)ethoxy]ethoxy}ethoxy)pyrrolidin-1-yl]ethyl}acetamide

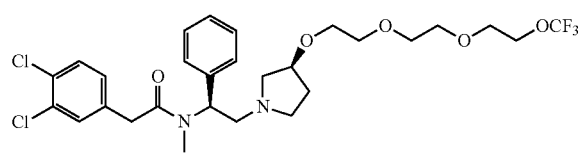 [SMILES: CN(C(=O)Cc1ccc(Cl)c(Cl)c1)[C@H](CN1CC[C@H](OCCOCCOCCOC(F)(F)F)C1)c1ccccc1]

Step 1: Preparation of 2-(2-(2-(trifluoromethoxy)ethoxy)ethoxy)ethyl methanesulfonate

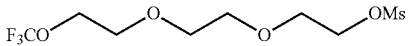

Step 1a: Preparation of O-(2-(2-(2-(benzyloxy)ethoxy)ethoxy)ethyl)S-methyl carbonodithioate

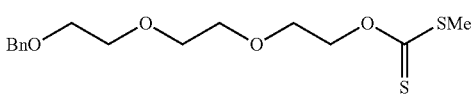 [SMILES: CSC(=S)OCCOCCOCCOCc1ccccc1]

2-(2-(2-(Benzyloxy)ethoxy)ethoxy)ethanol (T. Shiyama et al., *Bioorg. Med. Chem.* (2004), #12, 2831) (13.0 g, 54.1 mmol) is dissolved in 250 mL of tetrahydrofuran and sodium hydride (2.6 g of 60% in mineral oil, 65 mmol) is added into the solution. The mixture is stirred for ten minutes at room temperature and then cooled to 0° C. Carbon disulfide (4.25 mL, 70.33 mmol) is then added under stirring. After stirring for one hour, methyl iodide (4.38 mL, 70.33 mmol) is added drop wise at 0° C. The mixture is stirred for 18 hours at ambient temperature, and concentrated. The residue is dissolved in ethyl acetate (200 mL), the ethyl acetate solution is washed with water (2×300 mL), brine (300 mL) and dried over anhydrous sodium sulfate. Evaporation of the solvent and purification of the residue by flash chromatography yields O-(2-(2-(2-(benzyloxy)ethoxy)ethoxy)ethyl)S-methyl carbonodithioate.

Step 1b: Preparation of 2-(2-(2-(trifluoromethoxy)ethoxy)ethoxy)ethanol

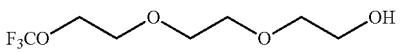 [SMILES: OCCOCCOCCOC(F)(F)F]

To a cooled (to −78° C.) suspension of 1,3-dibromo-5,5-dimethylhydantoin (38.63 g, 136.35 mmol) in dichloromethane (300 mL), HF-pyridine (45.5 mL, 1600 mmol) and O-(2-(2-(2-(benzyloxy)ethoxy)ethoxy)ethyl)S-methyl carbonodithioate (15.0 g, 45.45 mmol) is added into the reaction mixture at −78° C. After the addition, the mixture is stirred at −78° C. for one hour, warmed to 0° C., and stirred for two hours. Dichloromethane (150 mL) is added into the reaction mixture. The solution is washed with water (100 mL×3), saturated sodium bisulfite and dried over anhydrous sodium sulfate. The crude product is then dissolved in methanol and hydrogenated at ambient temperature with addition of 10% Pd/C (50% wet) (1.5 g) under a hydrogen atmosphere. The reaction mixture is filtered and concentrated under vacuum to give 2-(2-(2-(trifluoromethoxy)ethoxy)ethoxy)ethanol.

Step 1c: Preparation of 2-(2-(2-(trifluoromethoxy)ethoxy)ethoxy)ethyl methanesulfonate

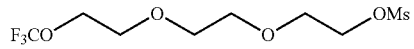

To a mixture of 2-(2-(2-(trifluoromethoxy)ethoxy)ethoxy)ethanol (8.0 g, 36.7 mmol) and TEA (6.64 mL, 47.7 mmol) in dichloromethane (150 mL), is added methane sulfonyl chloride (3.12 mL, 40.37 mmol) at 0° C. The reaction mixture is stirred at ambient temperature for one hour. Dichloromethane (150 mL) is added into the reaction mixture, is washed with water (200 mL×3) and is dried over anhydrous sodium sulfate. Evaporation of the solvent and purification of the residue by flash chromatography yields 2-(2-(2-(trifluoromethoxy)ethoxy)ethoxy)ethyl methanesulfonate.

Step 2: Preparation of (3S)-3-(2-{2-[2-(trifluoromethoxy)ethoxy]ethoxy)}ethoxy)pyrrolidine

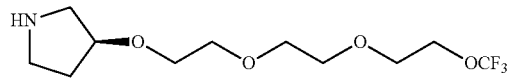 [SMILES: FC(F)(F)OCCOCCOCCO[C@H]1CCNC1]

(S)-tert-Butyl-3-hydroxypyrrolidine-1-carboxylate is dissolved in tetrahydrofuran and the solution is cooled to 0° C. Sodium hydride (60% in mineral oil, 1.2 equivalents) is added and the reaction mixture is stirred for thirty minutes. 2-(2-(2-(Trifluoromethoxy)ethoxy) ethoxy)ethyl methanesulfonate (1.5 equivalents), dissolved in tetrahydrofuran, is added to the above mixture while maintaining the temperature at 0° C. The reaction mixture is stirred for an additional one hour at 0° C., and then allowed to equilibrate to room temperature. After overnight stirring at room temperature, the reaction mixture is concentrated under reduced pressure. The residue is dissolved in dichloromethane and the resulting solution is washed with water. The organic portion is dried over anhydrous sodium sulfate and concentrated under reduced pressure. The residue is dissolved in dichloromethane/trifluoroacetic acid (2:1) and stirred for four hours at room temperature. The solution is concentrated under reduced pressure. The residue is dissolved in water and the pH of the solution is adjusted to 9 with sodium carbonate. The solution is saturated with sodium chloride and extracted with dichloromethane. The organic portion is dried over anhydrous sodium sulfate and concentrated under reduced pressure. The residue is purified by chromatography to give (3S)-3-(2-{2-[2(trifluoromethoxy)ethoxy]ethoxy}y ethoxy) pyrrolidine.

Step 3: Preparation of benzyl {(1S)-2-oxo-1-phenyl-2-[(3S)-3-(2-{2-[2-(trifluoromethoxy)ethoxy]ethoxy}ethoxy)pyrrolidin-1-yl]ethyl}carbamate

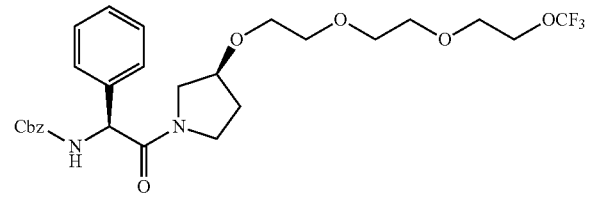 [SMILES: O=C(N[C@H](C(=O)N1CC[C@H](OCCOCCOCCOC(F)(F)F)C1)c1ccccc1)OCc1ccccc1]

(3S)-3-(2-{2-[2(Trifluoromethoxy)ethoxy]ethoxy}ethoxy)pyrrolidine (1.0 equivalent), (S)-2-(((benzyloxy)carbonyl)amino)-2-phenylacetic acid (1.0 equivalent) and diisopropylethylamine (3.0 equivalents) are dissolved in acetonitrile. The solution is stirred for 15 minutes at 22-25° C. and is then cooled to 0° C. O-(Benzotriazol-1-yl)-N,N,N',N'-tetramethyluronium tetrafluoroborate (1.2 equivalents) is added to the solution. The reaction mixture is stirred for one hour at 0° C. and then for four hours at room temperature. The reaction mixture is concentrated under reduced pressure. The resulting residue is dissolved in dichloromethane and washed with brine. The solution is dried over anhydrous sodium sulfate and concentrated. The residue is then purified by chromatography to give benzyl {(1S)-2-oxo-1-phenyl-2-[(3S)-3-(2-{2-[2-(trifluoromethoxy)ethoxy]ethoxy}ethoxy)pyrrolidin-1-yl] ethyl}carbamate.

Step 4: Preparation of (1S)—N-methyl-1-phenyl-2-[(3S)-3-(2-{2-[2-(trifluoromethoxy)ethoxy]ethoxy}ethoxy)pyrrolidin-1-yl]ethanamine

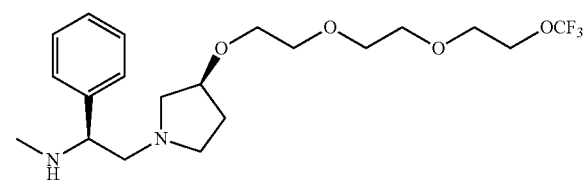 [SMILES: CN[C@H](CN1CC[C@H](OCCOCCOCCOC(F)(F)F)C1)c1ccccc1]

Benzyl {(1S)-2-oxo-1-phenyl-2-[(3S)-3-(2-{2-[2-(trifluoromethoxy)ethoxy]ethoxy}ethoxy)pyrrolidin-1-yl]ethyl) }carbamate is dissolved in tetrahydrofuran. The mixture is cooled to 0° C. Lithium aluminum hydride (2.0 M in tetrahydrofuran, 5.0 equivalents) is added to the above mixture and the mixture is stirred for 15 minutes at 0° C. and then heated to 65° C. and maintained at that temperature for four hours. A 3N aqueous sodium carbonate solution is added cautiously until effervescence ceases. The solid is removed by filtration and is washed with dichloromethane. The filtrate is concentrated under reduced pressure and the residue is dissolved in dichloromethane. The solution is washed with brine, and dried over anhydrous sodium sulfate. The organic portion is filtered and concentrated under reduced pressure. The residue is purified by chromatography to give (1S)—N-methyl-1-phenyl-2-[(3S)-3-(2-{2-[2-(trifluoromethoxy)ethoxy]ethoxy}ethoxy)pyrrolidin-1-yl] ethanamine.

Step 5: Preparation of 2-(3,4-dichlorophenyl)-N-methyl-N-{(1S)-1-phenyl-2-[(3S)-3-(2-{2-[2-(trifluoromethoxy)ethoxy]ethoxy}ethoxy)pyrrolidin-1-yl]ethyl}acetamide

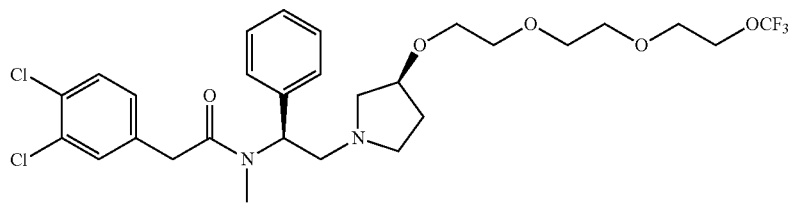 [SMILES: CN(C(=O)Cc1ccc(Cl)c(Cl)c1)[C@H](CN1CC[C@H](OCCOCCOCCOC(F)(F)F)C1)c1ccccc1]

(1S)—N-methyl-1-phenyl-2-[(3S)-3-(2-{2-[2-(trifluoromethoxy)ethoxy]ethoxy}ethoxy)pyrrolidin-1-yl]ethanamine (1.0 equivalent), 2-(3,4-dichlorophenyl)acetic acid (1.0 equivalent), and N,N-diisopropylethylamine (2.0 equivalents) are dissolved in acetonitrile. The resulting solution is stirred for 15 minutes at 22-25° C. and then cooled to 0° C. O-(Benzotriazol-1-yl)-N,N,N',N'-tetramethyluronium tetrafluoroborate (1.2 equivalents) is added to the solution. The reaction mixture is stirred for four hours at 22-25° C. and is then concentrated under reduced pressure. The residue is dissolved in dichloromethane and is washed with water. The organic portion is dried over anhydrous sodium sulfate. The organic portion is filtered and concentrated under reduced pressure. The residue is purified by chromatography to give 2-(3,4-dichlorophenyl)-N-methyl-N-{(1S)-1-phenyl-2-[(3S)-3-(2-{2-[2-(trifluoromethoxy)ethoxy]ethoxy}ethoxy)pyrrolidin-1-yl]ethyl}acetamide.

Prophetic Example 17

Preparation of 2-(3,4-Dichlorophenyl)-N-{(1S)-1-[4-(2-hydroxyethoxy)phenyl]-2-[(3S)-3-(2-{2-[2-(trifluoromethoxy)ethoxy]ethoxy}ethoxy)pyrrolidin-1-yl]ethyl}-N-methylacetamide Step 1: Preparation of tert-butyl {(1S)-1-(4-hydroxyphenyl)-2-oxo-2-[(3S)-3-(2-{2-[2-(trifluoromethoxy)ethoxy]ethoxy}ethoxy)pyrrolidin-1-yl]ethyl}carbamate

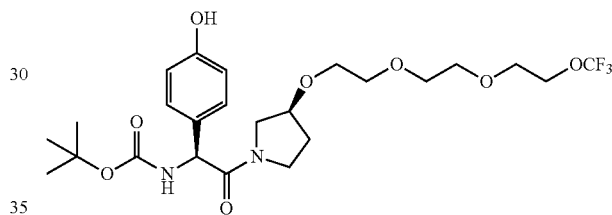

(3S)-3-(2-{2-[2-(Trifluoromethoxy)ethoxy]ethoxy}ethoxy)pyrrolidine (1.0 equivalent) and N,N-diisopropylethylamine (2.0 equivalents) are dissolved in dichloromethane. (S)-2-((Tert-butoxycarbonyl)amino)-2-(4-hydroxyphenyl)acetic acid (1.0 equivalent) is added to the solution and the mixture is cooled in an ice-bath under stirring. O-(Benzotriazol-1-yl)-N,N,N',N'-tetramethyluronium tetrafluoroborate (1.2 equivalents) is added and the reaction mixture is stirred for four hours at room temperature. Dichloromethane is added and the resultant mixture is

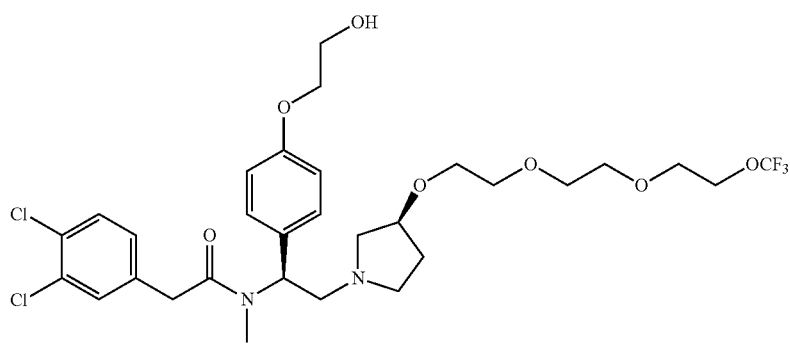 [SMILES: CN(C(=O)Cc1ccc(Cl)c(Cl)c1)[C@H](CN1CC[C@H](OCCOCCOCCOC(F)(F)F)C1)c1ccc(OCCO)cc1]

washed with water. The organic portion is dried over anhydrous sodium sulfate, and is then filtered and concentrated under reduced pressure. The residue is purified by chromatography to give tert-butyl {(1S)-1-(4-hydroxyphenyl)-2-oxo-2-[(3S)-3-(2-{2-[2-(trifluoromethoxy)ethoxy]ethoxy}ethoxy)pyrrolidin-1-yl]ethyl}carbamate.

Step 2: Preparation of tert-butyl {(1S)-1-[4-(2-{[tert-butyl(dimethyl)silyl]oxy}ethoxy)phenyl]-2-oxo-2-[(3S)-3-(2-{2-[2-(trifluoromethoxy)ethoxy]ethoxy}ethoxy)pyrrolidin-1-yl]ethyl}carbamate

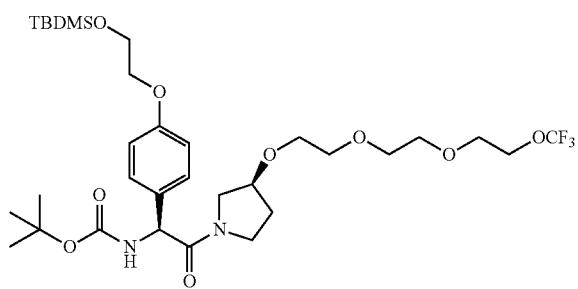 [SMILES: CC(C)(C)OC(=O)N[C@H](C(=O)N1CC[C@H](OCCOCCOCCOC(F)(F)F)C1)c1ccc(OCCO[Si](C)(C)C(C)(C)C)cc1]

To a solution of tert-butyl {(1S)-1-(4-hydroxyphenyl)-2-oxo-2-[(3S)-3-(2-{2-[2-(trifluoromethoxy)ethoxy]ethoxy}ethoxy)pyrrolidin-1-yl]ethyl}carbamate (1.0 equivalent) and (2-bromoethoxy)(tert-butyl)dimethylsilane (5.0 equivalents) in acetone is added potassium carbonate (5.0 equivalents). The mixture is stirred at 70° C. overnight. After this period, the reaction mixture is cooled to room temperature and dichloromethane is added and the resultant mixture is washed with water. The organic portion is dried over anhydrous sodium sulfate, and is then filtered and concentrated under reduced pressure. The residue is purified by chromatography to give tert-butyl {(1S)-1-[4-(2-{[tert-butyl(dimethyl)silyl]oxy}ethoxy)phenyl]-2-oxo-2-[(3S)-3-(2-{2-[2-(trifluoromethoxy)ethoxy]ethoxy}ethoxy)pyrrolidin-1-yl]ethyl}carbamate.

Step 3: Preparation of 2-(4-{(1S)-1-(Methylamino)-2-[(3S)-3-(2-{2-[2-(trifluoromethoxy)ethoxy]ethoxy}ethoxy)pyrrolidin-1-yl]ethyl}phenoxy)ethanol

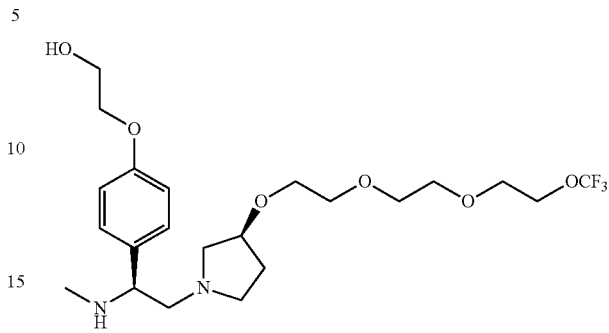

tert-Butyl {(1S)-1-[4-(2-{[tert-butyl(dimethyl)silyl]oxy}ethoxy)phenyl]-2-oxo-2-[(3S)-3-(2-{2-[2-(trifluoromethoxy)ethoxy]ethoxy}ethoxy)pyrrolidin-1-yl]ethyl}carbamate (1.0 equivalent) is dissolved in tetrahydrofuran. A 2.0 M solution of lithium aluminum hydride (7.0 equivalents) is added to the solution at room temperature. The mixture is stirred at 65° C. for four hours. A 3N solution of sodium carbonate is added cautiously until effervescence ceases. Dichloromethane is added to the mixture. The solid is filtered and washed with dichloromethane. The filtrate is washed with saturated sodium chloride solution and is dried over sodium sulfate. The organic portion is filtered and concentrated under reduced pressure to give 2-(4-{(1S)-1-(methylamino)-2-[(3S)-3-(2-{2-[2-(trifluoromethoxy)ethoxy]ethoxy}ethoxy)pyrrolidin-1-yl]ethyl}phenoxy)ethanol.

Step 4: Preparation of 2-(3,4-dichlorophenyl)-N-{(1S)-1-[4-(2-hydroxyethoxy)phenyl]-2-[(3S)-3-(2-{2-[2-(trifluoromethoxy)ethoxy]ethoxy}ethoxy)pyrrolidin-1-yl]ethyl}-N-methylacetamide

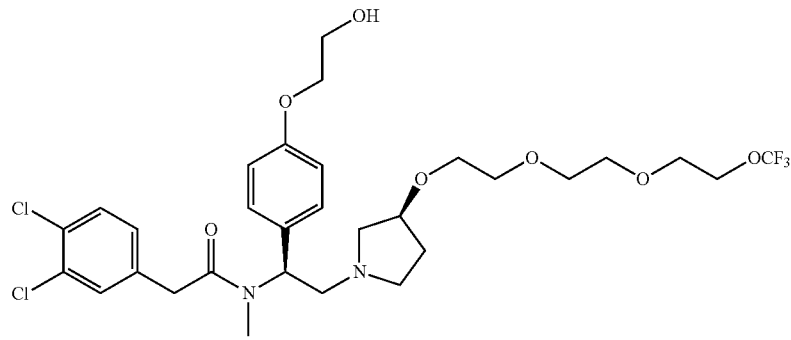 [SMILES: CN(C(=O)Cc1ccc(Cl)c(Cl)c1)[C@H](CN1CC[C@H](OCCOCCOCCOC(F)(F)F)C1)c1ccc(OCCO)cc1]

2-(4-{(1S)-1-(methylamino)-2-[(3S)-3-(2-{2-[2-(trifluoromethoxy)ethoxy]ethoxy)}ethoxy)pyrrolidin-1-yl]ethyl)}phenoxy)ethanol (1.0 equivalent), 3,4-dichlorophenylacetic acid (1.0 equivalent), and N,N-diisopropylethylamine (2.0 equivalents) are dissolved in acetonitrile. The solution is stirred for ten minutes at room temperature and then cooled to 0° C. O-(Benzotriazol-1-yl)-N,N,N',N'-tetramethyluronium tetrafluoroborate (1.2 equivalents) is added to the solution. The reaction mixture is stirred for one hour at 0° C. and then overnight. Dichloromethane is added and the mixture is washed with water and dried over sodium sulfate. The organic portion is dried over anhydrous sodium sulfate, and is then filtered and concentrated under reduced pressure. The residue is purified by chromatography to give 2-(3,4-dichlorophenyl)-N-{(1S)-

1-[4-(2-hydroxyethoxy)phenyl]-2-[(3S)-3-(2-{2-[2-(trifluoromethoxy)ethoxy]ethoxy}ethoxy)pyrrolidin-1-yl]ethyl}-N-methylacetamide.
Prophetic Example 18
Preparation of 2-(3,4-Dichlorophenyl)-N-(2-[(3S)-3-{2-[2-(2-methoxyethoxy)ethoxy]ethoxy}pyrrolidin-1-yl]-1-{4-[(2-methoxyethyl)amino]phenyl}ethyl)-N-methylacetamide
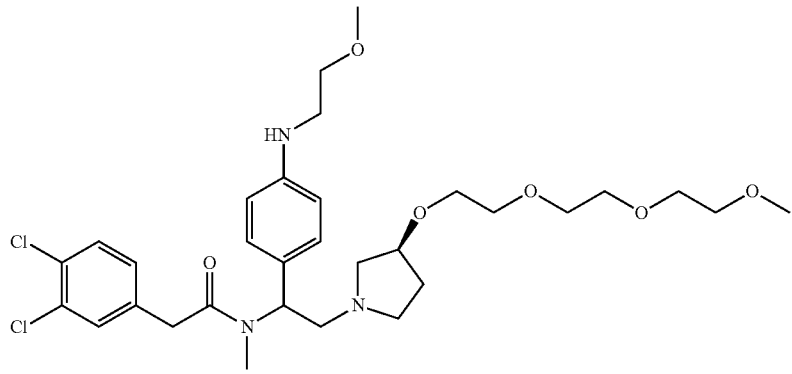 [SMILES: COCCNc1ccc(C(CN2CC[C@H](OCCOCCOCCOC)C2)N(C)C(=O)Cc2ccc(Cl)c(Cl)c2)cc1]
Using the procedure outlined in the schematic below, the named compound can be prepared.
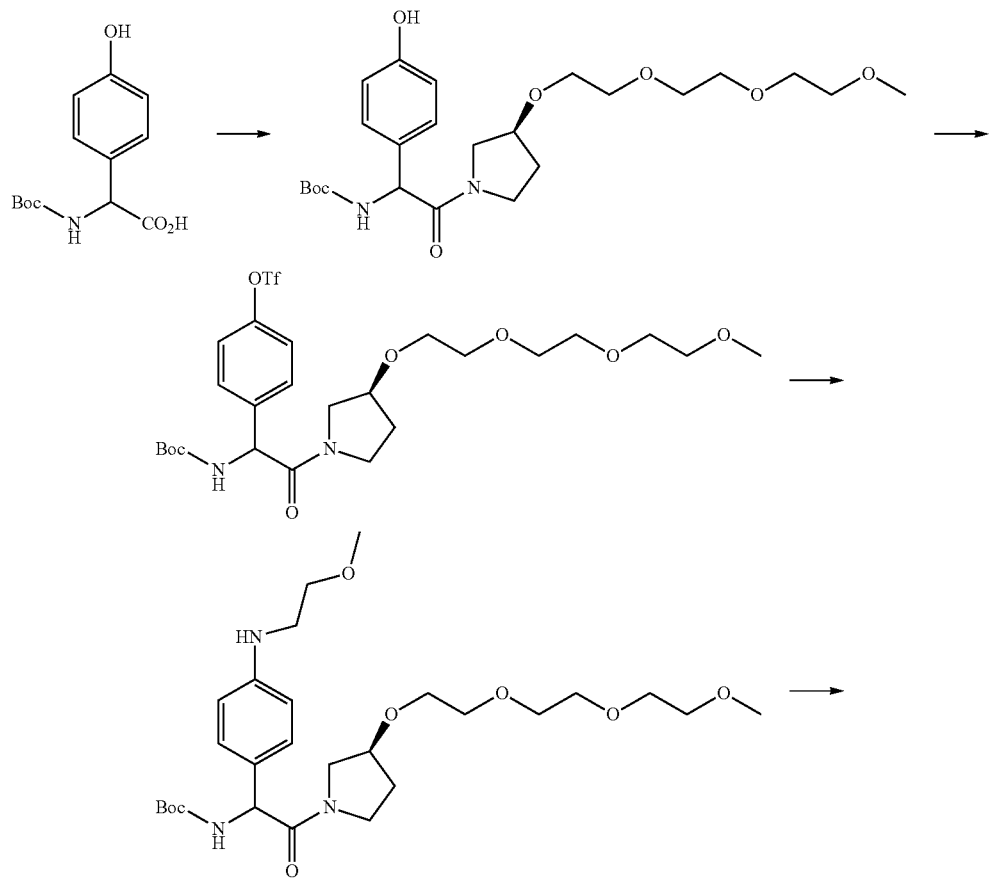

-continued

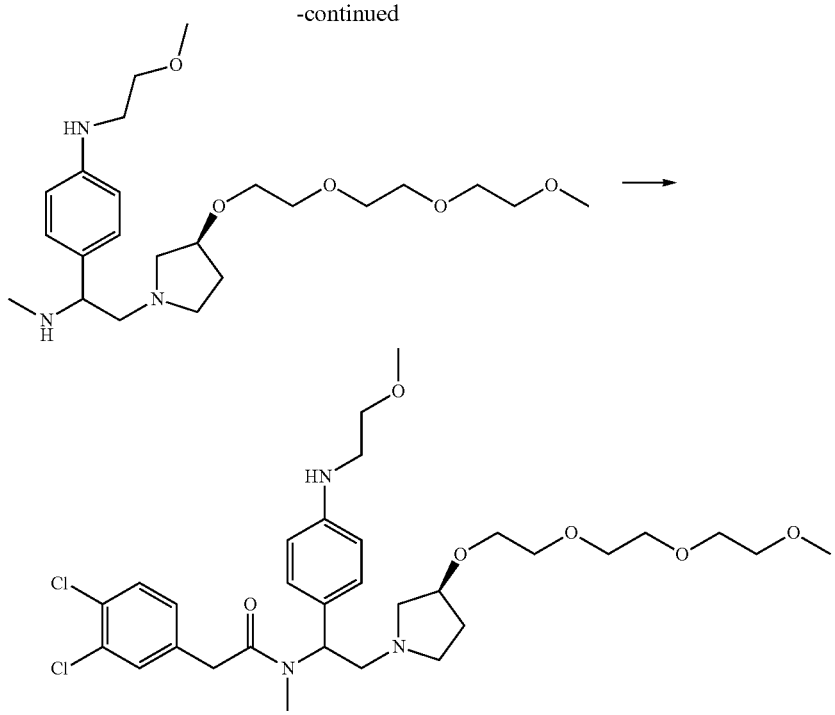

Step 1: Preparation of tert-Butyl {1-(4-hydroxyphenyl)-2-[(3S)-3-{2-[2-(2-methoxyethoxy)ethoxy]ethoxy}pyrrolidin-1-yl]-2-oxoethyl}carbamate

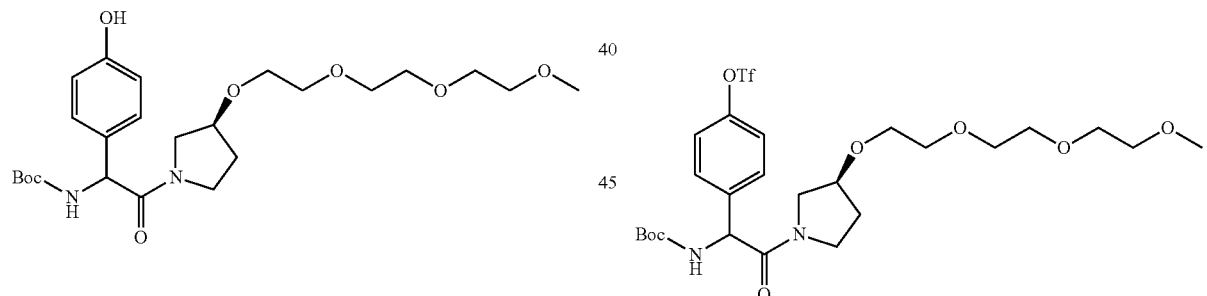

[(tert-Butoxycarbonyl)amino](4-hydroxyphenyl)acetic acid (1.0 equivalent), (S)-3-(2-(2-(2-methoxyethoxy)ethoxy)ethoxy)pyrrolidine (1.0 equivalent) and DIPEA (3.0 equivalents) are dissolved in acetonitrile. The above mixture is stirred for 15 minutes at 22-25° C. and then is cooled to 0° C. O-(Benzotriazol-1-yl)-N,N,N',N'-tetramethyluronium tetrafluoroborate (1.2 equivalents) is added into the solution. The reaction mixture is stirred for one hour at 0° C. and then at four hours at room temperature. The reaction mixture is concentrated under reduced pressure. The resulting residue is dissolved in DCM and washed with brine. The solution is dried over anhydrous sodium sulfate and is concentrated. The obtained residue is then purified by column chromatography to give tert-butyl {1-(4-hydroxyphenyl)-2-[(3S)-3-{2-[2-(2-methoxyethoxy)ethoxy]ethoxy}pyrrolidin-1-yl]-2-oxoethyl)}carbamate.

Step 2: Preparation of 4-{1-[(tert-butoxycarbonyl)amino]-2-[(3S)-3-{2-[2-(2-methoxyethoxy)ethoxy]ethoxy}pyrrolidin-1-yl]-2-oxoethyl}phenyl trifluoromethanesulfonate (tert-Butyl {1-(4-hydroxyphenyl)-2-[(3S)-3-{2-[2-(2-methoxyethoxy)ethoxy]ethoxy}pyrrolidin-1-yl]-2-oxoethyl}carbamate (1.0 equivalent) and cesium carbonate (1.5 equivalents) are dissolved in tetrahydrofuran. Then, 1,1,1-trifluoro-N-phenyl-N-((trifluoromethyl)sulfonyl)methanesulfonamide (1.5 equivalents) is added to the mixture and the reaction is stirred under nitrogen at 70° C. for five hours. The tetrahydrofuran is removed under reduced pressure. To the residue is added dichloromethane, followed by water. The organic portion is washed with brine and is dried over sodium sulfate. The solvent is removed and the crude product is purified by chromatography to give 4-{1-[(tert-Butoxycarbonyl)amino]-2-[(3S)-3-{2-[2-(2-methoxyethoxy)ethoxy]ethoxy}pyrrolidin-1-yl]-2-oxoethyl}phenyl trifluoromethanesulfonate.

Step 3: Preparation of tert-butyl (2-[(3S)-3-{2-[2-(2-methoxyethoxy)ethoxy]ethoxy}pyrrolidin-1-yl]-1-{4-[(2-methoxyethyl)amino]phenyl}-2-oxoethyl)carbamate

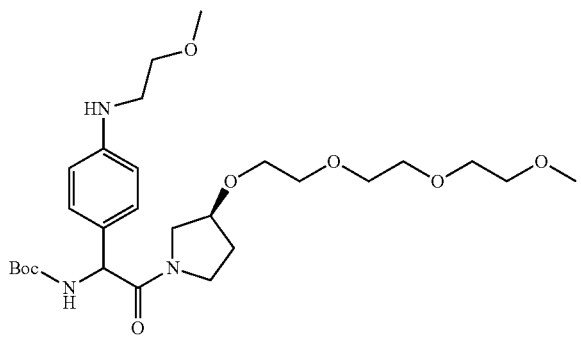 [SMILES: COCCNc1ccc(C(NC(=O)OC(C)(C)C)C(=O)N2CC[C@H](OCCOCCOCCOC)C2)cc1]

4-{1-[(tert-Butoxycarbonyl)amino]-2-[(3S)-3-{2-[2-(2methoxyethoxy)ethoxy]ethoxy}pyrrolidin-1-yl]-2-oxoethyl}phenyl trifluoromethanesulfonate (1.0 equivalent) and 2-methoxyethanamine (3.0 equivalents) are dissolved in anhydrous toluene. Cesium carbonate (3.0 equivalents), di-tert-butyl(2',4',6'-triisopropyl-3,6-dimethoxy-[1,1'-biphenyl]-2-yl)phosphine (0.2 equivalents), and diacetoxypalladium (0.1 equivalents) are added. The reaction mixture is purged with nitrogen. The mixture is stirred at 90° C. for five hours. Water and saturated sodium chloride solution are added into the reaction mixture. The mixture is extracted with dichloromethane. The organic portion is dried over anhydrous sodium sulfate and is then concentrated under reduced pressure. The residue is purified by chromatography to give tert-butyl (2-[(3S)-3-{2-[2-(2-methoxyethoxy)ethoxy]ethoxy}pyrrolidin-1-yl]-1-{4-[(2-methoxyethyl)amino]phenyl}-2-oxoethyl)carbamate.

Step 4: Preparation of 4-{2-[(3S)-3-{2-[2-(2-methoxyethoxy)ethoxy]ethoxy}pyrrolidin-1-yl]-1-(methylamino)ethyl}-N-(2-methoxyethyl)aniline

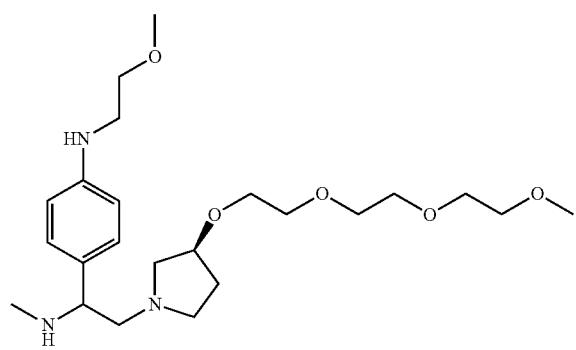

tert-Butyl (2-[(3S)-3-{2-[2-(2-methoxyethoxy)ethoxy]ethoxy}pyrrolidin-1-yl]-1-{4-[(2-methoxyethyl)amino]phenyl}-2-oxoethyl)carbamate (1.0 equivalent) in tetrahydrofuran is added dropwise to a stirred 2.0 M solution of lithium aluminum hydride (7.0 equivalents). The mixture is stirred for thirty minutes at room temperature and then is heated to 65° C. for four hours. A 3N solution of sodium carbonate is added cautiously until effervescence ceases. The solid is filtered out and washed with dichloromethane. The filtrate is concentrated and the residue is dissolved in dichloromethane. The resulting solution is dried over sodium sulfate. The organic portion is filtered and concentrated under reduced pressure. The residue is purified by chromatography to give 4-{2-[(3S)-3-{2-[2-(2-methoxyethoxy)ethoxy]ethoxy}pyrrolidin-1-yl]-1-(methylamino)ethyl}-N-(2-methoxyethyl)aniline.

Step 5: Preparation of 2-(3,4-Dichlorophenyl)-N-(2-[(3S)-3-{2-[2-(2-methoxyethoxy)ethoxy]ethoxy}pyrrolidin-1-yl]-1-{4-[(2-methoxyethyl)amino]phenyl}ethyl)-N-methylacetamide

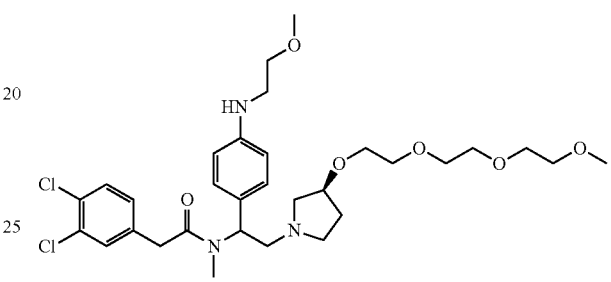

4-{2-[(3S)-3-{2-[2-(2-Methoxyethoxy)ethoxy]ethoxy}pyrrolidin-1-yl]-1-(methylamino)ethyl}-N-(2-methoxyethyl)aniline (1.1 equivalents), 2-(3,4-dichlorophenyl)acetic acid (1.0 equivalent), and N,N-diisopropylethylamine (2.2 equivalents) are dissolved in acetonitrile. The mixture is stirred for ten minutes at room temperature and then cooled to 0° C. O-(Benzotriazol-1-yl)-N,N,N',N'-tetramethyluronium tetrafluoroborate (1.3 equivalents) is added into the solution. The reaction mixture is stirred for four hours at 0° C. Dichloromethane is added into the solution and the solution is washed with water and dried over sodium sulfate. Evaporation of the solvent and purification of the residue by flash chromatography gives 2-(3,4-Dichlorophenyl)-N-(2-[(3S)-3-{2-[2-(2-methoxyethoxy)ethoxy]ethoxy}pyrrolidin-1-yl]-1-{4-[(2-methoxyethyl)amino]phenyl}ethyl)-N-methylacetamide.

Prophetic Example 19

Preparation of 2-(3,4-dichlorophenyl)-N-{(1S)-2-[(3S)-3-{2-[2-(2-hydroxyethoxy)ethoxy]ethoxy}pyrrolidin-1-yl]-1-[4-(2-hydroxyethoxy)phenyl]ethyl}-N-methylacetamide

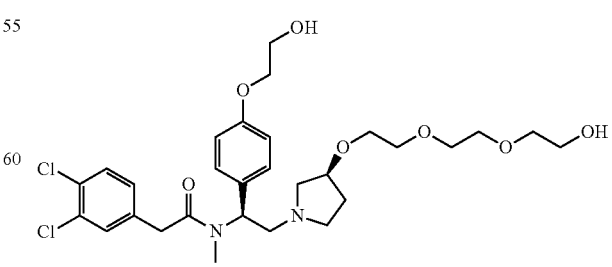

Using the procedure outlined in the schematic below, the named compound can be prepared.

201                                                                                             202
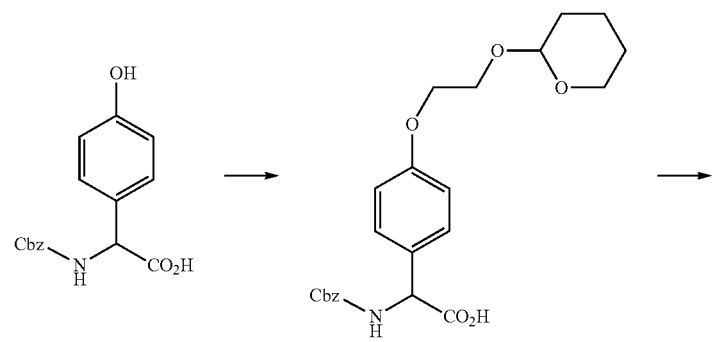
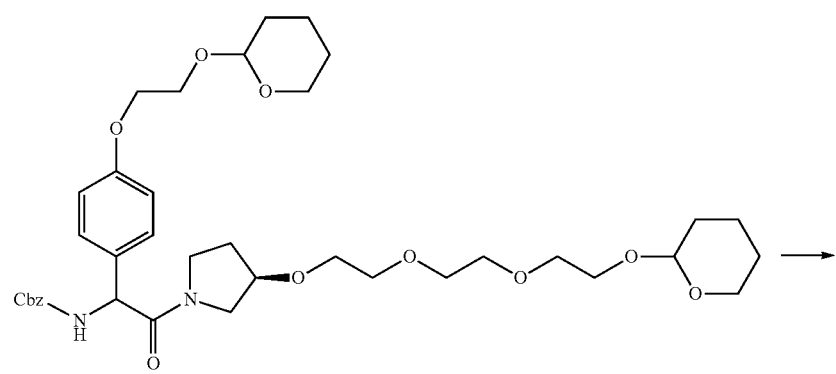
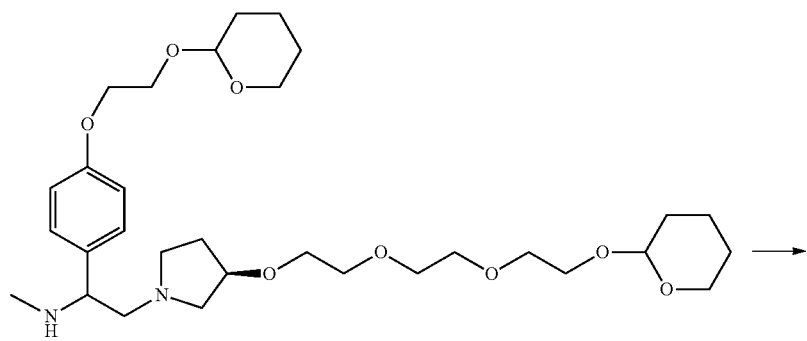
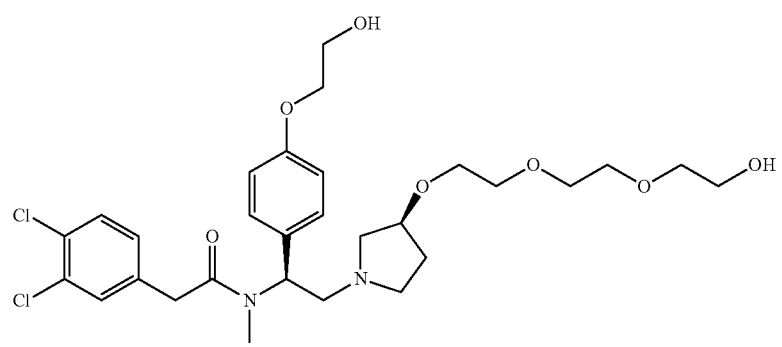

Step 1: Preparation of (2S)-{[(Benzyloxy)carbonyl]amino}{4-[2-(tetrahydro-2H-pyran-2-yloxy)ethoxy]phenyl}acetic acid

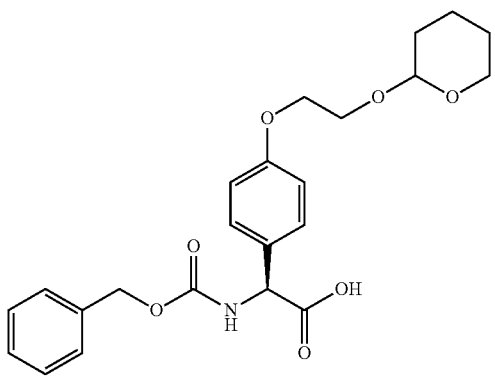 [SMILES: O=C(N[C@H](C(=O)O)c1ccc(OCCOC2CCCCO2)cc1)OCc1ccccc1]

(2S)-{[(Benzyloxy)carbonyl]amino}(4-hydroxyphenyl)acetic acid is dissolved in dimethylformamide and the solution is cooled in an ice bath. Sodium hydride (60% in mineral oil, 2.2 equivalents) is added in portions. The mixture is stirred for thirty minutes at 0° C. and then 2-(2-bromoethoxy)tetrahydro-2H-pyran (1.1 equivalents) in dimethylformamide is added in portions. The reaction mixture is stirred at room temperature overnight. The reaction mixture is diluted with ice/water. The mixture is extracted with ethyl acetate. The aqueous layer is cooled in an ice bath and acidified using 1.5 M aqueous potassium hydrogen sulfate to pH 2-3. The resulting mixture is extracted with ethyl acetate. The organic portion is washed with water, brine, and dried over sodium sulfate. The organic portion is filtered and concentrated under reduced pressure to give (2S)-{[(Benzyloxy)carbonyl]amino}{4-[2-(tetrahydro-2H-pyran-2-yloxy)ethoxy]phenyl}acetic acid.

Step 2: Preparation of (3S)-3-(2-{2-[2-(tetrahydro-2H-pyran-2-yloxy)ethoxy]ethoxy}ethoxy)pyrrolidin

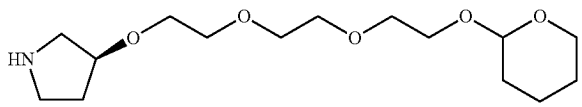 [SMILES: C1CCC(OCCOCCOCCO[C@H]2CCNC2)OC1]

Benzyl (3S)-3-hydroxypyrrolidine-1-carboxylate (6.0 g, 32.04 mmol) is dissolved in tetrahydrofuran. The solution is cooled to 0° C. and sodium hydride (60% in mineral oil, 1.2 equivalents) is added in portions. The solution is stirred at 0° C. for 30 minutes. 2-{2-[2-(Tetrahydro-2H-pyran-2-yloxy)ethoxy]ethoxy}ethyl methanesulfonate (Lu, *J. Journal of Drug Targeting*, 2010, vol. 18, #7, 520-535) (1.5 equivalents) in tetrahydrofuran is added to the solution while maintaining the temperature at 0° C. The reaction mixture is stirred for additional one hour at 0° C. and is allowed to warm to 22-25° C. The reaction is then heated to 60° C. and is stirred for six hours. The reaction mixture is concentrated under reduced pressure. The residue is dissolved in dichloromethane and the resulting solution is washed with water. The organic portion is dried over anhydrous sodium sulfate and concentrated under reduced pressure. Benzyl (3S)-3-(2-{2-[2-(tetrahydro-2H-pyran-2-yloxy)ethoxy]ethoxy}ethoxy)pyrrolidine-1-carboxylate is dissolved in ethanol in a hydrogenation flask, and charged with Pd/C (10%). The mixture is hydrogenated on a Parr shaker (50 psi) for 24 hours. The mixture is purged with nitrogen and filtered through a celite pad. The celite pad is further washed with more ethanol. The filtrate is concentrated under reduced pressure to give (3S)-3-(2-{2-[2-(Tetrahydro-2H-pyran-2-yloxy)ethoxy]ethoxy}ethoxy)pyrrolidine.

Step 3: Preparation of benzyl (2-oxo-2-[(3R)-3-(2-{2-[2-(tetrahydro-2H-pyran-2-yloxy)ethoxy]ethoxy}ethoxy)pyrrolidin-1-yl]-1-{4-[2-(tetrahydro-2H-pyran-2-yloxy)ethoxy]phenyl}ethyl)carbamate

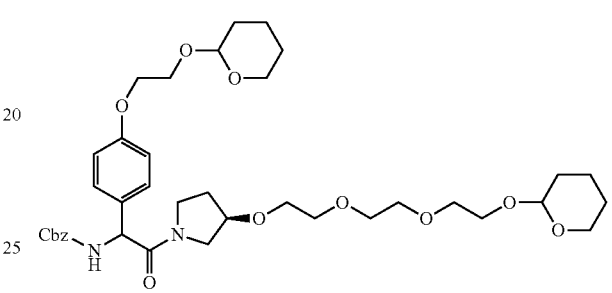

(2S)-{[(Benzyloxy)carbonyl]amino}{4-[2-(tetrahydro-2H-pyran-2-yloxy)ethoxy]phenyl}acetic acid (1.0 equivalent), (3S)-3-(2-{2-[2-(Tetrahydro-2H-pyran-2-yloxy)ethoxy]ethoxy}ethoxy)pyrrolidine (1.1 equivalents), and N,N-diisopropylethylamine (2.0 equivalents) are dissolved in acetonitrile. The mixture is stirred for ten minutes at room temperature and is then cooled to 0° C. O-(Benzotriazol-1-yl)-N,N,N',N'-tetramethyluronium tetrafluoroborate (1.2 equivalents) is added into the solution. The reaction mixture is stirred for two hours under an ice bath and the reaction is continued at room temperature for four hours. Dichloromethane is added into the reaction mixture, and the resulting solution is washed with water. The solution is dried over sodium sulfate and concentrated. The residue is purified by chromatography to give benzyl (2-oxo-2-[(3R)-3-(2-{2-[2-(tetrahydro-2H-pyran-2-yloxy)ethoxy]ethoxy}ethoxy)pyrrolidin-1-yl]-1-{4-[2-(tetrahydro-2H-pyran-2-yloxy)ethoxy]phenyl}ethyl)carbamate.

Step 4: Preparation of N-methyl-2-[(3R)-3-(2-{2-[2-(tetrahydro-2H-pyran-2-yloxy)ethoxy]ethoxy}ethoxy)pyrrolidin-1-yl]-1-{4-[2-(tetrahydro-2H-pyran-2-yloxy)ethoxy]phenyl}ethanamine

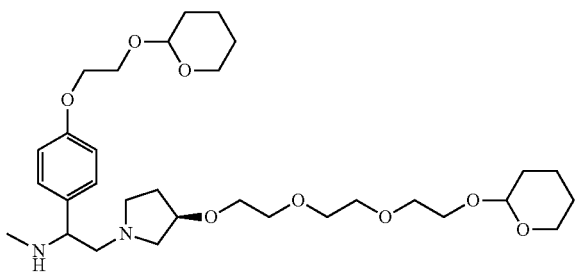 [SMILES: CNC(CN1CC[C@@H](OCCOCCOCCOC2CCCCO2)C1)c1ccc(OCCOC2CCCCO2)cc1]

tert-Butyl (2-oxo-2-[(3R)-3-(2-{2-[2-(tetrahydro-2H-pyran-2-yloxy)ethoxy]ethoxy}ethoxy)pyrrolidin-1-yl]-1-

{4-[2-(tetrahydro-2H-pyran-2-yloxy)ethoxy]phenyl}ethyl)carbamate (1.0 equivalent) is dissolved in tetrahydrofuran. A 2.0 M solution of lithium aluminum hydride (6.0 equivalents) is added into the solution at room temperature. The mixture is stirred at 65° C. for four hours. A 3N solution of sodium carbonate is added cautiously until effervescence ceases. Ethyl acetate is added into the mixture. The solid is filtered out and washed with ethyl acetate. The filtrate is washed with saturated sodium chloride solution and is dried over sodium sulfate. The organic portion is filtered and concentrated under reduced pressure. The residue is purified by chromatography to give N-Methyl-2-[(3R)-3-(2-{2-[2-(tetrahydro-2H-pyran-2-yloxy)ethoxy]ethoxy}ethoxy)pyrrolidin-1-yl]-1-{4-[2-(tetrahydro-2H-pyran-2-yloxy)ethoxy]phenyl}ethanamine.

Step 5: Preparation of 2-(3,4-dichlorophenyl)-N-{(1S)-2-[(3S)-3-{2-[2-(2-hydroxyethoxy)ethoxy]ethoxy}pyrrolidin-1-yl]-1-[4-(2-hydroxyethoxy)phenyl]ethyl}-N-methylacetamide

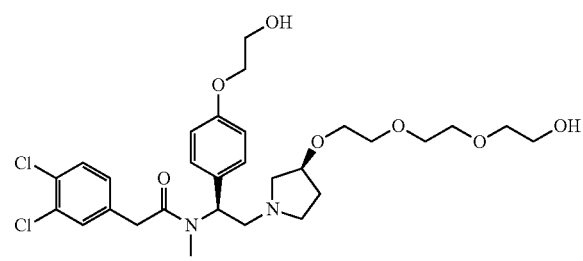 [SMILES: CN(C(=O)Cc1ccc(Cl)c(Cl)c1)[C@H](CN1CC[C@H](OCCOCCOCCO)C1)c1ccc(OCCO)cc1]

N-Methyl-2-[(3R)-3-(2-{2-[2-(tetrahydro-2H-pyran-2-yloxy)ethoxy]ethoxy}ethoxy)pyrrolidin-1-yl]-1-{4-[2-(tetrahydro-2H-pyran-2-yloxy)ethoxy]phenyl}ethanamine (1.0 equivalent), 3,4-dichlorophenylacetic acid (1.0 equivalent), and N,N-diisopropylethylamine (2.0 equivalents) are dissolved in acetonitrile. The mixture is stirred for ten minutes at room temperature and then cooled to 0° C. O-(Benzotriazol-1-yl)-N,N,N',N'-tetramethyluronium tetrafluoroborate (1.2 equivalents) is added into the solution. The reaction mixture is stirred for three hours under an ice-bath. Dichloromethane is added into the solution and the resultant solution is washed with water and dried over anhydrous sodium sulfate. The organic portion is filtered and is concentrated under reduced pressure. The residue is dissolved in methanol. p-Toluenesulfonic acid (2.0 equivalents) is added into the solution. The mixture is stirred for one hour at room temperature. Dichloromethane is added into the solution and the solution is washed with sodium carbonate (10%), water and is dried over anhydrous sodium sulfate. The organic portion is filtered and concentrated under reduced pressure. The residue is purified by chromatography to give 2-(3,4-dichlorophenyl)-N-{(1S)-2-[(3S)-3-{2-[2-(2-hydroxyethoxy)ethoxy]ethoxy}pyrrolidin-1-yl]-1-[4-(2-hydroxyethoxy)phenyl]ethyl}-N-methylacetamide.

Prophetic Example 20

In Situ Rat Brain Perfusion

The in situ perfusion experiment measures the relative permeability of compounds across a model of the blood-brain barrier. In situ perfusion of opioids into rat brain is performed as described in Summerfield et al., *J Pharmacol Exp Ther* 322: 205-213 (2007).

Adult male Sprague Dawley rats are used for the study. Rats are anaesthetized and the left common carotid artery is surgically cannulated for perfusion. Test compounds are perfused at concentrations of 5-50 µM in a Krebs Ringer perfusion buffer (pH 7.4). Atenolol and antipyrine are included as low and moderate permeability markers, respectively. At the end of a 30 second perfusion, the brains are removed, the left brain hemisphere is excised and homogenized. Test compounds are extracted and analyzed using LC-MS/MS. The brain permeability of the test compounds is calculated as follows:

$P = Kin/S$, where P is the permeability in cm/s, Kin is the unidirectional transfer constant (ml/min/gram), and S is the luminal area of the brain vascular space.

The relative permeability as determined in the in situ brain perfusion experiment provides information regarding the rates at which compounds enter the central nervous system from the periphery. It is used to characterize and compare the degree to which compounds of the present invention penetrate the BBB as compared to known compounds or analogs of the tested compounds.

Prophetic Example 21

Acetic Acid Writhing

An analgesic assay may be used to determine whether a given compound can reduce and/or prevent visceral pain in mice. The assay utilizes CD-1 male mice (5-8 mice per group), each mouse being approximately 0.015-0.030 kg on the study day. Mice are treated according to standard protocols.

Mice are given a single "pretreatment" dose of a compound of the present invention, a known compound, such as morphine (which is a known analgesic which has been shown to reduce writhing behavior in this model), or control solution (IV, SC, IP or orally) fifteen to thirty minutes prior to the administration of the acetic acid solution. The animal is given an IP injection of an irritant (acetic acid) that induces "writhing" which may include: contractions of the abdomen, twisting and turning of the trunk, arching of the back and the extension of the hindlimbs. Mice are given a single IP injection (0.1 mL/10 g bodyweight) of a 0.5% acetic acid solution. After the injection the animals are returned to their observation enclosure and their behavior is observed. Contractions are counted between 0 and 20 minutes after the injection. The animals are used once. Each test article may be dose at multiple doses to determine a dose response curve.

What is claimed is:

1. A compound according to Formula I:

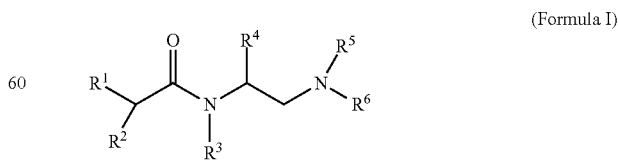

(Formula I)

wherein:
R$^1$ is an optionally substituted phenyl;
R$^2$ is hydrogen or phenyl;

R³ is selected from hydrogen and an optionally substituted lower alkyl;

R⁴ is a phenyl substituted with —X-POLY;

R⁵ and R⁶ together with the nitrogen to which they are attached form an optionally substituted pyrrolidinyl or azetidinyl ring;

X is an optional linker selected from a covalent bond; —C(O)NH—; —C(O)NHCH₂—; —C(O)NHCH₂CH₂—; —OC(O)NH—; —C(O)NH—; —O—; —NHC(O)—; —NHC(O)CH₂—; —NHC(O)CH₂O—; —NHC(O)CH₂CH₂—; —NH—; or —NHS(O)₂—; and POLY is a poly(alkylene oxide) oligomer comprising 2 to 10 alkylene oxide monomers;

or pharmaceutically acceptable salts and solvates thereof.

2. The compound of claim 1, wherein R¹ is substituted with 1, 2, or 3 halogen atoms.

3. The compound of claim 1, wherein R³ is methyl.

4. The compound of claim 1, wherein R⁵ and R⁶ are taken together to form an optionally substituted pyrrolidinyl.

5. The compound claim 1, wherein the poly(alkylene oxide) oligomer is a poly(ethylene oxide) oligomer.

6. The compound of claim 1, wherein POLY is end-capped with a hydroxyl group, a lower alkoxy group, or a trifluoromethoxy group.

7. The compound of claim 1 according to the following formula:

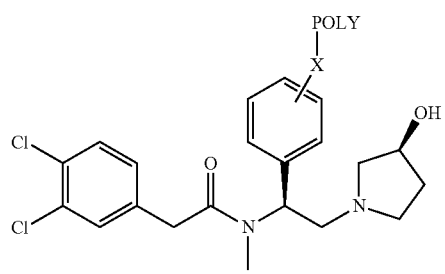

wherein:
POLY is —(CH₂CH₂O)ₙ—Y;
n is an integer from 2 to 10; and
Y is hydrogen, methyl, or trifluoromethoxy;
or pharmaceutically acceptable salts and solvates thereof.

8. The compound of claim 7 according to the following formula:

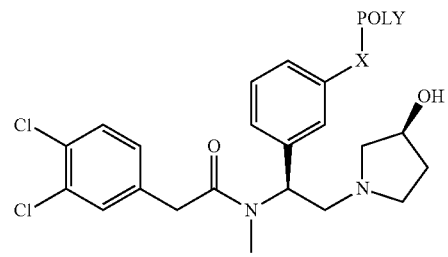

or pharmaceutically acceptable salts and solvates thereof.

9. The compound of claim 1 according to the following formula:

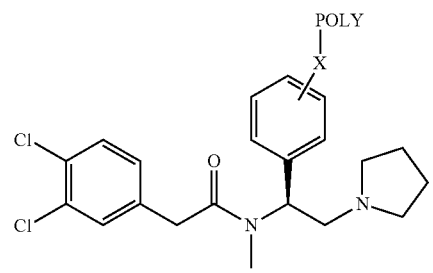

wherein:
POLY is —(CH₂CH₂O)ₙ—Y;
n is an integer from 42 to 10; and
Y is hydrogen, methyl, or trifluoromethoxy;
or pharmaceutically acceptable salts and solvates thereof.

10. The compound of claim 9 according to the following formula:

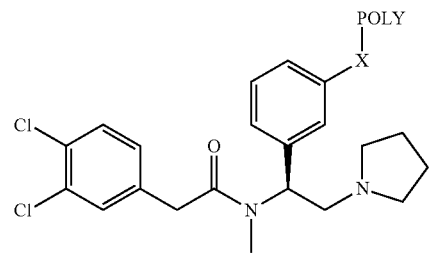

or pharmaceutically acceptable salts and solvates thereof.

11. The compound of claim 1 according to any of the following formulas:

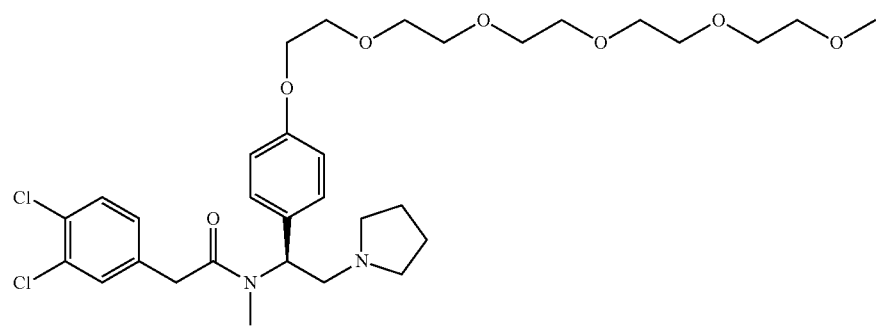

-continued
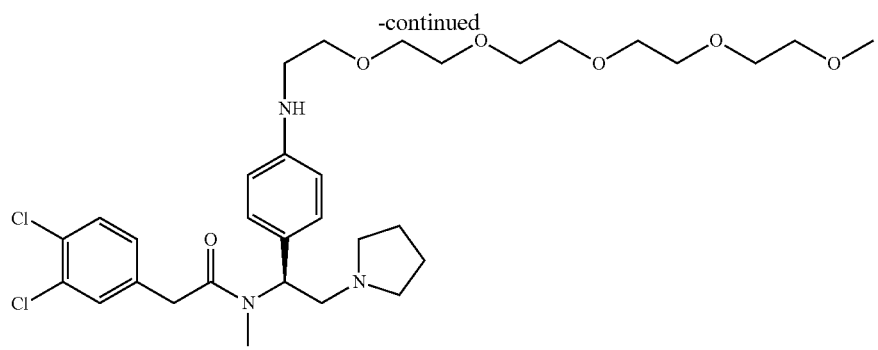
or pharmaceutically acceptable salts and solvates thereof.
12. A pharmaceutical composition comprising a compound of claim 1 and at least one pharmaceutically acceptable excipient.
13. A method of treating pain or inflammation comprising administering a compound of claim 1 to a patient in need thereof.
* * * * *